(12) United States Patent
Ferren et al.

(10) Patent No.: US 9,408,530 B2
(45) Date of Patent: Aug. 9, 2016

(54) PARAMETER-BASED NAVIGATION BY A LUMEN TRAVELING DEVICE

(75) Inventors: Bran Ferren, Beverly Hills, CA (US); W. Daniel Hillis, Encino, CA (US); Roderick A. Hyde, Redmond, WA (US); Muriel Y. Ishikawa, Livermore, CA (US); Edward K. Y. Jung, Bellevue, WA (US); Eric C. Leuthardt, St Louis, MO (US); Nathan P. Myhrvold, Bellevue, WA (US); Thomas J. Nugent, Jr., Bellevue, WA (US); Elizabeth A. Sweeney, Seattle, WA (US); Clarence T. Tegreene, Bellevue, WA (US); Lowell L. Wood, Jr., Bellevue, WA (US); Victoria Y. H. Wood, Livermore, CA (US)

(73) Assignee: Gearbox, LLC, Bellevue, WA (US)

( * ) Notice: Subject to any disclaimer, the term of this patent is extended or adjusted under 35 U.S.C. 154(b) by 0 days.

(21) Appl. No.: 13/136,680

(22) Filed: Aug. 5, 2011

(65) Prior Publication Data

US 2012/0035440 A1 Feb. 9, 2012

Related U.S. Application Data

(60) Continuation-in-part of application No. 11/403,230, filed on Apr. 12, 2006, now Pat. No. 9,011,329, and a continuation-in-part of application No. 11/417,898, filed on May 4, 2006, now Pat. No. 8,353,896, and a (Continued)

(51) Int. Cl.
*A61B 5/00* (2006.01)
*A61B 1/04* (2006.01)

(Continued)

(52) U.S. Cl.
CPC ............... *A61B 1/041* (2013.01); *A61B 5/0022* (2013.01); *A61B 5/0031* (2013.01); *A61B 5/062* (2013.01); *A61B 5/07* (2013.01); *A61B 5/073* (2013.01); *A61B 5/076* (2013.01); *A61B 5/082* (2013.01); *A61B 5/14546* (2013.01);

(Continued)

(58) Field of Classification Search
USPC ......................................................... 600/300
See application file for complete search history.

(56) References Cited

U.S. PATENT DOCUMENTS 3,391,697 A 7/1968 Greatbatch
3,802,417 A 4/1974 Lang (Continued)

FOREIGN PATENT DOCUMENTS

CN 99810271.7 10/2001
EP 1 245 201 A1 10/2002

(Continued)

OTHER PUBLICATIONS

U.S. Appl. No. 12/930,916, Wood, Jr., Lowell.

(Continued)

*Primary Examiner* — Patricia Mallari
*Assistant Examiner* — Karen Toth

(57) ABSTRACT

Methods of controlling the operation of a device traveling in a body tube tree, including sensing parameters from possible directions of travel and selecting the direction of travel based on the sensed parameters, implemented with a control system located partially or fully on the lumen traveling device. Various actions can be performed by the device for, e.g., medical or therapeutic purposes. Machine-readable media including instructions for performing the methods are also described.

17 Claims, 99 Drawing Sheets

Related U.S. Application Data continuation-in-part of application No. 11/478,368, filed on Jun. 28, 2006, now abandoned, and a continuation-in-part of application No. 11/485,619, filed on Jul. 11, 2006, now Pat. No. 9,173,837, and a continuation-in-part of application No. 11/645,358, filed on Dec. 21, 2006, now Pat. No. 8,000,784, and a continuation-in-part of application No. 11/651,946, filed on Jan. 9, 2007, now Pat. No. 7,998,060, and a continuation-in-part of application No. 11/725,982, filed on Mar. 19, 2007, which is a continuation-in-part of application No. 11/645,357, filed on Dec. 21, 2006, now Pat. No. 7,857,767, application No. 13/136,680, which is a continuation of application No. 11/726,025, filed on Mar. 19, 2007, now Pat. No. 8,512,219, which is a continuation-in-part of application No. 11/645,357, filed on Dec. 21, 2006, now Pat. No. 7,857,767, application No. 13/136,680, which is a continuation-in-part of application No. 11/726,031, filed on Mar. 19, 2007, now abandoned, and a continuation-in-part of application No. 12/319,882, filed on Jan. 12, 2009, now Pat. No. 8,019,413, which is a division of application No. 11/726,031, filed on Mar. 19, 2007, now abandoned, application No. 13/136,680, which is a continuation-in-part of application No. 12/319,881, filed on Jan. 12, 2009, now Pat. No. 8,024,036, which is a division of application No. 11/726,031, filed on Mar. 19, 2007, now abandoned, application No. 13/136,680, which is a continuation-in-part of application No. 13/136,677, filed on Aug. 5, 2011, now abandoned, and a continuation-in-part of application No. 13/136,679, filed on Aug. 5, 2011, now Pat. No. 9,198,563, and a continuation-in-part of application No. 13/136,676, filed on Aug. 5, 2011, now abandoned, and a continuation-in-part of application No. 13/136,675, filed on Aug. 5, 2011, now abandoned, and a continuation-in-part of application No. 13/136,674, filed on Aug. 5, 2011, now abandoned, and a continuation-in-part of application No. 13/136,678, filed on Aug. 5, 2011, now abandoned.

(51) Int. Cl.

| | | |
|---|---|---|
| *A61B 5/06* | (2006.01) | |
| *A61B 5/07* | (2006.01) | |
| *A61B 5/08* | (2006.01) | |
| *A61B 10/00* | (2006.01) | |
| *A61B 10/04* | (2006.01) | |
| *A61B 18/20* | (2006.01) | |
| *A61B 5/02* | (2006.01) | |
| *A61B 5/0215* | (2006.01) | |
| *A61B 5/026* | (2006.01) | |
| *A61B 5/03* | (2006.01) | |
| *A61B 5/145* | (2006.01) | |
| *A61B 7/00* | (2006.01) | |
| *A61B 17/22* | (2006.01) | |
| *A61B 10/02* | (2006.01) | |
| *A61B 17/00* | (2006.01) | |
| *A61B 19/00* | (2006.01) | |
| *A61F 2/82* | (2013.01) | |
| *A61N 1/40* | (2006.01) | |
| *A61N 7/00* | (2006.01) | |

(52) U.S. Cl.
CPC .............. *A61B 5/4064* (2013.01); *A61B 5/411* (2013.01); *A61B 5/4839* (2013.01); *A61B 10/0045* (2013.01); *A61B 10/04* (2013.01); *A61B 17/22012* (2013.01); *A61B 18/20* (2013.01); *A61B 34/73* (2016.02); *A61B 5/0071* (2013.01); *A61B 5/026* (2013.01); *A61B 5/02007* (2013.01); *A61B 5/0215* (2013.01); *A61B 5/03* (2013.01); *A61B 5/14539* (2013.01); *A61B 5/418* (2013.01); *A61B 7/00* (2013.01); *A61B 17/22* (2013.01); *A61B 2010/0077* (2013.01); *A61B 2010/0225* (2013.01); *A61B 2017/00022* (2013.01); *A61B 2017/00345* (2013.01); *A61B 2019/2253* (2013.01); *A61F 2/82* (2013.01); *A61N 1/406* (2013.01); *A61N 7/00* (2013.01)

(56) References Cited

U.S. PATENT DOCUMENTS

| | | |
|---|---|---|
| 3,821,469 A | 6/1974 | Whetstone et al. |
| 3,837,339 A | 9/1974 | Aisenberg et al. |
| 3,941,127 A | 3/1976 | Froning |
| 3,983,474 A | 9/1976 | Kuipers |
| 4,054,881 A | 10/1977 | Raab |
| 4,119,900 A | 10/1978 | Kremnitz |
| 4,202,349 A | 5/1980 | Jones |
| 4,262,306 A | 4/1981 | Renner |
| 4,267,831 A | 5/1981 | Aguilar |
| 4,314,251 A | 2/1982 | Raab |
| 4,317,078 A | 2/1982 | Weed et al. |
| 4,339,953 A | 7/1982 | Iwasaki |
| 4,367,741 A | 1/1983 | Michaels |
| 4,396,885 A | 8/1983 | Constant |
| 4,403,321 A | 9/1983 | Krüger |
| 4,418,422 A | 11/1983 | Richter et al. |
| 4,431,005 A | 2/1984 | McCormick |
| 4,585,652 A | 4/1986 | Miller et al. |
| 4,628,928 A | 12/1986 | Lowell |
| 4,638,798 A | 1/1987 | Shelden et al. |
| 4,642,786 A | 2/1987 | Hansen |
| 4,651,732 A | 3/1987 | Frederick |
| 4,658,214 A | 4/1987 | Petersen |
| 4,714,460 A | 12/1987 | Calderon |
| 4,717,381 A | 1/1988 | Papantonakos |
| 4,733,661 A | 3/1988 | Palestrant |
| 4,763,667 A | 8/1988 | Manzo |
| 4,769,006 A | 9/1988 | Papantonakos |
| 4,771,772 A | 9/1988 | DeWitt |
| 4,785,806 A | 11/1988 | Deckelbaum |
| 4,800,898 A | 1/1989 | Hess et al. |
| 4,805,615 A | 2/1989 | Carol |
| 4,817,601 A | 4/1989 | Roth et al. |
| 4,871,351 A | 10/1989 | Feingold |
| 4,889,526 A | 12/1989 | Rauscher et al. |
| 4,905,689 A | 3/1990 | Stack et al. |
| 4,943,296 A | 7/1990 | Funakubo et al. |
| 4,944,659 A | 7/1990 | Labbe et al. |
| 4,962,453 A | 10/1990 | Pong et al. |
| 4,981,138 A | 1/1991 | Deckelbaum et al. |
| 4,994,071 A | 2/1991 | MacGregor |
| 5,019,372 A | 5/1991 | Folkman et al. |
| 5,031,109 A | 7/1991 | Gloton |
| 5,042,494 A | 8/1991 | Alfano |
| 5,046,501 A | 9/1991 | Crilly |
| 5,051,906 A | 9/1991 | Evans, Jr. et al. |
| 5,078,140 A | 1/1992 | Kwoh |
| 5,086,401 A | 2/1992 | Glassman et al. |
| 5,115,137 A | 5/1992 | Andersson-Engels et al. |
| 5,153,827 A | 10/1992 | Coutre et al. |
| 5,165,064 A | 11/1992 | Mattaboni |
| 5,176,638 A | 1/1993 | Don Michael |
| 5,188,111 A | 2/1993 | Yates et al. |
| 5,204,814 A | 4/1993 | Noonan et al. |
| 5,234,457 A | 8/1993 | Andersen |
| 5,269,303 A | 12/1993 | Wernicke et al. |
| 5,275,594 A | 1/1994 | Baker et al. |
| 5,279,607 A | 1/1994 | Schentag et al. |
| 5,289,557 A | 2/1994 | Sheinis et al. |

(56) References Cited

U.S. PATENT DOCUMENTS

| | | |
|---|---|---|
| 5,293,872 A | 3/1994 | Alfano et al. |
| 5,310,404 A | 5/1994 | Gyory et al. |
| 5,313,835 A | 5/1994 | Dunn |
| 5,314,451 A | 5/1994 | Mulier |
| 5,321,614 A | 6/1994 | Ashworth |
| 5,335,657 A | 8/1994 | Terry, Jr. et al. |
| 5,337,732 A | 8/1994 | Grundfest et al. |
| 5,338,625 A | 8/1994 | Bates et al. |
| 5,339,051 A | 8/1994 | Koehler et al. |
| 5,350,375 A | 9/1994 | Deckelbaum et al. |
| 5,353,807 A | 10/1994 | DeMarco |
| 5,374,285 A | 12/1994 | Vaiani et al. |
| 5,381,786 A | 1/1995 | Spears |
| 5,386,741 A | 2/1995 | Rennex |
| 5,395,390 A | 3/1995 | Simon et al. |
| 5,398,670 A | 3/1995 | Ortiz et al. |
| 5,403,311 A | 4/1995 | Abele et al. |
| 5,411,551 A | 5/1995 | Winston et al. |
| 5,437,660 A | 8/1995 | Johnson et al. |
| 5,476,450 A | 12/1995 | Ruggio |
| 5,497,147 A | 3/1996 | Arms et al. |
| 5,502,638 A | 3/1996 | Takenaka |
| 5,507,287 A | 4/1996 | Palcic et al. |
| 5,522,394 A | 6/1996 | Zurbrügg |
| 5,551,953 A | 9/1996 | Lattin et al. |
| 5,554,914 A | 9/1996 | Miyazawa |
| 5,569,968 A | 10/1996 | Lal et al. |
| 5,574,347 A | 11/1996 | Neubauer |
| 5,589,932 A | 12/1996 | Garcia-Rubio et al. |
| 5,593,434 A | 1/1997 | Williams |
| 5,599,324 A | 2/1997 | McAlister et al. |
| 5,610,488 A | 3/1997 | Miyazawa |
| 5,624,398 A | 4/1997 | Smith et al. |
| 5,632,754 A | 5/1997 | Farley et al. |
| 5,634,920 A | 6/1997 | Hohla |
| 5,643,296 A | 7/1997 | Hundertmark et al. |
| 5,662,587 A | 9/1997 | Grundfest et al. |
| 5,669,874 A | 9/1997 | Feiring |
| 5,674,276 A | 10/1997 | Andersen et al. |
| 5,688,269 A | 11/1997 | Newton et al. |
| 5,695,457 A | 12/1997 | St. Goar et al. |
| 5,697,967 A | 12/1997 | Dinh et al. |
| 5,702,432 A | 12/1997 | Chen et al. |
| 5,705,293 A | 1/1998 | Hobson |
| 5,728,089 A | 3/1998 | Lal et al. |
| 5,735,276 A | 4/1998 | Lemelson |
| 5,737,279 A | 4/1998 | Carter |
| 5,758,298 A | 5/1998 | Guldner |
| 5,782,798 A | 7/1998 | Rise |
| 5,804,563 A | 9/1998 | Still et al. |
| 5,807,395 A | 9/1998 | Mulier et al. |
| 5,819,736 A | 10/1998 | Avny et al. |
| 5,827,190 A | 10/1998 | Palcic et al. |
| 5,830,179 A | 11/1998 | Mikus et al. |
| 5,830,207 A | 11/1998 | Leeb et al. |
| 5,831,012 A | 11/1998 | Nilsson et al. |
| 5,833,603 A | 11/1998 | Kovacs et al. |
| 5,843,139 A | 12/1998 | Goedeke et al. |
| 5,855,801 A | 1/1999 | Lin et al. |
| 5,865,754 A | 2/1999 | Sevick-Muraca et al. |
| 5,865,828 A | 2/1999 | Jeng |
| 5,873,835 A | 2/1999 | Hastings et al. |
| 5,908,027 A | 6/1999 | Butterfield et al. |
| 5,921,982 A | 7/1999 | Lesh et al. |
| 5,947,119 A | 9/1999 | Reznick |
| 5,951,600 A | 9/1999 | Lemelson |
| 5,954,675 A | 9/1999 | Dellagatta |
| 5,964,773 A | 10/1999 | Greenstein |
| 6,004,269 A | 12/1999 | Crowley et al. |
| 6,016,449 A | 1/2000 | Fischell et al. |
| 6,019,729 A | 2/2000 | Itoigawa et al. |
| 6,022,316 A | 2/2000 | Eppstein et al. |
| 6,053,873 A | 4/2000 | Govari et al. |
| 6,058,932 A | 5/2000 | Hughes |
| 6,086,528 A | 7/2000 | Adair |
| 6,102,845 A | 8/2000 | Woodard et al. |
| 6,108,597 A | 8/2000 | Kirchner et al. |
| 6,111,520 A | 8/2000 | Allen et al. |
| 6,128,538 A | 10/2000 | Fischell et al. |
| 6,134,474 A | 10/2000 | Fischell et al. |
| 6,149,603 A | 11/2000 | Parker |
| 6,159,230 A | 12/2000 | Samuels |
| 6,164,284 A | 12/2000 | Schulman et al. |
| 6,165,170 A | 12/2000 | Wynne et al. |
| 6,170,488 B1 | 1/2001 | Spillman, Jr. et al. |
| 6,175,757 B1 | 1/2001 | Watkins et al. |
| 6,179,789 B1 | 1/2001 | Tu et al. |
| 6,185,452 B1 | 2/2001 | Schulman et al. |
| 6,186,986 B1 | 2/2001 | Berg et al. |
| 6,187,599 B1 | 2/2001 | Asher et al. |
| 6,197,013 B1 | 3/2001 | Reed et al. |
| 6,219,577 B1 | 4/2001 | Brown, III et al. |
| 6,221,099 B1 | 4/2001 | Andersen et al. |
| 6,240,312 B1 | 5/2001 | Alfano et al. |
| 6,240,316 B1 | 5/2001 | Richmond et al. |
| 6,248,345 B1 | 6/2001 | Goldenheim et al. |
| 6,249,076 B1 | 6/2001 | Madden et al. |
| 6,255,361 B1 | 7/2001 | Rajagopalan et al. |
| 6,255,793 B1 | 7/2001 | Peless et al. |
| 6,258,576 B1 | 7/2001 | Richards-Kortum et al. |
| 6,263,245 B1 | 7/2001 | Snell |
| 6,278,379 B1 | 8/2001 | Allen et al. |
| 6,280,386 B1 | 8/2001 | Alfano et al. |
| 6,289,270 B1 | 9/2001 | Baumgarten |
| 6,290,668 B1 | 9/2001 | Gregory et al. |
| 6,295,990 B1 | 10/2001 | Lewis et al. |
| 6,296,638 B1 | 10/2001 | Davison et al. |
| 6,322,532 B1 | 11/2001 | D'Sa et al. |
| 6,337,997 B1 | 1/2002 | Rise |
| 6,372,248 B1 | 4/2002 | Qin et al. |
| 6,383,162 B1 | 5/2002 | Sugarbaker |
| 6,384,741 B1 | 5/2002 | O'Leary, Sr. |
| 6,385,472 B1 | 5/2002 | Hall et al. |
| 6,398,280 B1 | 6/2002 | Parker et al. |
| 6,402,678 B1 | 6/2002 | Fischell et al. |
| 6,409,674 B1 | 6/2002 | Brockway et al. |
| 6,417,641 B2 | 7/2002 | Peless et al. |
| 6,436,120 B1 | 8/2002 | Meglin |
| 6,442,413 B1 | 8/2002 | Silver |
| 6,450,937 B1 | 9/2002 | Mercereau et al. |
| 6,453,199 B1 | 9/2002 | Kobozev |
| 6,464,687 B1 | 10/2002 | Ishikawa et al. |
| 6,475,639 B2 | 11/2002 | Shahinpoor et al. |
| 6,490,483 B2 | 12/2002 | Willis |
| 6,491,618 B1 | 12/2002 | Ganz |
| 6,493,607 B1 | 12/2002 | Bourne et al. |
| 6,497,714 B1 | 12/2002 | Ishikawa et al. |
| 6,500,174 B1 | 12/2002 | Maguire et al. |
| 6,512,949 B1 | 1/2003 | Combs et al. |
| 6,512,950 B2 | 1/2003 | Li et al. |
| 6,514,237 B1 | 2/2003 | Maseda |
| 6,530,950 B1 | 3/2003 | Alvarado et al. |
| 6,547,723 B1 | 4/2003 | Ouchi |
| 6,547,825 B1 | 4/2003 | Shimizu et al. |
| 6,548,982 B1 | 4/2003 | Papanikolopoulos et al. |
| 6,554,798 B1 | 4/2003 | Mann et al. |
| 6,575,969 B1 | 6/2003 | Rittman, III et al. |
| 6,585,763 B1 | 7/2003 | Keilman et al. |
| 6,591,137 B1 | 7/2003 | Fischell et al. |
| 6,592,567 B1 | 7/2003 | Levin et al. |
| 6,597,954 B1 | 7/2003 | Pless et al. |
| 6,607,553 B1 | 8/2003 | Healy et al. |
| 6,612,982 B1 | 9/2003 | Ouchi |
| 6,616,676 B2 | 9/2003 | Bashiri et al. |
| 6,623,519 B2 | 9/2003 | Edwin et al. |
| 6,632,216 B2 | 10/2003 | Houzego et al. |
| 6,638,273 B1 | 10/2003 | Farley et al. |
| 6,648,908 B2 | 11/2003 | Dobak, III et al. |
| 6,666,860 B1 | 12/2003 | Takahashi |
| 6,669,683 B2 | 12/2003 | Santini, Jr. et al. |
| 6,673,042 B1 | 1/2004 | Samson et al. |
| 6,673,363 B2 | 1/2004 | Luo et al. |
| 6,679,893 B1 | 1/2004 | Tran |
| 6,709,388 B1 | 3/2004 | Mosse et al. |

(56) References Cited

U.S. PATENT DOCUMENTS

| | | |
|---|---|---|
| 6,711,423 B2 | 3/2004 | Colvin, Jr. |
| 6,712,835 B2 | 3/2004 | Mazzocchi et al. |
| 6,719,684 B2 | 4/2004 | Kim et al. |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,743,211 B1 | 6/2004 | Prausnitz et al. |
| 6,754,536 B2 | 6/2004 | Swoyer et al. |
| 6,755,802 B2 | 6/2004 | Bell |
| 6,755,803 B1 | 6/2004 | Le et al. |
| 6,764,441 B2 | 7/2004 | Chiel et al. |
| 6,770,071 B2 | 8/2004 | Woloszko et al. |
| 6,773,429 B2 | 8/2004 | Sheppard, Jr. et al. |
| 6,776,165 B2 | 8/2004 | Jin |
| 6,797,522 B1 | 9/2004 | Still et al. |
| 6,802,811 B1 | 10/2004 | Slepian |
| 6,816,632 B1 | 11/2004 | Slice |
| 6,817,998 B2 | 11/2004 | LaHaye |
| 6,824,508 B2 | 11/2004 | Kim et al. |
| 6,824,510 B2 | 11/2004 | Kim et al. |
| 6,824,561 B2 | 11/2004 | Soykan et al. |
| RE38,670 E | 12/2004 | Asah et al. |
| 6,834,118 B2 | 12/2004 | Kim |
| 6,849,183 B2 | 2/2005 | Gorsuch et al. |
| 6,855,115 B2 | 2/2005 | Fonseca et al. |
| 6,860,867 B2 | 3/2005 | Seward et al. |
| 6,861,001 B2 | 3/2005 | Lee et al. |
| 6,866,626 B2 | 3/2005 | Long et al. |
| 6,869,430 B2 | 3/2005 | Balbierz et al. |
| 6,875,209 B2 | 4/2005 | Zvuloni et al. |
| 6,882,881 B1 | 4/2005 | Lesser et al. |
| 6,889,091 B2 | 5/2005 | Hine et al. |
| 6,890,303 B2 | 5/2005 | Fitz |
| 6,898,464 B2 | 5/2005 | Edell et al. |
| 6,911,004 B2 | 6/2005 | Kim et al. |
| 6,911,496 B2 | 6/2005 | Rhee et al. |
| 6,920,359 B2 | 7/2005 | Meadows et al. |
| 6,921,413 B2 | 7/2005 | Mahadevan-Jansen et al. |
| 6,925,357 B2 | 8/2005 | Wang et al. |
| 6,929,636 B1 | 8/2005 | Von Alten |
| 6,936,003 B2 | 8/2005 | Iddan |
| 6,939,290 B2 | 9/2005 | Iddan |
| 6,939,376 B2 | 9/2005 | Shulze et al. |
| 6,950,707 B2 | 9/2005 | Whitehurst |
| 6,953,589 B1 | 10/2005 | Trautman et al. |
| 6,958,034 B2 | 10/2005 | Iddan |
| 6,959,215 B2 | 10/2005 | Gliner et al. |
| 6,960,227 B2 | 11/2005 | Jones et al. |
| 6,963,792 B1 | 11/2005 | Green |
| 6,984,205 B2 | 1/2006 | Gazdzinski |
| 6,984,952 B2 | 1/2006 | Peless et al. |
| 6,991,617 B2 | 1/2006 | Hektner et al. |
| 7,003,352 B1 | 2/2006 | Whitehurst |
| 7,013,177 B1 | 3/2006 | Whitehurst et al. |
| 7,020,231 B1 | 3/2006 | Frey et al. |
| 7,027,134 B1 | 4/2006 | Garcia-Rubio et al. |
| 7,037,343 B2 | 5/2006 | Imran |
| 7,039,453 B2 | 5/2006 | Mullick et al. |
| 7,042,184 B2 | 5/2006 | Oleynikov et al. |
| RE39,133 E | 6/2006 | Clayton et al. |
| 7,060,793 B2 | 6/2006 | Tsien et al. |
| 7,066,180 B2 | 6/2006 | Aylsworth et al. |
| 7,083,578 B2 | 8/2006 | Lewkowicz et al. |
| 7,101,386 B2 | 9/2006 | Dobak, III |
| 7,115,109 B2 | 10/2006 | Gerdts et al. |
| 7,118,531 B2 | 10/2006 | Krill |
| 7,125,382 B2 | 10/2006 | Zhou et al. |
| 7,131,979 B2 | 11/2006 | DiCarlo et al. |
| 7,160,258 B2 | 1/2007 | Imran et al. |
| 7,171,285 B2 | 1/2007 | Kim et al. |
| 7,181,261 B2 | 2/2007 | Silver et al. |
| 7,194,063 B2 | 3/2007 | Dilmanian et al. |
| 7,195,641 B2 | 3/2007 | Palmaz et al. |
| 7,212,110 B1 | 5/2007 | Martin et al. |
| 7,214,182 B2 | 5/2007 | Shimizu et al. |
| 7,228,162 B2 | 6/2007 | Ward et al. |
| 7,236,821 B2 | 6/2007 | Cates et al. |
| 7,244,232 B2 | 7/2007 | Connelly et al. |
| 7,245,954 B2 | 7/2007 | Glukhovsky |
| 7,297,113 B1 | 11/2007 | Russell et al. |
| 7,341,577 B2 | 3/2008 | Gill |
| 7,359,574 B2 | 4/2008 | Lennon et al. |
| 7,365,509 B2 | 4/2008 | Park et al. |
| 7,365,614 B2 | 4/2008 | McCorquodale et al. |
| 7,383,071 B1 | 6/2008 | Russell et al. |
| 7,398,734 B1 | 7/2008 | Jean |
| 7,451,537 B2 | 11/2008 | Liu et al. |
| 7,486,967 B2 | 2/2009 | Pan et al. |
| 7,510,699 B2 | 3/2009 | Black et al. |
| 7,572,228 B2 | 8/2009 | Wolinsky et al. |
| 7,596,403 B2 | 9/2009 | Horn |
| 7,625,338 B2 | 12/2009 | Gilad et al. |
| 7,684,840 B2 | 3/2010 | Palti |
| 7,713,196 B2 | 5/2010 | Baker, Jr. |
| 7,736,300 B2 | 6/2010 | Ziegler et al. |
| 7,744,542 B2 | 6/2010 | Piaget et al. |
| 7,801,626 B2 | 9/2010 | Moser |
| 7,840,271 B2 | 11/2010 | Kieval et al. |
| 7,857,767 B2 | 12/2010 | Ferren et al. |
| 7,967,016 B2 | 6/2011 | Anderson et al. |
| 8,019,413 B2 | 9/2011 | Ferren et al. |
| 8,024,036 B2 | 9/2011 | Ferren et al. |
| 8,036,731 B2 | 10/2011 | Kimchy et al. |
| 8,055,329 B2 | 11/2011 | Kimchy et al. |
| 8,140,141 B2 | 3/2012 | McGreevy et al. |
| 8,180,436 B2 | 5/2012 | Boyden et al. |
| 2001/0029348 A1 | 10/2001 | Willis |
| 2001/0039385 A1 | 11/2001 | Ellenz |
| 2001/0051766 A1 | 12/2001 | Gazdzinski |
| 2002/0026188 A1 | 2/2002 | Balbierz et al. |
| 2002/0049370 A1 | 4/2002 | Laufer et al. |
| 2002/0065509 A1 | 5/2002 | Lebel et al. |
| 2002/0068080 A1 | 6/2002 | Lerner |
| 2002/0077369 A1 | 6/2002 | Noolandi et al. |
| 2002/0090388 A1 | 7/2002 | Humes et al. |
| 2002/0103417 A1 | 8/2002 | Gazdzinski |
| 2002/0116029 A1 | 8/2002 | Miller et al. |
| 2002/0116034 A1 | 8/2002 | Miller et al. |
| 2002/0147480 A1 | 10/2002 | Mamayek |
| 2002/0156462 A1 | 10/2002 | Stultz |
| 2002/0165592 A1 | 11/2002 | Glukhovsky et al. |
| 2002/0169436 A1 | 11/2002 | Gurm et al. |
| 2002/0171385 A1 | 11/2002 | Kim et al. |
| 2002/0188323 A1 | 12/2002 | Penner et al. |
| 2002/0193679 A1 | 12/2002 | Malave et al. |
| 2002/0193874 A1 | 12/2002 | Crowley |
| 2002/0198470 A1 | 12/2002 | Imran et al. |
| 2002/0198521 A1 | 12/2002 | Maguire |
| 2002/0198604 A1 | 12/2002 | Schulman et al. |
| 2003/0004403 A1 | 1/2003 | Drinan et al. |
| 2003/0023150 A1 | 1/2003 | Yokoi et al. |
| 2003/0024534 A1 | 2/2003 | Silvestri et al. |
| 2003/0040704 A1 | 2/2003 | Dorros et al. |
| 2003/0065250 A1 | 4/2003 | Chiel et al. |
| 2003/0065358 A1 | 4/2003 | Frecker et al. |
| 2003/0069475 A1 | 4/2003 | Banik et al. |
| 2003/0069523 A1 | 4/2003 | Williams et al. |
| 2003/0078485 A1* | 4/2003 | Hartlep ............... 600/378 |
| 2003/0093031 A1 | 5/2003 | Long et al. |
| 2003/0151524 A1 | 8/2003 | Clark |
| 2003/0152823 A1 | 8/2003 | Heller |
| 2003/0153866 A1 | 8/2003 | Long et al. |
| 2003/0158584 A1 | 8/2003 | Cates et al. |
| 2003/0163177 A1 | 8/2003 | Eggers et al. |
| 2003/0167000 A1 | 9/2003 | Mullick et al. |
| 2003/0191430 A1 | 10/2003 | D'Andrea et al. |
| 2003/0214579 A1* | 11/2003 | Iddan ............... 348/81 |
| 2003/0214580 A1 | 11/2003 | Iddan |
| 2003/0220556 A1 | 11/2003 | Porat et al. |
| 2003/0220557 A1 | 11/2003 | Cleary et al. |
| 2004/0008853 A1 | 1/2004 | Pelrine et al. |
| 2004/0018508 A1 | 1/2004 | Friedman |
| 2004/0019374 A1 | 1/2004 | Hojeibane et al. |
| 2004/0034332 A1 | 2/2004 | Uhland |

(56) References Cited

U.S. PATENT DOCUMENTS

| | | |
|---|---|---|
| 2004/0064093 A1 | 4/2004 | Hektner et al. |
| 2004/0073177 A1 | 4/2004 | Hickle |
| 2004/0073190 A1 | 4/2004 | Deem et al. |
| 2004/0092825 A1 | 5/2004 | Madar et al. |
| 2004/0097805 A1 | 5/2004 | Verard et al. |
| 2004/0097819 A1 | 5/2004 | Duarte |
| 2004/0098030 A1 | 5/2004 | Makower et al. |
| 2004/0111019 A1 | 6/2004 | Long |
| 2004/0133147 A1 | 7/2004 | Woo |
| 2004/0138517 A1 | 7/2004 | Osorio et al. |
| 2004/0147939 A1 | 7/2004 | Rabkin et al. |
| 2004/0148034 A1 | 7/2004 | Kagan et al. |
| 2004/0152988 A1 | 8/2004 | Weirich |
| 2004/0162469 A1 | 8/2004 | Imran |
| 2004/0162501 A1 | 8/2004 | Imran |
| 2004/0176664 A1 | 9/2004 | Iddan |
| 2004/0193010 A1 | 9/2004 | Fujimori et al. |
| 2004/0193235 A1 | 9/2004 | Altshuler et al. |
| 2004/0199246 A1 | 10/2004 | Chu et al. |
| 2004/0225325 A1 | 11/2004 | Bonutti |
| 2004/0225326 A1 | 11/2004 | Weiner et al. |
| 2004/0260278 A1 | 12/2004 | Anderson et al. |
| 2004/0260391 A1 | 12/2004 | Santini, Jr. et al. |
| 2004/0267240 A1 | 12/2004 | Gross et al. |
| 2005/0004474 A1 | 1/2005 | Iddan |
| 2005/0004553 A1 | 1/2005 | Douk |
| 2005/0021023 A1 | 1/2005 | Guglielmi et al. |
| 2005/0027236 A1 | 2/2005 | Douk |
| 2005/0043583 A1 | 2/2005 | Killmann et al. |
| 2005/0058701 A1 | 3/2005 | Gross et al. |
| 2005/0062562 A1 | 3/2005 | Ries |
| 2005/0065592 A1 | 3/2005 | Holzer |
| 2005/0069925 A1 | 3/2005 | Ford et al. |
| 2005/0079132 A1 | 4/2005 | Wang et al. |
| 2005/0096712 A1 | 5/2005 | Abraham-Fuchs et al. |
| 2005/0105870 A1 | 5/2005 | Wang et al. |
| 2005/0113460 A1 | 5/2005 | Glick |
| 2005/0121411 A1 | 6/2005 | Cohen |
| 2005/0126916 A1 | 6/2005 | Lockard et al. |
| 2005/0149170 A1 | 7/2005 | Tassel et al. |
| 2005/0151524 A1 | 7/2005 | Sae-Ueng et al. |
| 2005/0171418 A1 | 8/2005 | Lin |
| 2005/0171434 A1 | 8/2005 | Madden et al. |
| 2005/0177223 A1 | 8/2005 | Palmaz |
| 2005/0182482 A1 | 8/2005 | Wang et al. |
| 2005/0203613 A1 | 9/2005 | Arney et al. |
| 2005/0215911 A1 | 9/2005 | Alfano et al. |
| 2005/0216074 A1 | 9/2005 | Sahatjian et al. |
| 2005/0221529 A1 | 10/2005 | Bang et al. |
| 2005/0228259 A1 | 10/2005 | Glukhovsky et al. |
| 2005/0234393 A1 | 10/2005 | Wood, Jr. |
| 2005/0234440 A1 | 10/2005 | Wood, Jr. |
| 2005/0238689 A1 | 10/2005 | Carpenter et al. |
| 2005/0272806 A1 | 12/2005 | Falotico et al. |
| 2005/0272974 A1 | 12/2005 | Iddan |
| 2005/0277839 A1 | 12/2005 | Alderman et al. |
| 2005/0278020 A1 | 12/2005 | Wang et al. |
| 2006/0004395 A1 | 1/2006 | Chiel et al. |
| 2006/0009810 A1 | 1/2006 | Mann et al. |
| 2006/0015146 A1 | 1/2006 | Girouard et al. |
| 2006/0037617 A1 | 2/2006 | Walke et al. |
| 2006/0058647 A1* | 3/2006 | Strommer et al. ............ 600/434 |
| 2006/0074479 A1 | 4/2006 | Bailey et al. |
| 2006/0119304 A1 | 6/2006 | Farritor et al. |
| 2006/0152309 A1 | 7/2006 | Mintchev et al. |
| 2006/0167339 A1 | 7/2006 | Gilad et al. |
| 2006/0169294 A1 | 8/2006 | Kaler et al. |
| 2006/0195015 A1 | 8/2006 | Mullick et al. |
| 2006/0235275 A1 | 10/2006 | Rabinovitz et al. |
| 2006/0241577 A1 | 10/2006 | Balbierz et al. |
| 2006/0252987 A1 | 11/2006 | Hasegawa et al. |
| 2007/0010868 A1 | 1/2007 | Ferren et al. |
| 2007/0066929 A1 | 3/2007 | Ferren et al. |
| 2007/0083099 A1* | 4/2007 | Henderson et al. ........... 600/407 |
| 2007/0088334 A1 | 4/2007 | Hillis et al. |
| 2007/0156211 A1 | 7/2007 | Ferren et al. |
| 2007/0213613 A1 | 9/2007 | Ishida et al. |
| 2007/0213698 A1 | 9/2007 | Altshuler et al. |
| 2007/0225634 A1 | 9/2007 | Ferren et al. |
| 2008/0063703 A1 | 3/2008 | Gross et al. |
| 2008/0066929 A1 | 3/2008 | Costa et al. |
| 2008/0103440 A1 | 5/2008 | Ferren et al. |
| 2008/0121054 A1 | 5/2008 | Goldenberg et al. |
| 2008/0241847 A1 | 10/2008 | Hoon et al. |
| 2008/0243056 A1 | 10/2008 | Hillis et al. |
| 2008/0266106 A1 | 10/2008 | Lim et al. |
| 2009/0054883 A1 | 2/2009 | Stolen et al. |
| 2009/0062646 A1 | 3/2009 | Creighton, IV et al. |
| 2009/0069821 A1 | 3/2009 | Farritor et al. |
| 2009/0082652 A1 | 3/2009 | Koh et al. |
| 2009/0105686 A1 | 4/2009 | Snow et al. |
| 2009/0182388 A1 | 7/2009 | Von Arx et al. |
| 2013/0274658 A1 | 10/2013 | Steinke et al. |
| 2013/0304446 A1* | 11/2013 | Rabinovitz et al. ............ 703/11 |

FOREIGN PATENT DOCUMENTS

| | | |
|---|---|---|
| EP | 1 618 831 A2 | 1/2006 |
| EP | 2 163 206 A1 | 3/2010 |
| JP | 2001-506871 | 3/1998 |
| JP | 10-099261 | 4/1998 |
| JP | 2002-010990 | 1/2002 |
| JP | 2002-153569 | 5/2002 |
| JP | 2003-111720 A | 4/2003 |
| JP | 2005-74229 | 3/2005 |
| KR | 2002-0010990 A | 2/2002 |
| WO | WO 96/39999 | 12/1996 |
| WO | WO 98/09582 | 3/1998 |
| WO | WO 98/14243 | 4/1998 |
| WO | WO 99/20335 | 4/1999 |
| WO | WO 99/44665 | 9/1999 |
| WO | WO 00/69515 | 11/2000 |
| WO | WO 01/08548 A1 | 2/2001 |
| WO | WO 01/24731 A1 | 4/2001 |
| WO | WO 03/072157 A1 | 9/2003 |
| WO | WO 03/090618 A2 | 11/2003 |
| WO | WO 03/106966 A2 | 12/2003 |
| WO | WO 2004/028335 A2 | 4/2004 |
| WO | WO 2004/058041 A2 | 7/2004 |
| WO | WO 2004/086958 A1 | 10/2004 |
| WO | WO 2005/082248 A1 | 9/2005 |

OTHER PUBLICATIONS

U.S. Appl. No. 12/928,455, Wood, Jr., Lowell L.
U.S. Appl. No. 12/075,480, Hillis et al.
U.S. Appl. No. 11/891,573, Wood, Jr., Lowell L.
U.S. Appl. No. 11/891,371, Wood, Jr., Lowell L.
U.S. Appl. No. 11/891,356, Wood, Jr., Lowell L.
U.S. Appl. No. 11/891,355, Wood, Jr., Lowell L.
U.S. Appl. No. 11/891,334, Wood, Jr., Lowell L.
U.S. Appl. No. 11/891,333, Wood, Jr., Lowell L.
U.S. Appl. No. 11/726,031, Ferren et al.
U.S. Appl. No. 11/726,025, Ferren et al.
U.S. Appl. No. 11/725,982, Ferren et al.
U.S. Appl. No. 11/651,946, Ferren et al.
U.S. Appl. No. 11/645,358, Ferren et al.
U.S. Appl. No. 11/645,357, Ferren et al.
U.S. Appl. No. 11/541,492, Jung et al.
U.S. Appl. No. 11/541,452, Jung et al.
U.S. Appl. No. 11/541,448, Jung et al.
U.S. Appl. No. 11/541,378, Jung et al.
U.S. Appl. No. 11/541,377, Jung et al.
U.S. Appl. No. 11/526,203, Jung et al.
U.S. Appl. No. 11/526,201, Jung et al.
U.S. Appl. No. 11/526,144, Jung et al.
U.S. Appl. No. 11/526,089, Jung et al.
U.S. Appl. No. 11/485,619, Hillis et al.
U.S. Appl. No. 11/478,368, Ferren et al.
U.S. Appl. No. 11/455,010, Jung et al.
U.S. Appl. No. 11/454,343, Jung et al.

(56) References Cited

OTHER PUBLICATIONS

U.S. Appl. No. 11/417,898, Hillis et al.
U.S. Appl. No. 10/949,186, Hillis et al.
U.S. Appl. No. 10/827,578, Wood, Jr., Lowell L.
U.S. Appl. No. 10/827,576, Wood, Jr., Lowell L.
U.S. Appl. No. 10/827,572, Wood, Jr., Lowell L.
U.S. Appl. No. 10/827,390, Wood, Jr., Lowell L.
"001_08 Comparison of Capsule Cameras: M2A (Given Imaging) vs. NORIKA3 (RF System lab)" RF System lab; bearing dates of 2001-2004; pp. 1-2; located at http://www.rfnorika.com/eng/system/sys_008.html; printed on May 4, 2006.
"A Hydrogel-based CO2 sensor"; BIOS—The lab on a chip group; bearing a date of Aug. 29, 2005; pp. 1-2; located at: http://bios.ewj.utwente.nl/research/analysissystemssenors/ahydrogelbased.doc/index.html; printed on Apr. 25, 2006; University of Twente; The Netherlands.
Agarwal, Abhishek K.; Atencia, Javier; Beebe, David J.; Jiang, Hongrui; "Magnetically-driven temperature-controlled microfluidic actuators"; pp. 1-5; located at: http://www.unl.im.dendai.ac.jp/INSS2004/INSS2004_papers/OralPresentations/C2.pdf.
"Agile new plastics change shape with heat"; MIT News Office; Nov. 20, 2006; pp. 1-4; Massachusetts Institute of Technology; printed on Nov. 22, 2006; located at http://web.mit.edu/newsoffice/2006/triple-shape.html.
"Agile new plastics change shape with heat"; MIT Tech Talk; Nov. 22, 2006; p. 5 (1 page).
Ananthaswamy, Anil; "First robot moved by muscle power"; bearing a date of Feb. 27, 2004; pp. 1-3; New Scientist; located at http://www.newscientist.com/article.ns?id=dn4714; printed on Sep. 12, 2006.
Arkin, Ronald C.; "Towards the Unification of Navigational Planning and Reactive Control"; Working Notes of the AAAI Spring Symposium on Robot Navigation; bearing dates of Mar. 20-28, 1989; pp. 1-6.
Arleo et al.; "Spatial Cognition and Neuro-Mimetic Navigation: A Model of Hippocampal Place Cell Activity"; bearing a date of Oct. 28, 1999; pp. 1-13.
Asari, Vijayan K.; Kumar, Sanjiv; Kassim, Irwan M.; "A Fully Autonomous Microrobotic Endoscopy System"; Journal of Intelligent and Robotic Systems; bearing a date of 2000; pp. 325-341; vol. 28; Kluwer Academic Publishers.
Balakrishnan et al.; "Spatial Learning and Localization in Rodents: A Computational Model of the Hippocampus and its Implications for Mobile Robots"; Adaptive Behavior; bearing a date of 1999; pp. 173-216 plus cover page; vol. 7, No. 2; SAGE Publications.
Behkam, Bahareh; Sitti, Metin; "Towards Hybrid Swimming Microrobots: Bacteria Assisted Propulsion of Polystyrene Beads"; Proceedings of the 28th IEEE EMBS Annual International Conference; bearing dates of Aug. 30, 2006-Sep. 3, 2006 and 2006; pp. 2421-2424; IEEE.
Bellin et al.; "Polymeric triple-shape materials"; PNAS; bearing dates of Nov. 18, 2006 and 2006; pp. 18043-18047; vol. 103, No. 48; The National Academy of Sciences of the USA; located at www.pnas.org/cgi/doi/10.1073/pnas.0608586103.
Berlinger, Norman T.; "Robotic Surgery—Squeezing into Tight Places"; New England Journal of Medicine; bearing dates of May 17, 2006, May 18, 2006, and 2006; pp. 2099-2101; Massachusetts Medical Society; located at www.nejm.org.
Berman et al.; "Decentralized Autonomous AGV System for Material Handling"; iFirst; bearing a date of Oct. 2002; pp. 3995-4006 (Only the Abstract is being provided); vol. 40, No. 15; located at: http://www.informaworld.com/smpp/content~content=a713846479~db=ai; printed on Apr. 24, 2007.
Bezrouk, A.; Hanuš, J.; Záhora, J.; "Temperature Characteristics of Nitinol Spiral Stents"; Scripta Medica (BRNO); bearing dates of Aug. 2005, Oct. 2005; pp. 219-226; vol. 78, No. 4.
Bialek, William; Rieke, Fred; De Ruyter Van Steveninck, Rob R.; Warland, David; "Reading a Neural Code"; Science; bearing a date of Jun. 28, 1991; pp. 1854-1857; vol. 252.
Bianco et al.; "Carbon Nanotube-based Vectors for Delivering Immunotherapeutics and Drugs"; Nanotechnologies for the Live Sciences: Nanomaterials for Medical Diagnosis and Therapy; bearing a date of 2007; Chapter 3; pp. 85-142.; vol. 10; Wiley-VCH Verlag GmbH & Co. KGaA; Weinheim.
Breslin et al.; "Autofluorescence and Diffuse Reflectance Properties Malignant and Benign Breast Tissues"; Annals of Surgical Oncology; bearing dates of 2003 and 2004; pp. 65-70; vol. 11, No. 1; Lippincott Williams & Wilkin.
Bright et al.; "Automated Pipe Inspection Robot"; Industrial Robot: An International Journal; bearing a date of Aug. 1997; pp. 285-289 (Only the Abstract is being provided); vol. 24, No. 4; located at: http://www.emeraldinsight.com/10.1108/01439919710176372; printed on Apr. 23, 2007.
Brinn, David; "A incredible journey from an Israeli robotics team"; ISRAEL21c: A Focus Beyond; bearing a date of Nov. 12, 2006; pp. 1-3; ISRAEL21c.org.
Brown et al.; "Performance Test Results of an Integrated GPS/MEMS Inertial Navigation Package"; Proceedings of ION GNSS 2004, bearing a date of Sep. 2004; pp. 1-8.
Bucher, Volker; Graf, Michael; Stelzle, Martin; Nisch, Wilfried; "Low-Impedance Thin-Film Polycrystalline Silicon Microelectrodes for Extracellular Stimulation and Recording"; Biosensors and Bioelectronics; bearing a date of 1999; pp. 639-649; vol. 14; Elsevier Science S.A.; located at: www.elsevier.com/locate/bios.
Budgett et al.; "Novel technology for the provision of power to implantable physiological devices"; Journal of Applied Physiology; bearing dates of Jan. 27, 2006, Jan. 5, 2007, and 2007; pp. 1658-1663; vol. 102; The American Physiological Society.
Bullitt et al.; "Analysis of Time-Varying Images Using 3D Vascular Models"; Proceedings 30th Applied Imagery Pattern Recognition Workshop; bearing a date of Apr. 2001; pp. 9-14; IEEE Computer Society; Piscataway, NJ.
Burke et al.; "Towards a single-chip, implantable RFID system: is a single-cell radio possible?"; Biomed Microdevices; bearing a date of 2009; pp. 1-8; Springer.
Butson, Christopher R.; McIntyre, Cameron C.; "Role of Electrode Design on the Volume of Tissue Activated During Deep Brain Stimulation"; Journal of Neural Engineering; bearing a date of 2006; vol. 3; pp. 1-8; IOP Publishing Ltd.
Cady et al.; "Optimized linkage and quenching strategies for quantum dot molecular beacons"; Molecular and Cellular Probes; bearing dates of Jul. 5, 2006, Sep. 7, 2006, Sep. 17, 2006, 2006, and 2007; pp. 116-124; vol. 21; Elsevier Ltd.
Cavalcanti et al.; "Autonomous Multi-Robot Sensor-Based Cooperation for Nanomedicine"; Nanotechnology Special Edition; bearing a date of Aug. 2002; pp. 1-4; International Journal of Nonlinear Science and Numerical Stimulation.
Chang, Suk Tai; Paunov, Vesselin N.; Petsev, Dimiter N.; Velev, Orlin D.; "Articles: Remotely Powered Self-Propelling Particles and Micropumps Based on Miniature Diodes"; Nature Materials; bearing a date of 2007; pp. 1-6; Nature Publishing Group; located at: www.nature.com/naturematerials.
Chen, Ting; Barton, Scott Calabrese, Binyamin, Gary; Gao, Zhiqiang; Zhang, Yongchao, Kim, Hyug-Han; Heller, Adam; "A Miniature Biofuel Cell"; Journal of the American Chemical Society; Aug. 11, 2001; pp. 8630-8631; vol. 123; 2001 American Chemical Society.
Chen, Haitao; Ebner, Armin D.; Ritter, James A.; Kaminski, Michael D.; Rosengart, Axel J.; "Sequestration of Blood-Borne Magnetic Drug Carrier Particles Using Magnetizable Intravascular Stents"; Collaborative Investigators for Applied Nanotechnology in Medicine; pp. 1; Chicago, Illinois.
Chen et al.; "Review on the Achievements in Simultaneous Localization and Map Building for Mobile Robot" CSA Illumina; bearing a date of Jun. 2005; pp. 455-460 (Only the Abstract is being provided); vol. 22, No. 3; ProQuest-CSA LLC; located at: http://mdl.csa.com/partners/viewrecord.php?requester=gs&collection=TRD&recid=A056354818AH&recid=2005134422784EA&q=Review+on+the+Achievements+in+Simultaneous+Localization+and+Map+Building+for+Mobile+Robot&uid=790366044&setcookie=yes.
Chiyo et al.; "Effective detection of bronchial preinvasive lesions by a new autofluorescence imaging bronchovideoscope system"; Lung Cancer; bearing dates of May 12, 2004, Nov. 17, 2004, Nov. 23, 2004, 2004, and 2005; pp. 307-313; vol. 48; Elsevier Ireland Ltd.

(56) References Cited

OTHER PUBLICATIONS

Christensen, Bill; "Musclebot: Microrobot with a Heart"; Technovelgy.com; pp. 1-2; bearing a date of Feb. 27, 2004; located at http://www.technovelgy.com/ct/Science-Fiction-News. asp?NewsNum=46; printed on Sep. 12, 2006.
Christensen, Bill; "Propulsion System for 'Fantastic Voyage' Robot"; Technovelgy.com; pp. 1-4; Technovelgy.com; located http://www.technovelgy.com/ct/Science-Fiction-News.asp?NewsNum=811; printed on Jan. 4, 2007.
Chung et al.; "Advanced Optical Imaging Requiring No Contrast Agents-A New Armamentarium for Medicine and Surgery"; Current Surgery; bearing dates of May/Jun. 2005 and 2005; pp. 365-370; vol. 62, No. 3; Elsevier Inc.
Costamagna; Guido M.D.; "PillCam™ SB Capsule Endoscopy"; Given Imaging.com; bearing dates of 2001-2006; pp. 1-4; located at http://www.givenimaging.com/Cultures/en-US/Given/English/Products/CapsuleEndoscopy/; printed on May 4, 2006.
Cui, Xinyan; Hetke, Jamille F.; Wiler, James A.; Anderson, David J.; Martin, David C.; "Electrochemical Deposition and Characterization of Conducting Polymer Polypyrrole/PPS on Multichannel Neural Probes"; Sensors and Actuators A Physical; bearing a date of 2001; pp. 8-18; vol. 93; Elsevier Science B.V.; located at: www.elsevier.com/locate/sna.
Dacosta et al.; "Autofluorescence characterisation of isolated whole crypts and primary cultured human epithelial cells from normal, hyperplastic, and adenomatous colonic mucosa"; Journal of Clinical Pathology; bearing dates of 2004 and 2005; pp. 766-774; vol. 58.
Dario, P.; Carrozza, M.C.; Lencioni, L.; Magnani, B.; D'Attanasio, S.; "A Micro Robotic System for Colonoscopy"; Proceedings of the 1997 IEEE International Conference on Robotics and Automation; bearing dates of Apr. 1997 and 1997; pp. 1567-1572; IEEE.
Degani et al.; "Minimalistic, Dynamic, Tube Climbing Robot"; 2010 IEEE International Conference on Robotics and Automation; bearing dates of May 3-8, 2010 and 2010; pp. 1100-1101; IEEE.
Desouza et al.; "Vision for Mobile Robot Navigation: A Survey"; IEEE Transactions on Pattern Analysis and Machine Intelligence; bearing a date of Feb. 2002; pp. 237-267 (Only the Abstract is being provided); vol. 24, No. 2; located at: http://csdl2.computer.org/persagen/DLAbsToc.jsp?resourcePath=/dl/trans/tp/&toc=comp/trans/tp/2002/02/i2toc.xml&DOI=10.1109/34.982903; printed on Apr. 23, 2007.
Diard et al.; "A theoretical comparison of probabilistic and biomimetic models of mobile robot navigation"; Proceedings of the 2004 IEEE International Conference on Robotics & Automation; bearing dates of Apr. 2004 and 2004; pp. 933-938; IEEE.
Dillier, Norbert; Lai, Wai Kong; Almqvist, Bengt; Frohne, Carolin; Müller-Deile, Joachim; Stecker, Matthias; Von Wallenberg, Ernst; "Measurement of the Electrically Evoked Compound Action Potential Via a Neural Response Telemetry System"; Annals of Otology Rhinology and Laryngology; bearing a date of May 2002; pp. 407-414; vol. 111, No. 5; Annals Publishing Company.
Dongxiang, Chi; Guozheng, Yan; "An earthworm based miniature robot for intestinal inspection"; Proceedings of SPIE; bearing dates of Nov. 7, 2001-Nov. 9, 2001; pp. 396-400; vol. 4601; SPIE.
Donoghue, John P.; "Review: Connecting Cortex to Machines: Recent Advances in Brain Interfaces"; Nature Neuroscience Supplement; bearing a date on Nov. 2002; pp. 1085-1088; vol. 5; Nature Publishing Group; located at: http://www.nature.com/natureneuroscience.
Dweik et al.; "Exhaled breath analysis: the new frontier in medical testing"; Journal of Breath Research; bearing a date of 2008; pp. 1-3; vol. 2; IOP Publishing Ltd; UK.
Edwards, Lin; "Spider pill to seek out disease"; PhysOrg.com; bearing dates of Oct. 16, 2009 and 2009; p. 1.
Eker et al.; "Clinical spectral characterisation of colonic mucosal lesions using autofluorescence and δ aminolevulinic acid sensitization"; Gut; bearing dates of 1998 and 1999; pp. 511-518; vol. 44.
Eulenstein et al.; "Ultrasound-Based Navigation System Incorporating Preoperative Planning for Liver Surgery"; International Congress Series CARS 2004—Computer Assisted Radiology and Surgery, Proceedings of the 18$^{th}$ International Congress and Exhibition; bearing a date of 2004; pp. 758-763; vol. 1268.
Fang, Zi-Ping; Mortimer, J. Thomas; "Selective Activation of Small Motor Axons by Quasitrapezoidal Current Pulses"; IEEE Transactions on Biomedical Engineering; bearing a date of Feb. 1991; pp. 168-174; vol. 38, No. 2; IEEE.
Fiaccabrino, G.C.; Tang, X.-M.; Skinner, N.; De Rooij, N.F.; Koudelka-Hep, M.; "Electrochemical Characterization of Thin-Film Carbon Interdigitated Electrode Arrays"; Analytica Chimica Acta; bearing a date of 1996; pp. 155-160; vol. 326; Elsevier Science B.V.
Filliat et al.; "Map Based Navigation in Mobile Robots: I. A Review of Localization Strategies"; Science Direct-Cognitive Systems Research; bearing dates of Feb. 12, 2003 and Dec. 2003; pp. 1-58; vol. 4, No. 4; Elsevier Science.
Foxlin et al.; "Miniature 6-DOF inertial system for tracking HMDs"; Helmet and Head-Mounted Displays III, AeroSense 98; bearing dates of Apr. 13-14, 1998; pp. 1-15; vol. 3362; SPIE.
Freitas Jr., Robert A.; "8.2.1.2 Arteriocenous Microcirculation"; "9.4.3.5 Legged Ambulation"; "9.4.3.6 Tank-Tread Rolling"; "9.4. 3.7 Amoeboid Locomotion"; "9.4.3.8 Inchworm Locomotion"; "Nanomedicine vol. I: Basic Capabilities"; bearing a date of 1999; pp. 211-214, pp. 316-318; Landes Bioscience; Georgetown, Texas, USA.
Gabrecht et al.; "Detection of early bronchial cancer by autofluorescence: results in patients with H&N cancer"; Diagnostic Optical Spectroscopy in Biomedicine IV, Proc. SPIE-OSA Biomedical Optics; bearing a date of 2007; pp. 1-8; vol. 6628; SPIE-OSA.
Gao et al., "A Micro Sensing Probe for Detecting Individual Biological Cells"; Proceedings of the 25$^{th}$ Annual International Conference of the IEEE EMBS; bearing dates of Sep. 17-21, 2003 and 2003; pp. 3348-3351; IEEE.
Gillenwater et al.; "Noninvasive Diagnosis of Oral Neoplasia Based on Fluorescence Spectroscopy and Native Tissue Autofluorescence"; Archives of Otolaryngology-Head & Neck Surgery; bearing a date of Nov. 1998 and 1998; pp. 1251-1258; vol. 124.
Gitter, Alfred H.; Fromm, Michael; Schulzke, Jörg-Dieter; "Impedance Analysis for the Determination of Epithelial and Subepithelial Resistance in Intestinal Tissues"; Journal of Biochemical and Biophysical Methods, bearing a date of 1998; pp. 35-46; vol. 37; Elsevier Science B.V.
Goda, Yukiko; Colicos, Michael A.; "Protocol: Photoconductive Stimulation of Neurons Cultured on Silicon Wafers"; Nature Protocols; bearing a date of 2006; pp. 461-467; vol. 1, No. 1; Nature Publishing Group; located at: http://www.nature.com/natureprotocols.
Gozani, Shai N.; Miller, John P.; "Optimal Discrimination and Classification of Neuronal Action Potential Waveforms from Multiunit, Multichannel Recordings Using Software-Based Linear Filters"; IEEE Transactions on Biomedical Engineering; bearing a date of Apr. 1994; pp. 358-372; vol. 41, No. 4; IEEE.
Gray, Charles M.; Maldonado, Pedro E.; Wilson, Mathew; McNaughton, Bruce; "Tetrodes Markedly Improve the Reliability and Yield of Multiple Single-Unit Isolation from Multi-Unit Recordings in Cat Striate Cortex"; Journal of Neuroscience Methods; bearing a date of 1995; pp. 43-54; vol. 63; Elsevier Science B.V.
Grifantini, Kristina; "Voyage of the Bacteria Bots"; Technology Review; bearing a date of Oct. 31, 2008; pp. 1-4; Technology Review.
Groothuis et al.; "The entry of antiviral and antiretroviral drugs into the central nervous system"; Journal of NeuroVirology; bearing a date of 1997; pp. 387-400; vol. 3; Journal of NeuroVirology, Inc.
"Guessing Robots Predict Their Environments, Navigate Better"; PhysOrg.com; printed on Sep. 16, 2008; pp. 1-2; original story found at www.phyorg.com/news100887209.html.
Gur, Amir; "The Nanobots are Coming"; TFOT; bearing a date of Jul. 9, 2007; pp. 1-2; The Future of Things.
Hagleitner, C.; Hierlemann, A.; Lange, D.; Kummer, A.; Kerness, N.; Brand, O.; Baltes, H.; "Smart single-chip gas sensor microsystem"; Nature; Nov. 15, 2001; pp. 293-296; vol. 414; Macmillan Magazines Ltd.; www.nature.com.
Hanna, Darrin M.; Oakley, Barbara A.; Stryker, Gabrielle A.; "Using a System-on-Chip Implantable Device to Filter Circulating Infected

(56) References Cited

OTHER PUBLICATIONS

Cells in Blood or Lymph"; IEEE Transactions on Biomedical Engineering; bearing dates of Jan. 25, 2003, Mar. 2003; pp. 6-13; vol. 2, No. 1; IEEE.
Hattori, Kevin; "Robot Can Crawl Through Human Body"; American Technion Society; bearing a date of Jul. 7, 2009; pp. 1-2; American Technion Society; located at http://www.ats.org/site/News2?page=NewsArticle&id=6063&news_iv_ctrl=1161&printer_friendly=1.
Herth et al.; "Successful Bronchoscopic Placement of Tracheobronchial Stents Without Fluoroscopy*"; Chest; bearing a date of Jun. 2001; pp. 1910-1912; vol. 119, No. 6; American College of Chest Physicians.
Hertzberg et al.; "Landmark-Based Autonomous Navigation in Sewerage Pipes"; Proceedings of EUROBOT; bearing a date of 1996; pp. 68-73; IEEE.
Hirsch et al.; "A new device with PZT ultrasonic transducers in MEMS technology"; Journal of Physics: Conference Series 34, International MEMS Conference 2006; bearing a date of 2006; pp. 475-480; IOP Publishing Ltd.
Hodgkin, A.L.; Huxley, A.F.; "A Quantitative Description of Membrane Current and its Application to Conduction and Excitation in Nerve"; Journal of Physiology; bearing a date of 1952; pp. 500-544; vol. 117.
Høeg, H.D.; Slatkin, A.B.; Burdick, J.W.; Grundfest, Dr. Warren S.; "Biomechanical Modeling of the Small Intestine as Required for the Design and Operation of a Robotic Endoscope"; Proceedings ICRA '00 IEEE International Conference on Robotics and Automation; Apr. 24, 2000-Apr. 28, 2000; pp. 1-8; vol. 2.
Hofmann, U.G.; Folkers, A.; Mösch, F.; Höhl, D.; Kindlundh, M.; Norlin, P.; "A 64(128)-Channel Multisite Neuronal Recording System"; bearing a date of 2002; pp. 1-4.
Hollings et al.; "Diagnostic imaging of lung cancer"; European Respiratory Journal; bearing a date of 2002, pp. 722-742; vol. 19; ERS Journals Ltd.
Hornyak, Tim; "RFID Powder"; Scientific American Magazine; bearing dates of Feb. 2008 and 2008; pp. 68-71; Scientific American, Inc.
Hosseini-Khayat, Saied; "A Lightweight Security Protocol for Ultralow Power ASIC Implementation for Wireless Implantable Medical Devices"; 2011 Symposium on Medical Information and Communication Technology (ISMICT); bearing dates of 2011 and Mar. 27-30, 2011; pp. 6-9; IEEE.
Howell et al.; "Practical Mobile Robot Self-Localization"; Proceedings of the IEEE International Conference on Robotics and Automation, 2000; bearing dates of Apr. 24-28, 2000; pp. 3485-3492; vol. 4.
Ikeuchi, K.; Yoshinaka, K.; Hashimoto, S.; Tomita, N.; "Locomotion of Medical Micro Robot with Spiral Ribs Using Mucus"; Seventh International Symposium on Micro Machine and Human Science; bearing a date of 1996; pp. 217-222; IEEE.
Inmann, Andreas; Haugland, Morten; Haase, Jens; Biering-Sørensen, Fin; Sinkjaer, Thomas; "NeuroReport: Signals from Skin Mechanoreceptors used in Control of a Hand Grasp Neuroprosthesis"; Motor Systems; bearing a date of Sep. 17, 2001; pp. 2817-2819; vol. 12, No. 13; Lippincott Williams & Wilkins.
Jaiswal et al.; "Long-term multiple color imaging of live cells using quantum dot bioconjugates"; Nature Biotechnology; bearing dates of Jan. 2003 and 2003; pp. 47-51; vol. 21; Nature Publishing Group.
Janders, M.; Egert, U.; Stelze, M.; Nisch, W.; "Novel Thin Film Titanium Nitride Micro-Electrodes with Excellent Charge Transfer Capability for Cell Stimulation and Sensing Applications"; IEEE Engineering in Medicine and Biology Society; bearing a date of 1996; pp. 245-247; IEEE.
Japanese Office Action; Japanese App. No. 2007-533572; Sep. 22, 2010 (received by our Agent on Sep. 28, 2010); pp. 1-4; (no English translation currently available).
"Japanese Researchers Unveil Medical Mini Robot"; Yahoo! News; bearing a date of Mar. 8, 2007; pp. 1-2; Yahoo! Inc.; located at: http://news.yahoo.com/s/afp/20070308/hl_afp/afplifestyleshealthscience; printed on Mar. 8, 2007.
Ji, Jin; Najafi, Khalil, Wise, Kensall D.; "A Low-Noise Demultiplexing System for Active Multichannel Microelectrode Arrays"; IEEE Transactions of Biomedical Engineering; bearing a date of Jan. 1991; pp. 77-81; vol. 38, No. 1; IEEE.
Jovanov et al.; "A wireless body area network of intelligent motion sensors for computer assisted physical rehabilitation"; Journal of NeuroEngineering and Rehabilitation; bearing dates of Mar. 1, 2005, Jan. 28, 2005, Mar. 1, 2005, and 2005; pp. 1-10; vol. 2, No. 6; BioMed Central Ltd.
Karino et al.; "Flow Patterns in Vessels of Simple and Complex Geometries*"; Annals of the New York Academy of Sciences; bearing a date of 1987; pp. 422-441; vol. 516.
Kassim, Irwan; Phee, Louis; NG, Wan S.; Gong, Feng; Dario, Paolo; Mosse, Charles A.; "Locomotion Techniques for Robotic Colonoscopy"; IEEE Engineering in Medicine and Biology Magazine; bearing dates of May/Jun. 2006 and 2006; pp. 49-56; IEEE.
Kawaguchi et al.; "Internal Pipe Inspection Robot"; IEEE Xplore; bearing dates of May 21, 1995-May 27, 1995 and 2005; pp. 857-862 (Only the Abstract is being provided); vol. 1; IEEE; located at: http://ieeexplore.ieee.org/xpls/abs_all.jsp?rnumber=525390; printed on Apr. 23, 2007.
Kennedy, P.R.; Bakay, R.A.E.; Moore, M.M.; Adams, K.; Goldwaithe, J.; "Direct Control of a Computer from the Human Central Nervous System"; IEEE Transactions on Rehabilitation Engineering; bearing a date of Jun. 2000; pp. 198-202; vol. 8, No. 2; IEEE.
Kharitonov et al.; "Exhaled Markers of Pulmonary Disease"; American Journal of Respiratory and Critical Care Medicine; bearing dates of Sep. 5, 2000, Jan. 24, 2001, and 2001; pp. 1693-1722; vol. 163.
Kim et al.; "Inchworm-Like Microbot for Capsule Endoscope"; Proceedings of the 2004 IEEE International Conference on Robotics and Biomimetics; bearing dates of Aug. 22-26, 2004 and 2004; pp. 458-463; IEEE.
Kim et al.; "Ultrasensitive carbon nanotube-based biosensors using antibody-binding fragments"; Analytical Biochemistry; bearing a date of 2008; pp. 193-198; vol. 381; Elsevier Inc.
Kirchner et al.; "A Prototype Study of an Autonomous Robot Platform for Sewerage System Maintenance"; Autonomous Robots; bearing a date of 1997; pp. 319-331; vol. 4; Kluwer Academic Publishers.
Kitaoka et al.; "A three-dimensional model of the human airway tree"; Journal of Applied Physiology; bearing a date of 1999; pp. 2207-2217; vol. 87; The American Physiological Society.
Kitching, John; "Time for a Better Receiver: Chip-Scale Atomic Frequency References"; GPS World; bearing a date of Nov. 2007; pp. 52-57.
Knappe, Svenja; "Emerging Topics: MEMS Atomic Clocks"; Comprehensive Microsystems; bearing a date of 2007; pp. 571-612; vol. 3; Elsevier B.V.; Netherlands.
Kobetic, Rudi; Triolo, Ronald J.; Uhlir, James P.; Bieri, Carole; Wibowo, Michael; Polando, Gordie; Marsolais, E. Byron; Davis Jr., John A.; Ferguson, Kathleen A.; Sharma, Mukut; "Implanted Functional Electrical Stimulation System for Mobility in Paraplegia: A Follow-Up Case Report"; IEEE Transactions on Rehabilitation Engineering; bearing a date of Dec. 1999; pp. 390-398; vol. 7, No. 4; IEEE.
Koenig et al.; "Laser-Induced Autofluorescence for Medical Diagnosis"; Journal of Fluorescence; bearing a date of 1994, pp. 17-40; vol. 4, No. 1; Plenum Publishing Corporation.
Krueger, Curtis; "New light on blood testing"; Oct. 20, 2006; pp. 1-2; St. Petersburg Times; printed on Oct. 24, 2006; located at http://www.sptimes.com/2006/10/20news_pf/Tampabay/New_light_on_blood_te.shtml.
Kuipers et al.; "A Robot Exploration and Mapping Strategy Based on a Semantic Hierarchy of Spatial Representations"; Robotics and Autonomous Systems; bearing a date of 1981; pp. 47-63; vol. 8; Elsevier Science Publishers B.V.
Kuntze et al.; "Experiences With the Development of a Robot for Smart Multisensoricpipe Inspection"; IEEE Xplore; bearing dates of May 16, 1998-May 20, 1998 and 2005; pp. 1773-1778 (Only the Abstract is being provided); vol. 2; IEEE; located at: http://ieeexplore.ieee.org/xpls/abs_all.jsp?rnumber=677423; printed on Apr. 23, 2007.

(56) References Cited

OTHER PUBLICATIONS

Langer, Robert; Peppas, Nicholas A.; "Advances in Biomaterials, Drug Delivery, and Bionanotechnology"; AIChE Journal—Bioengineering, Food, and Natural Products; Dec. 2003; pp. 2990-3006; vol. 49, No. 12.
Latombe, Jean-Claude; "Chapter 1: Introduction and Overview"; Robot Motion Planning; bearing a date of 1991; 11 pages total, pp. 12-20; Kluwer Academic Publishers.
Laumond et al.; "Robot Motion Planning and Control"; bearing a date of 1998; pp. 1-343 plus cover page, foreword and table of contents (353 total pages); Springer.
Leong et al.; "Tetherless thermobiochemically actuated microgrippers"; PNAS; bearing dates of Jan. 20, 2009 and 2009; pp. 703-708; vol. 106, No. 3; The National Academy of Sciences of the USA; located at www.pnas.org_cgi_doi_10.1073_pnas.0807698106.
Loeb, G.E.; Peck, R.A.; Martyniuk, J.; "Toward the Ultimate Metal Microelectrode"; Journal of Neuroscience Methods; bearing a date of 1995; pp. 175-183; vol. 63; Elsevier Science B.V.
Loeb, Gerald E.; Peck, Raymond A.; Moore, William H.; Hood, Kevin; "BION System for Distributed Neural Prosthetic Interfaces"; Medical Engineering and Physics; bearing a date of 2001; pp. 9-18; vol. 23; Elsevier Science Ltd.; located at: www.elsevier.com/locate/medengphy.
Lu, Zhao; Martel, Sylvain; "Preliminary Investigation of Bio-carriers Using Magnetotactic Bacteria"; Proceedings of the 28$^{th}$ IEEE EMBS Annual International Conference; bearing dates of Aug. 30, 2006-Sep. 3, 2006 and 2006; pp. 3415-3418; IEEE.
Luckevich, Mark, "MEMS microvalves: the new valve world"; Valve-World; bearing a date of May 2007; pp. 79-83.
Lynch et al.; "Design of Piezoresistive MEMS-Based Accelerometer for Integration with Wireless Sensing Unit for Structural Monitoring"; Journal of Aerospace Engineering; bearing a date of Jul. 2003; pp. 108-114; vol. 3; ASCE.
Machado et al., "Detection of Lung Cancer by Sensor Array Analyses of Exhaled Breath"; American Journal of Respiratory and Critical Care Medicine; bearing a date of 2005; pp. 1286-1291; vol. 171.
Mangan, Elizabeth V.; Kingsley, Dan A.; Quinn, Roger D.; Chiel, Hillel J.; "Development of a Peristaltic Endoscope"; IEEE International Conference on Robotics & Automation 2002; pp. 1-6; located at http://biorobots.cwru.edu/publications/ICRA02_Mangan_Endoscope.pdf.
Marcu et al.; "In vivo detection of macrophages in a rabbit atherosclerotic model by time-resolved laser-induced fluorescence spectroscopy"; Atherosclerosis; bearing a date of 2005, pp. 295-303; vol. 181; Elsevier Ireland Ltd.
Marks, William B.; Loeb, Gerald E.; "Action Currents, Internodal Potentials, and Extracellular Records of Myelinated Mammalian Nerve Fibers Derived from Node Potentials"; Biophysical Journal; 1976; pp. 655-668; vol. 16.
Martel, Sylvain; "Fundamental Principles and Issues of High-speed Piezoactuated Three-legged Motion for Miniature Robots Designed for Nanometer-scale Operations"; The International Journal of Robotics Research; bearing dates of Jul. 2005 and 2005; pp. 575-588; vol. 24, No. 7; Sage Publications.
Martel, Sylvain; "Fundamentals of high-speed piezo-actuated three-legged motion for miniature robots designed for nanometer-scale operations"; pp. 1-8.
Martel, Sylvain; "Towards MRI-Controlled Ferromagnetic and MC-1 Magnetotactic Bacterial Carriers for Targeted Therapies in Arteriolocapillar Networks Stimulated by Tumoral Angiogenesis"; Proceedings of the 28$^{th}$ IEEE EMBS Annual International Conference; bearing dates of Aug. 30, 2006-Sep. 3, 2006 and 2006; pp. 3399-3402; IEEE.
Martel, Sylvain; Mathieu, Jean-Baptiste; Felfoul, Ouajdi; Chanu, Arnaud; Aboussouan, Eric; Tamaz, Samer; Pouponneau, Pierre; "Automatic Navigation of an Untethered Device in the Artery of a Living Animal using a Conventional Clinical Magnetic Resonance Imaging System"; Applied Physics Letters; 2007; pp. 114105-1-114105-3; vol. 90, No. 114105; American Institute of Physics.

Mataric, Maja J.; "Integration of Representation into Goal-Driven Behavior-Based Robots"; IEEE Transactions on Robotics and Automation; bearing dates of Jun. 1992 and 1992; pp. 304-312; vol. 8, No. 3; IEEE.
Mathieu, J-B.; Martel, S.; Yahia, L'H.; Soulez, G.; Beaudoin, G.; "MRI Systems as a Mean of Propulsion for a Microdevice in Blood Vessels"; bearing a date of 2003; pp. 3419-3422; IEEE.
Matsui, Takemi; Matsumura, Kouji; Hagisawa, Kousuke; Ishihara, Masayuki; Ishizuka, Toshiaki; Suzuki, Minoru; Kurita, Akira; Kikuchi, Makoto; "A Novel Ferromagnetic Thermo-Stent for Plaque Stabilization That Self-Regulates the Temperature"; IEEE Transactions on Biomedical Engineering; bearing dates of Jun. 2002 and 2002; pp. 621-623; vol. 49, No. 6; IEEE.
Mattley et al.; "Blood Characterization using uv/vis Spectroscopy"; Advances in Fluorescence Sensing Technology II (Proceedings Volume); bearing a date of 1995; pp. 462-470; vol. 2388; SPIE.
McNeal, Donald R.; "Analysis of a Model for Excitation of Myelinated Nerve"; IEEE Transactions on Biomedical Engineering; bearing a date of Jul. 1976; pp. 329-337; vol. BME-23, No. 4.
Mehmood et al.; "Autonomous Navigation of Mobile Agents Using RFID-Enabled Space Partitions"; ACMGIS '08; bearing dates of Nov. 5-7, 2008 and 2008; pp. 1-10; ACM.
Meier, P.; Oberthür, S.; Lang, M.; "Development of a compliant device for minimally invasive surgery"; Proceedings of the 28$^{th}$ IEEE EMBS Annual International Conference; bearing dates of Aug. 30, 2006-Sep. 3, 2006 and 2006; pp. 331-334; IEEE.
"MEMS at the cutting edge®, Patent Pending"; VERIMETRA; pp. 1-2; located at http://www.verimetra.com/flow.htm; printed on May 4, 2006.
Menciassi, A.; Park, Jong H.; Lee, S.; Gorini, S.; Dario, P.; Park, Jong-Oh; "Robotic Solutions and Mechanisms for a Semi-Autonomous Endoscope"; Proceedings of the 2002 IEEE/RSJ International Conference on Intelligent Robots and Systems; bearing a date of 2002; pp. 1379-1384; IEEE.
Menciassi et al.; "Towards Active Capsular Endoscopy: Preliminary Results on a Legged Platform"; Proceedings of the 28$^{th}$ IEEE EMBS Annual International Conference; bearing dates Aug. 30, 2006-Sep. 3, 2006 and 2006; pp. 2215-2218; IEEE.
Meyer et al.; "Map-Based Navigation in Mobile Robots: II. A Review of Map-Learning and Path-Learning Strategies"; Science Direct-Cognitive Systems Research; bearing dates of Feb. 12, 2003 and Dec. 4, 2003; pp. 1-51; vol. 4, No. 4; Elsevier Science.
Mohan et al., "Bokode: Imperceptible Visual tags for Camera Based Interaction from a Distance"; ACM Transactions on Graphics (Proceedings of SIGGRAPH 2009); bearing dates of Aug. 3-7, 2009; pp. 1-8.
Mohseni, Kamran; "Biomimetic & Bio-Inspired Aerial and Underwater Vehicles"; bearing a date of Sep. 23, 2006; pp. 1-10; printed on Jan. 4, 2007; located at http://enstrophy.colorado.edu/~mohseni/MicroVehiclesl.html#UUV1#UUV1.
Mok et al.; "Recent Progress in Nucleic Acid Aptamer-Based Biosensors and Bioassays"; Sensors; bearing a date of 2008; pp. 7050-7084; vol. 8.
Morrison et al., "Clinical Applications of Micro- and Nanoscale Biosensors"; Biomedical Nanostructures; bearing a date of 2008; Chapter 17; pp. 433-454; John Wiley & Sons, Inc.
Mosse, Charles; Mills, Tim; Appleyard, Mark; Swain, Paul; "Electrostimulation to move endoscopes in the small bowel"; Proceedings of SPIE; bearing a date of 2001; pp. 24-28; vol. 4158.
Motomiya et al.; "Flow Patterns in the Human Carotid Artery Bifurcation"; Stroke; bearing dates of Jan.-Feb. 1984; pp. 50-56; vol. 15, No. 1.
Murthy, S. Narasimha; Hiremath, Shobha Rani R.; "Physical and Chemical Permeation Enhancers in Transdermal Delivery of Terbutaline Sulphate"; AAPS PharmSciTech; bearing a date of 2001; pp. 1-5; vol. 2001, 2(1); Technical Note 1; located at http://www.pharmscitech.com/.
Nakayama, Yasuhide; Ji-Youn, Kim; Nishi, Shogo; Ueno, Hikaru; Matsuda, Takehisa; "Development of high-performance stent: gelatinous photogel-coated stent that permits drug delivery and gene transfer"; J Biomed Mater Res; bearing dates of Nov. 13, 2000, Apr. 23, 2001, May 10, 2001 and 2001; pp. 559-566; vol. 57; John Wiley & Sons, Inc.

(56) References Cited

OTHER PUBLICATIONS

Naqvi, Nasir H.; Rudrauf, David; Damasio, Hanna; Bechara, Antoine; "Damage to the Insula Disrupts Addiction to Cigarette Smoking"; Science; bearing a date of Jan. 26, 2007; pp. 531-534; vol. 315, No. 531; located at: www.sciencemag.org; printed on Jan. 25, 2007.

Nehmzow et al.; "Robot Navigation in the Real World: Experiments with Manchester's *FortyTwo* in Unmodified, Large Environments"; Robotics and Autonomous Systems; bearing a date of 2000; pp. 223-242; vol. 33; Elsevier Science B.V.

Neto, A.M. Figueiredo; Godinho, M.H.; Toth-Katona, T.; Palffy-Muhoray, P.; "Optical, Magnetic and Dielectric Properties of Non-Liquid Crystalline Elastomers Doped with Magnetic Colloids"; Brazilian Journal of Physics; Bearing a date of Mar. 2005; pp. 184-189; vol. 35, No. 1.

"New Medical Device Combines Wireless and MEMS Technology"; Georgia Institute of Technology; pp. 1-4; PhysOrg.com; located at: http://www.physorg.com/printnews.php?newsid=10533; printed on Feb. 20, 2006.

Nguyen, Clark T.-C.; "MEMS Technology for Timing and Frequency Control"; IEEE Transactions on Ultrasonics, Ferroelectrics, and Frequency Controls; bearing dates of Feb. 2007 and 2007; pp. 251-270; vol. 54, No. 2; IEEE.

Nieuwenhuizen-Berkovits, P.; "lubrelastic medical appliances"; Lubrelastic Medical Appliances; pp. 1-4; located at: http://www.xs4all.nl/~plien070/caeng.html; printed on Feb. 20, 2006.

Nordstrom et al.; "Identification of Cervical Intraepithelial Neoplasia (CIN) Using UV-Excited Fluorescence and Diffuse-Reflectance Tissue Spectroscopy"; Lasers in Surgery and Medicine; bearing a date of 2001; pp. 118-127; vol. 29; Wiley-Liss, Inc.

Nowinski et al.; "Three-dimensional Atlas of the Brain Anatomy and Vasculature[1]"; RadioGraphics; bearing dates of Jan.-Feb. 2005 and 2005; pp. 263-271; vol. 25, No. 1; RSNA.

Nyitrai, Zsolt; Illyefalvi-Vitéz, Zsolt; Pinkola, János; "Preparing Stents with Masking & Etching Technology"; 26th International Spring Seminar on Electronics Technology; bearing dates of May 8, 2003-May 11, 2003 and 2003; pp. 321-324; IEEE.

Olsson III, R.H.; Gulari, M.N.; Wise, K.D.; "Poster 114: Silicon Neural Recording Arrays with On-Chip Electronics for In-Vivo Data Acquisition"; Microtechnologies in Medicine and Biology; bearing dates of May 2, 2002-May 4, 2002; pp. 237-240; IEEE.

Oweiss, Karim G.; Anderson, David J.; "A New Technique for Blind Source Separation Using Subband Subspace Analysis in Correlated Multichannel Signal Environments"; bearing a date of 2001; pp. 2813-2816; IEEE.

Pan et al.; "A magnetically driven PDMS micropump with ball check-valves"; Journal of Micromechanics and Microengineering; bearing a date of 2005, pp. 1021-1026; vol. 15; IOP Publishing Ltd.

Patronik, N.A.; Ota, T.; Zenati, M.A.; Riviere, C.N.; "Improved Traction for a Mobile Robot Traveling on the Heart"; Proceedings of the 28th IEEE EMBS Annual International Conference; bearing dates of Aug. 30, 2006-Sep. 3, 2006 and 2006; pp. 339-342; IEEE.

Pavlidis, N.; "The diagnostic and therapeutic management of leptomeningeal carcinomatosis"; Annals of Oncology; bearing a date of 2004; pp. iv285-iv291; vol. 15 (Supp. 4); European Society for Medical Oncology.

PCT International Search Report; International App. No. PCT/US 07/10969; Nov. 10, 2008; pp. 1-2.

PCT International Search Report; International App. No. PCT/US2007/008993; Sep. 30, 2008; pp. 1-3.

PCT International Search Report; International App. No. PCT/US2007/008993; Sep. 29, 2008; pp. 1-3.

PCT International Search Report; International App. No. PCT/US07/10819; Aug. 27, 2008; pp. 1-3.

PCT International Search Report; International App. No. PCT/US07/10824; Aug. 21, 2008; pp. 1-3.

PCT International Search Report; International App. No. PCT/US07/10942; Aug. 15, 2008; pp. 1-3.

PCT International Search Report; International App. No. PCT/US07/10936; Jul. 24, 2008; pp. 1-3.

PCT International Search Report; International App. No. PCT/US07/10857; Jul. 21, 2008; pp. 1-2.

PCT International Search Report; International App. No. PCT/US05/13349; Apr. 28, 2008; pp. 1-2.

PCT International Search Report; International App. No. PCT/US05/13348; Dec. 27, 2006; pp. 1-3.

PCT International Search Report; International App. No. PCT/US05/13346; Dec. 26, 2006; pp. 1-3.

PCT International Search Report; International App. No. PCT/US05/13347; Dec. 11, 2006; pp. 1-3.

PCT International Search Report; International App. No. PCT/US05/33475; Sep. 5, 2006; pp. 1-2.

Peckham, P. Hunter; Knutson, Jayme S.; "Functional Electrical Stimulation for Neuromuscular Applications"; Annual Review Biomedical Engineering; bearing a date of 2005; pp. 327-360; vol. 7; Annual Reviews.

Peng et al.; "Ultraviolet light-emitting diodes operating in the 340 nm wavelength range and application to time-resolved fluorescence spectroscopy"; Applied Physics Letters; bearing dates of Aug. 23, 2004 and 2004; pp. 1436-1438; vol. 85, No. 8; American Institute of Physics.

Pfister et al.; "Weighted Line Fitting Algorithms for Mobile Robot Map Building and Efficient Data Representation"; Proceedings of the 2003 IEEE International Conference on Robotics and Automation; bearing a date of Sep. 14-19, 2003; pp. 1-8.

"Philips develops "intelligent pill""; Reuters; bearing a date of Nov. 11, 2008; p. 1; Thomson Reuters.

"Philips' intelligent pill targets drug development and treatment for digestive tract diseases"; PhysOrg.com; bearing a date of Nov. 11, 2008; pp. 1-3; located at http://www.physorg.com/news145640874.html.

Phillips et al.; "Detection of Lung Cancer With Volatile Markers in the Breath*"; Chest; bearing dates of Jun. 2003 and 2003; pp. 2115-2123; vol. 123, No. 6; American College of Chest Physicians.

Pisupati et al.; "A Central Axis Algorithm for 3D Bronchial Tree Structures"; Proceedings of the International Symposium on Computer Vision; bearing a date of 1995; pp. 259-264; IEEE.

Psathakis et al.; "8-Isoprostane, a Marker of Oxidative Stress, Is Increased in the Expired Breath Condensate of Patients With Pulmonary Sarcoidosis*"; Chest; bearing dates of Mar. 2004 and 2004, pp. 1005-1011; vol. 125, No. 3; American College of Chest Physicians.

Quaglia et al.; "An endoscopic capsule robot: a meso-scale engineering case study"; Journal of Micromechanics and Microengineering; bearing a date of 2009; pp. 1-11; vol. 19; IOP Publishing Ltd.

Quirini et al.; "Design of a Pill-Sized 12-legged Endoscopic Capsule Robot"; 2007 IEEE International Conference on Robotics and Automation; bearing dates of Apr. 10-14, 2007 and 2007; pp. 1856-1862; IEEE.

Raman et al.; "In Vivo Atherosclerotic Plaque Characterization Using Magnetic Susceptibility Distinguishes Symptom-Producing Plaques"; JACC: Cardiovascular Imaging; bearing dates of Jan. 2008 and 2008; pp. 49-57; vol. 1, No. 1; Elsevier.

Rasmussen et al.; "Proximity-based Access Control for Implantable Medical Devices"; CCS '09, Proceedings of the 16th ACM Conference on Computer and Communications Security; bearing dates of Nov. 9-13, 2009 and 2009; pp. 1-10.

Rattay, Frank; "Analysis of Models for Extracellular Fiber Stimulation"; IEEE Transactions on Biomedical Engineering; bearing a date of Jul. 1989; pp. 676-682; vol. 36, No. 7; IEEE.

Rattay, F.; "The Basic Mechanism for the Electrical Stimulation of the Nervous System"; Neuroscience; 1999; pp. 335-346; vol. 98. No. 2; Elsevier Science Ltd; printed on Mar. 15, 2007.

Rattay, Frank, Aberham, Matthias; "Modeling Axon Membranes from Functional Electrical Stimulation"; IEEE Transactions on Biomedical Engineering; bearing a date of Dec. 1993; pp. 1201-1209; vol. 40, No. 12; IEEE.

"Remote-Control Electrostimulation Capsule"; Popular Science; bearing dates of 2002 and 2003; pp. 1-2; located at http://www.popsci.com/popsci/brown/2003/article/0,18881,537028,00.html; printed on May 4, 2006.

"Remote-controlled capsule endoscope safely examines the stomach"; PhysOrg.com; bearing a date of Jan. 18, 2011; pp. 1-2; located

(56) References Cited

OTHER PUBLICATIONS at http://www.physorg.com/news-2011-01-remote-controlled-capsule-endoscope-safely-stomach.html.
"Researchers Create Tiny, Self-Propelled Devices"; PhysOrg.com; printed on Feb. 12, 2007; pp. 1-3; located at: http://www.physorg.com/printnews.php?newsid=90521279.
"Researchers: Squid-Inspired Vortex Generators Could Mean Better Propulsion for Unmanned Underwater Vehicles"; UnderwaterTimes.com; Dec. 12, 2006; pp. 1-2; UnderwaterTimes.com; printed on Jan. 4, 2007; located at http://www.underwatertimes.com/print.php?article_id=51030782641.
Rice, Mike; "Implantable Neurostimulation Device Market Poised for Explosive Growth"; Future Fab International; Jan. 7, 2006; pp. 1-4; printed on Oct. 6, 2006; located at http://www.future-fab.com/documents.asp?d_ID=3725.
Rice, Mike; "New Products, Emphasis on Miniaturization Driving Medical Device Innovation"; bearing a date Aug. 23, 2006; pp. 1-3; Advantage Business Media; located at http://www.mdtmag.com/scripts/ShowPR.asp?PUBCODE=046&ACCT=0006109&ISSUE=0603&RELTYPE=PR&PRODCODE=0790&PRODLETT=A; printed on Aug. 23, 2006.
Riedmüller, J.; Bolz, A.; Rebling, H.; Schaldach, M.; "Improvement of Stimulation and Sensing Performance of Bipolar Pacemaker Leads"; IEEE Eng. Med. Biol. Soc.; 1992; pp. 2364-2365; IEEE.
Robinson, David A.; "The Electrical Properties of Metal Microelectrodes"; Proceedings of the IEEE; bearing a date of Jun. 1968; pp. 1065-1071; vol. 56, No. 6.
Roh et al.; "Strategy for Navigation Inside Pipelines With Differential-Driveinpipe Robot"; IEEE Xplore; 2002 and 2005; pp. 2575-2580 (Only the Abstract is being provided); vol. 3; IEEE; located at: http://ieeexplore.ieee.org/xpls/abs_all.jsp?arnumber=1013619; printed on Apr. 23, 2007.
Roh et al.; "Actively Steerable In-Pipe Inspection Robots for Underground Urban Gas Pipelines"; IEEE Xplore; bearing dates of 2001 and 2005; pp. 761-766 (Only the Abstract is being provided); vol. 1; IEEE; located at: http://ieeexplore.ieee.org/xpls/abs_all.jsp?arnumber=932642; printed on Apr. 23, 2007.
Rolfe, Brigitte; "Toward Nanometer-Scale Sensing Systems: Natural and Artificial Noses as Models for Ultra-Small, Ultra-Dense Sensing Systems"; Advances in Computers; bearing dates of Nov. 2004, 2004, and 2007; pp. 11-46; vol. 71; Elsevier, B.V.
Rousche, Patrick J.; Pellinen, David S.; Pivin, David P.; Williams, Justin C.; Vetter, Rio J.; Kipke, Daryl R.; "Flexible Polyimide-Based Intracortical Electrode Arrays with Bioactive Capability"; IEEE Transactions on Biomedical Engineering; bearing a date Mar. 2001; pp. 361-371; vol. 48, No. 3; IEEE.
Rutten, Wim; Mouveroux, Jean-Marie; Buitenweg, Jan; Heida, Ciska; Ruardij, Teun; Marani, Enrico; Lakke, Egbert; "Neuroelectronic Interfacing with Cultured Multielectrode Arrays Toward a Cultured Probe"; Proceedings of the IEEE; bearing a date of Jul. 2001; pp. 1013-1029; vol. 89, No. 7; IEEE.
Saltzman, John R.; "Endoscopic Advances—A View Toward the Future"; bearing dates of May 4, 2006, May 17, 2005, and 2005; pp. 1-4; Medscape; located at http://www.medscape.com/viewarticle/505100; printed on May 4, 2006.
Schertler et al.; "Effects of ECG Gating and Postprocessing Techniques on 3D MDCT of the Bronchial Tree"; AJR; bearing a date of Jul. 2004; pp. 83-89; vol. 183; American Roentgen Ray Society.
Schmidt, W.; Behrens, P.; Behrend, D.; Schmitz, K.-P.; Andresen, R.; "Experimental Study of Peripheral, Balloon-expandable Stent Systems"; Progress in Biomedical Research; bearing a date of May 2001; pp. 246-255.
Schnakenberg et al.; "Intravascular pressure monitoring system"; Sensors and Actuators A: Physical; bearing a date of 2004; pp. 61-67; vol. 110; Elsevier B.V.
Schoonhoven, R.; Stegeman, D.F.; "Models and Analysis of Compound Nerve Action Potentials"; Critical Reviews in Biomedical Engineering; bearing a date of 1991; pp. 47-111; vol. 19, No. 1; CRC Press, Inc.
Schwartz, John; "In the Lab: Robots That Slink and Squirm"; The New York Times: Science; bearing a date of Mar. 27, 2007; pp. 1-4; The New York Times Company; located at: http://www.nytimes.com/2007/03/27/science/27robo.html?ex=1332648000&en=d4541141c174b454&ei=5124&partner=digg&exprod=digg; printed on Mar. 27, 2007.
Senel, Sevda; Hincal, A. Atilla; "Drug permeation enhancement via buccal route: possibilities and limitations"; Journal of Controlled Release; bearing a date of 2001; pp. 133-144; vol. 72 (2001); Elsevier; located at www.elsevier.com/locate/jconrel.
Serruya, Mijail D.; Hatsopoulos, Nicholas G.; Paninski, Liam; Fellows, Matthew R.; Donoghue, John P.; "Brief Communications: Instant Neural Control of a Movement Signal"; Nature; bearing a date of Mar. 14, 2002; pp. 141-142; vol. 416; Macmillan Magazines Ltd; located at: www.nature.com.
Serruys, Patrick W.; Kutryk, Michael J.B.; Ong, Andrew T.L.; "Coronary-Artery Stents"; The New England Journal of Medicine; bearing a date of Feb. 15, 2006; pp. 483-495; vol. 354;5; Massachusetts Medical Society.
Shabalovskaya, Svetlana, A.; "Surface, corrosion and biocompatibility aspects of Nitinol as an implant material"; Bio-Medical Materials and Engineering; bearing dates of Apr. 4, 2001, and 2002; pp. 69-109; vol. 12; IOS Press.
Shahinpoor, Mohsen; Kim, Kwang J.; Ionic polymer-metal composites: IV. Industrial and medical applications; Smart Materials and Structures; 2005; pp. 197-214; vol. 14; Institute of Physics Publishing.
Smith, Michael; "PAS: Nasal Spray Flu Vaccine Seems Safe and Effective in Young"; May 2, 2006; pp. 1-2; MedPage Today, LLC; bearing dates of 2004-2006; printed on May 4, 2006; located at http://www.medpagetoday.com/tbprint.cfm?tbid=3213.
Snoek, GJ; Ijzerman, MJ; In 'T Groen, Facg; Stoffers, TS; Zilvold, G; "Use of the NESS Handmaster to Restore Handfunction in Tetraplegia: Clinical Experiences in Ten Patients"; Spinal Cord; bearing a date of 2000; pp. 244-249; vol. 38; International Medical Society of Paraplegia.
Snow, E.S.; Perkins, F.K.; Houser, E.J.; Badescu, S.C.; Reinecke, T. L.; "Chemical Detection with a Single-Walled Carbon Nanotube Capacitor"; Science; Mar. 25, 2005; pp. 1942-1945; vol. 307; www.sciencemag.org.
"Spider pill to seek out diseases"; PhysOrg.com; bearing a date of Oct. 16, 2009 and 2009; p. 1; located at http://www.physorg.com/news174893082.html.
Stoeckel, Dieter; Pelton, Alan; Duerig, Tom; "Self-expanding nitinol stents: material and design considerations"; European Radiology; bearing dates of Jan. 28, 2003, May 22, 2003, Jul. 1, 2003, Sep. 3, 2003, Feb. 2004 and 2004; pp. 292-301(1-2); vol. 14, No. 2; Springer-Verlag GmbH-SpringerLink—Article; located at: http://www.springerlink.com/(1begg455gtgjfseqqntyb43m)/app/home/contribution.asp?referrer=parent&backto=issue,17,26;journal,27,147;browsepublicationsresults, 444,1551; printed on Feb. 22, 2006.
Strauss, Bradley H., M.D., Ph.D.; Li, Chris, M.D.; Whittingham, Heather A., M.Sc; Tio, Fermin O., M.D.; Kutryk, Michael J.B., M.D., Ph.D.; Janicki, Christian, Ph.D.; Sparkes, John, D., M.Sc.; Turnlund, Todd, B.Sc.; Sweet, William L., M.D.; "Late Effects of Low-Energy Gamma-Emitting Stents in a Rabbit Iliac Artery Model"; Int. J. Radiation Oncology Biol. Phys.; bearing dates of Oct. 23, 2001, May 13, 2002 and May 15, 2002 and 2002; pp. 551-561; vol. 54, No. 2; Elsevier Science Inc.
Struijk, Johannes Jan; "The Extracellular Potential of a Myelinated Nerve Fiber in an Unbounded Medium and in Nerve Cuff Models"; Biophysical Journal; bearing a date of Jun. 1997; pp. 2457-2469; vol. 72; Biophysical Society.
Sun et al.; "A Miniature RF Communication System for Micro Gastrointestinal Robots"; Journal of Medical Engineering & Technology; bearing a date of 2003; pp. 160-163; vol. 27.
Suzumori et al.; "Micro Inspection Robot for 1-in Pipes"; IEEE/ASME Transactions on Mechatronics; bearing dates of Sep. 1999 and 1999; pp. 286-292; vol. 4, No. 3; IEEE.
Tang et al.; "Cerebral Vascular Tree Matching of 3D-RA Data Based on Tree Edit Distance"; Medical Imaging and Augmented Reality; bearing a date of 2006; pp. 116-123.

(56) References Cited

OTHER PUBLICATIONS

Taylor, Dawn M.; Helms Tillery, Stephen I.; Schwartz, Andrew B.; "Research Article: Direct Cortical Control of 3D Neuroprosthetic Devices"; Science; bearing a date of Jun. 7, 2002; pp. 1829-1832; vol. 296; located at: www.sciencemag.org.
The Biomedical Engineering Handbook, Second Edition; bearing a date of 2000; pp. IV-1-43-31; vol. I; CRC Press LLC.
The Biomedical Engineering Handbook, Second Edition; bearing a date of 2000; pp. V-1-51-9; vol. I; CRC Press LLC.
Thrun, Sebastian; "Learning Metric-Topological Maps for Indoor Mobile Robot Navigation"; Artificial Intelligence; bearing a date of 1998; pp. 21-71; vol. 99; Elsevier Science B.V.
Thrun, Sebastian; "Probabilistic Algorithms in Robotics"; AI Magazine; bearing dates of Winter 2000 and 2000; pp. 93-109; vol. 21, No. 4; American Association for Artificial Intelligence.
Thrun, Sebastian; "Robotic Mapping: A Survey"; Exploring Artificial Intelligence in the New Millenium; bearing a date of Feb. 2002; pp. 1-29 (31 total pages); Morgan Kaufmann.
Thrun et al.; "A Real-Time Algorithm for Mobile Robot Mapping With Applications to Multi-Robot and 3D Mapping"; IEEE International Conference on Robotics and Automation; bearing a date of Apr. 2000; pp. 1-8.
Thrun et al.; "Integrating Topological and Metric Maps for Mobile Robot Navigation: A Statistical Approach"; pp. 1-7.
"Tiny Robot Reduces Need for Surgery"; Pink Tentacle; bearing a date of Feb. 26, 2007; p. 1; located at: http://www.pinktentacle.com/2007/02/tiny-robot-reduces-need-for-surgery; printed on Mar. 8, 2007.
Tomatis et al.; "Simultaneous Localization and Map Building: A Global Topological Model with Local Metric Maps"; Robotics Autonomous Systems; bearing a date of 2003; pp. 1-6; vol. 44.
"Trying to control pain can be a double-edged sword, say scientists"; PhysOrg.com; printed on Nov. 2, 2006; pp. 1-2; located at http://www.physorg.com/printnews.php?newsid=81599312.
Tsuruta et al.; "Control Circuit in an In-Pipe Wireless Micro Inspection Robot"; IEEE Xplore; bearing dates of 2000 and 2005; pp. 59-64 (Only the Abstract is being provided); IEEE; located at: http://ieeexplore.ieee.org/xpls/abs_all.jsp?arnumber=903290; printed on Apr. 23, 2007.
Tummala, R. Lal; Mukherjee, R.; Aslam, D.; Xi, Ning; Mahadevan, S.; Weng, J.; "Reconfigurable Adaptable Micro-robot"; IEEE; bearing a date of 1999; pp. 687-691.
Twardoch, U.M.; "Integrity of Ultramicro-Stimulation Electrodes Determined from Electrochemical Measurements"; Journal of Applied Electrochemistry; bearing a date of 1994; pp. 835-857; vol. 24; Chapman & Hall.
UK Intellectual Property Office Examination Report under Section 18(3); App. No. GB0821521.2; Jan. 12, 2011 ; 4 pages.
UK Intellectual Property Office Combined Search and Examination Report Under Sections 17 & 18(3); App. No. GB1016383.0; Nov. 1, 2010; pp. 1-4.
UK Intellectual Property Office Examination Report Under Section 18(3); App. No. GB0821519.6; Oct. 19, 2010; 1 page.
UK Intellectual Property Office Examination Report Under Section 18(3); App. No. GB0821530.3; Aug. 27, 2010 ; pp. 1-6.
UK Intellectual Property Office Examination Report Under Section 18(3); App. No. GB0821524.6; Aug. 9, 2010; pp. 1-2.
UK Intellectual Property Office Examination Report Under Section 18(3); App. No. GB0821519.6; Aug. 9, 2010; pp. 1-3.
UK Intellectual Property Office Examination Report Under Section 18(3); App. No. GB0821526.1; bearing a date of Jul. 15, 2010; pp. 1-2.
UK Examination Report Under Section 18(3); App. No. GB0821524.6; bearing a date of May 6, 2010; pp. 1-3.
UK Intellectual Property Office Examination Report Under Section 18(3); App. No. GB0706802.6; Nov. 23, 2009; pp. 1-2.
UK Intellectual Property Office Examination Report Under Section 18(3); App. No. GB0821519.6; Nov. 12, 2009; 1-4.
UK Intellectual Property Office Examination Report Under Section 18(3); App. No. GB0821526.1; Nov. 11, 2009; 1-5.
UK Intellectual Property Office Examination Report Under Section 18(3), App. No. GB0821523.8; Jul. 2, 2009; pp. 1-2.
UK Intellectual Property Office Examination Report Under Section 18(3); App. No. GB0706802.6; bearing a date of Dec. 1, 2008; pp. 1-2.
Ulrich et al.; "Appearance-Based Place Recognition for Topological Localization"; IEEE International Conference on Robotics and Automation; bearing a date of Apr. 2000; pp. 1023-1029.
Verheye et al.; "Selective Clearance of Macrophages in Atherosclerotic Plaques by Autophagy"; Journal of the American College of Cardiology; bearing dates of Feb. 13, 2007 and 2007; pp. 706-715; vol. 49, No. 6; Elsevier Inc.
Wacharasindhu et al.; "Radioisotope microbattery based on liquid semiconductor"; Applied Physics Letters; bearing dates of Dec. 11, 2008, Jun. 9, 2009, Jul. 6, 2009, Dec. 8, 2009 and 2009; pp. 014103-1-014103-3; vol. 95; American Institute of Physics.
Wakimoto et al.; "A Micro Snake-Like Robot for Small Pipe Inspection"; International Symposium on Micromechatronics and Human Science; bearing a date of 2003; pp. 303-308; IEEE.
Wang et al.; "A MEMS-based Air Flow Sensor with a Free-standing Micro-cantilever Structure"; Sensors; bearing dates of Aug. 27, 2007, Oct. 10, 2007, Oct. 17, 2007, and 2007; pp. 2389-2401; vol. 7; MDPI.
Warland, David K.; Reinagel, Pamela; Meister, Markus; "Decoding Visual Information from a Population of Retinal Ganglion Cells"; bearing a date of 1997; pp. 2336-2350; The American Physiological Society.
Watson et al.; "Piezoelectric ultrasonic resonant motor with stator diameter less than 250 µm: The *Proteus* motor"; Journal of Micromechanics and Microengineering; bearing dates of Sep. 25, 2008, Nov. 18, 2008, Jan. 20, 2009, and 2009; pp. 1-5; vol. 19; IOP Publishing Ltd.
Weingandt et al.; "Autofluorescence spectroscopy for the diagnosis of cervical intraepithelial neoplasia"; BJOG: an International Journal of Obstetrics and Gynaecology; bearing dates of Aug. 2002 and 2002; pp. 947-951; vol. 109; RCOG.
Weis, Rolf; Müller, Bernt; Fromherz, Peter; "Neuron Adhesion on a Silicon Chip Probed by an Array of Field-Effect Transitors"; Physical Review Letters; bearing a date of Jan. 8, 1996; pp. 327-330; vol. 76, No. 2; The American Physical Society.
Wessberg, Johan; Stambaugh, Christopher R.; Kralik, Jerald D.; Beck, Pamela D.; Laubach, Mark; Chapin, John K.; Kim, Jung; Biggs, S. James; Srinivasan, Mandayam A.; Nicolelis, Miguel A.L.; "Letters to Nature: Real-Time Prediction of Hand Trajectory by Ensembles of Cortical Neurons in Primates"; Nature; bearing a date of Nov. 16, 2000; pp. 361-365; vol. 408; Macmillan Magazines Ltd; located at: www.nature.com.
White, Dave; "Mini Robot Explores, Gives you Medicine from Within"; Mobile Magazine; bearing a date of Feb. 27, 2007; p. 1; located at: http://www.mobilemag.com/content/100/313/C11869/; printed on Mar. 8, 2007.
Xi et al.; "Self-assembled microdevices driven by muscle"; Nature Materials; bearing dates of Feb. 2005 and 2005; pp. 180-184 (10 pages total); vol. 4; Nature Publishing Group.
Yang et al.; "Power generation with laterally packaged piezoelectric fine wires"; Nature Nanotechnology; bearing dates of Nov. 9, 2008, Jan. 2009, and 2009; pp. 34-39; vol. 4; Macmillan Publishers Limited.
Yang et al.; "Converting Biomechanical Energy into Electricity by a Muscle-Movement-Driven Nanogenerator"; Nano Letters; bearing dates of Dec. 25, 2008, Jan. 31, 2009, and 2009; pp. 1201-1205; vol. 9, No. 3; American Chemical Society.
Yavari, Nazila; "Optical spectroscopy for tissue diagnostics and treatment control"; Doctoral Thesis; Department of Physics and Technology; University of Bergen; bearing a date of Apr. 2006; 130 pages.
Yu et al.; "System for the analysis and visualization of large 3D anatomical trees"; Computers in Biology and Medicine; bearing dates of Oct. 6, 2006, May 31, 2007, Jun. 4, 2007, and 2007; pp. 1802-1820; vol. 37; Elsevier Ltd.
Yusa, Go; Muraki, Koji; Takashina, Kei; Hashimoto, Katsushi; Hirayama, Yoshiro; "Controlled multiple quantum coherences of

(56) References Cited

OTHER PUBLICATIONS nuclear spins in a nanometre-scale device"; Nature; Apr. 21, 2005; pp. 1001-1005; vol. 434; 2005 Nature Publishing Group; www.nature.com/nature.

Zhao et al.; "Physicist Develops Natural Motor Technique"; PhysOrg.com; bearing dates of Apr. 21, 2007 and 2007; 1 page; United Press International; located at: http://www.physorg.com/news96357975.html; printed on Apr. 23, 2007.

Zheng et al.; "Design and Fabrication of a Micro Coulter Counter with Thin Film Electronics"; Proceedings of 2006 International Conference on Microtechnologies in Medicine and Biology; bearing dates of May 9-12, 2006 and 2006; pp. 16-19; IEEE.

Zhu et al.; "Flattening Maps for the Visualization of Multibranched Vessels"; IEEE Transactions on Medical Imaging; bearing dates of Feb. 10, 2004, Sep. 27, 2004, Feb. 2005, and 2005; pp. 191-198; vol. 24, No. 2; IEEE.

Zrimec et al.; "3D Modelling and Visualization of the Human Lung"; Proceedings of the 2nd International Symposium on 3D Data Processing, Visualization, and Transmission (3DPVT'04); bearing a date of 2004; pp. 110-115; IEEE.

Zyga, Lisa; "Microswimmer Propels Itself With Near-Zero Friction"; PhysOrg.com; bearing dates of Jun. 4, 2007 and 2007; pp. 1-2; PhyOrg.com; located at: http://www.physorg.com/news100176842.html; printed on Jun. 6, 2007.

"Zyvex NanoEffector Microgrippers"; Nanotechnology at Zyvex; printed on Dec. 7, 2006; pp. 1-2; located at http://www.zyvex.com/Products/Grippers_Features.html.

"Zyvex NanoEffector Microgrippers"; Zyvex.com; bearing a date of 2006; pp. 1-2; Zyvex Corporation.

U.S. Appl. No. 13/136,679, Ferren et al.
U.S. Appl. No. 13/136,677, Ferren et al.
U.S. Appl. No. 13/136,676, Ferren et al.
U.S. Appl. No. 13/136,675, Ferren et al.
U.S. Appl. No. 13/136,678, Ferren et al.
U.S. Appl. No. 13/136,674, Ferren et al.
U.S. Appl. No. 13/135,694, Ferren et al.
U.S. Appl. No. 13/135,696, Ferren et al.

Mosby's Dictionary of Medicine, Nursing & Health Professions; "endoscopy"; 2009; Credo Reference. Web. Jun. 29, 2011; 1 page; Elsevier Health Sciences.

Hammer-Wilson et al.; "Fluorescence Diagnostics of *Helicobacter pylori*-Infected Human Gastric Mucosa: Establishing Technique and Validity"; Scandinavian Journal of Gastroenterology; bearing a date of 2007, accepted Jan. 2, 2007; pp. 941-950; vol. 42; Taylor & Francis.

So, Peter TC; "Two-Photon Fluorescence Light Microscopy"; Encyclopedia of Life Sciences; bearing a date of 2002; pp. 1-5; Macmillan Publishers Ltd, Nature Publishing Group; located at: http://web.mit.edu/solab/Documents/Assets/So-2PF%20light%20microscopy.pdf.

Thomas et al.; "Detection and Analysis of Tumor Fluorescence Using a Two-Photon Optical Fiber Probe"; Biophysical Journal; bearing a date of Jun. 2004; 7 pages (3959-3965); vol. 86, No. 6.

European Patent Office, Supplementary European Search Report, Pursuant to Rule 62 EPC; App. No. EP 08795525; Jan. 21, 2015; pp. 1-7.

\* cited by examiner

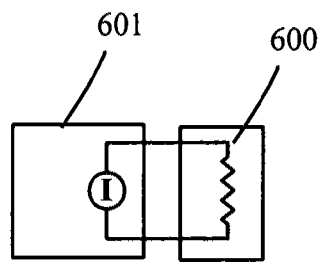
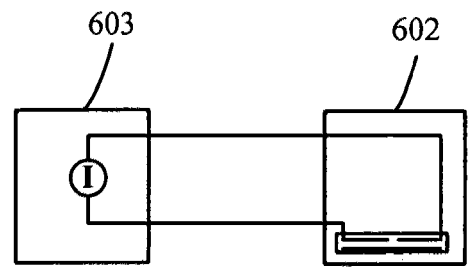
FIG. 6A  FIG. 6B
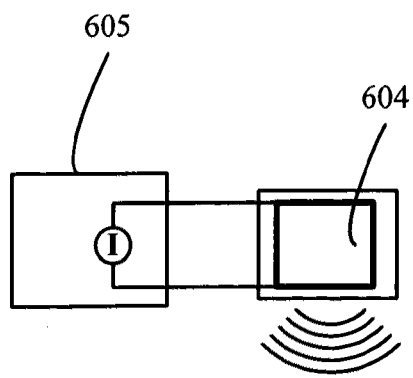
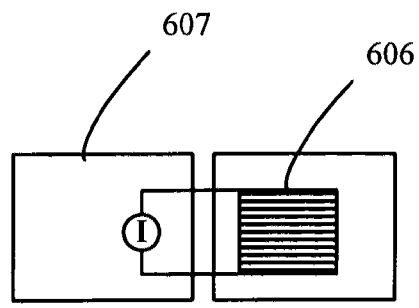
FIG. 6C  FIG. 6D

1100 A system comprising:

1102 non-transitory machine readable media for use in a lumen traveling device control system 1104
    one or more instructions that cause the lumen traveling device control system to activate a propelling mechanism on a lumen traveling device to propel the lumen traveling device within a body tube tree;

one or more instructions that cause the lumen traveling device control system to determine an arrival of the lumen traveling device at a branch point in the body tube tree based upon a signal from at least one arrival sensor on the lumen traveling device, the branch point including at least two branch channels;

one or more instructions that cause the lumen traveling device control system to select one of the at least two branch channels substantially randomly;

one or more instructions that cause the lumen traveling device control system to direct the propelling mechanism on the lumen traveling device to move the lumen traveling device into the selected branch channel;

one or more instructions that cause the lumen traveling device control system to store information regarding at least one of the at least two branch channels;

one or more instructions that cause the lumen traveling device control system to direct the sensing of a local parameter value from a parameter sensor on the lumen traveling device; and one or more instructions that cause the lumen traveling device control system to direct an active portion of the lumen traveling device to perform an action based at least in part upon the local parameter value 1106 computer readable media 1108 recordable-type media

1300 Sensing and Storing Information

1302 Sensing one or more position indicator signals

- a signal from inertial navigation system 1304
- a magnetic signal originating from a remote source 1306
- an electromagnetic signal from a remote source 1312
  - RF beacon 1314
  - Personal Area Network 1318
  - Wireless Network 1317
- Sensing an encrypted signal 1319
- an ultrasonic signal originating from a remote source 1308
- a radiological signal originating from a remote source 1310
- GPS 1316
- Body Area Network 1320

1322 Sensing one or more local parameters

- Concentration of analyte 1324
- Fluid Flow 1326
- Temperature 1328
- Pressure 1330
- Acoustic signal 1332
- Optical signal 1334
- Electrical field 1336
- Magnetic field 1338
- marker or label 1340
- Structure parameter 1342
- Electromagnetic field 1344
- Image 1345

1346 Storing information regarding at least one of the at least two branch channels

- Direction 1348
- Orientation 1350
- Branching pattern 1352
- Lumenal dimension 1354
- Length 1356
- Structural configuration 1358
- Distance from another branch point 1360
- Proximity to valve or channel restriction 1362

FIG. 15

1500 performing an action with an active portion of the lumen traveling device 1502 wherein performing an action with the active portion includes transmitting a signal to a remote location 1505 wherein performing an action with the active portion includes delivering a material to a wall region of the body tube tree.

1504 wherein performing an action with the active portion includes releasing a material.

1506 wherein the material includes at least one of adhesive, a filler, a polymer, a hydrogel, an antibiotic, an antibody, an antiviral, a pharmaceutical compound, a nutrient, a hormone, a growth factor, a catalyst, a drug, a therapeutic compound, a chemical, a biomaterial, a biological label, an enzyme, a protein, a nuclueic acid, an oligonucleotide, a polynucleotide, a polypeptide, a genetic material, a cell, a fraction of a cell, a cell fragment, a complex, a vaccine, a vitamin, a neurotransmitter, a neurotropic agent, a neuroactive material, a cytokine, a chemokine, a hormone, a cell-signaling material, a pro-apoptotic agent, an anti-apoptotic agent, an immunological mediator, an anti-inflammatory agent, a salt, an ion, an electrolyte, an antioxidant, an imaging agent, a labeling agent, a diagnostic compound, a nanomaterial, an inhibitor, a lipid, an alcohol, a sterol, a steroid, a carbohydrate, a sugar, a gas, or a blocker.

1500 performing an action with an active portion of the lumen traveling device 1602 wherein performing an action with the active portion includes collecting a material from the body lumen 1604 wherein performing an action with the active portion includes collecting a sample from a fluid within the body lumen 1606 wherein performing an action with the active portion includes collecting a sample from a wall region of the body lumen 1608 wherein performing an action with the active portion includes producing heating.

1610 wherein performing an action with an active portion includes producing heating to ablate an atherosclerotic plaque 1612 wherein performing an action with an active portion includes producing heating to ablate a cancerous lesion 1614 wherein performing an action with an active portion includes heating in male reproductive system to destroy gametes 1616 wherein performing an action with the active portion includes producing cooling.

1618 wherein performing an action with the active portion includes securing the lumen traveling device into position within the body lumen.

FIG. 16 performing an action with an active portion of the lumen traveling device
1500 wherein performing an action with the active portion includes emitting acoustic energy.
1802 wherein performing an action with the active portion includes emitting ultrasonic acoustic energy.
1804 wherein performing an action with the active portion includes applying pressure to the body lumen
1806 wherein performing an action with the active portion includes modulating the flow of fluid through at least a portion of the body lumen.
1808 wherein modulating the flow of fluid through at least a portion of the body lumen includes blocking the flow of fluid through at least a portion of the body lumen.
1810 wherein modulating the flow of fluid through at least a portion of the body lumen includes modifying the direction of flow of fluid through at least a portion of the body lumen.
1812 wherein modulating the flow of fluid through at least a portion of the body lumen includes modifying the amount of turbulent flow.
1814

FIG. 18

| performing an action with an active portion of the lumen traveling device 1500 |||
|---|---|---|
| wherein performing an action with the active portion includes at least partly removing specific components from at least a portion of a fluid within the body lumen 1902 | wherein performing an action with the active portion includes activating at least one catalyst 1904 | wherein performing an action with the active portion includes generating a localized electric field 1906 |
| wherein performing an action with the active portion includes generating a localized magnetic field 1908 | wherein performing an action with the active portion includes removing tissue from at least a portion of the body lumen 1910 | wherein performing an action with the active portion includes cutting at least a portion of the body lumen 1912 |
| wherein performing an action with the active portion includes releasing a man-made structure from the lumen traveling device 1914  
wherein performing an action with the active portion includes attaching the man-made structure to a wall of the body lumen 1916 | wherein performing an action with the active portion includes delivering a material or structure to a receiving portion of a man-made device 1918 | wherein performing an action with the active portion includes receiving a material or structure from a delivery portion of a man-made device 1920 |
| including transmitting power to the lumen traveling device 1922 | including transmitting a signal to the lumen traveling device 1924  
Transmitting an encrypted signal 1925 | including receiving a signal from a remote source with the lumen traveling device 1926  
Receiving an encrypted signal 1927 | including receiving power from a remote source with the lumen traveling device 1928 |

FIG. 19

2100 A system comprising:

2102 non-transitory machine readable media for use in a lumen traveling device control system 2104
    one or more instructions that cause the lumen traveling device control system to activate a propelling mechanism on a lumen traveling device to propel the lumen traveling device within a body tube tree;
    one or more instructions that cause the lumen traveling device control system to determine a time based on a signal from a timing device; and
    one or more instructions that cause the lumen traveling device control system to direct the active portion of the lumen traveling device to perform at least one action based at least in part upon the determined time 2106 computer readable media 2108 recordable-type media

FIG. 21

2400 A system comprising:

2402 non-transitory machine readable media for use in a lumen traveling device control system 2404
    one or more instructions that cause the lumen traveling device control system to identify at least two possible directions of travel of a lumen traveling device through a body tube tree, the body tube tree including a plurality of branched, interconnected channels, the at least two possible directions of travel corresponding to at least two of the branched, interconnected channels;
    one or more instructions that cause the lumen traveling device control system to receive information related to whether at least one of the at least two possible directions of travel of the lumen traveling device through the body tube tree has previously been traveled by the lumen traveling device;
    one or more instructions that cause the lumen traveling device control system to select a direction of travel from the at least two possible directions of travel based at least in part on the information related to whether or not at least one of the at least two possible directions of travel of the lumen traveling device through the body tube tree has previously been traveled by the lumen traveling device; and
    one or more instructions that cause the lumen traveling device control system to direct at least one of a steering mechanism and a propelling mechanism on the lumen traveling device to cause the lumen traveling device to move through the body tube tree in the selected direction of travel 2406 computer readable media 2408 recordable-type media

FIG. 24 directing at least one of a steering mechanism and a propelling mechanism on the lumen traveling device to cause the lumen traveling device to move through the body tube tree in the selected direction of travel 2508

| wherein the directing is performed under the control of motion control circuitry located on-board the lumen traveling device 2509 | wherein the directing is performed under the control of motion control circuitry located in part on-board the lumen traveling device and in part on a remote device 2510 | wherein the directing is performed under the control of motion control circuitry located on a remote device 2511 |

| directing at least one of the steering mechanism and the propelling mechanism on the lumen traveling device to cause the lumen traveling device to move through the body tube tree in the selected direction of travel for a pre-determined distance 2512 | directing at least one of the steering mechanism and the propelling mechanism on the lumen traveling device to cause the lumen traveling device to move through the body tube tree in the selected direction of travel for a pre-determined duration 2513 |

| directing at least one of the steering mechanism and the propelling mechanism on the lumen traveling device to cause the lumen traveling device to move through the body tube tree in the selected direction of travel until a stop instruction is received from a remote device 2514 | generating an instruction to turn the lumen traveling device 2515 |

| directing at least one of the steering mechanism and the propelling mechanism on the lumen traveling device to cause the lumen traveling device to continue moving in a current direction of travel 2516 | directing at least one of the steering mechanism and the propelling mechanism on the lumen traveling device to cause the lumen traveling device to continue moving in a current direction of travel until a branch point is reached 2517 | directing at least one of the steering mechanism and the propelling mechanism on the lumen traveling device to cause the lumen traveling device to reverse its direction of travel 2518

FIG. 25B selecting a direction of travel from the at least two possible directions of travel based at least in part on the information related to whether or not at least one of at least two possible directions of travel of the lumen traveling device through the body tube tree has previously been traveled by the lumen traveling device 2506 selecting a direction of travel that has not previously been traveled by the lumen traveling device 2530 selecting a direction of travel that is the least frequently traveled by the lumen traveling device of the at least two directions of travel 2531 selecting a direction of travel that is the most frequently traveled by the lumen traveling device of the at least two directions of travel 2532 selecting a direction of travel that is the least recently traveled by the lumen traveling device of the at least two directions of travel 2533 selecting a direction of travel that is the most recently traveled by the lumen traveling device of the at least two directions of travel 2534 avoiding at least one portion of the body tube tree having a dimension less than a specified minimum dimension 2535 storing a record of the selected direction of travel 2536    2510 directing an active portion of the lumen traveling device to mark or label the selected direction of travel 2537 directing an active portion of the lumen traveling device to mark or label the selected direction of travel by marking or labeling a selected body lumen with a chemical marker or label 2538

Chemical marker or label includes a biochemical marker or label 2539 biochemical marker or label includes a nucleic acid 2540 biochemical marker or label includes a protein 2541 chemical marker or label includes a radioactive marker or label 2542 directing an active portion of the lumen traveling device to mark or label the selected direction of travel by marking or labeling a selected body lumen with a physical marker or label 2543 physical marker or label includes a magnetic marker or label 2544 physical marker or label includes an optically detectable marker or label 2545 physical marker or label includes a magnetically detectable marker or label 2546 physical marker or label includes an electrically detectable marker or label 2548

FIG. 25D

```
┌─────────────────────────────────────────────────────────────────────────────┐
│                                                                      2510   │
│  ┌───────────────────────────────────────────────────────────────────────┐  │
│  │ sensing a local parameter value with a parameter sensor on the lumen  │  │
│  │ traveling device 2550                                                 │  │
│  └───────────────────────────────────────────────────────────────────────┘  │
│                                                                             │
│  ┌───────────────────────────────────────────────────────────────────────┐  │
│  │ identifying a stop condition based at least in part on the sensed     │  │
│  │ local parameter value; and directing at least one of the steering     │  │
│  │ mechanism and the propelling mechanism on the lumen traveling device  │  │
│  │ to cause the lumen traveling device to stop movement of the lumen     │  │
│  │ traveling device through the body tube tree based at least in part on │  │
│  │ the identified stop condition 2551                                    │  │
│  └───────────────────────────────────────────────────────────────────────┘  │
│                                                                             │
│  ┌───────────────────────────────────────────────────────────────────────┐  │
│  │ storing data representing the sensed local parameter value in a       │  │
│  │ memory location on the lumen traveling device 2552                    │  │
│  └───────────────────────────────────────────────────────────────────────┘  │
│                                                                             │
│  ┌───────────────────────────────────────────────────────────────────────┐  │
│  │ transmitting data representing the sensed local parameter value from  │  │
│  │ the lumen traveling device to a remote device 2553                    │  │
│  └───────────────────────────────────────────────────────────────────────┘  │
│                                                                             │
│  ┌───────────────────────────────────────────────────────────────────────┐  │
│  │ storing motion control instructions for directing operation of at     │  │
│  │ least one of the steering mechanism and the propelling mechanism in   │  │
│  │ a memory location on the lumen traveling device 2554                  │  │
│  └───────────────────────────────────────────────────────────────────────┘  │
│                                                                             │
│  ┌───────────────────────────────────────────────────────────────────────┐  │
│  │ transmitting motion control instructions for directing operation of   │  │
│  │ at least one of the steering mechanism and the propelling mechanism   │  │
│  │ on the lumen traveling device to a remote device 2555                 │  │
│  └───────────────────────────────────────────────────────────────────────┘  │
│                                                                             │
│  ┌───────────────────────────────────────────────────────────────────────┐  │
│  │ receiving at least one of instructions or data from a remote device   │  │
│  │ 2556                                                                  │  │
│  └───────────────────────────────────────────────────────────────────────┘  │
│                                                                             │
│  ┌───────────────────────────────────────────────────────────────────────┐  │
│  │ wherein the method steps are performed by the lumen traveling device  │  │
│  │ 2557                                                                  │  │
│  └───────────────────────────────────────────────────────────────────────┘  │
│                                                                             │
│  ┌───────────────────────────────────────────────────────────────────────┐  │
│  │ wherein a portion of the method steps are performed by the lumen      │  │
│  │ traveling device and a portion of the method steps are performed at   │  │
│  │ least in part by a remote device 2558                                 │  │
│  └───────────────────────────────────────────────────────────────────────┘  │
│                                                                             │
└─────────────────────────────────────────────────────────────────────────────┘
```

FIG. 25E

2700 A system comprising:

2702 non-transitory machine readable media for use in a lumen traveling device control system 2704
    one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of the branched, interconnected channels;
    one or more instructions that cause the lumen traveling device control system to receive data representing at least one parameter value sensed from at least one of the at least two possible directions of travel of the lumen traveling device through the body tube tree;
    one or more instructions that cause the lumen traveling device control system to select a direction of travel from the at least two directions of travel based at least in part on the data representing at least one parameter value sensed from at least one of the at least two possible directions of travel of the lumen traveling device through the body tube tree; and
    one or more instructions that cause the lumen traveling device control system to direct at least one of the steering mechanism and the propelling mechanism on the lumen traveling device to cause the lumen traveling device to move through the body tube tree in the selected direction of travel 2706 computer readable media 2708 recordable-type media

FIG. 27 directing at least one of a steering mechanism and a propelling mechanism on the lumen traveling device to cause the lumen traveling device to move through the body tube tree in the selected direction of travel 2808 directing at least one of the steering mechanism and the propelling mechanism on the lumen traveling device to cause the lumen traveling device to move through the body tube tree in the selected direction of travel for a pre-determined distance 2822 directing at least one of the steering mechanism and the propelling mechanism on the lumen traveling device to cause the lumen traveling device to move through the body tube tree in the selected direction of travel for a pre-determined duration 2823 directing at least one of the steering mechanism and the propelling mechanism on the lumen traveling device to cause the lumen traveling device to move through the body tube tree in the selected direction of travel until an stop instruction is received from a remote device by the lumen traveling device 2824 directing at least one of the steering mechanism and the propelling mechanism on the lumen traveling device to cause the lumen traveling device to turn 2825 directing at least one of the steering mechanism and the propelling mechanism on the lumen traveling device to cause the lumen traveling device to continue moving in a current direction of travel 2826 directing at least one of the steering mechanism and the propelling mechanism on the lumen traveling device to cause the lumen traveling device to reverse its direction of travel 2827 directing at least one of the steering mechanism and the propelling mechanism on the lumen traveling device to cause movement of the lumen traveling device based on a previous movement direction 2828 directing at least one of the steering mechanism and the propelling mechanism on the lumen traveling device to cause the lumen traveling device to move in a different direction the direction it was previously instructed to move 2829 directing at least one of the steering mechanism and the propelling mechanism on the lumen traveling device to cause the lumen traveling device to move in the same direction it was previously directed to move 2830

FIG. 28C

2810 receiving data representing at least one parameter value sensed from at least one of the at least two possible directions of travel of the lumen traveling device through the body tube tree 2831 receiving data representing an analyte 2832 receiving data representing an analyte selected from the list consisting of a chemical, a biomaterial, an ion, an electrolyte, a biological marker, an antibody, a polypeptide, a protein, a nuclueic acid, an oligonucleotide, a polynucleotide, a complex, a pathogen, a signaling material, a lipid, an alcohol, a sterol, a steroid, a carbohydrate, a sugar, a drug, a therapeutic, a gas, a metabolite, a cytokine, a chemokine, a hormone, an inflammatory molecule, a cell, and a cell fragment 2833 receiving data representing a temperature 2834 receiving data representing a pressure 2835 receiving data representing a fluid flow 2836 receiving data representing a structural parameter of at least one of the plurality of branched interconnected channels 2837 receiving data representing a length, width, diameter, thickness, direction, orientation, structural configuration, branching pattern, distance from a branch point, proximity to a valve, or proximity to a channel restriction of at least one of the plurality of branched interconnected channels 2838 receiving data representing an electrical field 2839 receiving data representing a magnetic field 2840 receiving data representing an electromagnetic signal 2841 receiving data representing an acoustic signal 2842 receiving data representing an optical signal 2843 receiving data from at least one parameter sensor on the lumen traveling device 2844 receiving data from a remote device 2845 receiving data representing at least one parameter value sensed from at least one of the at least two possible directions of travel at at least two different times, and wherein selecting a direction of travel from the at least two directions of travel based at least in part on the data includes selecting the direction of travel based on the value of a function of the at least one parameter at the at least two different times 2846

FIG. 28D selecting a direction of travel from the at least two directions of travel based at least in part on the data representing at least one parameter value sensed from at least one of the at least two possible directions of travel of the lumen traveling device through the body tube tree 2806 avoiding at least one direction of travel if the data representing the at least one parameter value sensed from the at least one direction of travel indicates that the at least one direction of travel is non-navigable by the lumen traveling device 2850 selecting the direction of travel based on the value of a function of the at least one parameter 2851 selecting the direction of travel having the lowest value of the function of the at least one parameter 2852 selecting the direction of travel having the highest value of the function of the at least one parameter 2853 selecting the direction of travel having a value of the function of the at least one parameter that falls within a specified range of values 2854 selecting a direction of travel from the at least two directions of travel based at least in part on the data representing parameter values sensed at two or more times by comparing a rate of change of at least one parameter from the at least two possible directions of travel and selecting the direction of travel having the lowest rate of change of the at least one parameter 2855 selecting a direction of travel from the at least two directions of travel based at least in part on the data representing parameter values sensed at two or more times by comparing a rate of change of at least one parameter from the at least two possible directions of travel and selecting the direction of travel having the highest rate of change of the at least one parameter 2856

FIG. 28E

2810 identifying a stop condition based at least in part on the data representing at least one parameter value sensed from at least one of the at least two possible directions of travel of the lumen traveling device through the body tube tree; and
directing at least one of the steering mechanism and the propelling mechanism on the lumen traveling device to cause the lumen traveling device to stop moving through the body tube tree 2860 storing the data representing at least one parameter value sensed from at least one of the at least two possible directions of travel of the lumen traveling device through the body tube tree in a memory location on the lumen traveling device 2861 storing instructions related to directing at least one of the steering mechanism and the propelling mechanism on the lumen traveling device to cause movement of the lumen traveling device in a memory location on the lumen traveling device 2862 transmitting the data representing at least one parameter value sensed from at least one of the at least two possible directions of travel of the lumen traveling device through the body tube tree from the lumen traveling device to a remote device 2863 transmitting instructions related to directing at least one of the steering mechanism and the propelling mechanism on the lumen traveling device to cause movement of the lumen traveling device from the lumen traveling device to a remote device 2864 receiving at least one of instructions or data from a remote device 2865 receiving information related to whether or not at least one of at least two possible directions of travel of the lumen traveling device through the body tube tree has previously been traveled by the lumen traveling device; and
selecting the direction of travel from the at least two possible directions of travel based at least in part on the information related to whether or not at least one of at least two possible directions of travel of the lumen traveling device through the body tube tree has previously been traveled by the lumen traveling device 2866

FIG. 28F

2900 A system comprising:

2902 non-transitory machine readable media for use in a lumen traveling device control system 2904
    one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of the branched, interconnected channels;

one or more instructions that cause the lumen traveling device control system to receive data representing a stored parameter value relating to a previous event associated with at least one of the at least two possible directions of travel;

one or more instructions that cause the lumen traveling device control system to select a direction of travel from the at least two directions of travel based at least in part on the data representing a stored parameter value relating to a previous event associated with at least one of the at least two possible directions of travel; and one or more instructions that cause the lumen traveling device control system to direct at least one of a steering mechanism and a propelling mechanism on the lumen traveling device to cause the lumen traveling device to move through the body tube tree in the selected direction of travel 2906 computer readable media 2908 recordable-type media

FIG. 29

3010 identifying a stop condition based at least in part on the data;
and
directing at least one of the steering mechanism and the propelling mechanism on the lumen traveling device to cause to cause the lumen traveling device to stop moving through the body tube tree 3030 storing the data in a memory location on the lumen traveling device 3031 storing motion control instructions for directing operation of at least one of the steering mechanism and the propelling mechanism in a memory location on the lumen traveling device 3032 transmitting the data from the lumen traveling device to a remote device 3033 transmitting motion control instructions for directing operation of at least one of the steering mechanism and the propelling mechanism from the lumen traveling device to a remote device 3034 receiving at least one of instructions or data from a remote device 3035 receiving information related to whether or not at least one of at least two possible directions of travel of the lumen traveling device through the body tube tree has previously been traveled by the lumen traveling device; and
selecting the direction of travel from the at least two possible directions of travel based at least in part on the information related to whether or not at least one of at least two possible directions of travel of the lumen traveling device through the body tube tree has previously been traveled by the lumen traveling device 3036

FIG. 30C directing at least one of the steering mechanism and the propelling mechanism on the lumen traveling device to cause the lumen traveling device to move through the body tube tree in the selected direction of travel for a pre-determined duration 3008 directing at least one of the steering mechanism and the propelling mechanism on the lumen traveling device to cause the lumen traveling device to move through the body tube tree in the selected direction of travel for a pre-determined distance 3040 directing at least one of the steering mechanism and the propelling mechanism on the lumen traveling device to cause the lumen traveling device to move through the body tube tree in the selected direction of travel for a pre-determined duration 3041 directing at least one of the steering mechanism and the propelling mechanism on the lumen traveling device to cause the lumen traveling device to move through the body tube tree in the selected direction of travel until an stop instruction is received from a remote device by the lumen traveling device 3042 directing at least one of the steering mechanism and the propelling mechanism on the lumen traveling device to cause the lumen traveling device to turn 3043 directing at least one of the steering mechanism and the propelling mechanism on the lumen traveling device to cause the lumen traveling device to continue moving in a current direction of travel 3044 directing at least one of the steering mechanism and the propelling mechanism on the lumen traveling device to cause to cause the lumen traveling device to reverse its direction of travel 3045

FIG. 30D

3100 A system comprising:

3102 non-transitory machine readable media for use in a lumen traveling device control system 3104
one or more instructions that cause the lumen traveling device control system to receive data including at least one target parameter value representing a target location in a body tube tree, the body tube tree including a plurality of branched, interconnected channels, the target location being located within the body tube tree;
one or more instructions that cause the lumen traveling device control system to direct the sensing of at least one parameter value representative of a current location of the lumen traveling device within the body tube tree;
one or more instructions that cause the lumen traveling device control system to determine whether the current location of the lumen traveling device is the target location;
one or more instructions that cause the lumen traveling device control system to direct an active portion of the lumen traveling device to perform an action if the current location is the target location; and
one or more instructions that cause the lumen traveling device control system to direct at least one of a steering mechanism and a propelling mechanism on the lumen traveling device to cause the lumen traveling device to move through the body tube tree in a selected direction of travel if the current location is not the target location 3106 computer readable media 3108 recordable-type media

FIG. 31 sensing at least one parameter value representative of a current location of the lumen traveling device 3204 sensing at least one parameter value representative of an orientation of at least a portion of the body tube tree 3221 sensing at least one parameter value representative of an orientation of at least a portion of the body tube tree within a absolute coordinate system 3222 sensing at least one parameter value representative of an orientation of at least a portion of the body tube tree within a relative coordinate system 3223 sensing at least one parameter value representative of an orientation of at least a portion of the body tube tree relative to at least one other portion of the body tube tree 3224 sensing at least one parameter value representative of an orientation of at least a portion of the body tube tree relative to at least one other portion of the body tube tree 3225 sensing at least one parameter value representative of a rate of fluid flow through of at least a portion of the body tube tree 3226 sensing at least one parameter value representative of a direction of fluid flow through of at least a portion of the body tube tree 3227 sensing at least one parameter value representative of a chemical 3228 sensing of at least one parameter value representative of at least one of a biological marker, a biomaterial, a carbohydrate, a sugar, a cell, a cell fragment, microbe, a microbial fragment, a virus, a viral fragment, a chemical, a chemokine, a hormone, a complex, a cytokine, a drug, a gas, a lipid, a metabolite, a pathogen, a signaling material, a polypeptide, a protein, a nuclueic acid, an oligonucleotide, a polynucleotide, a steroid, a hormone, a therapeutic, an alcohol, an antibody, an electrolyte, an inflammatory molecule, or an ion 3229

FIG. 32C sensing at least one parameter value representative of a current location of the lumen traveling device 3204 sensing at least one parameter value representative of a concentration gradient of at least one of a biological marker, a biomaterial, a carbohydrate, a sugar, a cell, a cell fragment, microbe, a microbial fragment, a virus, a viral fragment, a chemical, a chemokine, a hormone, a complex, a cytokine, a drug, a gas, a lipid, a metabolite, a pathogen, a signaling material, a polypeptide, a protein, a nuclueic acid, an oligonucleotide, a polynucleotide, a steroid, a hormone, a therapeutic, an alcohol, an antibody, an electrolyte, an inflammatory molecule, or an ion 3230 sensing at least one parameter value representative of a temperature 3231 sensing at least one parameter value representative of a temperature gradient 3232 sensing at least one parameter value representative of a lumenal dimension 3233 sensing at least one parameter value representative of a material in or on a lumen wall 3234 sensing at least one parameter value representative of a lumen wall mechanical property 3235 sensing at least one parameter value representative of a position signal 3236 sensing at least one parameter value representative of an electromagnetic field 3237 sensing at least one parameter value representative of a the presence of a marker or label 3238

FIG. 32D determining whether the current location of the lumen traveling device is the target location 3206 comparing the at least one parameter value representative of a current location of the lumen traveling device with the at least one target parameter value representing a target location toward which the lumen traveling device is to travel 3239

| target parameter value representing the target location includes a temperature 3240 | target parameter value representing the target location includes a pressure 3241 | target parameter value representing the target location includes a fluid flow 3242 | target parameter value representing the target location includes an optical absorption 3243 |
|---|---|---|---|
| target parameter value representing the target location includes an optical emission 3244 | target parameter value representing the target location includes a fluorescence 3245 | target parameter value representing the target location includes a phosphorescence 3246 | target parameter value representing the target location includes an index of refraction 3247 |
| target parameter value representing the target location includes an electrical resistivity 3248 | target parameter value representing the target location includes a density 3249 | target parameter value representing the target location includes a sound speed 3250 | target parameter value representing the target location includes a pH 3251 |

| target parameter value representing the target location includes an osmolality or concentration 3252 | target parameter value representing the target location includes at least one of temperature, pressure, fluid flow, optical absorption, optical emission, fluorescence, phosphorescence, index of refraction at at least one wavelength, electrical resistivity, density, sound speed, pH, osmolality, or concentration 3253 |
|---|---|

FIG. 32E directing an active portion of the lumen traveling device to perform an action if the current location is the target location 3208

- directing the active portion of the lumen traveling device to release a material 3255
  - adhesive, a filler, a polymer, a hydrogel, an antibiotic, an antibody, an antiviral, a pharmaceutical compound, a nutrient, a hormone, a growth factor, a catalyst, a drug, a therapeutic compound, a chemical, a biomaterial, a biological label, an enzyme, a protein, a nuclueic acid, an oligonucleotide, a polynucleotide, a polypeptide, a genetic material, a cell, a fraction of a cell, a cell fragment, a complex, a vaccine, a vitamin, a neurotransmitter, a neurotropic agent, a neuroactive material, a cytokine, a chemokine, a hormone, a cell-signaling material, a pro-apoptotic agent, an anti-apoptotic agent, an immunological mediator, an anti-inflammatory agent, a salt, an ion, an electrolyte, an antioxidant, an imaging agent, a labeling agent, a diagnostic compound, a nanomaterial, an inhibitor, a lipid, an alcohol, a sterol, a steroid, a carbohydrate, a sugar, a gas, or a blocker 3256

- directing the active portion of the lumen traveling device to release a device or structure 3257

- directing the active portion of the lumen traveling device to release energy 3258

- directing the active portion of the lumen traveling device to collect a sample 3259
  - directing the active portion of the lumen traveling device to collect at least one of a fluid sample or a sample from a wall region of the body tube tree 3260

- directing the active portion of the lumen traveling device to collect a device or structure 3261

- directing the active portion of the lumen traveling device to attach a structure to a wall of the body tube tree 3262

- directing the active portion of the lumen traveling device to deliver a material or structure to a receiving portion of a man-made device 3263

- directing the active portion of the lumen traveling device to receive a material or structure from a delivery portion of a man-made device 3264

- directing the active portion of the lumen traveling device to deliver a material to a wall region of the body tube tree 3298

- directing the active portion of the lumen traveling device to receive a signal from a remote source 3265

- directing the active portion of the lumen traveling device to receive power from a remote source 3266

- directing the active portion of the lumen traveling device to transmit a signal to a remote location 3267

- directing the active portion of the lumen traveling device to perform a surgical step or procedure 3268

FIG. 32F directing an active portion of the lumen traveling device to perform an action if the current location is the target location 3208

| directing the active portion of the lumen traveling device to remove tissue from at least a portion of the body tube tree 3269 | directing the active portion of the lumen traveling device to remove specific components from at least a portion of a fluid within the body tube tree 3270 | directing the active portion of the lumen traveling device to perform an action includes exposing a catalyst 3271 | directing the active portion of the lumen traveling device to generate a localized electric field 3272 |

| directing the active portion of the lumen traveling device to generate a localized magnetic field 3273 | directing the active portion of the lumen traveling device to produce heating 3274 | directing the active portion of the lumen traveling device to cause cooling 3275 | directing the active portion of the lumen traveling device to emit electromagnetic radiation 3276 |

| directing the active portion of the lumen traveling device to emit acoustic energy 3277 | directing the active portion of the lumen traveling device to apply pressure to at least a portion of the body tube tree 3278 | directing the active portion of the lumen traveling device to modulate the flow of fluid through at least a portion of the body tube tree 3279 |

FIG. 32G directing at least one of a steering mechanism and a propelling mechanism on the lumen traveling device to cause the lumen traveling device to move through the body tube tree in a selected direction of travel if the current location is not the target location 3210 directing at least one of the steering mechanism and the propelling mechanism on the lumen traveling device to cause the lumen traveling device to stop 3280 directing at least one of the steering mechanism and the propelling mechanism on the lumen traveling device to cause the lumen traveling device to advance 3281 directing at least one of the steering mechanism and the propelling mechanism on the lumen traveling device to cause the lumen traveling device to reverse direction 3282 directing at least one of the steering mechanism and the propelling mechanism on the lumen traveling device to cause the lumen traveling device to turn 3283

FIG. 32H

3212 receiving map data representing a map of at least a portion of the body tube tree 3284 receiving map data from a data storage location on the lumen traveling device 3285 receiving map data from a remote source 3286

Wherein the map data is encrypted 3297 receiving data representing at least one parameter value sensed from at least one of at least two possible directions of travel of the lumen traveling device through the body tube tree;
and
selecting a direction of travel from the at least two directions of travel based at least in part on the data 3287 selecting the direction of travel from the at least two directions of travel based at least in part on the data includes avoiding at least one of the at least two directions of travel if at least one of the at least two directions of travel is non-navigable by the lumen traveling device 3288 receiving information indicating whether or not at least one of at least two possible directions of travel of the lumen traveling device through the body tube tree has previously been traveled by the lumen traveling device; and
selecting a direction of travel from the at least two directions of travel based at least in part on the information indicating whether or not at least one of at least two possible directions of travel of the lumen traveling device through the body tube tree has previously been traveled by the lumen traveling device 3289

FIG. 32I

3212 storing the data in a memory location on the lumen traveling device 3289 storing motion control instructions for directing operation of at least one of the steering mechanism and the propelling mechanism in a memory location on the lumen traveling device 3290 transmitting the data from the lumen traveling device to a remote device 3291 transmitting motion control instructions for directing operation of at least one of the steering mechanism and the propelling mechanism from the lumen traveling device to a remote device 3292 receiving at least one of instructions or data from a remote device 3293

Wherein the instructions or data are encrypted 3299 determining the current location of the lumen traveling device on a map of at least a portion of a body tube tree, the lumen traveling device located within the body tube tree represented by the map; and
planning a path of travel for the lumen traveling device, the path of travel leading at least a portion of the way between the current location and the target location, wherein directing at least one of a steering mechanism and a propelling mechanism on the lumen traveling device to cause the lumen traveling device to move through the body tube tree in a selected direction of travel if the current location is not the target location along the planned path of travel 3294

FIG. 32J

3300 A system comprising:

3302 non-transitory machine readable media for use in a lumen traveling device control system 3304
one or more instructions that cause the lumen traveling device control system to obtain a map of at least a portion of a body tube tree including a plurality of branched, interconnected channels;

one or more instructions that cause the lumen traveling device control system to determine a current location of a lumen traveling device on the map with an operation performed on-board the lumen traveling device, the lumen traveling device located within the body tube tree represented by the map;

one or more instructions that cause the lumen traveling device control system to determine a target location for the lumen traveling device within the body tube tree;

one or more instructions that cause the lumen traveling device control system to plan a path of travel for the lumen traveling device, the path of travel leading at least a portion of the way between the current location and the target location; and one or more instructions that cause the lumen traveling device control system to direct at least one of a steering mechanism and a propelling mechanism on the lumen traveling device to cause the lumen traveling device to move through the body tube tree along the path of travel 3306 computer readable media 3308 recordable-type media

FIG. 33

3402 obtaining a map of at least a portion of a body tube tree including a plurality of branched, interconnected channels

| the map includes a topological map 3421 | the map includes a metric map 3422 | the map includes a conformal map 3440 | generating a map of at least a portion of the body tube tree through exploration of the body tube tree with the lumen traveling device 3423 receiving a map of at least a portion of the body tube tree from a remote source 3424 receiving a map of at least a portion of the body tube tree from another lumen traveling device 3425

3406 determining a target location for the lumen traveling device within the body tube tree wherein determining a target location for the lumen traveling device within the body tube tree includes receiving at least one instruction regarding a target location from a remote device 3426

FIG. 34D

3408 planning a path of travel for the lumen traveling device, the planned path of travel leading at least a portion of the way between the current location and the target location planning a path between the current location and the target location 3427 planning a path between the current location and a second location in the body tube tree, the second location intermediate between the current location and the target location on a map of the body tube tree 3429 the target location is a selected anatomical location 3428 planning a path between a first branch point at the current location and a second branch point at the second location 3430 planning a first path of travel leading between the current location and an intermediate location and a planning a second path of travel leading between the intermediate location and the target location and wherein causing movement of the lumen traveling device through the body tube tree along the path of travel includes causing the lumen traveling device to move along the first path of travel leading between the current location and an intermediate location and causing the lumen traveling device to move along the second path of travel leading between the intermediate location and the target location 3431 wherein causing the lumen traveling device to move along the first path of travel travel includes controlling the movement of the lumen traveling device according to a first algorithm and causing the lumen traveling device to move along the second path of travel includes controlling the movement of the lumen traveling device according to a second algorithm, wherein the first algorithm is different than the second algorithm 3432 wherein the first algorithm is a Markov localization algorithm and the second algorithm is a Kalman filtering algorithm 3433 wherein obtaining a map of at least a portion of a body tube tree includes receiving the map of at least a portion of a body tube tree from a remote device 3434 wherein obtaining a map of at least a portion of a body tube tree includes receiving the map of at least a portion of a body tube tree from a data storage location on the lumen traveling device 3435 wherein obtaining a map of at least a portion of a body tube tree includes generating a map of at least a portion of the body tube tree through exploration of the body tube tree with the lumen traveling device 3436

FIG. 34E

3800 Planning a path of travel

3802 Planning path to specific location

3804 Planning optimal path to target location based on known graph-search-based planning techniques (map)

3806 Planning path along gradient of specific parameter

3808 Choosing local branch / direction that leads in desired direction on gradient of specific parameter

3810 Planning path based on previous event

3812 Planning path based on whether direction has been previously traveled

3814 Planning path based on previous action, movement, and/or previously sensed parameter

3816 Planning a 'Random' walk

3818 Choosing branch / direction substantially at random

FIG. 38

3900 A system comprising:

3902 non-transitory machine readable media for use in a lumen traveling device control system 3304
    one or more instructions that cause the lumen traveling device control system to obtain a map of at least a portion of a body tube tree including a plurality of branched, interconnected channels;

one or more instructions that cause the lumen traveling device control system to determine a current location of a lumen traveling device on the map with an operation performed on-board the lumen traveling device, the lumen traveling device located within the body tube tree represented by the map;

one or more instructions that cause the lumen traveling device control system to determine a target location for the lumen traveling device within the body tube tree;

one or more instructions that cause the lumen traveling device control system to plan a path of travel for the lumen traveling device, the path of travel leading at least a portion of the way between the current location and the target location;

3904
    wherein the one or more instructions that cause the lumen traveling device control system to plan a path of travel for the lumen traveling device include
        one or more instructions that cause the lumen traveling device control system to determine a first path of travel leading between the current location and an intermediate location; and
        one or more instructions that cause the lumen traveling device control system to determine a second path of travel leading between the intermediate location and the target location and
    one or more instructions that cause the lumen traveling device control system to direct at least one of a steering mechanism and a propelling mechanism on the lumen traveling device to cause the lumen traveling device to move through the body tube tree along the path of travel 3906 computer readable media 3908 recordable-type media

FIG. 39

4300 A system comprising:

4302 non-transitory machine readable media for use in a lumen traveling device control system for controlling a lumen traveling device including a light emitting diode, an imaging sensor, a reservoir containing a therapeutic agent for treatment of an atherosclerotic plaque, and a propelling mechanism 4304
    one or more instructions that cause the lumen traveling device control system to activate the propelling mechanism to cause the lumen traveling device to travel through the vasculature of the subject;
    one or more instructions that cause the lumen traveling device control system to direct the light emitting diode to emit a first wavelength of electromagnetic radiation;
    one or more instructions that cause the lumen traveling device control system to direct the detection of an atherosclerotic plaque by sensing a second wavelength of electromagnetic radiation emitted by the atherosclerotic plaque with the imaging sensor; and
    one or more instructions that cause the lumen traveling device control system to release the therapeutic agent from the reservoir of the lumen traveling device in response to detection of an atherosclerotic plaque 4306 computer readable media 4308 recordable-type media

FIG. 43

4600 A system comprising:

4602 non-transitory machine readable media for use in a lumen traveling device control system 4604
one or more instructions that cause the lumen traveling device control system
    to direct a sensor including an electronic nose on a lumen traveling
    device to sense a analyte indicative of a lesion in a bronchial airway
    of a subject while the lumen traveling device moves through the
    bronchial airway;
one or more instructions that cause the lumen traveling device control system
    to determine a concentration gradient of the analyte;
one or more instructions that cause the lumen traveling device control system
    to direct at least one of a steering mechanism and a propelling
    mechanism on the lumen traveling device to move the lumen
    traveling device through the bronchial airway along the concentration
    gradient in the direction of the highest concentration of the analyte
    with a propelling mechanism on the lumen traveling device;
one or more instructions that cause the lumen traveling device control system
    to detect when the concentration gradient reverses direction;
one or more instructions that cause the lumen traveling device control system
    to reverse the direction of movement of the lumen traveling device
    when the concentration gradient changes direction;
one or more instructions that cause the lumen traveling device control system
    to direct at least one of the steering mechanism and the propelling
    mechanism on the lumen traveling device to move the lumen
    traveling device to the location of the lesion as determined by the
    change in direction of the concentration gradient; and
one or more instructions that cause the lumen traveling device control system
    to direct the lumen traveling device to deliver a treatment to the
    lesion 4606 computer readable media 4608 recordable-type media

FIG. 46

4900 A system comprising:

4902 non-transitory machine readable media for use in a lumen traveling device control system 4904
one or more instructions that cause the lumen traveling device control system to direct at least one of a steering mechanism and a propelling mechanism on the lumen traveling device to cause a lumen traveling device to travel through a cerebrospinal fluid flow route of a subject;
one or more instructions that cause the lumen traveling device control system to detect circulating tumor cells from a meningeal malignancy with a microelectromechanical system miniaturized Coulter counter on the lumen traveling device; and
one or more instructions that cause the lumen traveling device control system to release a chemotherapeutic agent from a reservoir on the lumen traveling device in response to detect circulating tumor cells with the microelectromechanical system miniaturized Coulter counter on the lumen traveling device 4906 computer readable media 4908 recordable-type media

START

↓ introducing a lumen traveling device into a cerebral ventricle of a subject
5002

↓ activating a propelling mechanism on the lumen traveling device to propel the lumen traveling device through the ventricle
5004

↓ detecting the binding of human immunodeficiency virus marker to one or more carbon nanotube-field effect transistors functionalized with an human immunodeficiency virus marker binding moiety on a fluid-contacting surface of the lumen traveling device
5006

↓ in response to detection of human immunodeficiency virus marker in the cerebrospinal fluid, releasing the one or more antiretroviral drugs from a reservoir in the lumen traveling device; wherein the activating a propelling mechanism, detecting the binding of human immunodeficiency virus mark, and releasing the one or more antiretroviral drugs in response to detection of human immunodeficiency virus marker are performed under the control of control circuitry on the lumen traveling device
5008

↓

END

FIG. 50

5100 A system comprising:

5102 non-transitory machine readable media for use in a lumen traveling device control system 5104
one or more instructions that cause the lumen traveling device control system to activate a propelling mechanism on a lumen traveling device to propel the lumen traveling device through a cerebral ventricle of a subject, the cerebral ventricle containing cerebrospinal fluid;
one or more instructions that cause the lumen traveling device control system to detect the binding of a disease marker to one or more carbon nanotube-field effect transistors functionalized with a disease marker binding moiety on a fluid-contacting surface of the lumen traveling device; and
one or more instructions that cause the lumen traveling device control system to release the one or more drugs from a reservoir in the lumen traveling device in response to detection of the disease marker in the cerebrospinal fluid 5106 computer readable media 5108 recordable-type media

FIG. 51

5300 A system comprising:

5302 non-transitory machine readable media for use in a lumen traveling device control system 2104
one or more instructions that cause the lumen traveling device control system to activate a propelling mechanism on a lumen traveling device to propel the lumen traveling device within a body tube tree;
one or more instructions that cause the lumen traveling device control system to determine a time based on a signal from a timing device; and
one or more instructions that cause the lumen traveling device control system to direct the active portion of the lumen traveling device to perform at least one action based at least in part upon the determined time 5304
one or more instructions that cause the lumen traveling device control system to detect an arrival of the lumen traveling device at a branch point in the body tube tree with at least one arrival sensor on the lumen traveling device, the branch point including at least two branch channels;
one or more instructions that cause the lumen traveling device control system to direct the propelling mechanism on the lumen traveling device to move the lumen traveling device into one of the at least two branch channels;
one or more instructions that cause the lumen traveling device control system to store information regarding at least one of the at least two branch channels;
one or more instructions that cause the lumen traveling device control system to direct the sensing of a position indicator signal;
one or more instructions that cause the lumen traveling device control system to direct the sensing of a local parameter value with a parameter sensor on the lumen traveling device; and
one or more instructions that cause the lumen traveling device control system to direct the active portion of the lumen traveling device to perform the action based at least in part upon at least one of the local parameter value and the position indicator signal 5306 computer readable media 5308 recordable-type media

FIG. 53

5500 A system comprising:

5502 non-transitory machine readable media for use in a lumen traveling device control system 3304 one or more instructions that cause the lumen traveling device control system to obtain a map of at least a portion of a body tube tree including a plurality of branched, interconnected channels;
    one or more instructions that cause the lumen traveling device control system to determine a current location of a lumen traveling device on the map with an operation performed on-board the lumen traveling device, the lumen traveling device located within the body tube tree represented by the map;
    one or more instructions that cause the lumen traveling device control system to determine a target location for the lumen traveling device within the body tube tree;
    one or more instructions that cause the lumen traveling device control system to plan a path of travel for the lumen traveling device, the path of travel leading at least a portion of the way between the current location and the target location; and
    one or more instructions that cause the lumen traveling device control system to direct at least one of a steering mechanism and a propelling mechanism on the lumen traveling device to cause the lumen traveling device to move through the body tube tree along the path of travel 5504 one or more instructions that cause the lumen traveling device control system to
    detect an arrival of the lumen traveling device at a branch point in the body tube tree with at least one arrival sensor on the lumen traveling device, the branch point including at least two branch channels;
    one or more instructions that cause the lumen traveling device control system to select at least one of the at least two branch channels;
    one or more instructions that cause the lumen traveling device control system to activate the propelling mechanism to propel the lumen traveling device into the selected branch channel;
    one or more instructions that cause the lumen traveling device control system to store information regarding at least one of the at least two branch channels;
    one or more instructions that cause the lumen traveling device control system to determine a time based on a signal from a timing device;
    one or more instructions that cause the lumen traveling device control system to direct the sensing of a local parameter value with a parameter sensor on the lumen traveling device; and
    one or more instructions that cause the lumen traveling device control system to direct the active portion of the lumen traveling device to perform an action based at least in part upon at least one of the local parameter value and the determined time 5506 computer readable media 5508 recordable-type media

FIG. 55

5700 A system comprising:

5702 non-transitory machine readable media for use in a lumen traveling device control system

2104
one or more instructions that cause the lumen traveling device control system to activate a propelling mechanism on a lumen traveling device to propel the lumen traveling device within a body tube tree;
one or more instructions that cause the lumen traveling device control system to determine a time based on a signal from a timing device; and
one or more instructions that cause the lumen traveling device control system to direct the active portion of the lumen traveling device to perform at least one action based at least in part upon the determined time

5704
one or more instructions that cause the lumen traveling device control system to determine a current location of a lumen traveling device on a map of at least a portion of a body tube tree including a plurality of branched, interconnected channels with an operation performed on-board the lumen traveling device, the lumen traveling device located within the body tube tree represented by the map;
one or more instructions that cause the lumen traveling device control system to determine a target location for the lumen traveling device within the body tube tree;
one or more instructions that cause the lumen traveling device control system to plan a path of travel for the lumen traveling device, the path of travel leading at least a portion of the way between the current location and the target location;
one or more instructions that cause the lumen traveling device control system to detect an arrival of the lumen traveling device at a branch point in the body tube tree with at least one arrival sensor on the lumen traveling device, the branch point including at least two branch channels;
one or more instructions that cause the lumen traveling device control system to select one of the at least two branch channels;
one or more instructions that cause the lumen traveling device control system to direct at least one of a steering mechanism on the lumen traveling device and the propelling mechanism to cause the lumen traveling device to move into the selected branch channel

5706 computer readable media

5708 recordable-type media

FIG. 57

5900 A system comprising:

5902 non-transitory machine readable media for use in a lumen traveling device control system 2704
    one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of the branched, interconnected channels;
    one or more instructions that cause the lumen traveling device control system to receive data representing at least one parameter value sensed from at least one of the at least two possible directions of travel of the lumen traveling device through the body tube tree;
    one or more instructions that cause the lumen traveling device control system to select a direction of travel from the at least two directions of travel based at least in part on the data representing at least one parameter value sensed from at least one of the at least two possible directions of travel of the lumen traveling device through the body tube tree; and
    one or more instructions that cause the lumen traveling device control system to direct at least one of the steering mechanism and the propelling mechanism on the lumen traveling device to cause the lumen traveling device to move through the body tube tree in the selected direction of travel 5904
    one or more instructions that cause the lumen traveling device control system to receive information related to whether or not at least one of at least two possible directions of travel of the lumen traveling device through the body tube tree has previously been traveled by the lumen traveling device; and
    one or more instructions that cause the lumen traveling device control system to select a direction of travel from the at least two possible directions of travel based at least in part on the information related to whether or not at least one of at least two possible directions of travel of the lumen traveling device through the body tube tree has previously been traveled by the lumen traveling device 5906 computer readable media 5908 recordable-type media

FIG. 59

6100 A system comprising:

6102 non-transitory machine readable media for use in a lumen traveling device control system 2904
one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of the branched, interconnected channels;

one or more instructions that cause the lumen traveling device control system to receive data representing a stored parameter value relating to a previous event associated with at least one of the at least two possible directions of travel;

one or more instructions that cause the lumen traveling device control system to select a direction of travel from the at least two directions of travel based at least in part on the data representing a stored parameter value relating to a previous event associated with at least one of the at least two possible directions of travel; and one or more instructions that cause the lumen traveling device control system to direct at least one of a steering mechanism and a propelling mechanism on the lumen traveling device to cause the lumen traveling device to move through the body tube tree in the selected direction of travel 6104
one or more instructions that cause the lumen traveling device control system to receive information related to whether or not at least one of at least two possible directions of travel of the lumen traveling device through the body tube tree has previously been traveled by the lumen traveling device; and one or more instructions that cause the lumen traveling device control system to select a direction of travel from the at least two possible directions of travel based at least in part on the information related to whether or not at least one of at least two possible directions of travel of the lumen traveling device through the body tube tree has previously been traveled by the lumen traveling device 6106 computer readable media 6108 recordable-type media

FIG. 61

6300 A system comprising:

6302 non-transitory machine readable media for use in a lumen traveling device control system one or more instructions that cause the lumen traveling device control system to obtain a map of at least a portion of a body tube tree including a plurality of branched, interconnected channels;
one or more instructions that cause the lumen traveling device control system to determine a current location of a lumen traveling device on the map with an operation performed on-board the lumen traveling device, the lumen traveling device located within the body tube tree represented by the map;
one or more instructions that cause the lumen traveling device control system to determine a target location for the lumen traveling device within the body tube tree;
one or more instructions that cause the lumen traveling device control system to plan a path of travel for the lumen traveling device, the path of travel leading at least a portion of the way between the current location and the target location; and
one or more instructions that cause the lumen traveling device control system to direct at least one of a steering mechanism and a propelling mechanism on the lumen traveling device to cause the lumen traveling device to move through the body tube tree along the path of travel                3304 one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of the branched, interconnected channels;
one or more instructions that cause the lumen traveling device control system to receive information related to whether or not at least one of at least two possible directions of travel of the lumen traveling device through the body tube tree has previously been traveled by the lumen traveling device;
one or more instructions that cause the lumen traveling device control system to select a direction of travel from the at least two possible directions of travel based at least in part on the information related to whether or not at least one of at least two possible directions of travel of the lumen traveling device through the body tube tree has previously been traveled by the lumen traveling device, wherein the selected direction of travel is expected to lie along the planned path of travel; and
one or more instructions that cause the lumen traveling device control system to direct at least one of a steering mechanism and a propelling mechanism on the lumen traveling device to cause the lumen traveling device to move through the body tube tree in the selected direction of travel                6304

6306 computer readable media                6308 recordable-type media

FIG. 63

6500 A system comprising:

6502 non-transitory machine readable media for use in a lumen traveling device control system 3304
(SEE FIG. 39)

3904
(SEE FIG. 39)

wherein the one or more instructions that cause the lumen traveling device control system determine the first path of travel include:
    one or more instructions that cause the lumen traveling device control system to identify at least two possible directions of travel of the lumen traveling device through the body tube tree;
    one or more instructions that cause the lumen traveling device control system to receive information related to whether or not at least one of at least two possible directions of travel of the lumen traveling device through the body tube tree has previously been traveled by the lumen traveling device; and
    one or more instructions that cause the lumen traveling device control system to select a direction of travel from the at least two possible directions of travel based at least in part on the information related to whether or not at least one of at least two possible directions of travel of the lumen traveling device through the body tube tree has previously been traveled by the lumen traveling device, wherein the selected direction of travel is along the first path
6504

6506 computer readable media 6508 recordable-type media

FIG. 65

6700 A system comprising:

6702 non-transitory machine readable media for use in a lumen traveling device control system 3304 one or more instructions that cause the lumen traveling device control system to obtain a map of at least a portion of a body tube tree including a plurality of branched, interconnected channels;
    one or more instructions that cause the lumen traveling device control system to determine a current location of a lumen traveling device on the map with an operation performed on-board the lumen traveling device, the lumen traveling device located within the body tube tree represented by the map;
    one or more instructions that cause the lumen traveling device control system to determine a target location for the lumen traveling device within the body tube tree;
    one or more instructions that cause the lumen traveling device control system to plan a path of travel for the lumen traveling device, the path of travel leading at least a portion of the way between the current location and the target location; and
    one or more instructions that cause the lumen traveling device control system to direct at least one of a steering mechanism and a propelling mechanism on the lumen traveling device to cause the lumen traveling device to move through the body tube tree along the path of travel 6704 one or more instructions that cause the lumen traveling device control system to identify at least two possible directions of travel of a lumen traveling device through a body tube tree;
    one or more instructions that cause the lumen traveling device control system to receive information related to whether or not at least one of at least two possible directions of travel of the lumen traveling device through the body tube tree has previously been traveled by the lumen traveling device;
    one or more instructions that cause the lumen traveling device control system to receive data representing at least one parameter value sensed from at least one of the at least two possible directions of travel of the lumen traveling device through the body tube tree;
    one or more instructions that cause the lumen traveling device control system to select a direction of travel from the at least two possible directions of travel based at least in part on the data representing at least one parameter value and at least in part on the information related to whether or not at least one of at least two possible directions of travel of the lumen traveling device through the body tube tree has previously been traveled by the lumen traveling device; and
    one or more instructions that cause the lumen traveling device control system to direct at least one of the steering mechanism and the propelling mechanism on the lumen traveling device to cause the lumen traveling device to move through the body tube tree in the selected direction of travel 6706 computer readable media 6708 recordable-type media

FIG. 67

6800 A system comprising:

6802 non-transitory machine readable media for use in a lumen traveling device control system 3304
(SEE FIG. 39)

3904
(SEE FIG. 39)

6804
    one or more instructions that cause the lumen traveling device control system to identify at least two possible directions of travel of a lumen traveling device through the body tube tree;
    one or more instructions that cause the lumen traveling device control system to receive information related to whether or not at least one of at least two possible directions of travel of the lumen traveling device through the body tube tree has previously been traveled by the lumen traveling device;
    one or more instructions that cause the lumen traveling device control system to receive data representing at least one parameter value sensed from at least one of the at least two possible directions of travel of the lumen traveling device through the body tube tree;
    one or more instructions that cause the lumen traveling device control system to select a direction of travel from the at least two possible directions of travel based at least in part on the data and at least in part on the information related to whether or not at least one of at least two possible directions of travel of the lumen traveling device through the body tube tree has previously been traveled by the lumen traveling device; and
    one or more instructions that cause the lumen traveling device control system to direct at least one of a steering mechanism and a propelling mechanism on the lumen traveling device to cause the lumen traveling device to move through the body tube tree in the selected direction of travel 6806 computer readable media 6808 recordable-type media

FIG. 68

7000 A system comprising:

7002 non-transitory machine readable media for use in a lumen traveling device control system

3104
one or more instructions that cause the lumen traveling device control system to receive data including at least one target parameter value representing a target location in a body tube tree, the body tube tree including a plurality of branched, interconnected channels, the target location being located within the body tube tree;
one or more instructions that cause the lumen traveling device control system to direct the sensing of at least one parameter value representative of a current location of the lumen traveling device within the body tube tree;
one or more instructions that cause the lumen traveling device control system to determine whether the current location of the lumen traveling device is the target location;
one or more instructions that cause the lumen traveling device control system to direct an active portion of the lumen traveling device to perform an action if the current location is the target location; and
one or more instructions that cause the lumen traveling device control system to direct at least one of a steering mechanism and a propelling mechanism on the lumen traveling device to cause the lumen traveling device to move through the body tube tree in a selected direction of travel if the current location is not the target location

7004 one or more instructions that cause the lumen traveling device control system to determine the current location of a lumen traveling device on a map of at least a portion of the body tube tree including a plurality of branched, interconnected channels with an operation performed on-board the lumen traveling device, the lumen traveling device located within the body tube tree represented by the map;
one or more instructions that cause the lumen traveling device control system to determine the target location for the lumen traveling device within the body tube tree;
one or more instructions that cause the lumen traveling device control system to plan a path of travel for the lumen traveling device, the path of travel leading at least a portion of the way between the current location and the target location; and
one or more instructions that cause the lumen traveling device control system to direct at least one of the steering mechanism and the propelling mechanism on the lumen traveling device to cause movement of the lumen traveling device through the body tube tree along the path of travel

7006 computer readable media

7008 recordable-type media

FIG. 70

PARAMETER-BASED NAVIGATION BY A LUMEN TRAVELING DEVICE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 11/403,230, titled LUMENALLY-ACTIVE DEVICE, naming Bran Ferren, W. Daniel Hillis, Roderick A. Hyde, Muriel Y. Ishikawa, Edward K. Y. Jung, Nathan P. Myhrvold, Elizabeth A. Sweeney, Clarence T. Tegreene, Richa Wilson, Lowell L. Wood, Jr., and Victoria Y. H. Wood as inventors, filed 12 Apr. 2006, now U.S. Pat. No. 9,011,329, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/417,898, titled CONTROLLABLE RELEASE NASAL SYSTEM, naming W. Daniel Hillis, Roderick A. Hyde, Muriel Y. Ishikawa, Elizabeth A. Sweeney, Clarence T. Tegreene, Richa Wilson, Lowell L. Wood, Jr., and Victoria Y. H. Wood as inventors, filed 4 May 2006, now U.S. Pat. No. 8,353,896, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/478,368, titled LUMENALLY-ACTIVE DEVICE, naming Bran Ferren, W. Daniel Hillis, Roderick A. Hyde, Muriel Y. Ishikawa, Edward K. Y. Jung, Nathan P. Myhrvold, Elizabeth A. Sweeney, Clarence T. Tegreene, Richa Wilson, Lowell L. Wood, Jr., and Victoria Y. H. Wood as inventors, filed 28 Jun. 2006, now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/485,619, titled CONTROLLABLE RELEASE NASAL SYSTEM, naming W. Daniel Hillis, Roderick A. Hyde, Muriel Y. Ishikawa, Elizabeth A. Sweeney, Clarence T. Tegreene, Richa Wilson, Lowell L. Wood, Jr., and Victoria Y. H. Wood as inventors, filed 11 Jul. 2006, now U.S. Pat. No. 9,173,837, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/645,358, titled LUMEN-TRAVELING DEVICE, naming Bran Ferren, W. Daniel Hillis, Roderick A. Hyde, Muriel Y. Ishikawa, Edward K. Y. Jung, Eric C. Leuthardt, Nathan P. Myhrvold, Elizabeth A. Sweeney, Clarence T. Tegreene, Lowell L. Wood, Jr., and Victoria Y. H. Wood as inventors, filed 21 Dec. 2006, now U.S. Pat. No. 8,000,784, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/651,946, titled LUMEN-TRAVELING DELIVERY DEVICE, naming Bran Ferren, W. Daniel Hillis, Roderick A. Hyde, Muriel Y. Ishikawa, Edward K. Y. Jung, Eric C. Leuthardt, Nathan P. Myhrvold, Elizabeth A. Sweeney, Clarence T. Tegreene, Lowell L. Wood, Jr., and Victoria Y. H. Wood as inventors, filed 9 Jan. 2007, now U.S. Pat. No. 7,998,060, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/725,982, titled LUMEN-TRAVELING BIOLOGICAL INTERFACE DEVICE, naming Bran Ferren, W. Daniel Hillis, Roderick A. Hyde, Muriel Y. Ishikawa, Edward K. Y. Jung, Eric C. Leuthardt, Nathan P. Myhrvold, Clarence T. Tegreene, Lowell L. Wood, Jr., and Victoria Y. H. Wood as inventors, filed 19 Mar. 2007, which is currently co-pending, or is an application of which a currently co-pending application is entitled to the benefit of the filing date, and which is a continuation-in-part of U.S. patent application Ser. No. 11/645,357, titled LUMEN-TRAVELING DEVICE, naming Bran Ferren, W. Daniel Hillis, Roderick A. Hyde, Muriel Y. Ishikawa, Edward K. Y. Jung, Eric C. Leuthardt, Nathan P. Myhrvold, Elizabeth A. Sweeney, Clarence T. Tegreene, Lowell L. Wood, Jr., and Victoria Y. H. Wood as inventors, filed 21 Dec. 2006, now U.S. Pat. No. 7,857,767 issued 28 Dec. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/726,025, titled BIOELECTROMAGNETIC INTERFACE SYSTEM, naming Bran Ferren, W. Daniel Hillis, Roderick A. Hyde, Muriel Y. Ishikawa, Edward K. Y. Jung, Eric C. Leuthardt, Nathan P. Myhrvold, Clarence T. Tegreene, Lowell L. Wood, Jr., and Victoria Y. H. Wood as inventors, filed 19 Mar. 2007, now U.S. Pat. No. 8,512,219, which is currently co-pending, or is an application of which a currently co-pending application is entitled to the benefit of the filing date, and which is a continuation-in-part of U.S. patent application Ser. No. 11/645,357, titled LUMEN-TRAVELING DEVICE, naming Bran Ferren, W. Daniel Hillis, Roderick A. Hyde, Muriel Y. Ishikawa, Edward K. Y. Jung, Eric C. Leuthardt, Nathan P. Myhrvold, Elizabeth A. Sweeney, Clarence T. Tegreene, Lowell L. Wood, Jr., and Victoria Y. H. Wood as inventors, filed 21 Dec. 2006, now U.S. Pat. No. 7,857,767 issued 28 Dec. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/726,031, titled LUMEN-TRAVELING BIOLOGICAL INTERFACE DEVICE AND METHOD OF USE, naming Bran Ferren, W. Daniel Hillis, Roderick A. Hyde, Muriel Y. Ishikawa, Edward K. Y. Jung, Eric C. Leuthardt, Nathan P. Myhrvold, Clarence T. Tegreene, Lowell L. Wood, Jr., and Victoria Y. H. Wood as inventors, filed 19 Mar. 2007, now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/319,882, titled LUMEN-TRAVELING BIOLOGICAL INTERFACE DEVICE AND METHOD OF USE, naming Bran Ferren, W. Daniel Hillis, Roderick A. Hyde, Muriel Y. Ishikawa, Edward K. Y. Jung, Eric C. Leuthardt, Nathan P. Myhrvold, Clarence T. Tegreene, Lowell L. Wood, Jr., and Victoria Y. H. Wood as inventors, filed 12 Jan. 2009, now U.S. Pat. No. 8,019,413, which is currently co-pending, or is an application of which a currently co-pending application is entitled to the benefit of the filing date, and which is a divisional of U.S. patent application Ser. No. 11/726,031, titled LUMEN-TRAVELING BIOLOGICAL INTERFACE DEVICE AND METHOD OF USE, naming Bran Ferren, W. Daniel Hillis, Roderick A. Hyde, Muriel Y. Ishikawa, Edward K. Y. Jung, Eric C. Leuthardt, Nathan P. Myhrvold, Clarence T. Tegreene, Lowell L. Wood, Jr., and Victoria Y. H. Wood as inventors, filed 19 Mar. 2007, now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/319,881, titled LUMEN-TRAVELING BIOLOGICAL INTERFACE DEVICE AND METHOD OF USE, naming Bran Ferren, W. Daniel Hillis, Roderick A. Hyde, Muriel Y. Ishikawa, Edward K. Y. Jung, Eric C. Leuthardt, Nathan P. Myhrvold, Clarence T. Tegreene, Lowell L. Wood, Jr., and Victoria Y. H. Wood as inventors, filed 12 Jan. 2009, now U.S. Pat. No. 8,024,036, which is currently co-pending, or is an application of which a currently co-pending application is entitled to the benefit of the filing date, and which is a divisional of U.S. patent application Ser. No. 11/726,031, titled LUMEN-TRAVELING BIOLOGICAL INTERFACE DEVICE AND METHOD OF USE, naming Bran Ferren, W. Daniel Hillis, Roderick A. Hyde, Muriel Y. Ishikawa, Edward K. Y. Jung, Eric C. Leuthardt, Nathan P. Myhrvold, Clarence T. Tegreene, Lowell L. Wood, Jr., and Victoria Y. H. Wood as inventors, filed 19 Mar. 2007, now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/136,677, titled CONTROL OF A LUMEN TRAVELING DEVICE IN A BODY TUBE TREE, naming Bran Ferren, W. Daniel Hillis, Roderick A. Hyde, Muriel Y. Ishikawa, Edward K.Y. Jung, Eric C. Leuthardt, Nathan P. Myhrvold, Thomas J. Nugent, Jr., Elizabeth A. Sweeney, Clarence T. Tegreene, Lowell L. Wood, Jr., and Victoria Y. H. Wood as inventors, filed 5, Aug. 2011, now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/136,679, titled TEMPORAL CONTROL OF A LUMEN TRAVELING DEVICE IN A BODY TUBE TREE, naming Bran Ferren, W. Daniel Hillis, Roderick A. Hyde, Muriel Y. Ishikawa, Edward K.Y. Jung, Eric C. Leuthardt, Nathan P. Myhrvold, Thomas J. Nugent, Jr., Elizabeth A. Sweeney, Clarence T. Tegreene, Lowell L. Wood, Jr., and Victoria Y. H. Wood as inventors, filed 5, Aug. 2011, now U.S. Pat. No. 9,198,563, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/136,676, titled PATH SELECTION BY A LUMEN TRAVELING DEVICE IN A BODY TUBE TREE BASED ON PREVIOUS PATH, naming Bran Ferren, W. Daniel Hillis, Roderick A. Hyde, Muriel Y. Ishikawa, Edward K.Y. Jung, Eric C. Leuthardt, Nathan P. Myhrvold, Thomas J. Nugent, Jr., Elizabeth A. Sweeney, Clarence T. Tegreene, Lowell L. Wood, Jr., and Victoria Y. H. Wood as inventors, filed 5, Aug. 2011, now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/136,675, titled EVENT-BASED CONTROL OF A LUMEN TRAVELING DEVICE, naming Bran Ferren, W. Daniel Hillis, Roderick A. Hyde, Muriel Y. Ishikawa, Edward K.Y. Jung, Eric C. Leuthardt, Nathan P. Myhrvold, Thomas J. Nugent, Jr., Elizabeth A. Sweeney, Clarence T. Tegreene, Lowell L. Wood, Jr., and Victoria Y. H. Wood as inventors, filed 5, Aug. 2011, now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/136,674, titled NAVIGATION OF A LUMEN TRAVELING DEVICE TOWARD A TARGET, naming Bran Ferren, W. Daniel Hillis, Roderick A. Hyde, Muriel Y. Ishikawa, Edward K.Y. Jung, Eric C. Leuthardt, Nathan P. Myhrvold, Thomas J. Nugent, Jr., Elizabeth A. Sweeney, Clarence T. Tegreene, Lowell L. Wood, Jr., and Victoria Y. H. Wood as inventors, filed 5, Aug. 2011, now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/136,678, titled MAP-BASED NAVIGATION OF A BODY TUBE TREE BY A LUMEN TRAVELING DEVICE, naming Bran Ferren, W. Daniel Hillis, Roderick A.

Hyde, Muriel Y. Ishikawa, Edward K.Y. Jung, Eric C. Leuthardt, Nathan P. Myhrvold, Thomas J. Nugent, Jr., Elizabeth A. Sweeney, Clarence T. Tegreene, Lowell L. Wood, Jr., and Victoria Y. H. Wood as inventors, filed 5, Aug. 2011, now abandoned which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.goviwebiofficies/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

BACKGROUND

Devices and systems for use in various body lumens include catheters for performing a variety of sensing, material delivery or surgical tasks and stents which can be implanted in blood vessels for the purpose of preventing stenosis or restenosis of blood vessels. Capsules containing sensing and imaging instrumentation that may be swallowed by a subject and which travel passively through the digestive tract have also been developed. Robotic devices intended to move through the lower portion of the digestive tract under their own power are also under development.

SUMMARY

The present application describes methods for controlling movement of a lumen traveling device through a body tube tree, as well as associated systems and devices.

In an embodiment, a system includes non-transitory machine readable media, for use in a lumen traveling device control system, including one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of the branched, interconnected channels; one or more instructions that cause the lumen traveling device control system to receive data representing at least one parameter value sensed from at least one of the at least two possible directions of travel of the lumen traveling device through the body tube tree; one or more instructions that cause the lumen traveling device control system to select a direction of travel from the at least two directions of travel based at least in part on the data representing at least one parameter value sensed from at least one of the at least two possible directions of travel of the lumen traveling device through the body tube tree; and one or more instructions that cause the lumen traveling device control system to direct at least one of the steering mechanism and the propelling mechanism on the lumen traveling device to cause the lumen traveling device to move through the body tube tree in the selected direction of travel.

In an embodiment, a method of operating a lumen traveling device with a lumen traveling device control system includes identifying at least two possible directions of travel of a lumen traveling device through a body tube tree, the body tube tree including a plurality of branched, interconnected channels, and the at least two possible directions of travel corresponding to at least two of the branched, interconnected channels; receiving data representing at least one parameter value sensed from at least one of the at least two possible directions of travel of the lumen traveling device through the body tube tree; selecting a direction of travel from the at least two directions of travel based at least in part on the data representing at least one parameter value sensed from at least one of the at least two possible directions of travel of the lumen traveling device through the body tube tree; and directing at least one of the steering mechanism and the propelling mechanism on the lumen traveling device to cause the lumen traveling device to move through the body tube tree in the selected direction of travel.

In an embodiment, a method of detecting and treating a lesion in a bronchial airway of a subject includes introducing a lumen traveling device into the bronchial airway of the subject; sensing an analyte produced by the lesion in the exhaled breath of the subject with a sensor including an electronic nose on the lumen traveling device, as the lumen traveling device moves through the bronchial airway with a propelling mechanism on the lumen traveling device; determining a concentration gradient of the analyte with control circuitry on the lumen traveling device; moving the lumen traveling device through the bronchial airway along the concentration gradient in the direction of the highest concentration of the analyte; moving along the concentration gradient until the concentration gradient reverses direction; identifying the location of the lesion as the region of highest concentration of the analyte, wherein the region of highest concentration is identified by the change in direction of the concentration gradient; moving the lumen traveling device to the location of the lesion as determined by the change in direction of the concentration gradient; and delivering a treatment to the lesion with the lumen traveling device. For example, delivering a treatment to the lesion with the lumen traveling device can include releasing electromagnetic energy from an electromagnetic energy source on the lumen traveling device at the location of the lesion to produce ablation of the lesion, releasing a material, or taking various other actions as described herein.

In an embodiment, a system includes non-transitory machine readable media for use in a lumen traveling device control system, including: one or more instructions that cause the lumen traveling device control system to direct a sensor including an electronic nose on a lumen traveling device to sense an analyte indicative of a lesion in a bronchial airway of a subject while the lumen traveling device moves through the bronchial airway; one or more instructions that cause the lumen traveling device control system to determine a concentration gradient of the analyte; one or more instructions that cause the lumen traveling device control system direct at least one of a steering mechanism and a propelling mechanism on the lumen traveling device to move the lumen traveling device through the bronchial airway along the concentration gradient in the direction of the highest concentration of the analyte with a propelling mechanism on the lumen traveling device; one or more instructions that cause the lumen traveling device control system to detect when the concentration gradient reverses direction; one or more instructions that cause the lumen traveling device control system to reverse the direction of movement of the lumen traveling device when the concentration gradient changes direction; one or more instructions that cause the lumen traveling device control system to direct at least one of the steering mechanism and the propelling mechanism on the lumen traveling device to move the lumen traveling device to the location of the lesion as determined by the change in direction of the concentration gradient; and one or more instructions that cause the lumen traveling device control system to direct the lumen traveling device to deliver a treatment to the lesion.

In an embodiment, a method of detecting and treating a meningeal malignancy includes introducing a lumen traveling device into a cerebrospinal fluid flow route of a subject; causing the lumen traveling device to travel through the cerebrospinal fluid flow route; detecting circulating tumor cells from a meningeal malignancy with a microelectromechanical system miniaturized Coulter counter on the lumen traveling device, based upon differentiation of circulating tumor cells by volume; and in response to detection of circulating tumor cells, releasing a chemotherapeutic agent from a reservoir on the lumen traveling device.

In an embodiment, a system includes non-transitory machine readable media, for use in a lumen traveling device control system, including one or more instructions that cause the lumen traveling device control system to direct at least one of a steering mechanism and a propelling mechanism on the lumen traveling device to cause a lumen traveling device to travel through a cerebrospinal fluid flow route of a subject; one or more instructions that cause the lumen traveling device control system to detect circulating tumor cells from a meningeal malignancy with a microelectromechanical system miniaturized Coulter counter on the lumen traveling device; and one or more instructions that cause the lumen traveling device control system to release a chemotherapeutic agent from a reservoir on the lumen traveling device in response to detect circulating tumor cells with the microelectromechanical system miniaturized Coulter counter on the lumen traveling device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 6A-6D illustrate several embodiments of active portions of a lumen traveling;

FIG. 11 illustrates a block diagram of a system;

FIG. 13 illustrates embodiments of sensing and storing information;

FIG. 15 illustrates embodiments of performing an action with an active portion of a lumen traveling device;

FIG. 16 illustrates embodiments of performing an action with an active portion of a lumen traveling device;

FIG. 18 illustrates embodiments of performing an action with an active portion of a lumen traveling device;

FIG. 19 illustrates embodiments of performing an action with an active portion of a lumen traveling device;

FIG. 21 illustrates a block diagram of a system;

FIG. 24 illustrates a block diagram of a system;

FIGS. 25A-25E illustrate a method of operating a lumen traveling device and variants thereof;

FIG. 27 illustrates a block diagram of a system;

FIGS. 28A-28F illustrate a method of operating a lumen traveling device and variants thereof;

FIG. 29 illustrates a block diagram of a system;

FIGS. 30A-30D illustrate a method of operating a lumen traveling device and variants thereof;

FIG. 31 illustrates a block diagram of a system;

FIGS. 32A-32J illustrate a method of operating a lumen traveling device and variants thereof;

FIG. 33 illustrates a block diagram of a system;

FIGS. 34A-34E illustrate a method of operating a lumen traveling device and variants thereof;

FIG. 38 illustrates embodiments of planning a path of travel;

FIG. 39 illustrates a block diagram of a system;

FIG. 43 illustrates a block diagram of a system;

FIG. 46 illustrates a block diagram of a system;

FIG. 49 illustrates a block diagram of a system;

FIG. 50 illustrates a method of operating a lumen traveling device;

FIG. 51 illustrates a block diagram of a system;

FIG. 53 illustrates a block diagram of a system;

FIG. 55 illustrates a block diagram of a system;

FIG. 57 illustrates a block diagram of a system;

FIG. 59 illustrates a block diagram of a system;

FIG. 61 illustrates a block diagram of a system;

FIG. 63 illustrates a block diagram of a system;

FIG. 65 illustrates a block diagram of a system;

FIG. 67 illustrates a block diagram of a system;

FIG. 68 illustrates a block diagram of a system;

FIG. 70 illustrates a block diagram of a system.

DETAILED DESCRIPTION

Figure 1:
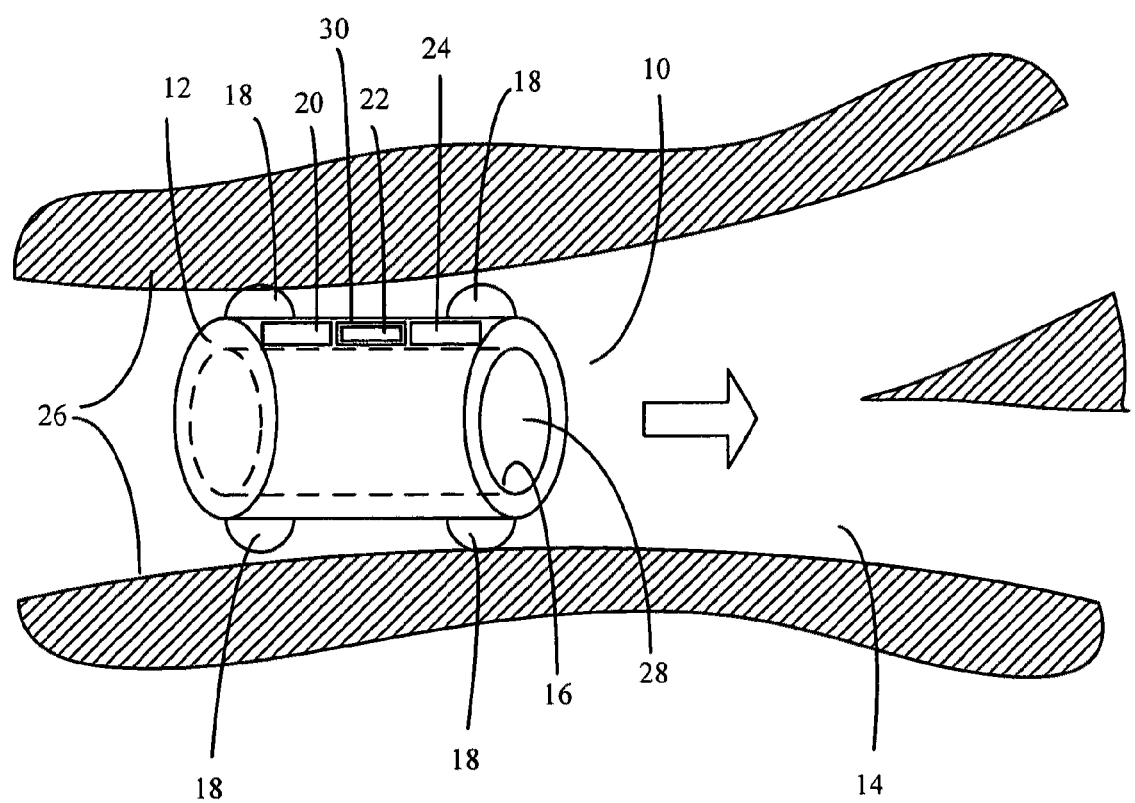
FIG. 1 illustrates an embodiment of a lumen traveling device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A lumen traveling device is an example of a lumenally active device. Lumenally active devices, and related methods and systems, are described in U.S. Patent Publication No. 2007/0066929 titled "Lumenally-Active Device," published Mar. 22, 2007, which is incorporated herein by reference.

An embodiment of a lumen traveling device 10 is illustrated in FIG. 1 and includes a structural element 12 configured to travel within at least a portion of a body lumen 14. The structural element 12 of lumen traveling device 10 includes a fluid-contacting portion 16 configured to contact fluid within the body lumen, a propelling mechanism 18 capable of producing movement of the structural element 12 through a body lumen 14 in which the structural element is deployed, a sensor 20 capable of sensing a local parameter value in the body lumen, on-board control circuitry 22 configured to control the operations of the lumen traveling device 10; and an active portion 24 operatively connected to on-board control circuitry 22 and capable of producing a response upon receipt of a signal from on-board control circuitry 22. Body lumen 14 is defined by wall portions 26, which are the walls of a blood vessel or other lumen, or a plurality of lumen defining a body tube tree within the body of an organism. In this example, a body fluid flows through body lumen 14 in the direction indicated by the arrow. Fluid flows through the central opening 28 of structural element 12, with the interior surface of the structural element 12 forming fluid-contacting portion 16. In the embodiment depicted in FIG. 1, sensor 20 and active portion 24 are located at a fluid-contacting portion 16. The on-board control circuitry 22 further includes one or more of motion control circuitry, mapping circuitry, and response control circuitry. On-board control circuitry 22 serves as a lumen-traveling device control system 30 that is located entirely on-board lumen traveling device 10 in this example. In this example, the propelling mechanism 18 is one or more rotating wheels that frictionally engage wall portions 26 and function to move lumen traveling device 10 through body lumen 14. In other aspects of lumen traveling devices, other structures and methods for engaging the lumen wall and/or propelling the lumen traveling device through the lumen may be employed.

A lumen traveling device or system is configured for use in (e.g., configured to fit within and travel within) the lumens of a body tube tree of an organism. Examples of body tube trees of an organism include but are not limited to the respiratory tract, the cardiovascular system (e.g., blood vessels), a portion of the cerebrospinal fluid (CSF) space of the nervous system (e.g., the central canal of the spinal cord, the ventricles of the brain, the subarachnoid space, intrathecal space, etc.), the urinary tract, the lymphatic system, a portion of the abdominal cavity, a portion of the thoracic cavity, the digestive tract, the female reproductive tract (e.g., a lumen of a fallopian tube), the male reproductive tract (including various lumens including but not limited to the epididymis, vas deferens or ductus deferens, efferent duct, ampulla, seminal duct, ejaculatory duct, or urethra), the biliary tract, a nostril or nasal cavity, the oral cavity, the tear ducts, or a glandular system. Other body lumens include those found in the auditory or visual system, or in interconnections thereof, e.g., the Eustachian tubes. Some of the devices and systems described herein can be used in a body tube tree through which fluid flows, but it is not intended that such devices or systems are limited to use in tubular lumen-containing structures containing moving fluid; in some applications a lumen traveling device can be used in a body tube tree containing relatively unmoving or intermittently moving fluid. In a further embodiment, the lumen traveling device can be used in a man-made lumen within the body, including, for example, vascular catheters, spinal fluid shunts, vascular grafts, bowel re-anastomoses, bypass grafts, indwelling stents of various types (e.g., vascular, gastrointestinal, tracheal, respiratory, ureteral, genitourinary, etc.) and surgically created fistulas.

The term fluid, as used herein, refers to liquid, gases or other compositions, mixtures, or materials exhibiting fluid behavior. The fluid within the lumen of a body tube tree can include a liquid, a gas or gaseous mixtures. As used herein, the term fluid can encompass liquids, gases, or mixtures thereof that also include solid particles in a fluid carrier. Liquids can include mixtures of two or more different liquids, solutions, slurries, or suspensions. Body fluids can include components such as, for example, cells, cellular fractions or components, collections or aggregations of cells, bacterial, viral or fungal species, ions, molecules, gas bubbles, dissolved gas, suspended particles, or a variety of other materials that may be present in the body fluid. Body fluid components can be materials that are normally present in the body fluid, materials that are naturally derived but not normally present in the body fluid, or foreign materials that have entered or been introduced to the body fluid (including but not limited to pathogens, toxins, pollutants, medications, for example). Examples of liquids present within body lumens include blood, lymph, serum, urine, semen, digestive fluids, tears, saliva, mucous, cerebrospinal fluid, intestinal contents, bile, epithelial exudate, or esophageal contents. Liquids present within body lumens can include synthetic or introduced liquids, such as blood substitutes, or drug, nutrient, or saline solutions. Fluids can include liquids containing dissolved gases or gas bubbles, or gasses containing fine liquid droplets or solid particles. Gases or gaseous mixtures found within body lumens can include inhaled and exhaled air, e.g., in the nasal or respiratory tract, or intestinal gases.

Figure 2:
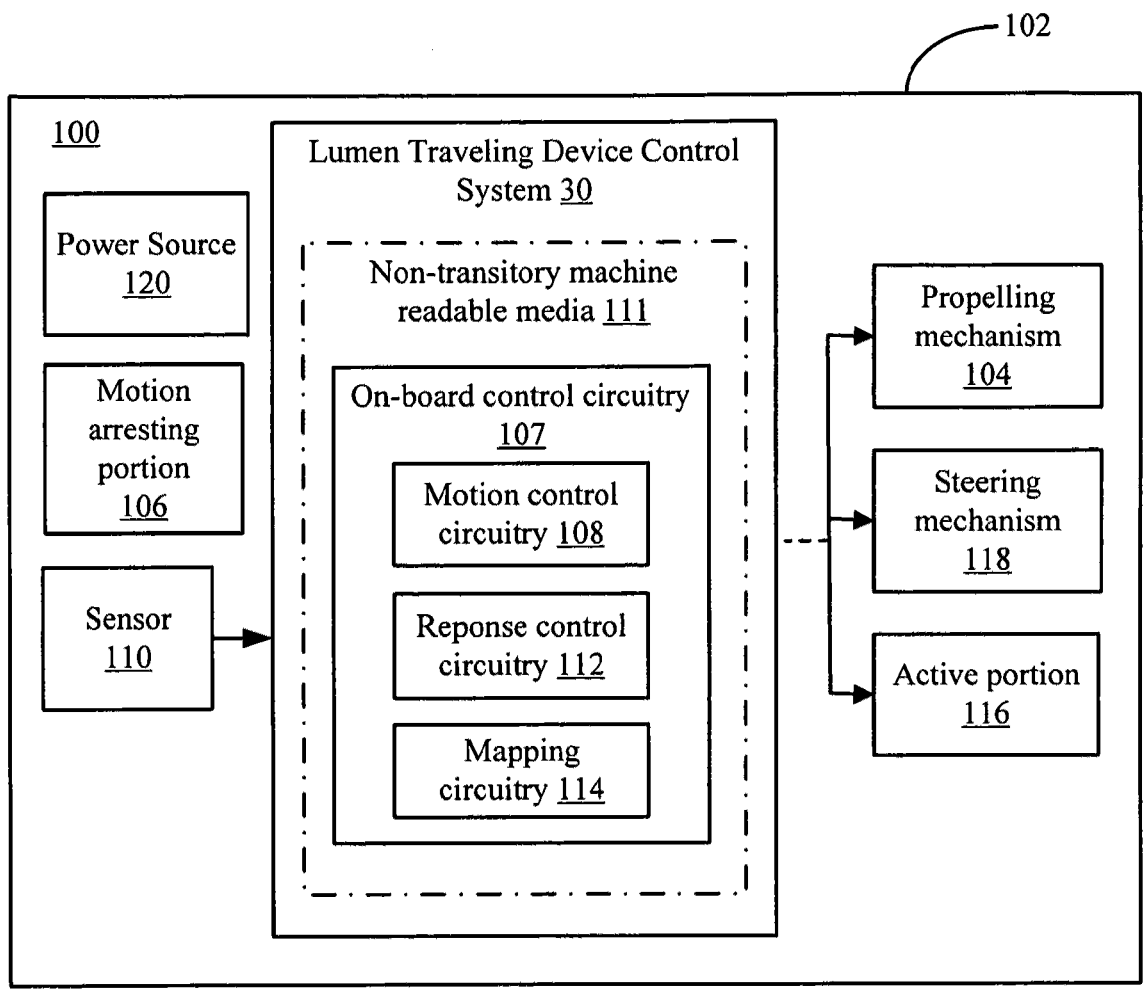
FIG. 2 is a block diagram an embodiment of a lumen traveling device.

FIG. 2 is a block diagram depicting components of an embodiment of lumen traveling device 100. Lumen traveling device 100 includes a fluid-contacting portion 102 configured to contact fluid within the lumen of the body tube tree and to at least intermittently permit flow of fluid through the lumen; a propelling mechanism 104 capable of producing movement of the lumen traveling device through the lumen of a body tube tree in which the lumen traveling device is deployed; a motion arresting portion 106 capable of stopping the movement of the lumen traveling device; motion control circuitry 108 carried at least in part by said lumen traveling device and configured to control propelling mechanism 104 and motion arresting portion 106 to control movement of the lumen traveling device through the lumen of a body tube tree; a sensor 110 capable of sensing a local parameter value in the lumen of a body tube tree and generating a sense signal indicating detection of the local parameter value; response control circuitry 112 operatively connected to sensor 110 and configured to generate a response control signal upon receipt of the sense signal indicating detection of a local parameter value in the lumen of a body tube tree; mapping circuitry 114 operatively connected to motion control circuitry 108 and configured to inform control of movement in the body tube tree based at least in part on a map of the body tube tree; and an active portion 116 operatively connected to response control circuitry 112 and capable of producing a response upon receipt of the response control signal. Motion control circuitry 108, response control circuitry 112, and mapping circuitry 114 make up part of on-board control circuitry 107, which can also include other components not specifically described herein. On-board control circuitry 107 in this embodiment also constitutes lumen traveling device control system 30. Lumen traveling device control system 30 includes non-transitory machine readable media 111, which stores instructions and/or data for implementation of/use by on-board control circuitry 107/lumen traveling device control system 30. The embodiment of FIG. 2 also includes a steering mechanism 118 under control of the motion control circuitry 108 and capable of modifying the direction of movement of the lumen traveling device through the body tube tree. The embodiment of FIG. 2 can include power source 120 configured to provide power to at least one of propelling mechanism 104, motion arresting portion 106, steering mechanism 118, motion control circuitry 108, mapping circuitry 114, sensor 110, response control circuitry 112 and active portion 116. Components of the embodiment of FIG. 2 can be generally as described elsewhere herein. The lumen traveling device depicted in schematic form in FIG. 2 is a self-contained and self-sufficient device that does not require connections to an external controller or power source, and is capable of untethered use. In some embodiments, methods and systems as described herein can be used in connection with untethered lumen traveling devices. In some embodiments, methods and systems as described herein can be used in connection with tethered lumen traveling devices (i.e., lumen traveling devices connected to a power source, controller, etc. located outside the body of the subject or, in some cases, at a location within the body of the subject but remote from the lumen traveling device) via a wire, cable, line, cord or the like.

A lumen traveling device as described for example in connection with FIG. 2 can be configured to fit within a particular lumen of a body tube tree through appropriate selection of device dimensions, material properties, and propelling mechanism. Configuration aspects can include size, shape, rigidity/flexibility, porosity, and biocompatibility, among others and may depend on both the materials and methods used to construct the lumen traveling device. The dimensions and mechanical properties (e.g., rigidity) of the lumen traveling device can be selected for compatibility with the location of use in order to provide for reliable movement and/or positioning of the device and to prevent damage to the lumen of the body tube tree. For example, the dimensions of a lumen traveling device may be selected to allow the device to fit within the smallest lumens expected to be found in the body tube tree of interest. Alternatively, the dimensions of a lumen traveling device may be selected to allow the device to fit into a subset of lumens of a body tube tree. As an example, the inner diameter of the lumen of the vascular body tube tree can range from about 2 to 2.5 centimeters within the aorta to less than 20 micrometers in the capillaries. In an embodiment, the lumen traveling device is capable of altering its dimensions (e.g. changing in length and diameter) to accommodate lumens of varying diameter. For example, see U.S. Patent Application 2005/0177223, which is incorporated herein by reference in its entirety. In a further embodiment, a lumen traveling device of fixed dimension can be designed for a particular application, or a set of lumen traveling devices in several sizes can be designed, from which the best size can be selected for a particular application and/or particular patient.

In an embodiment, the structural element of a lumen traveling device for use in a lumen of a body tube tree can be a substantially tubular structure and may include one or multiple lumens in fluid communication with the body lumen. Structural elements can have the form of a short cylinder, an annulus, an elongated cylinder, or a spiral, for example and can further include an adjustable diameter. Elongated forms such as cylinders or spirals may be suitable for use in tubular lumen-containing structures such as, for example, blood vessels. A spiral structure is disclosed, for example, in Bezrouk et al, *Scripta Medica* (BRNO) 2005, 78:219-226, which is incorporated herein by reference in its entirety.

In an embodiment, the structural element of the lumen traveling device can include a self-expanding material, a resilient material, a mesh material, or a combination thereof. The form as well as the material composition of the structural element can be configured to contribute to the expanding or flexing properties of the structural element. For example, the basic form of the structural element can include perforations, mesh, or slots, or a combination thereof that run along all or part of the length of the structural element and provide flexibility to the structural element. Spiral, mesh, or slotted structural elements formed from resilient material, for example, can be used to generate elastic, springy or self-expanding/self-contracting structural elements. A self expanding or self-contracting structural element can be used to facilitate positioning of the structural element within a body lumen of an organism. Flexible material having adjustable diameter, taper, and length properties can also be used. Structural elements that exhibit expansion/contraction properties can include mesh structures formed of various metals or plastics, and some polymeric materials, for example. Examples of shape change materials are described in Bellin et al., *Proc.*

*Natl. Acad. Sci. USA,* 2006, 103:18043-18047; and Shahinpoor & Kim *Smart Materials and Structures,* 2005, 14:197-214, each of which is incorporated herein by reference.

Lumen traveling devices are not limited to cylindrical structural elements having a single central opening. In an embodiment, a structural element can be configured to contact and move along a portion of a wall of a body lumen, contacting or engaging the lumen wall over a portion of its cross-section (as opposed to contacting the lumen wall along its entire cross-section) without obstructing the movement of fluid within the body lumen. Such an embodiment can be approximately hemi-spherical or hemi-elliptoid. In an embodiment, the lumen traveling device can be pill- or capsule-shaped, adapted to move through a central portion of a body lumen. In an embodiment, the lumen traveling device can have an elongated, flexible (e.g. worm- or snake-like) configuration. Other examples are described in U.S. Patent Application 2007/0156211, which is incorporated herein by reference.

The lumen-traveling device can be constructed from a variety of materials by a variety of manufacturing methods. Appropriate materials include, but are not limited to, metals, ceramics, polymers, and composite materials having suitable biocompatibility, sterilizability, mechanical, and physical properties. Examples of materials and selection criteria are described, for example, in *The Biomedical Engineering Handbook,* Second Edition, Volume I, J. D. Bronzino, Ed., Copyright 2000, CRC Press LLC, pp. IV-1-43-31, which is incorporated herein by reference. In a further embodiment, the structural element can include a bioactive component (such as a drug releasing coating or bioactive material attached to or incorporated into the structural element). Techniques for manufacturing the structural element include, but are not limited to, injection molding, extrusion, die-cutting, rapid-prototyping, self-assembly, etc., and will depend on the choice of material and device size and configuration. Sensing portions, active portions, and propelling mechanisms or structures of the lumen traveling device as well as associated circuitry can be fabricated on the structural element using various microfabrication and/or MEMS techniques, or can be constructed separately and subsequently assembled to the structural element, as one or more distinct components. Examples of microfabrication techniques include, for example, those disclosed in U.S. Patent Applications 2005/0221529; 2005/0121411; 2005/0126916; and Nyitrai et al., "Preparing Stents with Masking & Etching Technology," $26^{th}$ International Spring Seminar on Electronics Technology, IEEE, May 8-11, 2003, pp. 321-324, each of which is incorporated by reference.

The lumen-traveling device of FIG. 2 includes lumen traveling device control system 30 including on-board control circuitry 107 configured to control the operation of the lumen traveling device. The operations of the lumen traveling device include but are not limited to sensing, moving, mapping, transmitting, receiving, computing, responding and acting within the lumen of a body tube tree. The control circuitry can include but is not limited to, motion control circuitry, response control circuitry and mapping circuitry. The control circuitry making up lumen traveling device control system can include at least one microprocessor, and/or at least one of hardware, software, and firmware. The control circuitry can be electrical circuitry and/or other types of logic/circuitry including, but not limited to, fluid circuitry, chemo-mechanical circuitry, and other types of logic/circuitry that provide equivalent functionality. The control circuitry can be located in or on the structural element of the lumen traveling device, in or on a remote device separate from the structural element of the lumen traveling device, or in part in or on the lumen traveling device and in part in or on a remote device. Thus, while in the embodiments of FIGS. 1 and 2 the lumen traveling device control system 30 includes on-board control circuitry 22 and on-board control circuitry 107, respectively, in other embodiments, as will be discussed elsewhere here, the lumen traveling device control system can include control circuitry in multiple locations both on-board and remote from the lumen traveling device. Examples of devices and/or systems for communicating within devices in the body are described in U.S. Pat. Nos. 5,843,139; 6,409,674; or 7,125,382; U.S. Patent Application 2002/0198604, each of which is incorporated herein by reference.

The control circuitry of the lumen-traveling device can include motion control circuitry. The motion control circuitry can be configured to control one or more motion arresting portions, one or more propelling mechanisms and/or one or more steering mechanisms of the lumen traveling device. The motion control circuitry can be operatively connected to one or more sensors. The one or more sensors are configured to sense one or more parameter values in the body tube tree. The motion control circuitry is configured to control movement of the lumen traveling device at least in part in response to receipt of a sense signal indicating detection of a parameter value of interest in the lumen of the body tube tree.

The motion control circuitry component of the lumen traveling device control system can be connected to the mapping circuitry. The mapping circuitry of the lumen traveling device can be operatively connected to one or more sensor, and configured to use data regarding one or more sensed parameter values associated with the current position of the lumen traveling device to locate the lumen traveling device on a map of the body tube tree or to generate or make corrections to a map of the body tube tree. The mapping circuitry can be operatively connected to the motion control circuitry and configured to control at least one of a propelling mechanism, a steering mechanism, and/or a motion arresting portion and to control the movement of the lumen traveling device at least in part in response to receipt of data regarding the location of the lumen traveling device relative to a map of the body tube tree. In an embodiment, the mapping circuitry is incorporated into the lumen traveling device. In an embodiment, the mapping circuitry is incorporated into a remote device, which receives data regarding one or more sensed parameter values at the current location of the lumen traveling device, locates the lumen traveling device on a pre-existing map of the body tube tree, and transmits information to the motion control circuitry on the lumen traveling device to control movement of the lumen traveling device in a selected direction of travel.

The lumen traveling device can be propelled through the lumen of a body tube tree under control of the motion control circuitry using one or more propelling mechanisms. The propelling mechanism can be selected for the type and nature of the lumen to be traveled. For example, a lumen traveling device that walks or rolls along one side of a lumen or employs more than one mode of propulsion, for example, may adapt well to changes in lumen cross-section. Examples of propelling mechanisms are provided in U.S. Pat. Nos. 5,337,732; 5,386,741; 5,662,587; and 6,709,388; and in Kassim et al., "Locomotion Techniques for Robotic Colonoscopy," *Engineering in Medicine and Biology Magazine, IEEE,* May/June 2006 pp. 49-56; Xi et al., *Nat. Materials,* 2005, 4:180-184; and Freitas, "8.2.1.2 Arteriovenous Microcirculation"; "9.4.3.5 Legged Ambulation"; "9.4.3.6 Tank-Tread Rolling"; "9.4.3.7 Amoeboid Locomotion"; "9.4.3.8 Inchworm Locomotion"; "Nanomedicine Volume I: Basic Capabilities"; 1999; pp. 211-214, pp. 316-318; Landes Bioscience; Georgetown, Tex., USA; each of which is incorporated herein by reference.

The propelling mechanism of the lumen-traveling device can include one or more cilium-like structures, for example, as described in U.S. Patent Application 2004/0008853; Mathieu et al., "MRI Systems as a means of propulsion for a microdevice in blood vessels," *Engineering in Medicine and Biology Society,* 2003, *Proceedings of the 25th Annual International Conference of the IEEE,* Sep. 17-21, 2003, 4:3419-3422; Lu & Martel, "Preliminary Investigation of Bio-carriers Using Magnetotactic Bacteria," *Proceedings of the 28th IEEE EMBS Annual International Conference,* Aug. 30-Sep. 3, 2006, pp. 3415-3418; and MARTEL, S., "Towards MRI-controlled ferromagnetic and MC-1 magnetotactic bacterial carriers for targeted therapies in arteriolocapillary networks stimulated by tumoral angiogenesis," *Proceedings of the 28th IEEE EMBS Annual International Conference,* Aug. 30-Sep. 3, 2006, pp. 3399-3402, each of which is incorporated herein by reference. The propelling mechanism can include rollers or wheel-like structures, as shown in U.S. Pat. No. 7,042,184 and U.S. Patent Application 2006/0119304, each of which is incorporated herein by reference; screw-like structures, as disclosed in Ikeuchi et al., "Locomotion of Medical Micro Robot with Spiral Ribs Using Mucus," *Micro Machine and Human Science,* 1996, *Proceedings of the Seventh International Symposium,* Oct. 2-4, 1996, pp. 217-222, which is incorporated herein by reference; appendages capable of walking motion, as described, for example, in U.S. Pat. No. 5,574,347; Xi et al., *Nat. Materials,* 2005, 4:180-184; Martel, *Int. J. Robotics Res.* 2005, 24:575-588, and Edwards, Lin, "Spider pill to seek out disease," PhysOrg.com, 16 Oct. 2009; each of which is incorporated herein by reference. Appendage-like structures can be configured to intermittently engage the lumen wall and push the structural element with respect to the lumen wall with a walking-type motion, or can be configured to push against fluid within the lumen in a paddling or swimming motion. In an embodiment, the propelling mechanism can drive rotational movement of a lumen-wall-engaging structure with respect to the structural element, e.g., as in turning of a wheel or a screw element to propel the structural element through a lumen. Propelling mechanisms can include mechanical or micromechanical structures driven by at least one motor, micromotor, or molecular motor, or by expansion or change in configuration of a shape change polymer or metal. A molecular motor can be a biomolecular motor that runs on a biological chemical such as ATP, kinesin, RNA polymerase, myosin dynein, adenosinetriphosphate synthetase, rotaxanes, or a viral protein.

Figure 3:
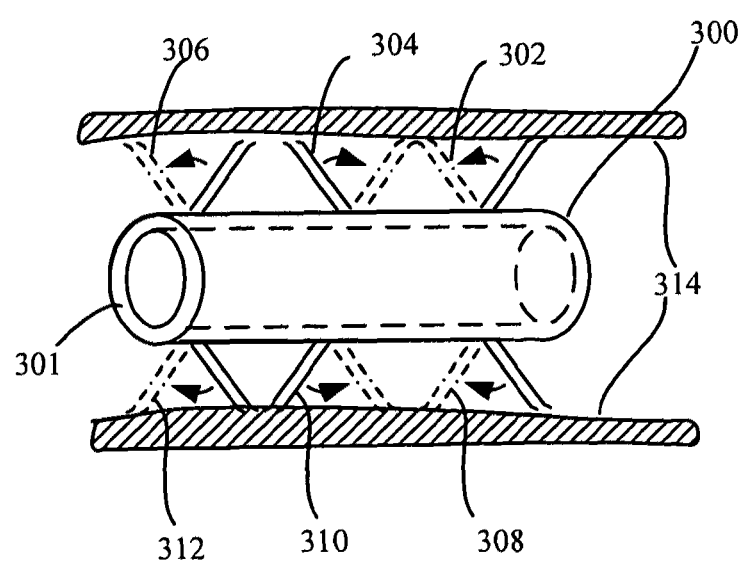
FIG. 3 illustrates an embodiment of a propelling mechanism.

FIG. 3 depicts an embodiment of a lumen traveling device adapted to travel through the lumen of a body tube tree with a propelling mechanism that produces walking-type motion. In this embodiment, lumen traveling device 300 includes a structural element 301 sized to travel within a lumen of a body tube tree; at least two lumen wall engaging structures operable to alternately engage and disengage the lumen wall 314 (in FIG. 3, 6 lumen-wall-engaging structures 302, 304, 306, 308, 310, and 312 are shown); and a propelling mechanism capable of producing relative extension and retraction of the at least two lumen-wall-engaging structures with respect to each other in combination with alternate engagement and disengagement of the lumen wall 314 to produce movement of the lumen traveling stimulation device with respect to the lumen wall 314. Lumen traveling device 300 may also include motion control circuitry carried at least in part by the lumen traveling device and configured to control the propelling mechanism to control movement of the lumen traveling device through the lumen of a body tube tree. The at least two lumen-wall-engaging structures may include at least two appendages configured for walking motion. In the embodiment shown in FIG. 3, legs (lumen-wall-engaging structures) 302 and 304 extend and retract with respect to each other, for example, so that as one leg swings forward, the other swings back. Larger or smaller numbers of legs, distributed in various patterns about the structural element, may be used to propel the lumen traveling device through the body tube tree, and the embodiment depicted in FIG. 3 represents one possible example. Lumen traveling devices that utilize a walking type propulsion mechanism for engaging surfaces of the gastrointestinal tract are disclosed in Quaglia et al., *J. Micromech. Microeng,* 2009, 19 105007 (11 pp), which is incorporated herein by reference.

Leg structures for lumen traveling devices can be formed of various materials and structures, including but not limited to, nanotubes and nanotube bundles, carbon fibers and carbon fiber bundles, silicon, metal, polymers, and other materials as described herein. The leg structures can be moved to produce walking motion by various mechanisms. In an embodiment, one or more legs can be formed from shape-changing material and moved through change in configuration of the leg structure itself. In an embodiment, the legs can have a substantially rigid or fixed configuration that move by a separate actuation mechanism. Shape-changing materials for use in leg structures or actuators can be of various types, including but not limited to, stacked piezoelectric elements, electroactive polymers, heat sensitive polymers, magnetic field responsive polymers, and ferromagnetic materials, as described elsewhere herein.

Figure 4A:
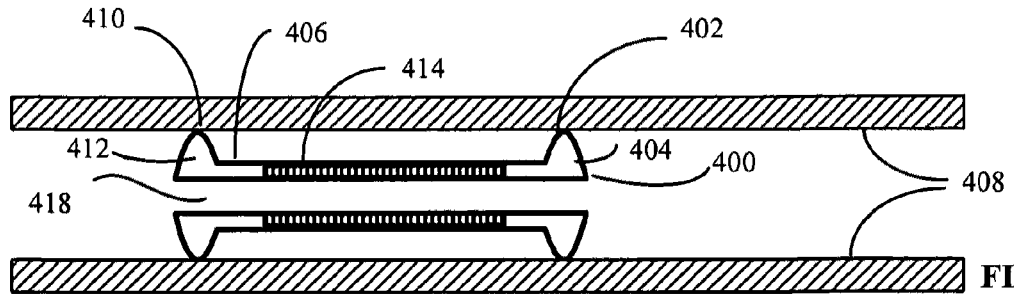
FIGS. 4A-4E illustrate an additional embodiment of a propelling mechanism.
Figure 4B:
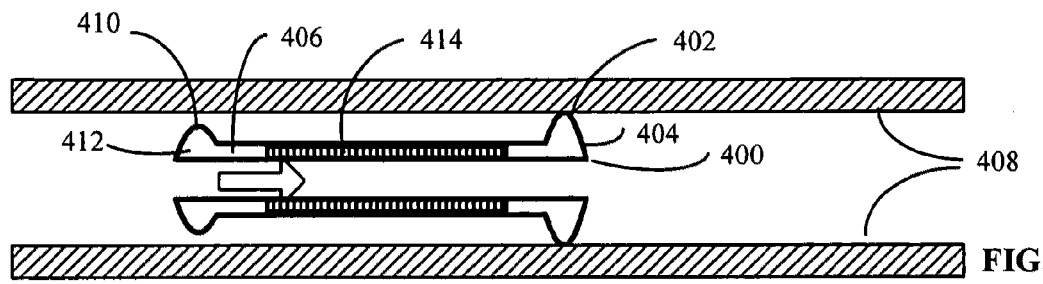
Figure 4C:
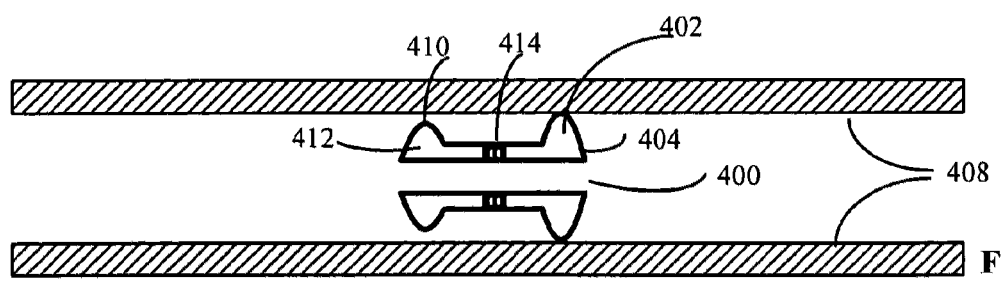
Figure 4D:
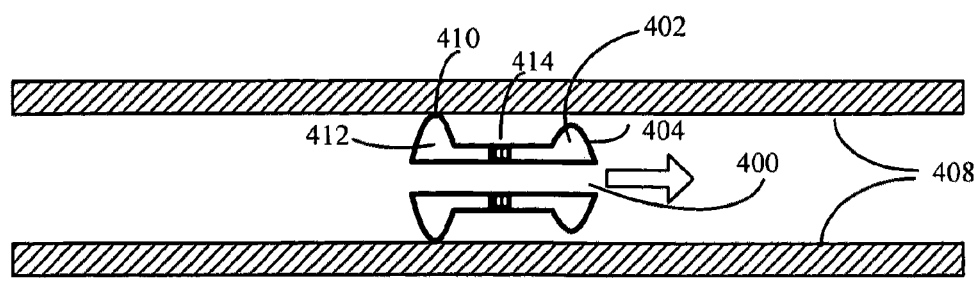
Figure 4E:
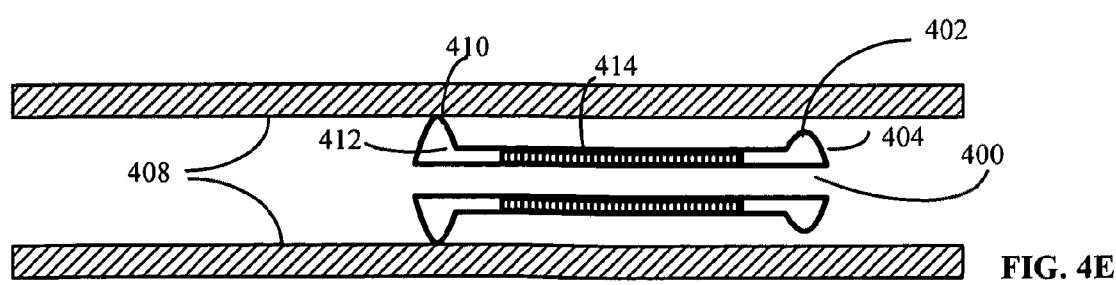

FIGS. 4A-4E depict (in cross-section) a further embodiment of propelling mechanism of a lumen traveling device using one or more motion-arresting portions and lengthening and shortening of the lumen traveling device to inch along the lumen wall. In this embodiment, lumen traveling device 400 includes a motion-arresting portion including a first lumen-wall-engaging structure 402 on first portion 404 of the lumen traveling device, capable of at least intermittently engaging the wall 408 of a lumen of a body tube tree in which the lumen traveling device 400 is deployed. The lumen traveling device may also include at least one second lumen-wall-engaging structure 410 on second portion 412 of the lumen traveling device, wherein the propelling mechanism produces lengthening and shortening of the distance, between the first lumen-wall-engaging structure 402 and the second lumen-wall-engaging structure 410 in coordination with alternate engagement of the first lumen-wall-engaging structure 402 and the second lumen-wall-engaging structure 410 with the wall 408 of the lumen of a body tube tree in which the lumen traveling device is deployed. In the present example, the lengthening and shortening of the distance between the first and second lumen-wall-engaging structures may take place in region 414, but in other embodiments, the distance between the first and second lumen-wall-engaging structures may change due to change in position of the lumen-wall-engaging structures, e.g., in limbs that move relative to each other to produce walking-type motion. Portions of the lumen traveling device (e.g. end portion 406) may be of fixed length, in order to provide a stable location for mounting of control circuitry (not shown). The alternate engagement and disengagement of the lumen wall by the first and second lumen-wall-engaging structures may produce inchworm-type propulsion of the lumen traveling device through the body lumen. Lumen traveling device 400 includes a propelling mechanism capable of producing relative extension and retraction of the at least two lumen-wall-engaging structures (402 and 410) with respect to each other in combination with alternate engagement and disengagement of the body lumen wall to produce inch-worm-like movement of the lumen traveling stimulation device with respect to the body lumen wall. The embodiment of the lumen traveling device depicted in FIGS. 4A-4E has a tubular structure with a central lumen 418, to permit movement of fluid through the lumen traveling device. FIG. 4A depicts a lumen traveling device in which lumen-wall-engaging structures 402 and 410 are extended to engage with the wall 408. In FIG. 4B, second lumen-wall-engaging structure 410 has been retracted, and region 414 shortened to cause movement of second portion 412 of lumen traveling device 400 in the direction indicated by the arrow, to attain the configuration shown in FIG. 4C. Second lumen-wall-engaging structure 410 is then extended to engage the wall 408, and first lumen-wall-engaging structure 402 is retracted, to attain the configuration shown in FIG. 4D. Then, as indicated in the arrow in FIG. 4D, region 414 is extend to move first portion 404 of lumen traveling device 400 in the direction indicated by the arrow in FIG. 4D. At the end of the movement cycle, lumen traveling device 400 has attained the configuration shown in FIG. 4E. First lumen-wall-engaging structure 402 may then be extended to engage wall 408, as depicted in FIG. 4A. It will be appreciated that by repeating the motion cycle illustrated in FIGS. 4A-4E, movement of the lumen traveling device through the lumen may be accomplished.

The lumen-wall-engaging structures 402 of FIG. 4 can be mechanical or micromechanical structures, expandable materials, inflatable structures, or shape-changing materials or structures. Structures that are specified as being expandable and inflatable can also be contractable or deflatable, and thus capable of reversible change in dimension. Reversible changes of dimension can be used in generating cyclical motions for propelling a lumen traveling device. Nevertheless, it is contemplated that, in some applications, materials and structures that change dimension in one direction (only expansion or only contraction) may be used.

In addition to lumen-wall-engaging structures that expand or extend, structures that engage the lumen wall through other mechanisms (for example, with suction mechanisms, adhesives, claws or hooks) may be used. See, for example, Dario et al., "A Micro Robotic System for Colonoscopy," *Robotics and Automation,* 1997, *Proceeding* 1997 *IEEE International Conference,* Apr. 20-25, 1997, 2:1567-1572 and Dongxiang & Guozheng, "An earthworm based miniature robot for intestinal inspection," *Micromachining and Microfabrication Process Technology Devices, Proceedings* Vol. 4601, Tien & Huang, Ed., pp. 396-400, 2001, each of which is incorporated herein by reference. Lumen traveling devices that utilize an inchworm-type propulsion mechanism with suction mechanisms for engaging the surface of the heart are disclosed in Patronik et al., "Improved Traction for a Mobile Robot Traveling on the Heart," *Proceedings of the 28th IEEE EMBS Annual International Conference,* Aug. 30-Sep. 3, 2006, pp. 339-342, which is incorporated herein by reference.

In an embodiment of a propelling mechanism, multiple lumen-wall-engaging structures, operating in sequence to alternately engage and disengage the lumen wall, can be configured to produce "peristaltic" motion of the lumen traveling device. Examples of devices that produce this type of motion are described in U.S. Pat. No. 6,764,441; U.S. Patent Application 2006/0004395; Mangan et al., "Development of a Peristaltic Endoscope," *Robotics and Automation,* 2002, *Proceedings, ICRA* '02, *IEEE International Conference,* 1:347-352; and Meier et al., "Development of a compliant device for minimally invasive surgery," *Proceedings of the 28th IEEE EMBS Annual International Conference,* Aug. 30-Sep. 3, 2006, pp. 331-334, each of which is incorporated herein by reference.

In an embodiment, the propelling mechanism of a lumen traveling device can be configured to drive movement of the lumen traveling device along a wire, catheter, cannula, or tube within the lumen of a body tube tree.

In an embodiment, the lumen traveling device can be propelled through the body tube tree by one or more paddles, propellers, flagella, cilia, or the like, which push against fluid contained within the lumen rather than engaging the wall of the lumen, e.g. as described in U.S. Pat. No. 6,240,312 or in Behkam & Sitti, "Towards hybrid swimming microrobots: Bacteria assisted propulsion of polystyrene beads," *Proceedings of the 28th IEEE EMBS Annual International Conference,* Aug. 30-Sep. 3, 2006, pp. 2421-2424, each of which is incorporated herein by reference. Other illustrative examples of propelling mechanisms for lumen traveling devices are described in U.S. Patent Application 2007/0156211, which is incorporated herein by reference. In many cases, the direction of movement produced by the various propelling mechanisms described herein may be reversed by simply reversing the operation of the propelling mechanisms.

Movement of the lumen traveling device in a given direction of travel can be reduced or stopped by one or more motion-arresting portions under control of the motion control circuitry. A motion-arresting portion can take various forms, including, for example, an anchor capable of attaching at least temporarily to a wall of the lumen, at least one hook or claw, at least one adhesive material or glue, a brake to oppose the action of the propelling mechanism, or a shutoff for the propelling mechanism. The motion-arresting portion can further include a reversal mechanism for the propelling mechanism, in that to arrest motion it may be necessary to provide sufficient propulsion in the reverse direction to oppose a flow of fluid through the body lumen. The motion-arresting portion can be a part of, or associated with, the propelling mechanism (e.g. a shutoff or reversal mechanism for the propelling mechanism) or it can be a separate mechanism (adhesive, hook- or claw-like structure, anchor, etc.).

The lumen traveling device can be configured to include a steering mechanism under control of the motion control circuitry. The steering mechanism can be any of various structures, depending on the type of propelling mechanism used. For example, if the propelling mechanism is a paddle or propeller that causes the lumen traveling device to move in the fluid in the lumen, the steering mechanism can be a rudder. If the propelling mechanism includes multiple wheels or limb-like structures, the wheels or limb-like structures can be activated differentially on different sides of the lumen traveling device to steer it in one direction or another. In an embodiment in which the lumen traveling device contacts the lumen walls on all sides of the lumen traveling device, the steering mechanism may be used only in the cases that the lumen traveling device encounters a branch point in the lumen, and once the front portion of the lumen traveling device (defined by the direction of travel) is steered to cause the device to enter a selected branch, the back portion of the device will follow without the need for additional steering.

As illustrated in FIG. 2, the control circuitry, including the motion control circuitry, the mapping circuitry, and the response control circuitry, is operatively connected to one or more sensors. The one or more sensors are configured to sense one or more local parameter values in the lumen of a body tube tree. Sensed local parameter values can be used in mapping and motion control functions, and to control use of the lumen traveling device to perform actions or deliver treatments with the active portion. The lumen traveling device can include various types of sensing or information gathering devices or structures, including but not limited to, one or more pressure sensors, temperature sensors, flow sensors, viscosity sensors, shear sensors (e.g., for measuring the effective shear modulus of the fluid at a frequency or strain-rate), pH sensors, gas sensors, chemical sensors for determining the presence and/or concentration of a chemical compound or species, optical sensors and/or image sensors (e.g., charged couple device (CCD) array), acoustic sensors, biosensors, electrical sensors, magnetic sensors, clocks or timers. Examples of sensor types are provided in U.S. Pat. Nos. 5,522,394; 5,873,835; 6,053,873; 6,409,674; 6,111,520; 6,278,379; 6,475,639; 6,802,811; 6,855,115, and U.S. Patent Applications 2005/0277839 and 2005/0149170, each of which is incorporated herein by reference. It will be appreciated that an "image sensor" includes any type of sensor that can detect or construct a two- or higher-dimensional representation of values of a parameter of interest, including but not limited to optical images, thermal images, acoustic images, and so forth. In some embodiments, an active portion of a lumen traveling device can include a sensing or information gathering device or structure, and the action performed by the active portion of the lumen traveling device can include detecting or sensing information; for example, an action performed by an active portion of a lumen traveling device can include detecting an image.

In an embodiment, the one or more sensors of the lumen traveling device are optical sensors. An optical sensor can be configured to measure the optical absorption, optical emission, fluorescence, or phosphorescence of at least a portion of the body tube tree, including for example, the fluid in the lumen, the surface of the lumen wall, the interior of the lumen wall, or a combination thereof. Such optical properties may be inherent optical properties of all or a portion of the fluid or lumen wall, or may be optical properties of materials added or introduced to the fluid or lumen wall, such as markers, labels, or tags for materials or structures of interest. Optical sensing of materials in blood, for example, is described in Mattley et al., "Blood characterization using UV/VIS spectroscopy," *Proc. SPIE Advances in Fluorescence Sensing Technology II*, Joseph R. Lakowicz, Ed., Vol. 2388, p. 462-470, 1995 and U.S. Pat. Nos. 5,589,932 and 7,027,134, each of which is incorporated herein by reference.

In an embodiment, the one or more sensors of the lumen traveling device are biosensors configured to sense materials including, but not limited to, a biological marker, an antibody, an antigen, a peptide, a polypeptide, a protein, a complex, a nucleic acid, oligonucleotide, a polynucleotide, a cell (and, in some cases, a cell of a particular type, e.g. by methods used in flow cytometry), a cell fragment, a cellular component, a platelet, an organelle, a gamete, a pathogen, a signaling material (including bacterial and viral signaling materials, for example, as well as endogenous cell-signaling materials), a lipid, a lipoprotein, an alcohol, an acid, an ion, an immunomodulator, a sterol, a steroid, a carbohydrate, a sugar, a polysaccharide, a glycoprotein, a metal, an electrolyte, a metabolite, an organic compound, an organophosphate, a drug, a therapeutic, a gas, a pollutant, or a tag. A biosensor can include one or more binding molecule, examples of which include antibodies, aptamers, receptors, ligands, synthetic antibodies, etc. (see, e.g., Mok & Li, *Sensors*, 2008, 8:7050-7084, which is incorporated herein by reference).

A sensor can include a single sensor or an array of sensors, and is not limited to a particular number or type of sensors. The one or more sensors can be very small, including a sensor or array that is a chemical sensor (Snow, *Science*, 2005, 307:1942-1945), a gas sensor (Hagleitner et al., *Nature*, 2001, 414:293-296), an electronic nose, a nuclear magnetic resonance imager (Yusa et al., *Nature*, 2005, 343:1001-1005). Each of the foregoing references is incorporated herein by reference. Further examples of sensors are provided in *The Biomedical Engineering Handbook*, Second Edition, Volume I, J. D. Bronzino, Ed., Copyright 2000, CRC Press LLC, pp. V-1-51-9; Morrison et al., "Clinical Applications of Micro- and Nanoscale Biosensors," in *Biomedical Nanostructures*, Edited by K. E. Gonsalves, C. L. Laurencin, C. R. Halberstadt, L. S. Nair. 2008, John Wiley & Sons, Inc.; and U.S. Pat. No. 6,802,811, each of which is incorporated herein by reference.

The one or more sensors are configured to send signals to the control circuitry of the lumen traveling device regarding local parameter values in the environment of the body tube tree through which the lumen traveling device is traveling. The control circuitry of the lumen traveling device further includes, but is not limited to, motion control circuitry, mapping circuitry and response control circuitry. In response to a signal from a sensor, the motion control circuitry can send one or more signals instructing the lumen traveling device to move or arrest. In response to a signal from a sensor, the mapping circuitry can send one or more signals instructing the lumen traveling device to move or to perform an action based on a pre-existing or evolving map of the body tube tree. In response to a signal from a sensor, the response control circuitry can send one or more signals instructing the lumen traveling device to perform an action using one or more of an active portion. In an embodiment, the control circuitry responsive to one or more sensors is located in or on the lumen traveling device. In a further embodiment, at least a portion of the control circuitry is located in or on a remote device in communication with the lumen traveling device.

The lumen traveling device can include one or more active portions under control of the response control circuitry (and, more generally, the lumen traveling device control system) and configured to perform an action. An active portion of the lumen traveling device is configured to perform an action including but not limited to releasing a material, releasing a device or structure, releasing an energy, collecting a sample, collecting a device or structure, attaching a structure to a wall of the body tube tree, delivering a material or structure to a receiving portion of a man-made device, receiving a material or structure from a delivery portion of a man-made device, receiving a signal from a remote source, receiving power from a remote source, transmitting a signal to a remote location, performing a surgical step or procedure, removing tissue from at least a portion of the body tube tree (e.g., by scraping, shaving, excising, resecting, aspirating, excising by core or punch, biopsying, etc.), removing components of at least a portion of a fluid from a body tube tree, exposing a catalyst, generating a localized electric field, generating a localized magnetic field, producing heat, causing cooling, emitting electromagnetic radiation, emitting acoustic energy, applying pressure to at least a portion of the body tube tree, modulating the flow of a fluid through at least a portion of the body tube tree, sensing a local parameter value (which may be the same or different than a previously sensed parameter value), stopping performance of an action if the local parameter value is within a specified range, and initiating performance of an action if the local parameter value is within a specified range. A number of illustrative examples of active portions of a lumen traveling device for performing an action are described in U.S. Patent Application 2007/0156211, which is incorporated herein by reference. As used herein, "exposing a catalyst" refers to any process by which a catalyst is made available or accessible to a reactant or reactants participating in a reaction catalyzed by the catalyst. For example, a catalyst may be exposed by being released from the active portion of the lumen traveling device into the body tube tree, or it may be exposed while remaining on or associated with the lumen traveling device. A catalyst may be exposed through the removal of a material or structure covering the catalyst, or by the creation or expansion of opening or apertures that permit access to the catalyst through a material or structure that covers or otherwise limits access to the catalyst.

As used herein, a "remote source" (e.g., from which power or a signal can be received, as discussed above) can be a remote device that forms a part of a lumen traveling device system, or it can be a remote source that is not a part of a lumen traveling device system. A remote source can be a power source, a signal source, or both. Examples of remote sources (particularly sources of position indicator signals) are described herein below.

In an embodiment, the active portion of the lumen traveling device performs an action that includes releasing a material. Examples of material released by the lumen traveling device include but are not limited to at least one of an adhesive, a filler, a polymer, a hydrogel, an antibiotic, an antibody, an antiviral, a pharmaceutical compound, a nutrient, a hormone, a growth factor, a catalyst, a drug, a therapeutic compound, a chemical, a biomaterial, a biological marker, label, or tag, an enzyme, a protein, a nuclueic acid, an oligonucleotide, a polynucleotide, a polypeptide, a genetic material, a cell, a fraction of a cell, a cell fragment, a complex, a vaccine, a vitamin, a neurotransmitter, a neurotropic agent, a neuroactive material, a cytokine, a chemokine, a hormone, a signaling material, a pro-apoptotic agent, an anti-apoptotic agent, an immunological mediator, an anti-inflammatory agent, a salt, an ion, an electrolyte, an antioxidant, an imaging agent, a labeling agent, a diagnostic compound, a nanomaterial, an inhibitor, a lipid, an alcohol, a sterol, a steroid, a carbohydrate, a sugar, a gas, or a blocker.

Figure 5:
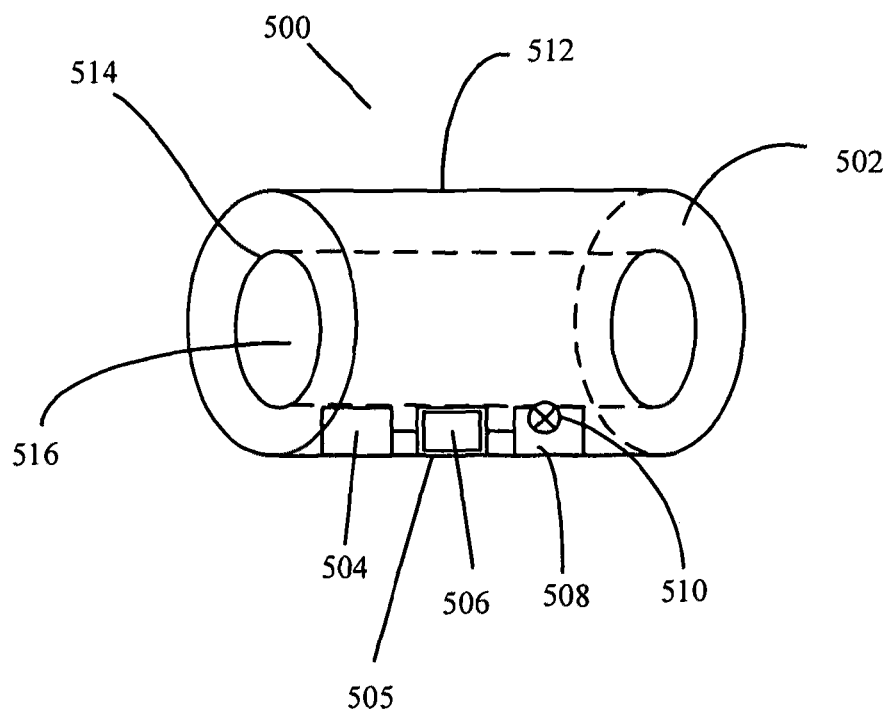
FIG. 5 illustrates an embodiment of a lumen traveling device.

An active portion of a lumen traveling device can include a material release structure operatively coupled to the response control circuitry and configured to release a material in response to receipt of a response control signal. FIG. 5 depicts a lumen traveling device 500 including a structural element 502, sensor 504, on-board control circuitry 505 including response control circuitry 506, and material release structure 508 including release mechanism 510. On-board control circuitry 505 can constitute the entirety of the lumen traveling device control system, or the lumen traveling device control system can include additional control circuitry located remotely (not shown in FIG. 5), as discussed elsewhere herein. Structural element 502 includes external surface 512, configured to fit within a body lumen, and internal surface 514 defining central opening 516, through which a fluid may flow. Upon sensing of a condition of interest in the fluid by sensor 504, response control circuitry 506 sends a response control signal to activate release mechanism 510, resulting in release of material from material release structure 508. Release mechanism 510 can include a variety of different types of release mechanisms, including, for example, a controllable valve. Various types of valves and microvalves are known to those of skill in the art, and can be used to regulate the release of material from material release structure 508 in response to a response initiation signal from response control circuitry 506. Examples of controllable valves or microvalves for microelectromechanical systems (MEMS) are provided in Luckevich, *Valve-World*, May 2007, 79-82, 2007, which is incorporated herein by reference. Response control circuitry 506 may activate release mechanism 510 by supplying a response control signal, which may be an electrical signal, for example. Other types of response control signals can be used, including magnetic signals, optical signals, acoustic signals, other types of signals, or combinations thereof. In an embodiment, response control circuitry 506 can cause release of material from material release structure 508 in response to passage of a certain amount of time, as monitored, for example, by a timekeeping device. In an embodiment, material release structure 508 can include a pressurized reservoir of material. In an embodiment, the material (or materials) to be released is generated within material release structure 508.

The material release structure of the lumen traveling device can include deformable, degradable, or rupturable barriers formed from a variety of materials, including, but not limited to, metals, polymers, crystalline materials, glasses, ceramics, semiconductors, etc. Release of materials through rupture or degradation of a barrier is also described in U.S. Pat. No. 6,773,429, and U.S. Patent Application 2004/0260391, each of which is incorporated herein by reference. Semipermeable barriers having variable permeability are described, for example, in U.S. Pat. No. 6,669,683, which is incorporated herein by reference. In an embodiment, barriers can be formed and operated reversibly through multiple release cycles. In an embodiment, a rupturable barrier can be used for a single-release functionality. Additional illustrative examples of lumen traveling device material release structures are provided in U.S. Patent Application 2007/0156211, which is incorporated herein by reference.

The lumen traveling device can further include a material for release that is dispersed in a carrier material. The material can be released from the carrier material upon activation of a release mechanism. Material can be released into a central opening of the lumen traveling device and/or into the area around the lumen traveling device. In an embodiment, the material(s) may diffuse away from the release structure along a concentration gradient. The carrier material can be, for example, a polymeric material such as a hydrogel into which the released material is dispersed or dissolved. Carrier materials can include particles or particle-like structures, e.g. particles, microparticles, nanoparticles, microspheres, nanospheres, liposomes, micelles, protein cages, dendrimers, etc. The release mechanism can be a heating element, for example a resistive element connected directly to response control circuitry, or an electrically or magnetically responsive material that can be moved, vibrated or heated, by an externally applied electromagnetic field, which in turn causes release of material from the carrier material. See, for example, U.S. Pat. Nos. 5,019,372 and 5,830,207, each of which is incorporated herein by reference. An example of a magnetically responsive polymer is described, for example, in Neto et al., *Brazilian Journal of Physics*, 2005, 35:184-189, which is incorporated herein by reference. Other exemplary materials and structures are described in Pan et al., *J. Micromech. Microeng.*, 2005, 15:1021-1026 or in U.S. Pat. No. 6,607,553, each of which is incorporated herein by reference.

In an embodiment, the permeability of the lumen wall to the released material can be increased by the use of retractable spines that penetrate the lumen wall, as described in U.S. Pat. No. 6,991,617, by hollow microneedles capable of penetrating the lumen wall, as described in U.S. Pat. No. 6,743,211, by a chemical permeability enhancer as described in U.S. Pat. No. 6,673,363, which may be released from the lumen traveling delivery device along with the material or from a separate reservoir or other source, or by an electrical permeability enhancer, such as a voltage source for producing electroporation, as in U.S. Pat. No. 6,512,950 or 6,022,316, all of which patents are incorporated herein by reference.

In an embodiment, the active portion of the lumen traveling device can include a heating element 600 as depicted in FIG. 6A, operatively coupled to the response control circuitry 601 and configured to produce heating in response to receipt of the response control signal. The heating element can be a resistive element that produces heat when current is passed through it, or it can be a magnetically active material that produces heat upon exposure to an electromagnetic field. Examples of magnetically active materials include permanently magnetizable materials, ferromagnetic materials such as iron, nickel, cobalt, and alloys thereof, ferrimagnetic materials such as magnetite, ferrous materials, ferric materials, diamagnetic materials such as quartz, paramagnetic materials such as silicate or sulfide, and antiferromagnetic materials such as canted antiferromagnetic materials which behave similarly to ferromagnetic materials; examples of electrically active materials include ferroelectrics, piezoelectrics and dielectrics. Heat can also be generated through an exothermic chemical reaction. U.S. Patent Applications 2002/0147480 and 2005/0149170, provide examples of heating and/or cooling mechanisms and structures, and are incorporated herein by reference. The heating element can be used to at least partially ablate and/or cauterize a target of interest within the lumen of a body tube tree.

In an embodiment, the active portion of the lumen traveling device can include a cooling element 602 as depicted in FIG. 6B, operatively coupled to the response control circuitry 603 and configured to cause cooling in response to receipt of the response control signal. Cooling can be caused by a number of mechanisms and/or structures. For example, cooling can be caused by an endothermic reaction (such as the mixing of ammonium nitrate and water) initiated by opening of a valve or actuation of a container in response to a control signal, which in turn removes energy from its surrounding. Other cooling elements that can be used for causing cooling include, but are not limited to, thermoelectric (Peltier Effect) and liquid-gas-vaporization (Joule-Thomson) devices.

In an embodiment, the active portion of the lumen traveling device can include an electromagnetic radiation source 604 as depicted in FIG. 6C, operatively coupled to the response control circuitry 605 and configured to emit electromagnetic radiation in response to receipt of the response control signal. Electromagnetic radiation sources can include light sources (e.g., light emitting diodes or laser diodes), or sources of other frequencies of electromagnetic energy or radiation including but not limited to radio waves, microwaves, ultraviolet rays, infra-red rays, optical rays, terahertz beams, and the like.

In an embodiment, the active portion of the lumen traveling device can include an acoustic energy source 606 (e.g. a piezoelectric element) as depicted in FIG. 6D, operatively coupled to the response control circuitry 607 and configured to emit acoustic energy in response to receipt of the response control signal. An acoustic energy source can generate pressure pulses of various frequencies, including auditory frequencies, subsonic frequencies, and ultrasonic frequencies. A microscale acoustic transducer may be constructed, for example, in U.S. Pat. No. 5,569,968, which is incorporated herein by reference.

In an embodiment, the active portion of the lumen traveling device can include an electric field source, operatively connected to the response control circuitry and configured to apply an electric field to the fluid and/or lumen wall or surrounding tissue in response to receipt of the response control signal. The electric field source may be a capacitor or other charge storing device, to generate a static electric field, or it may be current source capable of generating a dynamic electric field.

In an embodiment, the active portion of the lumen traveling device can include a magnetic field source operatively connected to the response control circuitry and configured to apply a magnetic field to the fluid and/or lumen wall or surrounding tissue in response to receipt of the response control signal. The magnetic field can be generated by running a current through a coil or other structure. In an embodiment, one or more fixed magnets are included in the magnetic field source.

In an embodiment, the active portion of the lumen traveling device can include a positioning element operatively coupled to the response control circuitry and configured to secure the lumen traveling device into position within the body lumen in response to receipt of the response control signal. Examples of positioning elements include but are not limited to claws, hooks, clips, tensioning elements, expanding elements, and adhesives. Certain positioning elements may be suited to retaining the lumen traveling device in a location for extended periods (e.g., an adhesive), while other positioning elements may be more suited to retaining the lumen traveling device in a location only briefly (e.g., a retractable hook). Other illustrative examples of positioning elements of a lumen traveling device are described in U.S. Patent Application 2007/0156211, which is incorporated herein by reference.

In an embodiment, the active portion of the lumen traveling device can include a separator operatively connected to the response control circuitry and configured to selectively remove specific components from the fluid or wall of the lumen in response to detection of the local condition of interest. Separators can include but are not limited to, one or more molecular sieve or mechanical filter (including, for example, screen, mesh, fiber, etc) having openings sized to allow passage of particles or structures of a particular size or size range, or one or more chemical or biochemical separators configured to separate materials based on binding affinity, charge, surface energy, etc. For example, U.S. Patent Application 2005/0126916 provides an example of a microfabricated mesh while U.S. Patent Application 2008/0241847 provides an example of a probe for in vivo collection of circulating molecules. Each of the foregoing references is incorporated herein by reference. A separator can be configured to remove undesirable components from the fluid. Alternatively, a separator can be configured to remove components for the purpose of collecting a sample for analysis.

In an embodiment the active portion of the lumen traveling device can include a sample collector for collecting fluid or solid samples. The liquid and/or solid sample can be immediately analyzed or placed in a sample collection structure for future analysis. Examples of sample collection structures and mechanisms are provided in U.S. Pat. Nos. 6,436,120 and 6,712,835, and Hanna et al., *IEEE Trans. Nanobioscience*, 2003, 2:6-13, each of which is incorporated herein by reference. The active portion can include a tool for collecting a solid sample (e.g., arterial plaque, tumor), for example, for biopsy and/or for removal of damaged, diseased, or otherwise unwanted tissue. The active portion can include one or more tools, especially surgical tools, e.g., for cutting, scraping, suturing, cauterizing, or injecting or aspirating. An example of a scraping tool is presented in JP 2005-74229, which is incorporated herein by reference. Other examples of biopsy tools associated with intralumenal devices are described in US Patent Application 2009/0069821 and U.S. Pat. No. 6,679,893, each of which is incorporated herein by reference.

In an embodiment, the active portion of the lumen traveling device can include a fluid capture portion operatively coupled to the response control circuitry and configured to capture a material of interest. A fluid capture portion can be a reservoir, for example, into which fluid is drawn by capillary action or by a negative pressure generated by a pump, for example. Captured fluid can be treated and released, or simply stored. In some applications, captured fluid may be subjected to analysis as described in U.S. Patent Application 2009/0082652, which is incorporated herein by reference. Fluid and/or constituents thereof, including cells or other biologics, can be passively collected within a matrix material associated with the lumen traveling device. The matrix material can include an absorbent such as cotton, cellulose, natural or artificial sponge, a gel (e.g., a natural gel such as agarose, a natural and/or synthetic polymer gel, or a hydrogel), a colloid, a gum base such as acacia gum, or micro particles. The sample collection portion can include a lipid monolayer, lipid bilayer, liposome, dendrimer, ligand affinity resin with conjugated peptide or antibody, ionophore, hydrosol, sol-gel, xerogel, aerogel, smart gel, hydrocarbon gel, or ferrogel. Alternatively, the sample collector can include a synthetic or natural adsorbent material such as a proteoglycan or charged polymer like polylysine, that promotes the adhesion of one or more fluid constituent, e.g. a cell or protein. Other materials include semi-specific or non-specific absorbers, such as silica ($SiO_2$) or alumina ($Al_2O_3$) gel or ion exchange resin, possibly as part of the matrix material. Further examples of materials for sample collection are disclosed in U.S. Pat. Nos. 6,861,001 and 6,475,639, each of which is incorporated herein by reference. Alternatively or in addition, the sample collector can include one or more recognition elements of a type able to recognize and/or specifically bind a constituent of the fluid. Examples of recognition elements include but are not limited to, staphylococcus protein A complex, which generally binds immunoglobulins; a binding peptide or protein like an immunoglobulin; a ligand; a receptor; a nucleic acid; a carbohydrate; a lipid; a conjugate; or a synthetic molecule like an artificial antibody or other mimetic. U.S. Pat. Nos. 6,255,361; 5,804,563; 6,797,522; and 5,831,012 and U.S. Patent Application 2004/0018508, each of which is incorporated herein by reference provide examples of such mimetics.

In an embodiment, the active portion of the lumen traveling device can be configured to suture a portion of the lumen of a body tube tree. Various examples of suturing tools are disclosed and described in U.S. Pat. Nos. 7,131,979 and 5,964,773, each of which is incorporated herein by reference. Tools may be micro-scale tools formed by MEMS manufacturing techniques, for example, as described in U.S. Pat. No. 5,728,089, which is incorporated herein by reference. It will be appreciated that various other active portions disclosed herein may also have surgical utility: for example, active portions for performing sample collection, material release, heating, cooling, etc. may all have surgical applications.

In an embodiment, the active portion of a lumen traveling device can include an attachment structure operatively coupled to the response control circuitry and configured to attach to a structure (particularly a man-made structure) present in the body lumen in response to receipt of the response control signal. The attachment structure can include various mechanical mechanisms, e.g., a grasper or hook, or be based on magnetic attraction, electrostatic forces, chemical bonding, surface interactions, etc. MicroScale structures for gripping or grasping are described in U.S. Pat. No. 6,398,280; and Leong et al., *Proc. Natl. Acad. Sci. USA,* 2009, 106:703-708, each of which is incorporated herein by reference.

Figure 7:
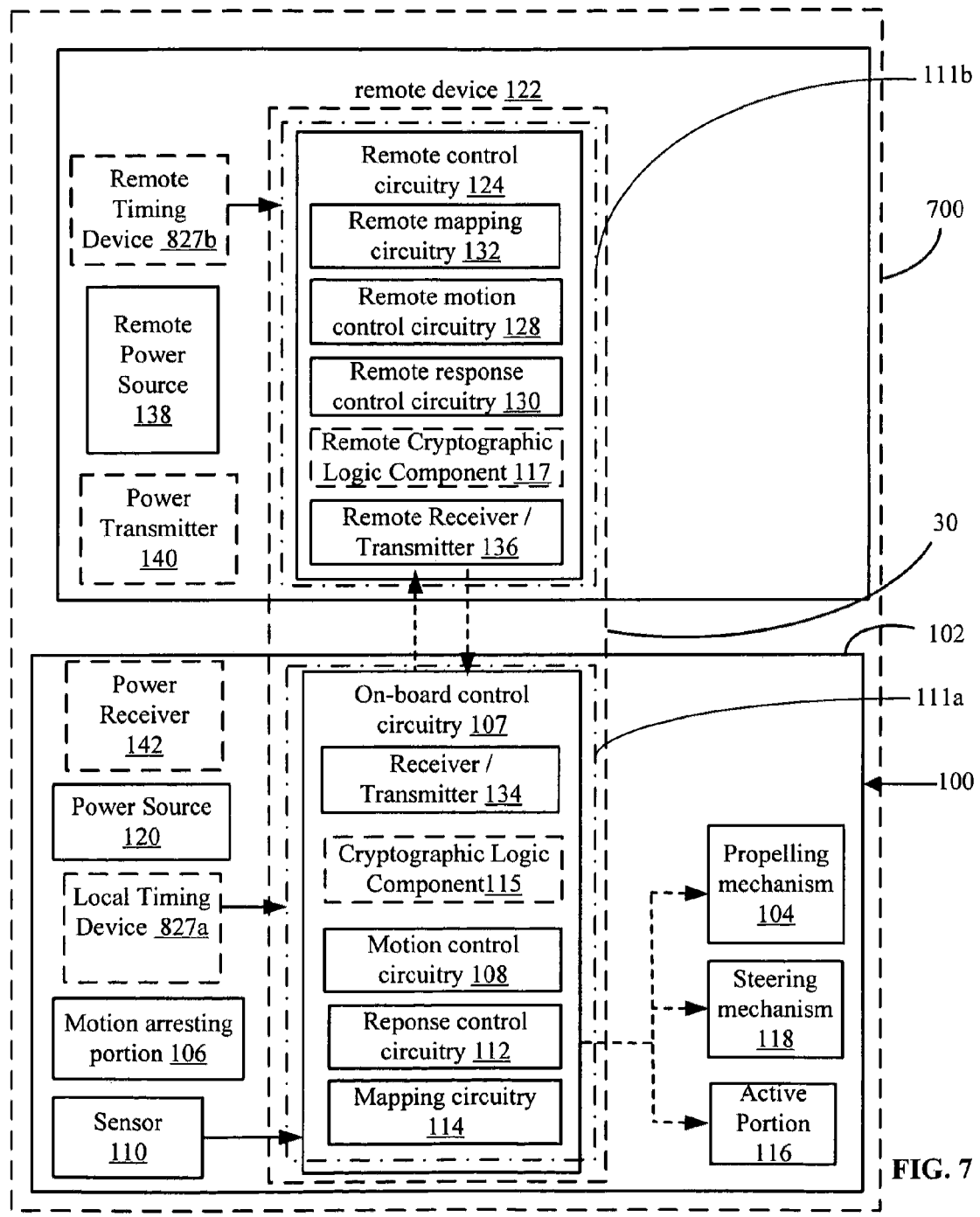
FIG. 7 illustrates an embodiment of a lumen traveling device system including a remote device.

The active portion as well as other operational components of the lumen traveling device is operatively coupled to the control circuitry. In an embodiment, as depicted in FIG. 7, at least a portion of the control circuitry that controls the operation of lumen traveling device 100 is located in remote device 122, outside the body of the subject, or at a location within the body of the subject at a distance from the lumen traveling device. In the embodiment depicted in FIG. 7, lumen traveling device system 700 includes lumen traveling device 100 and remote device 122. In general, a lumen traveling device system includes at least one lumen traveling device and at least one remote device, and in some embodiments can include multiple lumen traveling devices and/or multiple remote devices. Lumen traveling device control system 30 is thus distributed between lumen traveling device 100 and remote device 122.

In the embodiment of FIG. 7, lumen traveling device 100 includes a fluid-contacting portion 102 configured to contact fluid within the lumen of the body tube tree and to at least intermittently permit flow of fluid through the lumen; a propelling mechanism 104 capable of producing movement of the lumen traveling device through the lumen of a body tube tree in which the lumen traveling device is deployed; a motion arresting portion 106 capable of stopping the movement of the lumen traveling device; motion control circuitry 108 carried at least in part by said lumen traveling device and configured to control propelling mechanism 104 and motion arresting portion 106 to control movement of the lumen traveling device through the lumen of a body tube tree; a sensor 110 capable of sensing a local parameter value in the lumen of a body tube tree and generating a sense signal indicating detection of the local parameter value; response control circuitry 112 operatively connected to sensor 110 and configured to generate a response control signal upon receipt of the sense signal indicating detection of a local parameter value in the lumen of a body tube tree; mapping circuitry 114 operatively connected to motion control circuitry 108 and configured to inform control of movement in the body tube tree based at least in part on a map of the body tube tree; and an active portion 116 operatively connected to response control circuitry 112 and capable of producing a response upon receipt of the response control signal. Motion control circuitry 108, response control circuitry 112, and mapping circuitry 114 make up part of on-board control circuitry 107, which may also include other components not specifically described herein. The embodiment of FIG. 7 also includes a steering mechanism 118 capable of modifying the direction of movement of the lumen traveling device; wherein the motion control circuitry 108 can be configured to control the steering mechanism 118 to control movement of the lumen traveling device through the body tube tree. The embodiment of FIG. 7 includes power source 120 configured to provide power to at least one of propelling mechanism 104, motion arresting portion 106, steering mechanism 118, motion control circuitry 108, mapping circuitry 114, sensor 110, response control circuitry 112 and active portion 116. At least a portion of the control circuitry for lumen traveling device 100 can be remote control circuitry 124 located remote from lumen traveling device 100 in remote device 122. Remote control circuitry 124 can include a remote portion of the motion control circuitry, remote motion control circuitry 128, a remote portion of the response control circuitry, remote response control circuitry 130, and a remote portion of the mapping circuitry, remote mapping circuitry 132. Lumen traveling device 100 can include receiver/transmitter 134 with data reception and/or transmission circuitry configured to receive a wireless control signal from remote motion control circuitry 128, transmitted from remote receiver/transmitter 136. Receiver/transmitter 134 and remote receiver/transmitter 136 are parts of on-board control circuitry 107 and remote control circuitry 124, respectively. As shown in FIG. 7, lumen traveling device control system 30 includes remote control circuitry 124 and on-board control circuitry 107.

Lumen traveling device control system 30 may include non-transitory machine readable media 111*a*, which stores instructions and/or data for implementation of/use by on-board control circuitry 107 and non-transitory machine readable media 111*b*, which stores instructions and/or data for implementation of/use by remote control circuitry 124. Data, e.g., sensed parameter values, device location, etc., can be transmitted from lumen traveling device 100 to remote device 122 via receiver/transmitter 134. Remote device 122 includes a remote power source 138. In some embodiments, power can be transmitted to lumen traveling device 100 from remote device 122 via power transmitter 140 and power received 142. An example of a telemetry communication system using radiofrequency (RF) is described in Sun et al., *J. Med. Eng. Technol.*, 2003, 27:160-163, which is incorporated herein by reference.

In an embodiment of lumen traveling devices or systems, a lumen traveling device can be a self-contained device that includes all functionalities necessary for operation of the lumen traveling device, as illustrated in FIG. 2. In another embodiment, as illustrated in FIG. 7, a lumen traveling device system can include a lumen traveling device 100 configured to for placement in a body lumen, and at least one remote device 122 configured to perform at least some of the functionalities of the lumen traveling device system. The lumen traveling device control system 30 is located in part in lumen traveling device 100 and in part in one or more remote devices 122; e.g., lumen traveling device control system 30 includes on-board control circuitry 107 and remote control circuitry 124. In an embodiment, all functionalities essential for the operation of the lumen traveling device are located on the lumen traveling device in on-board control circuitry 107, with a subset of auxiliary functions located in the remote device in remote control circuitry 124. For example, the remote device 122, including remote control circuitry 124, can provide monitoring of the operation of the lumen traveling device, data collection or analysis and/or map building. Remote device 122 can be located within the body of the subject at a distance from the lumen traveling device, or outside the body of the subject. The remote device 122 can be located near the subject (e.g., carried or worn on the subject's body or placed on a table near the subject) or distant from the subject (e.g. in a different room or building, or in a different city, state or country). In an embodiment, the remote device can include a computing device, and can be a cell phone, mobile device, remote controller, a personal digital assistant (PDA), or other handheld device. In an embodiment, the remote device can be a computer system such as, for example, a laptop computer, computer pad, or a computer work station.

Lumen traveling device system 700 can include one or more timing devices, for example one or both of local timing device 827*a* on lumen traveling device 100 and remote timing device 827*b* on remote device 122. Local timing device 827*a* can form a part of on-board control circuitry 107, and similarly, remote timing device 827*b* can form a part of remote control circuitry 124.

Lumen traveling device 100 can include a transmitter and receiver (receiver/transmitter 134) operatively coupled to the control circuitry and configured to communicate with one or more remote devices 122. Data and/or power signals can be transmitted between lumen traveling device 100 and one or more remote devices 122 using electromagnetic or acoustic signals, or can be carried over electrical or optical links. It will be appreciated that by using a wireless link between the lumen traveling device 100 and remote device 122 lumen traveling device 100 can function as an untethered device that can move freely within the body without connecting cables, wires, lines, catheters, etc. Various types and/or combinations of types of communications methods and devices may be used, as are known to those of skill in the art. Transmission of information between lumen traveling device 100 and one or more remote devices 122 can be via multiple communication channels, in series or in parallel. In an embodiment, the remote device can be placed in a location where there is more space available than within the lumen of the body tube tree, or that is more readily accessible than the lumen of the body tube tree and can include a portion of the electrical circuitry portion of the lumen traveling device control system (e.g., hardware, firmware, software, or any combination thereof).

Communication of information between lumen traveling device 100 and at least one remote device 122 (e.g., via receiver/transmitter 134 and remote receiver/transmitter 136) can include communicating an image, communicating a sensed parameter value, communicating a measured parameter value, communicating a derived parameter value, communicating device status information, or communicating an action performed. The information transmitted by lumen traveling device 100 to a remote device 122 can be used to inform a medical caregiver about a condition of the subject so that suitable treatment may be provided by the caregiver. In some embodiments, the information transmitted by the lumen traveling device 100 to the remote device 122 can contain information usable by a lumen traveling device control system to control operation of the lumen traveling device 100. The information transmitted by the lumen traveling device 100 to a remote device 122 can also include information regarding the movement and location of the lumen traveling device 100 to aid in development of a map of the body tube tree by the remote device, e.g. by remote mapping circuitry 132.

The lumen traveling device 100 can further include a receiver coupled to the control circuitry and configured to receive a communication from one or more remote devices 122. Information communicated from the remote device 122 to the lumen traveling device 100 can include, but is not limited to, operating instructions, a map of a body tube tree, and/or image data or other parameter data collected by at least one remote device 122. In an embodiment, information can be transmitted to the lumen traveling device 100 by the remote device 122 in response to communications received from the lumen traveling device 100. In an embodiment, a medical caregiver can control communications to the lumen traveling device 100, sending specific instructions and information to the lumen traveling device 100 through the remote device. Implantable medical devices with wireless communication capabilities have been described (see, e.g., U.S. Pat. Nos. 6,263,245 and 7,486,967; U.S. Pat. Application 2009/0182388, each of which is incorporated herein by reference). Instructions, data, or other signals transmitted between a remote source (e.g., remote device 122) and lumen traveling device 100 can be encrypted. The lumen traveling device system 700 can include, lumen traveling device 100 including for example, but not limited to, one or more cryptographic logic component 115. Similarly, Remote device 122 can include remote cryptographic logic component 117. In an embodiment, at least one of the one or more cryptographic logic components 115 and 117 is configured to implement at least one cryptographic process, or cryptographic logic, or combinations thereof. Examples of a cryptographic process include, but are not limited to one or more process associated with cryptographic protocols, decryption protocols, encryption protocols, regulatory compliance protocols (e.g., FDA regulatory compliance protocols, or the like), regulatory use protocols, authentication protocols, authorization protocols, delivery protocols, activation protocols, encryption protocols, decryption protocols, and the like. Examples of a cryptographic logic include one or more crypto-algorithms signal-bearing media, crypto controllers (e.g., crypto-processors), cryptographic modules (e.g., hardware, firmware, or software, or combinations thereof for implementing cryptographic logic, or cryptographic processes), and the like. See, for example, Hosseini-Khayat, S., "A lightweight Security Protocoal for Ultra-low Power ASIC Implementation for Wireless Implantable Medical Devices," 2011 *Symposium on Medical Information and Communication Technology (IS-MICT)*, pages 6-9, 27-30 Mar. 2011, and Rasmussen, K. R., et al., "Proximity-based Access Control for Implantable Medical Devices," CCS '09, Proceedings of the 16$^{th}$ ACM Conference on Computer and Communications Security, Nov. 9-13, 2009, each of which is incorporated herein by reference.

Figure 8:
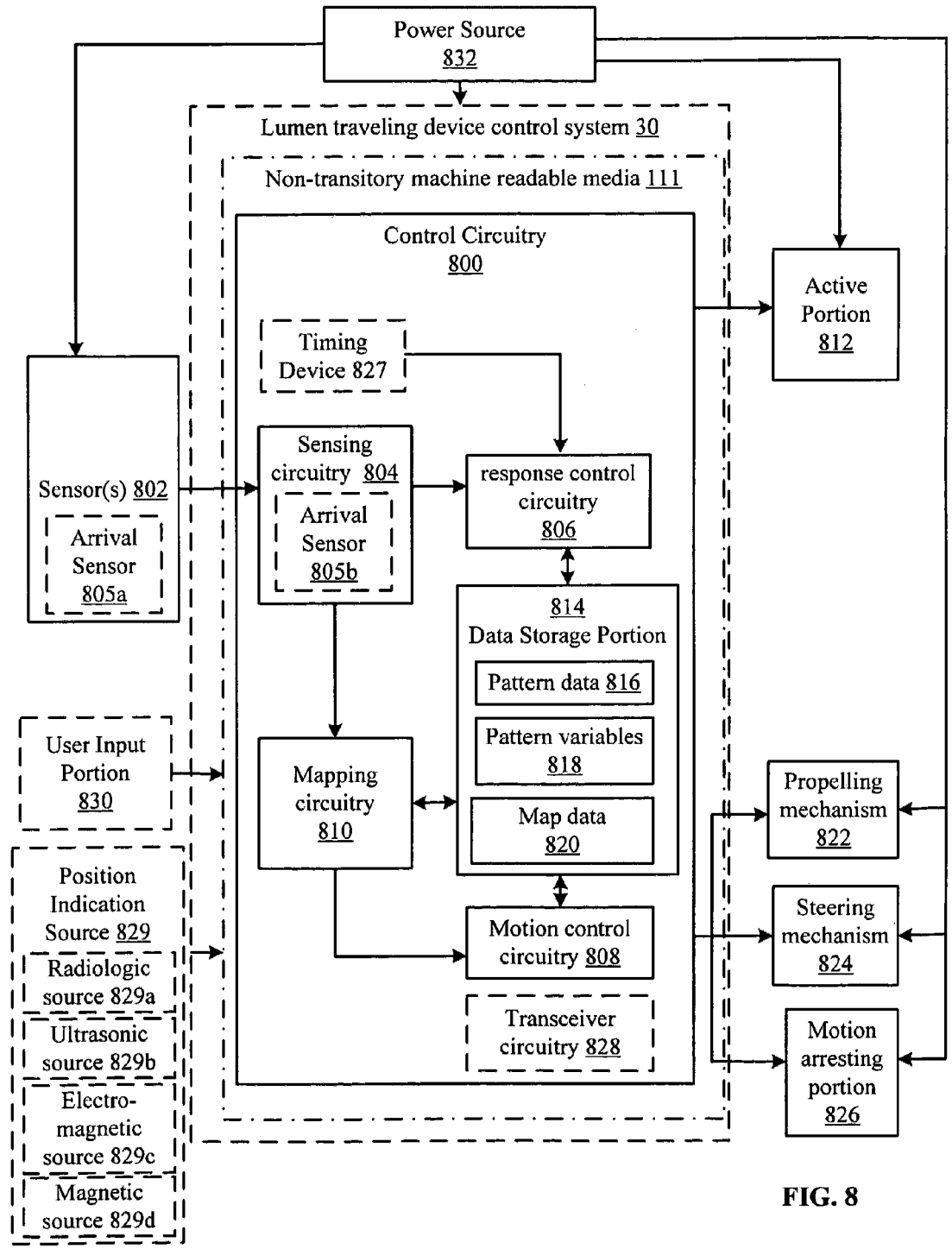
FIG. 8 illustrates an embodiment of control circuitry of a lumen-travel device system.

FIG. 8 is a block diagram illustrating in greater detail various circuitry components of a lumen traveling device system including lumen traveling device control system 30. As discussed elsewhere herein, the circuitry components of lumen traveling device control system 30 can be located entirely on the lumen traveling device, or can be distributed between the lumen traveling device and one or more remote devices that along with the lumen traveling device form a lumen traveling device system. Lumen traveling device control system 30 includes non-transitory machine readable media 111, which stores instructions and/or data for implementation of/use by control circuitry 800 and lumen traveling device control system 30. The control circuitry 800 of the lumen traveling device control system 30 is operationally linked to one or more sensor(s) 802. At least a portion of the one or more sensor(s) 802 are associated with the lumen traveling device, with a remote device, or a combination thereof. The signal generated by sensor(s) 802 may be transmitted to sensing circuitry 804, a component of control circuitry 800. Sensor(s) 802 can include arrival sensor 805a for detecting arrival of the lumen traveling device at a branch point in the body tube tree. Alternatively, or in addition, sensing circuitry 804 can include all or a portion of arrival sensor 805b, which may be, for example, processing circuitry configured to process signals from sensor(s) 802 to determine arrival of the lumen traveling device at a branch point in the body tube tree. In addition to sensing circuitry 804, the control circuitry 800 of the lumen traveling device control system 30 may include response control circuitry 806, motion control circuitry 808, and mapping circuitry 810. Response control circuitry 806 provides a response control signal to active portion 812. Motion control circuitry 808 provides control of propelling mechanism 822, and optionally steering mechanism 824 and/or motion arresting portion 826. Mapping circuitry 810 is operatively connected to motion control circuitry 808 and configured to control movement in the body tube tree based at least in part on a map of the body tube tree. Control circuitry 800 also includes data storage portion 814, which can, for example, be used to store pattern data 816 or pattern variables 818 for determining an activation pattern of active portion 812. Data storage portion 814 can also store map data 820, including, for example, a map of some or all of the relevant body tube tree(s) of the subject, the location of one or more target locations or landmarks on the map, and/or the current location of the lumen traveling device relative to the map. Map data 820 stored in data storage portion 814 can also include data relating to one or more pre-determined motion patterns for use by mapping circuitry 810 and motion control circuitry 808 to control movement of the lumen traveling device in a pre-determined pattern. Control circuitry 800 further includes transceiver circuitry 828, which provides for the transmission and reception of data and/or power signals between the lumen traveling device and one or more remote devices or external devices (e.g., monitoring or recording equipment). Control circuitry 800 can optionally include one or more timing device 827, which can be on board a lumen traveling device or on a remote device, e.g., as depicted in FIG. 7. In some embodiments, control circuitry 800 may alternatively, or in addition, receive a timing signal containing information relating to an absolute or relative time measure from a remote source. A timing signal may be received by sensor(s) 802, or by transceiver circuitry 828. Optionally, transceiver circuitry 828 can also receive one or more position indicator signal from position indication source(s) 829, which may be a radiologic source 829a, an ultrasonic source 829b, an electromagnetic source 829c (including but not limited to an RF beacon, a cellular communication source, a satellite communication source, a GPS, a personal area network, or a body area network), or a magnetic source 829d, for example. A user input portion 830 provides for the input of user instructions, parameters, and/or external data to control circuitry 800. Finally, one or more power source 832 is configured to provide power to at least one of the sensor, control circuitry, propelling mechanism, steering mechanism, motion arresting portion, and active portion. Some components of the lumen traveling device can be operated in whole or in part under software control, and control circuitry 800 can include hardware, software, firmware, or various combinations thereof. The lumen traveling device can include components that are primarily hardware-based, e.g., sensor 802, active portion 812, propelling mechanism 822, steering mechanism 824, motion arresting portion 826 and, optionally, user input portion 830. Hardware-based devices can include components that are electrical, mechanical, chemical, optical, electromechanical, electrochemical, electro-optical, and are not limited to the specific examples presented herein. As described elsewhere, portions of the control circuitry, including, for example, the motion control circuitry, the response control circuitry, and the mapping circuitry can be located entirely in or on the structural element of the lumen traveling device or can be located in part associated in a remote device.

A power source 832 as depicted in FIG. 8 can include one or more of a battery or microbattery, a fuel cell or biofuel cell, or a nuclear battery. One or more power sources of the same or different types can be included in the lumen traveling device, without limitation. Batteries can be located on the lumen traveling device, possibly a microbattery like those available from Quallion LLC (Sylmar, Calif.) or of the type designed as a film (U.S. Pat. Nos. 5,338,625 and 5,705,293), each of which is incorporated herein by reference. Alternatively, the power source could be one or more fuel cell such as an enzymatic, microbial, or photosynthetic fuel cell or other biofuel cell (US2003/0152823A1; WO03/106966A2; or Chen, T. et al., *J. Am. Chem. Soc.*, 2001, 123:8630-8631, each of which is incorporated herein by reference), and could be of any size, including the micro- or nano-scale. In an embodiment, the power source can include laterally packaged piezoelectric fine wires that convert biomechanical energy (e.g., stretching muscles, beating heart, walking) into electrical energy using a nanogenerator (see, e.g., Yang et al., *Nature Nanotechnol.*, 2009, 4:34-39 or Yang et al., *Nano Lett.*, 2009, 9:1201-1205, each of which is incorporated herein by reference). In another embodiment, the power source can include a pressure-rectifying mechanism that utilizes pulsatile changes in blood pressure or an acceleration-rectifying mechanism as used in self-winding watches, or other types of flow-rectifying mechanism capable of deriving energy from other flow parameters. In an embodiment, the power source can be a nuclear battery (see, e.g., Wacharasindhu et al., *Appl. Phys. Lett.*, 2009, 95:014103, which is incorporated herein by reference).

In an embodiment, the power source can be located remote from the structural element and can include an electrical power source connected to the structural element by a wire, an optical power source connected to the structural element by a fiber-optic line or cable, or a power receiver capable of receiving power from an acoustic source or electromagnetic source (e.g., infrared energy, or inductively coupled, as described in U.S. Pat. Nos. 6,170,488, and 7,212,110; U.S. Patent Application No. 2005/0228259; and Budgett et al., *J. Appl. Physiol.*, 2007, 102:1658-1663, each of which is incorporated herein by reference). In an embodiment, the lumen traveling device can include a power transmitter capable of transmitting power (e.g., acoustic power, electrical power, or optical power) from the lumen traveling device to a secondary location. The secondary location can be, for example, another device within the body, either in a body lumen or elsewhere, which includes a power receiver and structures for using, storing and/or re-transmitting the received power. A remote device of a lumen traveling device system can include its own power supply, whether or not it supplies power to a lumen traveling device.

Figure 9:
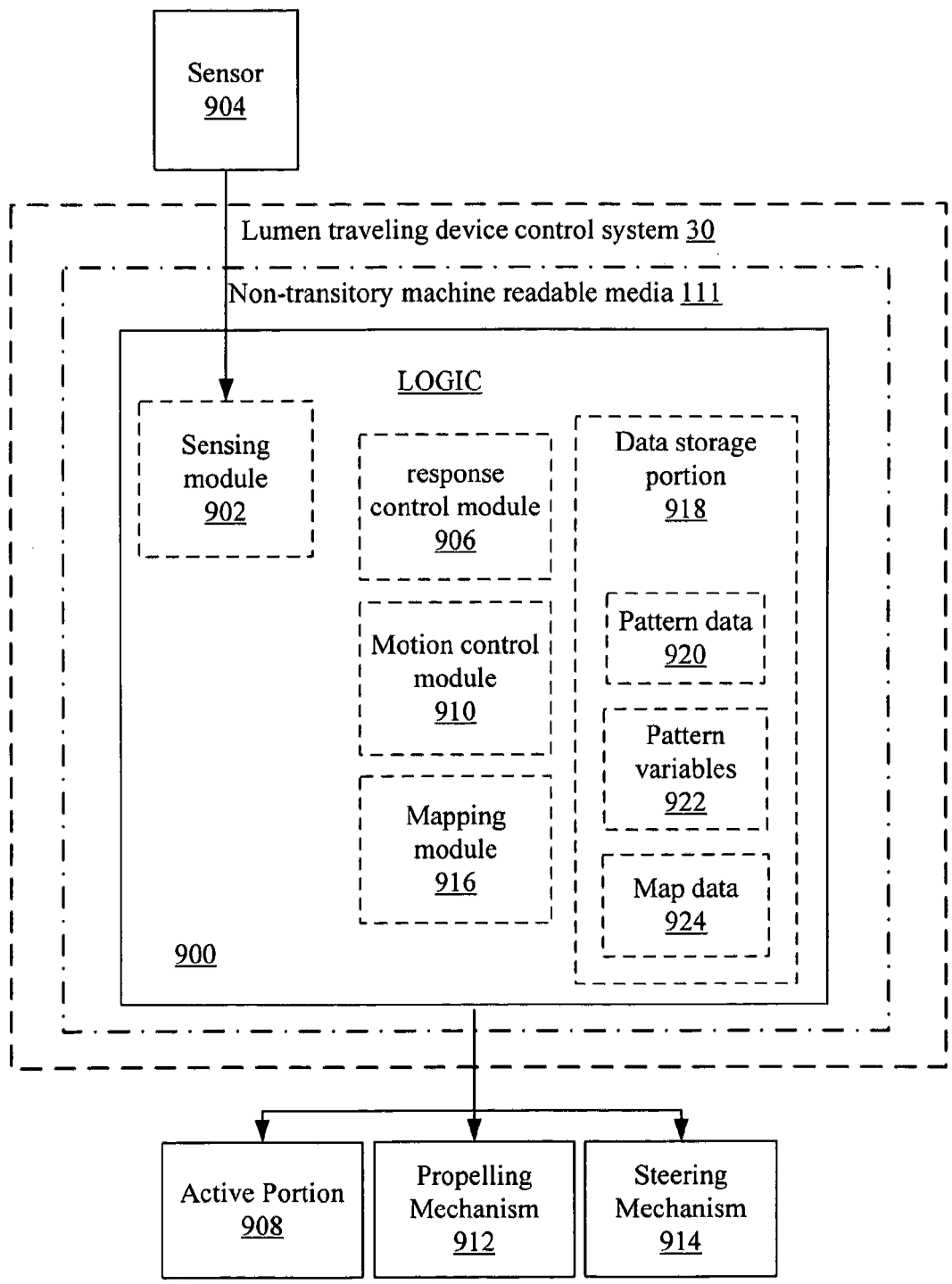
FIG. 9 illustrates an embodiment of logic for controlling a lumen traveling device system.

The lumen traveling device control system of the lumen traveling device, including on-board and/or remote control circuitry, as depicted in FIG. 8 can be implemented at least in part in the form of logic, including analog or digital logic circuitry and software, or a combination thereof. FIG. 9 depicts logic modules (which may include software or hardware) for use in lumen traveling device control system 30 as described herein. As shown in FIG. 9, logic 900 for controlling a lumen traveling device, can include, for example, a sensing module 902 capable of processing an input from a sensor 904 on the lumen traveling device to generate a sense signal indicating detection of a parameter value in the lumen of a body tube tree of an organism; a response control module 906 capable of receiving and processing the sense signal from the sensing module 902 and based at least in part upon the sense signal generating a response control signal configured for causing an action to be performed in the lumen of the body tube tree by an active portion 908 of the lumen traveling device; and a motion control module 910 capable of generating a signal for controlling at least one of a propelling mechanism 912 and a steering mechanism 914 on the lumen traveling device to control direction or rate of movement of the lumen traveling device through the body tube tree. The logic 900 for controlling a lumen traveling device can further include a mapping module 916 capable of receiving information from the sensing module 902 and configured to locate the lumen traveling device on an existing map of the body tube tree or to generate a map de novo of the body tube tree based at least in part upon the sense signal. The mapping module 916 is further capable of providing information to motion control module 910. Motion control module 910 is capable of producing an analog or digital signal that controls at least one of a propelling mechanism 912 and a steering mechanism 914 on the lumen traveling device. Control of the direction or rate of movement of the lumen traveling device can be based at least in part upon a map of the body tube tree. The mapping module 916 can include logic for constructing, extending, or refining at least one map, based on sensed parameter values and/or determining the location of the lumen traveling device on a map. Data storage portion 918, which may be, for example, a memory location on the lumen traveling device (like data storage portion 814 in FIG. 8) can contain pattern data 920, pattern variables 922, and map data 924. Map data 924 can include data representing a map generated by mapping module 916. Pattern data 920 and pattern variables 922 stored in data storage portion 918 can be used in the generation of or for directing operation of at least one of propelling mechanism 912 and steering mechanism 914, and/or in the generation of response control signals used in the control of active portion 908. For example, if the active portion 908 releases a drug, pattern data 920 can include a pattern for the rate of drug release over time, e.g. with the pattern including an array of data points in which each data point represents the rate of drug release at a particular time. Pattern variables 922 can include variables used for generating a pattern of action taken by the active portion. For example, variables can include duration and frequency of occurrence of pulses of drug release. Logic 900 may be implemented in digital circuitry, analog circuitry, software, or combinations thereof.

Data storage portions (e.g., data storage portion 918 and data storage portion 814 and other data storage portions or structures described elsewhere herein) can include various types of non-transitory machine readable media 111 for use in a lumen traveling device control system. In addition, other portions of lumen traveling device control system 30, including logic 900, may be stored in or implemented in non-transitory machine readable media 111, as depicted in FIG. 9.

Non-transitory machine readable media 111 as depicted in, e.g., FIGS., 2, 7, 8, 9, and 10, can be located on-board lumen traveling device or at least in part on a lumen traveling device and in part on one or more remote device, e.g. as depicted in FIG. 7, and can include any media that can be accessed by control circuitry and logic of the lumen traveling device, and/or remote devices. By way of example, and not of limitation, non-transitory machine readable media 111 can be computer readable media. By way of further example, non-transitory machine 111 readable media can be recordable-type media. Computer readable media may also be recordable-type media, and the qualities of being "computer readable" and "recordable-type" should not be construed as being mutually exclusive, though in some cases a computer readable media may not be a recordable-type media, and vice versa. Machine readable media include volatile and nonvolatile, removable and non-removable media implemented in any method or technology for storage of information such as machine readable instructions, data structures, program modules, or other data. Non-transitory machine readable media include, but are not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other media which can be used to store the desired information and which can be accessed by control circuitry 800 and/or logic 900, and/or be used in the implementation of logic 900. In a further embodiment, computer storage media may include a group of computer storage media devices. In an embodiment, machine readable media may include an information store. In an embodiment, an information store may include a quantum memory, a photonic quantum memory, or atomic quantum memory. Combinations of any of the above may also be included within the scope of non-transitory machine readable media. Machine readable media can be located on a lumen traveling device configured for placement in a body lumen. In an embodiment, machine readable media can be located at least in part on a lumen traveling device and at least in part on and one or more remote devices configured to perform at least some of the functionalities of the lumen traveling device control system 30, e.g. as depicted in and described in connection with FIG. 7.

Communication media may embody machine readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media may include wired media, such as a wired network and a direct-wired connection, and wireless media such as acoustic, RF, optical, and infrared media. Examples of communication media include digital and/or analog communication media (e.g., a fiber optic cable, a waveguide, a wired communications link, or a wireless communication link (e.g., transmitter, receiver, transmission logic, reception logic, etc.), etc.). Communication media can carry data between portions or components of a lumen traveling device, between a lumen traveling device and one or more remote devices, and/or between two or more remote devices. In some embodiments, machine readable instructions, data structures, program modules, or other data used in methods and systems as described herein can be implemented or distributed via communication media.

In a general sense, the various aspects described herein can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

In some embodiments described herein, logic and similar implementations may include software or other control structures suitable for operating the lumen traveling device. Electrical circuitry, for example, may include one or more paths of electrical current constructed and arranged to implement various logic functions as described herein. In some embodiments, one or more non-transitory machine readable media for use in a lumen traveling device control system are configured to bear an implementation detectable by a lumen traveling device including, for example, an instruction set for a lumen traveling device. In some embodiments, the non-transitory machine readable media is carried by the lumen traveling device. In other embodiments, the non-transitory machine readable media is carried in part by the lumen traveling device and in part by a remote device. The non-transitory machine readable media can include but is not limited to computer readable media, including, for example, non-volatile memory (e.g., ROM, PROM, EPROM, EEPROM, and Flash memory). In some variants, an implementation may include special-purpose hardware, software, firmware components, and/or general-purpose components executing or otherwise invoking special-purpose components. Logic and/or other implementations for operating a lumen traveling device can include logic and/or other implementations relating to update or other modification of existing software or firmware, or of gate arrays or other programmable hardware, by a reception of or a transmission of one or more instructions in relation to one or more operations of a lumen traveling device and/or remote device as described herein.

In some embodiments, logic and similar implementations may include executing a special-purpose instruction sequence or otherwise invoking circuitry for enabling, triggering, coordinating, requesting, or otherwise causing one or more occurrences of any of the sensing, responding, performing, moving and mapping operations of the lumen traveling device as described herein. In some variants, operational or other logical descriptions may be expressed directly as source code and compiled or otherwise used as an executable sequence of instructions. In some embodiments, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may include Verilog-type hardware description or other circuitry model before physical implementation in hardware.

Figure 10:
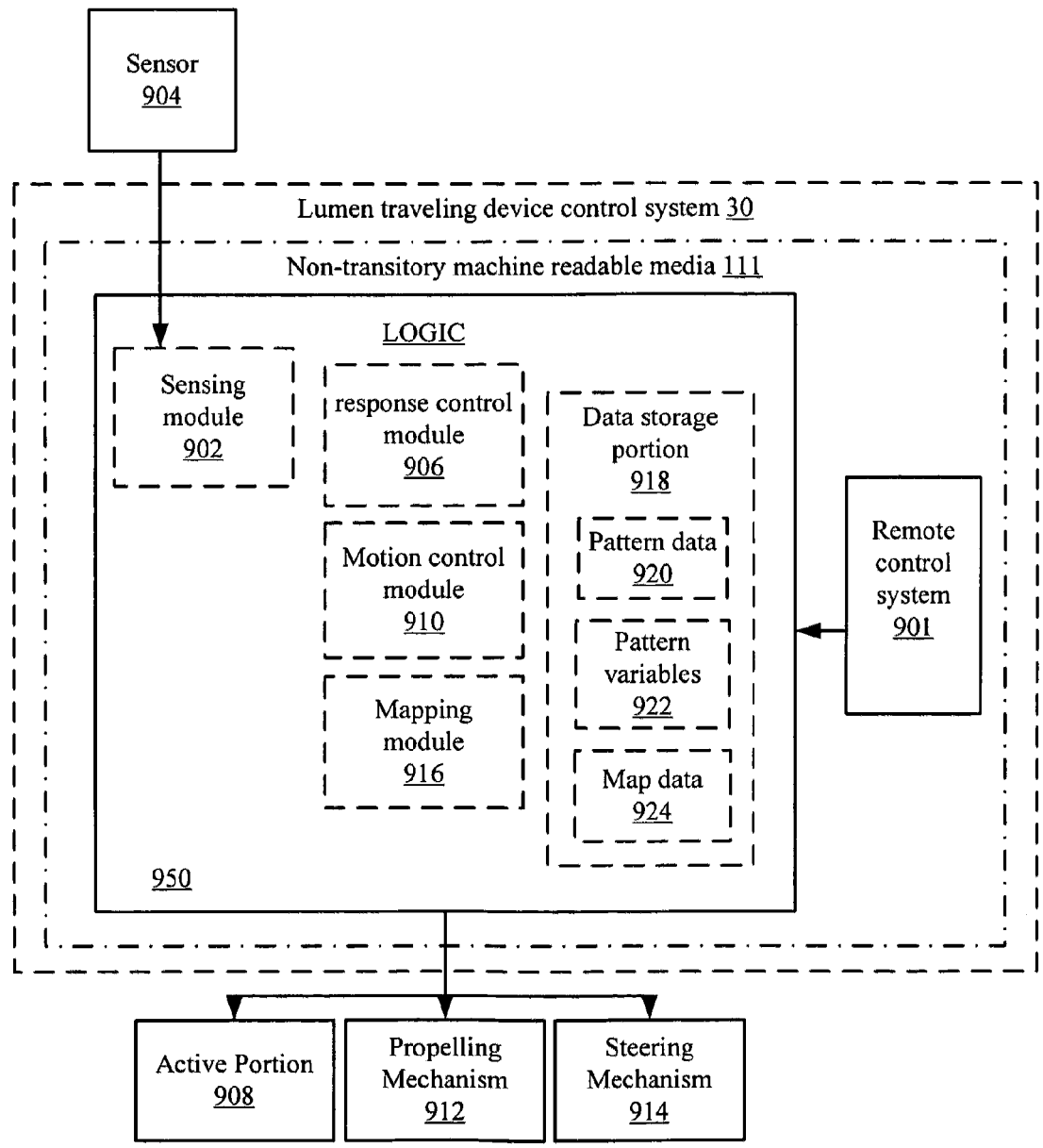
FIG. 10 illustrates an embodiment of logic for controlling a lumen traveling device.

In an embodiment shown in FIG. 10, lumen traveling device control system 30 includes motion control module 910 capable of controlling at least one of a propelling mechanism 912 and a steering mechanism 914 on the lumen traveling device based at least in part upon a motion control signal from a remote control system 901. Otherwise, the logic 950 is like that shown in FIG. 9, including sensing module 902 capable of processing an input from a sensor 904 on the lumen traveling device to generate a sense signal indicating detection of a parameter value in a lumen of a body tube tree of an organism; a response control module 906 capable of receiving the sense signal from the sensing module 902 and based at least in part upon the sense signal generating a response control signal configured for causing an action to be performed in the lumen of the body tube tree by an active portion 908 of the lumen traveling device; a motion control module 910 capable of controlling at least one of a propelling mechanism 912 and a steering mechanism 914 on the lumen traveling device to control direction or rate of movement of the lumen traveling device through the body tube tree; and a mapping module 916 capable of receiving data from a sensing module 902 and informing a motion control module 910 regarding the current location of the lumen traveling device on a map of a body tube tree. The mapping module 916 can further include control logic that uses a pre-programmed pattern which may be stored in a memory location on the lumen traveling device (like data storage portion 814 in FIG. 8). The logic 950 can include a data storage portion 918 that includes pattern data 920, pattern variables 922, and map data 924. The remote control system 901 may be operated by an operator such as, for example, a medical caregiver. In some embodiments, the remote control system 901 may be under complete control of remote device such as, for example, a general computer or microprocessor that receives data from the lumen traveling device, processes the data, and transmits an appropriate set of operational instructions to the lumen traveling device based on the data received. Logic and other aspects of lumen traveling device control system 30 can be stored in/implemented in non-transitory machine readable media 111 included in the lumen traveling device and/or remote control system 901.

At least a portion of the devices and/or processes described herein can be used in connection with an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

In some embodiments, the lumen traveling device may be used in connection with a data processing system. The data processing system may include one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The functionalities of the lumen traveling device control system can be distributed between hardware, firmware, and software located at two or more sites. An electrical circuitry portion of the lumen traveling device control system can include, but is not limited to, electrical circuitry associated with the sensor, control circuitry, and electronics associated with the propelling mechanism, steering mechanism, motion arresting portion, and active portion. While the control circuitry has been discussed within the context of electrical circuitry, it will be appreciated that in some embodiments other types of logic/circuitry can be used in place of or in addition to electrical circuitry, and the control circuitry described herein is not limited to electrical circuitry. For example, fluid circuitry, chemo-mechanical circuitry, and other types of logic/circuitry can provide equivalent functionality.

The lumen traveling device with control circuitry, logic and other components described herein can be part of a system that includes non-transitory machine readable media for use in a lumen traveling device control system including one or more instructions that cause the lumen traveling device control system to operate the lumen traveling device in the body tube tree of a subject.

FIG. 11 illustrates a block diagram of a system 1100 that includes a set of instructions 1104 for operating a lumen traveling device. An embodiment of system 1100 is provided using non-transitory machine readable media for use in a lumen traveling device control system 1102 including a set of instructions 1104 including one or more instructions that cause the lumen traveling device control system to activate a propelling mechanism on a lumen traveling device to propel the lumen traveling device within a body tube tree; one or more instructions that cause the lumen traveling device control system to determine an arrival of the lumen traveling device at a branch point in the body tube tree based upon a signal from at least one arrival sensor on the lumen traveling device, the branch point including at least two branch channels; one or more instructions that cause the lumen traveling device control system to select one of the at least two branch channels substantially randomly; one or more instructions that cause the lumen traveling device control system to direct the propelling mechanism on the lumen traveling device to move the lumen traveling device into the selected branch channel; one or more instructions that cause the lumen traveling device control system to store information regarding at least one of the at least two branch channels; one or more instructions that cause the lumen traveling device control system to direct the sensing of a local parameter value from a parameter sensor on the lumen traveling device; and one or more instructions that cause the lumen traveling device control system to direct an active portion of the lumen traveling device to perform an action based at least in part upon the local parameter value. The one or more instructions can be, for example, computer executable and/or logic-implemented instructions. The non-transitory machine readable media 1102 can include computer readable media 1106, or recordable-type media 1108, for example.

The system described herein includes non-transitory machine readable media for use in a lumen traveling device control system including one or more instructions relating to operation of a lumen traveling device in a body tube tree. In an embodiment, the non-transitory machine readable media is carried by the lumen traveling device. In a further embodiment, the non-transitory machine readable media is carried in part by the lumen traveling device and in part by a remote device. The non-transitory machine readable media can include computer readable media, which may be, for example, recordable-type media. In some instance, the non-transitory machine readable media carried by the lumen traveling device can include non-volatile memory selected from a ROM, PROM, EPROM, EEPROM, Flash memory, or the like.

Figure 12:
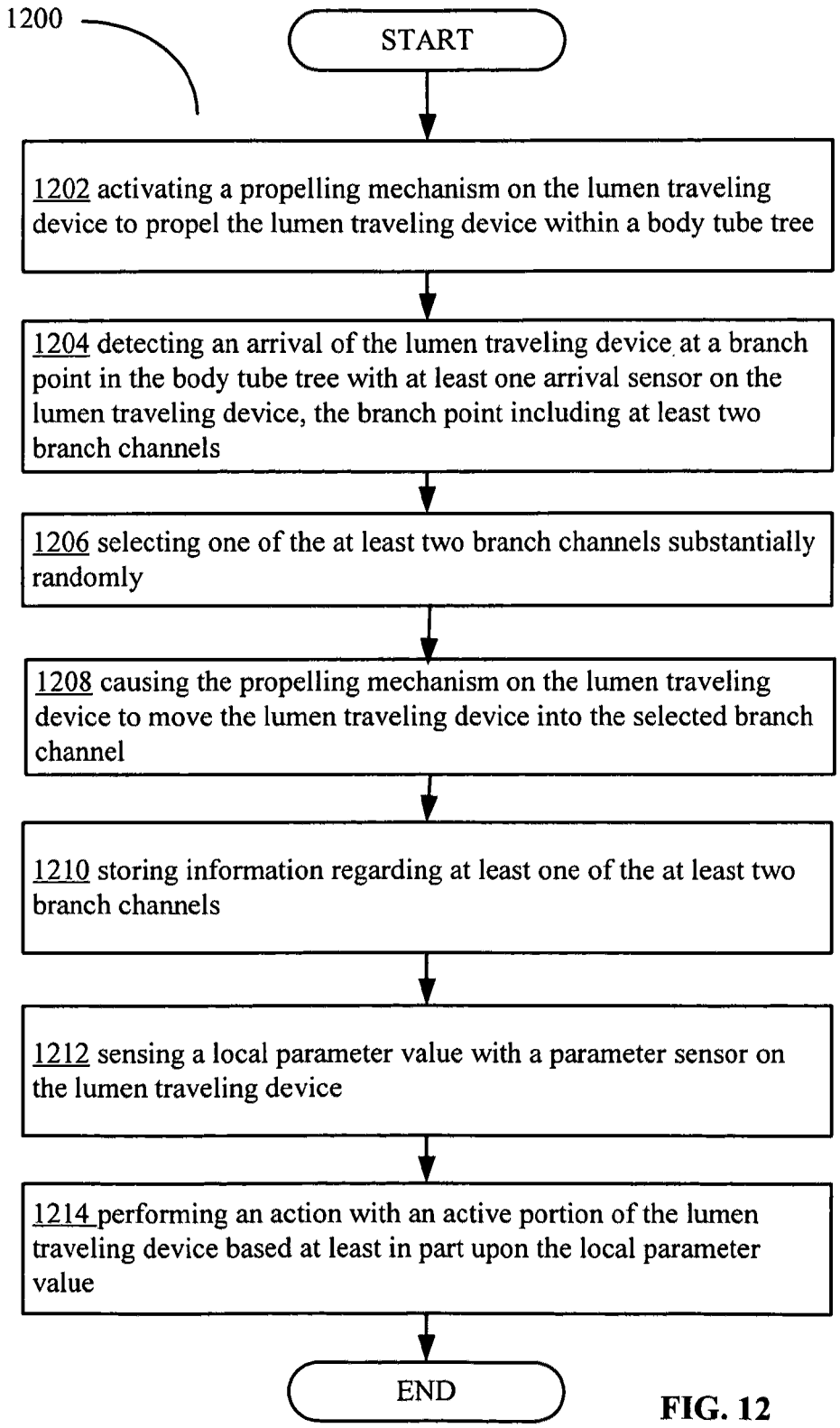
FIG. 12 illustrates a method of operating a lumen traveling device.

FIG. 12 illustrates the steps for a method 1200 of operating a lumen traveling device. The method includes activating a propelling mechanism on the lumen traveling device to propel the lumen traveling device within a body tube tree at 1202; detecting an arrival of the lumen traveling device at a branch point in the body tube tree with at least one arrival sensor on the lumen traveling device, the branch point including at least two branch channels at 1204; selecting one of the at least two branch channels substantially randomly at 1206; causing the propelling mechanism on the lumen traveling device to move the lumen traveling device into the selected branch channel at 1208; storing information regarding at least one of the at least two branch channels at 1210; sensing a local parameter value with a parameter sensor on the lumen traveling device at 1212; and performing an action with an active portion of the lumen traveling device based at least in part upon the local parameter value at 1214. The method of FIG. 12 can be performed under the control of control circuitry such as that depicted in FIG. 8.

The method of operating a lumen traveling device with a lumen traveling device control system includes one or more instructions for activating a propelling mechanism on the lumen traveling device. The one or more instructions for activating a propelling mechanism can originate from the motion control circuitry of the lumen traveling device and/or an associated remote device. The instructions can include but are not limited to, stop instructions, go instructions, speed up instructions, and/or slow down instructions. In an embodiment, the motion control circuitry is operatively connected to one or more steering mechanisms. Instructions originating from the motion control circuitry include instructions to the steering mechanism and include but are not limited to, instructions to turn right, turn left, turn a certain number of degrees, reverse, go up, go down, or a combination thereof. Movements can be defined relative to an axis (e.g., of the lumen traveling device, of the lumen, of the direction of travel, or the body of the subject) or relative to some other relative or absolute frame of reference. The propelling mechanism and the steering mechanism are activated by the motion control circuitry in response to signals received from one or more sensors associated with the lumen traveling device.

The lumen traveling device can include one or more sensors configured to sense one or more local parameter values in the lumen of a body tube tree. In an embodiment, the one or more local parameters can include a branch point in the body tube tree. The arrival of the lumen traveling device at a branch point in the body tube tree can be detected with one or more specialized arrival sensors. The one or more arrival sensors can include, but are not limited to, pressure sensors, temperature sensors, flow sensors, viscosity sensors, shear sensors, pH sensors, chemical sensors, optical sensors, acoustic sensors, biosensors, electrical sensors, magnetic sensors, clocks or timers. An arrival sensor can be configured to sense one or more parameter values characteristic of a branch point in a body tube tree. Examples of parameter values characteristic of a branch point in a body tube tree include but are not limited to changes in flow and/or pressure within the channel at the branch point (e.g., turbulence, eddies, etc.), changes in chemical composition at the branch point, interaction with and detection of a solid surface portion of the branch point (e.g., at a T-junction intersection or apex of the branch point) by either physically bouncing off the solid surface or bouncing a signal off of the surface, e.g., reflection of electromagnetic wave, ultrasonic echoes, etc. As used herein, an "arrival sensor" can include not only a sensor but also circuitry or logic for performing signal processing or analysis for sensing arrival of the lumen traveling device at a branch point.

In an embodiment, the arrival sensor can be a charged coupled device (CCD), a complementary metal oxide semiconductor (CMOS) or other image capturing sensor on the lumen traveling device which captures images of the body tube tree at specified time and/or distance intervals as the lumen traveling device travels through the lumen of the body tube tree, used in combination with image analysis hardware and/or software. Image analysis can be used to recognize an image of a branch point (e.g., bifurcation, trifurcation, other) relative to an image of the lumen of the body tube tree.

In an embodiment, the arrival sensor can measure changes in flow and pressure of fluid or gas in a body tube tree. The flow of fluid or gas in a body tube tree is disrupted at branch points or bifurcations. In the arterial vasculature, for example, these disruptions are observed as turbulence, eddies, flow separation, stasis and transient flow reversals at various regions in proximity to the branch point (see, e.g., Motomiya & Karino, *Stroke,* 1984, 15:50-56 and Karino et al., *Ann. NY Acad. Sci.,* 1987, 516:422-441, each of which is incorporated herein by reference). These disruptions can be measured as changes in pressure and flow relative to pressure and flow measured in a non-bifurcated portion of the body tube tree. These relative changes can be used to identify a branch point. Examples of intravascular pressure and flow sensors have been described in U.S. Pat. Nos. 6,053,873 and U.S. Pat. No. 5,873,835 as well as in Schnakenberg et al., *Sensors and Actuators A: Physical,* 2004, 110: 61-67, each of which is incorporated herein by reference. The arrival sensor can include one or more anemometer-type flow transducer for measuring air flow in, for example, the bronchial body tube tree. Examples of microscale anemometer-type sensors are described in U.S. Pat. No. 7,451,537 and in Wang et al., *Sensors,* 2007 7:2389-2401, which is incorporated herein by reference. In an embodiment, the arrival sensor can be an ultrasonic sensor. In this instance, the lumen traveling device emits ultrasonic waves which reflect off surfaces in the path of the lumen traveling device, including lumen walls and branch points within the body tube tree. An example of a microscale ultrasonic sensor is described in Hirsch et al., *J Physics: Conf. Series,* 2006, 34:475-480, which is incorporated herein by reference.

In an embodiment, the lumen traveling device can move substantially randomly into one of two or more branch channels. As used herein, "moving substantially randomly" means powered and/or directed movement of lumen traveling device in which the direction of travel is selected at random from among two or more possible directions of travel. Selection of the direction of travel can be determined by control circuitry on the lumen traveling device or a remote device. For example, supposing the lumen traveling device has arrived at a branch point including two branch channels, so that there are two possible directions of travel to select from, the control circuitry can generate a random number that may be either even or odd. The first of the two possible directions of travel is selected if the random number is even, and the second of two possible directions of travel is selected if the random number is even. It will be appreciated that, while in the foregoing example a selection is made between two possible directions of travel, a random selection can be made from among more than two possible directions of travel, based upon suitable processing of a randomly generated number.

As the lumen traveling device moves through a branch channel of a body tube tree, information is collected regarding the properties of the branch channel and its surroundings using one or more sensors. Information collected by the lumen traveling device relating to properties of a branch channel can include but is not limited to the direction or orientation of the branch channel relative to some fixed point (e.g., point of origin, internal or external reference points) or other branched channels; the length of the branch channel; the structural configuration of the branch channel (e.g., straight, curved, a combination thereof); the branching pattern of the branch channel; the distance from one branch point to the next branch point; the luminal dimension of the branch channel; and the proximity of the branch channel to a valve or other channel restriction.

The distance traveled by the lumen traveling device can be measured using an odometer type sensor. In an embodiment, the odometer is a mechanical type odometer with a rotating element such as, for example, a wheel or a motor. For example, the lumen traveling device can include a wheel-like attachment that engages the surface of the lumen of the body tube tree and rotates with the movement of the device. The known circumference of the wheel and the number of rotations can be used to estimate the distance traveled by the lumen traveling device. In an embodiment, the rotating element can be a rotary-type motor component associated with the lumen traveling device. In a further embodiment, the odometer can calculate distance traveled using an image sensor to capture images at set intervals and measuring displacement between captured images as described in U.S. Pat. No. 7,171,285, which is incorporated herein by reference.

The dimensions of the lumen of a branch channel can be measured using electromagnetic radiation wherein the lumen traveling device is configured to emit a transverse ring of electromagnetic radiation which becomes incident upon a discrete cross section of the interior surface of the lumen and is visualized as a ring of electromagnetic radiation reflected back from the luminal surface as described in U.S. Pat. No. 5,381,786 which is incorporated herein by reference. The dimensions of the lumen of a branch channel can also be measured using an expandable structure such as a spiral coil or inflatable balloon as described in U.S. Pat. No. 6,175,757, which is incorporated herein by reference.

Information relating to properties of one of the two or more branch channels traveled by the lumen traveling device, including direction or orientation of the branch channel, length of the branch channel, the structural configuration of the branch channel, the branching pattern of the branch channel, the distance from one branch point to the next branch point, the luminal dimension of the branch channel, and the proximity of the branch channel to a valve or other channel restriction, can be stored in one or more data storage locations within the lumen traveling device. In a further embodiment, information relating to properties of one of the two or more branch channels traveled by the lumen traveling device is transmitted to and stored in one or more data storage locations of one or more remote devices in communication with the lumen traveling device. The information relating to properties of one of the two or more branch channels can be stored on non-transitory machine readable media, such as one or more recordable-type media (e.g., floppy disk, a hard disk drive, a compact disc, digital video, a digital tape, a computer memory); and/or non-volatile memory (e.g., ROM, PROM, EPROM, EEPROM, or Flash memory).

In addition to information relating to the properties of at least one of the two or more branch channels traveled by the lumen traveling device, information relating to the relative location of the lumen traveling device is collected. Information relating to the relative location of the lumen traveling device as well as information relating to properties of the branch channels can be used to generate a map of a body tube tree and/or to place the lumen traveling device on a preexisting map of the body tube tree. In an embodiment, the location of the lumen traveling device can be determined based on sensing a position indicator signal. In an embodiment, the position indicator signal can be at least one signal from an inertial navigation system associated with the lumen traveling device. Miniaturized inertial navigation systems using microelectromechanical (MEMS) accelerometers and gyroscopes have been described (see, e.g., U.S. Pat. No. 5,313,835; U.S. Patent Application 2008/0121054; Lynch et al., *J Aerospace Eng.*, 3:108-114, 2003; and Foxlin et al., "Miniature 6-DOF inertial system for tracking HMDs," SPIE vol. 3362, *Helmet and Head-Mounted Displays III, AeroSense 98*, Orlando, Fla., Apr. 13-14, 1998, each of which is incorporated herein by reference). The inertial navigation system can be combined with one or more other position indicator signal such as, for example, one or more global position system (GPS) signal (see, e.g., Brown et al., "Performance test results of an integrated GPS/MEMS inertial navigation package," *Proceedings of ION GNSS* 2004, Long Beach, Calif., September 2004, which is incorporated herein by reference).

In an embodiment, the position indicator signal can originate from a remote source. Examples of position indicator signals originating from one or more remote sources include but are not limited to radiological signals, ultrasonic signals, magnetic signals, and electromagnetic signals. Further examples of position indicator signals include a radiofrequency (RF) signal, a global positioning system (GPS) signal, a signal from a personal area network (PAN), or a signal from a body area network (BAN): A body area network can function generally as described, for example, in Jovanov, E., Milenkovic, A., Otto, C., and de Groen, P., "A wireless body area network of intelligent motion sensors for computer assisted physical rehabilitation," *J. of NeuroEngineering and Rehabilitation*, 2:6, Mar. 1, 2005, which is incorporated herein by reference. The signal can originate from a single remote source or a plurality of signals can originate from a plurality of remote sources. Signal sources that produce radiological signals, ultrasonic signals, magnetic signals, electromagnetic signals, RF, GPS signals known to those of skill in the relevant arts and are examples of remote sources. A position indicator signal can be received by a receiver on the lumen traveling device that is also used to receive data and/or power from a remote device (e.g., receiver/transmitter 134 in FIG. 7) or a position indicator signal can be received by a separate receiver.

In an embodiment, time of flight and or pulse measurements can be used to determine the current location of a lumen traveling device within a body tube tree. Time of flight measurements or pulse measurements are based on measuring the time of flight of a signal, e.g., a position indicator signal, from the measurement device to a target and back again. Trilateration is the technique of determining the position of a target by calculating the time of arrival from at least three different locations (i.e., readers). Multilateration, also known as hyperbolic positioning, is the process of locating a target by accurately computing the time difference of arrival of a signal emitted from the target to three or more receivers. It also refers to the case of locating a receiver by measuring the time difference of arrival of a signal transmitted from three or more synchronized transmitters. Alternatively, a triangulation method can be used to determine the current location of the lumen traveling device based on the plurality of position indicator signals from a plurality of remote sources. Triangulation, also called angle of arrival, is the process of finding the coordinates and the distance to a point by calculating the length of one side of a triangle (which is formed by that point and two other known reference points), based on measurements of the angles and the length of the sides of the triangle.

In an embodiment, the position indicator signals can be one or more radiofrequency signals. For example, the lumen traveling device can include one or more radiofrequency identification (RFID) tags. Miniaturized RFID tags with dimensions of 50 microns by 50 microns have been described by Burke & Rutherglen, *Biomed Microdevices*, Jan. 24, 2009 (Epub ahead of print), which is incorporated herein by reference. An example of implantable device with an RFID tag has been described in U.S. Pat. No. 7,596,403, which is incorporated herein by reference. Radiofrequency signals can also be used for navigation, as described, for example, in U.S. Patent Application 2008/0266106 and Mehmood et al., "Autonomous navigation of mobile agents using RFID-enabled space partitions," *ACMGIS '08*, Nov. 5-7, 2008, Irvine, Calif., USA, each of which is incorporated herein by reference. Navigation systems using ultrasound have been described in U.S. Patent Application 2009/0062646 and Eulenstein et al., "Ultrasound-based navigation system incorporating preoperative planning for liver surgery," *International Congress Series CARS* 2004-*Computer Assisted Radiology and Surgery, Proceedings of the 18th International Congress and Exhibition*, 2004, 1268:758-763, each of which is incorporated herein by reference. Navigation systems using magnetic field have been described in U.S. Pat. Nos. 6,776,165 and 4,658,214, each of which is incorporated herein by reference.

The lumen traveling device can be modified in such a way as to aide in determining the current location of the lumen traveling device in a body tube tree. In an embodiment, the lumen traveling device can include one or more labels, markers or tags detectable by an external imaging system or by a sensing device or structure within the body of the subject. Imaging of a body tube tree using an external imaging system can be combined with imaging of the lumen traveling device to provide a current location for the lumen traveling device within the body tube tree.

In an embodiment, at least a portion of the lumen traveling device can be constructed from a radiopaque metal capable of blocking radiation so that the lumen traveling device is visible in a body tube tree by x-ray imaging. In a further embodiment, the lumen traveling device can be at least partially coated with a radiopaque dye or contrast media. Examples of contrast agents, radiopaque dyes, and roentgenographic drugs used for x-ray imaging and computed tomography (CT) scans include, but are not limited to, barium sulfate and various iodine derivatives including diatrizoate meglumine, diatrizoate sodium, iodipamide meglumine, diatrizoic acid, ethiodized oil, iodipamide, iodixanol, iohexyl, iomeprol, iopamidol, iopanoic acid, iophendylate, iopromide, iothalamate meglumine, iothalamate sodium, iothalamic acid, ioversol, ioxaglate meglumine, and ioxaglate sodium.

In an embodiment, the lumen traveling device can be at least partially coated with one or more of a contrast agent used for magnetic resonance imaging (MRI) as exemplified by paramagnetic and supramagnetic agents with one or more unpaired electrons, typically including manganese, iron, or gadolinium in their structure. Examples of MRI contrast agents containing iron include, but are not limited to, ferumoxides (magnetite coated with dextran), ferumoxsil (magnetite coated with siloxane), ferumoxytol, ferumoxtran, ferucarbotran (RESOVIST), ferric chloride, and ferric ammonium citrate. Examples of MRI contrast agents containing gadolinium include, but are not limited to, gadopentetate dimeglumine (Gd-DTPA; MAGNEVIST), gadobutrol (GADOVIST), gadodiamide (Gd-DTPA-BMA; OMNISCAN), gadoteridol (PROHANCE), Gd-DOTA (DOTAREM), gadofosveset trisodium (VASOVIST), gadoversetamide (OPTIMARK), and gadobenate dimeglumine (MULTIHANCE). Examples of MRI contrast agents containing manganese include but are not limited to mangafodipir trisodium (TESLASCAN) and EVP 1001-1.

In an embodiment, the lumen traveling device can include one or more of a radioactive element used for diagnostic positron emission tomography (PET), single photon emission computed tomography (SPECT), or gamma camera imaging. Radioisotopes commonly used for PET, SPECT and gamma camera imaging include, but are not limited to, carbon-11; nitrogen-13; oxygen-15; and fluorine-18; salts of radioisotopes such as 1-131 sodium iodide, Tl-201 thallous chloride, Sr-89 strontium chloride; technetium Tc-99m; compounds containing iodine-123, iodine-124, iodine-125, and iodine-131; compounds containing indium-111 such as $^{111}$In-1,4,7,10-Tetraazacyclododecane-N,N',N'',N'''-tetraacetic acid and $^{111}$In-Diethylenetriamine pentaacetic acid; $^{177}$Lu-[R]-2-amino-3-(4-isothiocyanatophenyl)propyl]-trans-(S,S)-cyclohexane-1,2-diamine-pentaacetic acid) ($^{177}$Lu-CHX-A''-DTPA), $^{64}$Cu-DOTA, $^{89}$Zr, and $^{86}$Y-DOTA.

In an embodiment, the lumen traveling device can be at least partially coated with one or more agents used for diagnostic fluorescence imaging including, but not limited to, fluorescein (FITC), indocyanine green (ICG) and rhodamine B. Examples of other fluorescent dyes for use in fluorescence imaging include but are not limited to cyanine dyes such as Cy5, Cy5.5, and Cy7 (Amersham Biosciences, Piscataway, N.J., USA) and/or Alexa Fluor dyes such as Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., USA; see, e.g., U.S. Pat. App. No. 2005/0171434, incorporated herein by reference). Additional fluorophores include IRDye800, IRDye700, and IRDye680 (LI-COR, Lincoln, Nebr., USA), NIR-1 and 1C5-OSu (Dejindo, Kumamoto, Japan), LaJolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, Calif.), NIAD-4 (ICx Technologies, Arlington, Va.). Other fluorescing agents include BODIPY-FL, europium, green, yellow and red fluorescent proteins, and luciferase. Quantum dots of various emission/excitation properties are also available for fluorescence imaging (see, e.g., Jaiswal et al., *Nature Biotech.*, 2003, 21:47-51, which is incorporated herein by reference).

The non-transitory machine readable media of the system includes one or more instructions for storing information derived from one or more position indicator signals. Information relating to one or more position indicator signals representative of the current location of the lumen traveling device can be stored in one or more data storage locations within the lumen traveling device. Alternatively, information relating to one or more position indicator signals representative of the current location of the lumen traveling device can be transmitted to and stored in one or more remote devices associated with the lumen traveling device. Information relating to one or more position indicator signals representative of the current location of the lumen traveling device can be stored on one or more recordable-type media (e.g., floppy disk, a hard disk drive, a compact disc, digital video, a digital tape, a computer memory); or non-volatile memory (e.g., ROM, PROM, EPROM, EEPROM, or Flash memory).

Parameter sensors can include signal processing or analysis capabilities; a sensed parameter value may be the parameter value of interest or the sensed parameter value may be a parameter value indicative of a parameter value of interest, e.g., a parameter value from which the parameter value of interest can be computed or derived. Information relating to a local parameter value can include, for example, information regarding the presence, absence, quantity, rate of change, spatial or temporal pattern of distribution, or various other measures relating to or representative of a parameter of interest.

The lumen traveling device is further configured to sense and store information relating to one or more local parameter values as the lumen traveling device travels through a body tube tree. The local parameter can include an anatomical feature such as, for example, a branch point, a valve, a growth, a plaque, a polyp, a tumor, a discoloration of the lumen wall, or other distinct feature of the lumen of the body tube tree. The local parameter can include a man-made structure such as an implantable device of some sort, potentially including another lumen traveling device. The local parameter can further include one or more chemical or physical marker or label previously placed into the lumen of the body tube tree by the lumen traveling device. Alternatively, the local parameter can include one or more of an electrical field, magnetic field, temperature, flow condition, time, location, pressure, pH, presence or concentration of a chemical compound or species, or objects, cells, cellular components. The local parameter can include an image.

Sensing a local parameter value can include sensing the presence of a material of interest in the fluid within the lumen of a body tube tree, or in or on the wall of the body tube tree.

A material of interest in the fluid can include, for example, an object such as a blood clot, a thrombus, an embolus, a plaque, a lipid, a kidney stone, a dust particle, a pollen particle, an aggregate, a cell, a specific type of cell, a cell fragment, a cellular component, a platelet, an organelle, a collection or aggregation of cells or components thereof, a gamete, a pathogen, or a parasite.

The lumen traveling device can include one or more parameter sensors for sensing a local parameter value. Parameter sensors are operatively connected to logic circuitry (hardware, firmware, and/or software) and can be used to sense a local parameter value in or on the wall of the body lumen, in the tissue that forms or surrounds the body lumen, or in the fluid within the body lumen. A parameter sensor can be configured to measure various parameters, including, but not limited to, the electrical resistivity of fluid, tissue, or other material, the density of a material, the pH, the osmolality, or the index of refraction of the fluid at least one wavelength. Specific examples of a parameter sensor include a pressure sensor, a flow sensor, a temperature sensor, an image sensor, a biosensor, and a chemical sensor. The selection of a suitable parameter sensor for a particular application or use site is considered to be within the capability of a person having skill in the art. A parameter sensor can further include some signal processing or pre-processing capability integrated therewith.

Information relating to a local parameter can be collected using one or more sensing or information gathering devices or structures. The lumen traveling device can include one or more sensors of the same or different types, including but not limited to pressure sensors, temperature sensors, flow sensors, viscosity sensors, shear sensors, pH sensors, chemical sensors, optical sensors, an image sensor, acoustic sensors, biosensors, electrical sensors, magnetic sensors, clocks or timers. Examples of sensors are provided in U.S. Pat. Nos. 5,522,394; 5,873,835; 6,053,873; 6,409,674; 6,111,520; 6,278,379; 6,475,639; 6,802,811; 6,855,115, and U.S. Patent Applications 2005/0277839 and 2005/0149170, each of which is incorporated herein by reference.

Information relating to one or more local parameter values sensed by the lumen traveling device while traveling through a body tube tree can be stored in one or more data storage locations within the lumen traveling device. Alternatively, information relating to one or more local parameter values sensed by the lumen traveling device while traveling through a body tube tree can be transmitted to and stored in one or more remote devices associated with the lumen traveling device. Information relating to one or more local parameter values sensed by the lumen traveling device while traveling through a body tube tree can be stored on one or more recordable-type media (e.g., floppy disk, a hard disk drive, a compact disc, digital video, a digital tape, a computer memory); or non-volatile memory (e.g., ROM, PROM, EPROM, EEPROM, or Flash memory).

The block diagram in FIG. 13 summarizes the sensing and storing of information 1300 related to the position or the environment of the lumen traveling device as it moves through the body tube tree of a subject. Sensing and storing information 1300 can include sensing one or more position indicator signals 1302; sensing one or more local parameter values 1322; and storing information regarding at least one of the at least two branch channels of the body tube tree at step 1346. Sensing one or more position indicator signals 1302 can further include one or more of sensing a signal from an inertial navigation system 1304; sensing a magnetic signal originating from a remote source 1306; sensing an ultrasonic signal originating from a remote source 1308; sensing a radiological signal originating from a remote source 1310; and/or sensing an electromagnetic signal from a remote source 1312. Sensing an electromagnetic signal from a remote source 1312 can further include sensing signals from one or more of an RF beacon 1314, a GPS 1316, a wireless network 1317, a personal area network 1318, and/or a body area network 1320. Sensing a position indicator signal can include sensing an encrypted signal 1319. Sensing one or more local parameter value 1322 can include sensing one or more of concentration of analyte 1324; fluid flow 1326; temperature 1328; pressure 1330; acoustic signal 1332; optical signal 1334; electrical field 1336; magnetic field 1338; marker or label 1340; structure parameter 1342; electromagnetic field 1344, or image 1345. Storing information regarding at least one of the at least two branch channels 1346 of a body tube tree can include information regarding one or more of direction 1348, orientation 1350, branching pattern 1352, lumenal dimension 1354, length 1356, structural configuration 1358, distance from another branch point 1360, and proximity to valve or channel restriction 1362. Information relating to position indicator signals of a lumen traveling device, local parameters, and/or properties of branches of a body tube tree can be stored in one or more data storage locations within the lumen traveling device and/or stored in one or more remote devices. This information can be used to generate a map of at least a portion of a body tube tree.

Figure 14:
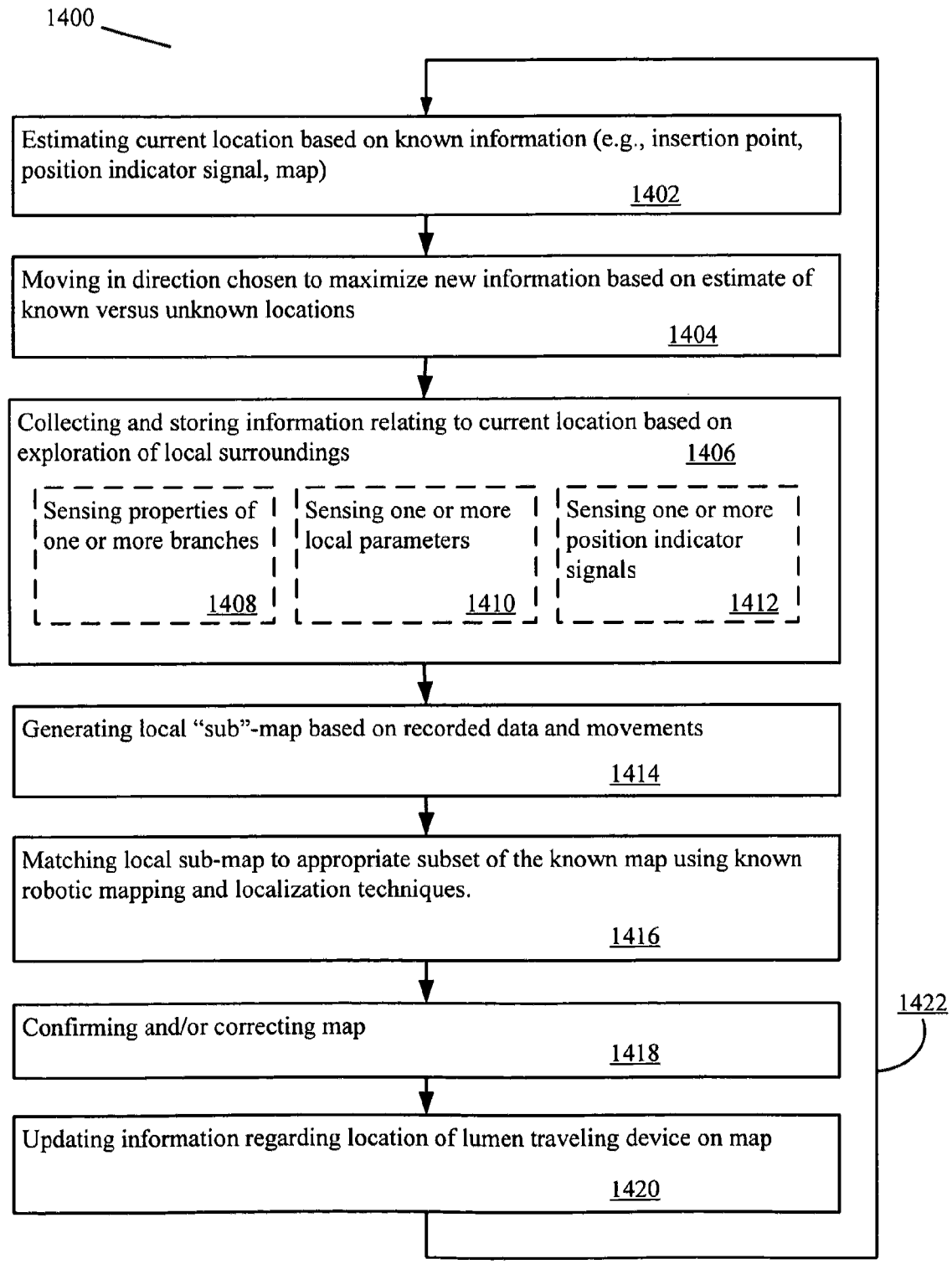
FIG. 14 illustrates a method of generating a map.

FIG. 14 illustrates generating a map 1400 of a body tube tree using exploration and information related to the position and/or the environment of the lumen traveling device, including the steps of estimating the current location of the lumen traveling device based on known information (e.g., injection point, position indicator signal, existing map) at step 1402; moving in a direction chosen to maximize new information based on an estimate of known versus unknown locations at step 1404; collecting and storing information relating to current location based on exploration of local surroundings at step 1406 wherein collecting and storing information includes sensing properties of one or more branches 1408, sensing one or more local parameters 1410, and/or sensing one or more position indicator signals 1412, as outlined in FIG. 13; generating a local "sub"-map based on recorded data and movements at step 1414; matching local sub-map to appropriate subset of the known map using known robotic mapping and localization techniques at step 1416; confirming and/or correcting map at step 1418; and updating information regarding location of lumen traveling device on the map at step 1420. The steps of generating a map by localization and exploration can be implemented in an iterative process 1422, which can be performed through multiple iterations as the lumen traveling device moves through the lumen of a body tube tree.

Information relating to the properties of the branch channels, the position of the lumen traveling device, and local parameters can be used to generate a map of at least a portion of a body tube tree. The map can be based on information collected and stored by the lumen traveling device as it travels through the various branches of the body tube tree. The lumen traveling device can use ultrasonic, radio, microwave and/or laser range finding to generate a map of the immediate environment of the device in the body tube tree. The lumen traveling device can use other sensors to perceive the immediate environment including but not limited to cameras, radar, tactile sensors, compasses and global positioning (GPS). The lumen traveling device can be placed at the origin of the map, and initial measurements taken at the origin are taken to be the initial map of the body tube tree. The lumen traveling device can be instructed by the motion control circuitry to move in a specific direction and to take another measurement. The new measurement can be fit into the existing map on the assumption that the features in the environment of the lumen traveling device have not changed significantly. The best fit returns a most likely location of the device relative to the origin; the measurements are then shifted by the device's now-known position, and contributed to the map. This cycle can be repeated indefinitely as the lumen traveling device explores the body tube tree. Measurements taken in the rearward direction of the device's path of travel aide in localizing the device on the evolving map, while measurements taken in the forward direction of the device's path contribute new information to the evolving map. See, e.g., Howell & Donald, *Proceedings of the IEEE International Conference on Robotic and Automation, 2000, ICRA '00*, Apr. 24-28, 2000, 4:3485-3492, which is incorporated herein by reference.

In an embodiment, the map generated by exploration and localization can be a metric map, a topographical map, or a combination thereof. See, e.g., Tomatis et al., *Robotics Autonomous Systems*, 44:3-14, 2003, which is incorporated herein by reference. A metric map captures the geometric properties of the environment traveled by an object and decomposes the properties into a two-dimensional (2D) or three-dimensional (3D) lattice of grids or cells, with each cell representing the probability of occupancy. A topological map describes the connectivity of different locations within the environment. Topographical maps are graph-oriented models with nodes representing structural features of the environment and vertices capturing adjacency and ordering information. In this instance, the structural features are the properties of the lumen sensed by the lumen traveling device as it travels through the body tube tree. A topological map may be computable from a metric map.

A number of map building algorithms have been described including but not limited to probabilistic frameworks, Bayesian frameworks, artificial neural networks, Cartesian symbolic-oriented approaches, Markov localization, simultaneous localization and mapping (SLAM), concurrent mapping and localization (CML), and expectation maximization (see, e.g., Thrun, "Robotic Mapping: A Survey," In *Exploring Artificial Intelligence in the New Millenium*, eds. Lakemeyer & Nebel, published by Morgan Kaufmann, 2002, which is incorporated herein by reference). The mapping algorithm can include a statistical framework for simultaneously solving the mapping problem and the problem of localizing the lumen traveling device relative to the growing map using Kalman filters to estimate the map and the device location. The resulting map describes the location of landmarks or significant features in the environment. Additional information regarding mapping is described in Thrun, *AI Magazine*, 2000, 21:93-109; Pfister et al., "Weighted line fitting algorithms for mobile robot map building and efficient data representation," *Proceedings of the 2003 IEEE International Conference on Robotics and Automation*, Taipei, Taiwan, Sep. 14-19, 2003; Thrun et al., "A real-time algorithm for mobile robot mapping with applications to multi-robot and 3D mapping," *Proceedings of the 2000 IEEE International Conference on Robotics and Automation*, San Francisco, Calif., April 2000, each of which is incorporated herein by reference. See also Filliat, D. and Meyer, J.-A., "Map-based navigation in mobile robots I. A review of localization strategies," *Cognitive Systems Research*, Vol. 4, Issue 4, December 2003, pages 243-282, Elsevier B. V. and Meyer, J.-A. and Filliat, D., "Map-based navigation in mobile robots II. A review of map-learning and path-planning strategies," *Cognitive Systems Research*, Vol. 4, Issue 4, December 2003, pages 283-317, Elsevier B. V., each of which is incorporated herein by reference.

Other maps and mapping techniques may be used instead of, or the mapping techniques described above. For example, a conformal map can be used in embodiments where it is desired to preserve information regarding angles or areas of mapped regions, for purposes of visualization of surface. (see, e.g., Zhu, L., Haker, S., and Tannenbaum, A., "Flattening Maps for the Visualization of Multibranched Vessels," *IEEE Transactions on Medical Imaging*, Vol. 24, No. 2, pp. 191-198, February 2005, which is incorporated herein by reference).

In response to sensing a local parameter value, the lumen traveling device, and in particular an active portion of the lumen traveling device, can be instructed by the response control circuitry to perform one or more actions. Examples of performing an action include but are not limited to releasing a material, releasing a device or structure, releasing an energy, collecting a sample, collecting a device or structure, attaching a structure to a wall of the body tube tree, delivering a material or structure to a receiving portion of a man-made device, receiving a material or structure from a delivery portion of a man-made device, receiving a signal from a remote source, receiving power from a remote source, transmitting a signal to a remote location, performing a surgical step or procedure, removing tissue from at least a portion of the body tube tree, removing specific components of at least a portion of a fluid from a body tube tree, exposing a catalyst, generating a localized electric field, generating a localized magnetic field, producing heat, causing cooling, emitting electromagnetic radiation, emitting acoustic energy, applying pressure to at least a portion of the body tube tree, modulating the flow of a fluid through at least a portion of the body tube tree, sensing a second local parameter value, stopping performance of an action if the local parameter value is within a specified range, and initiating performance of an action if the local parameter value is within a specified range. Examples of performing an action are shown in FIGS. 15-19.

As shown in FIG. 15, the step of performing an action with the active portion of the lumen traveling device (at step 1500) can include transmitting a signal to a remote location (at 1502), or releasing a material (at step 1504), which can be, for example, at least one of at least one of adhesive, a filler, a polymer, a hydrogel, an antibiotic, an antibody, an antiviral, a pharmaceutical compound, a nutrient, a hormone, a growth factor, a catalyst, a drug, a therapeutic compound, a chemical, a biomaterial, a biological label, an enzyme, a protein, a nucleic acid, an oligonucleotide, a polynucleotide, a polypeptide, a genetic material, a cell, a fraction of a cell, a cell fragment, a complex, a vaccine, a vitamin, a neurotransmitter, a neurotropic agent, a neuroactive material, a cytokine, a chemokine, a hormone, a cell-signaling material, a pro-apoptotic agent, an anti-apoptotic agent, an immunological mediator, an anti-inflammatory agent, a salt, an ion, an electrolyte, an antioxidant, an imaging agent, a labeling agent, a diagnostic compound, a nanomaterial, an inhibitor, a lipid, an alcohol, a sterol, a steroid, a carbohydrate, a sugar, a gas, or a blocker (as indicated at step 1506). As indicated at 1505, performing an action with an active portion of the lumen traveling device can include delivering a material to a wall region of the body tube tree. This can include delivering a material to tissue in, on, or behind the wall of the body tube tree, by injection, spraying, painting, printing, etc.

As shown in FIG. 16, performing an action with the active portion of the lumen traveling device 1500 can include collecting a material from the body lumen (as shown in step 1602), which can include collecting a sample from a fluid within the body lumen (as shown in step 1604), or collecting a sample from a wall region of the body lumen (as shown in step 1606). The method can include collecting a sample from beyond the wall region of the body lumen, e.g., with the use of a needle to penetrate the body lumen wall. As further shown in FIG. 16, performing an action with the active portion of the lumen traveling device 1500 can include producing heating or causing cooling, as shown in steps 1608 and 1616, respectively. Heating can be used in a variety of locations, for a variety of purposes, including but not limited to ablation or cauterization of tissue, or stimulation or inhibition of cellular functions. In one example, the method can include propelling the lumen traveling device through the body lumen to a location in the vicinity of an atherosclerotic plaque, wherein performing an action with the active portion can include producing heating to ablate the plaque, as shown in step 1610. In another example, performing an action with an active portion includes heating to ablate a cancerous lesion, as shown in step 1612. In another example, heating can be used in the male reproductive system to destroy gametes, as shown in step 1614.

Performing an action with the active portion can include securing the lumen traveling device into position within the body lumen as shown in step 1618, e.g., by using various positioning or lumen-wall-engaging structures, examples of which have been described herein.

Figure 17:
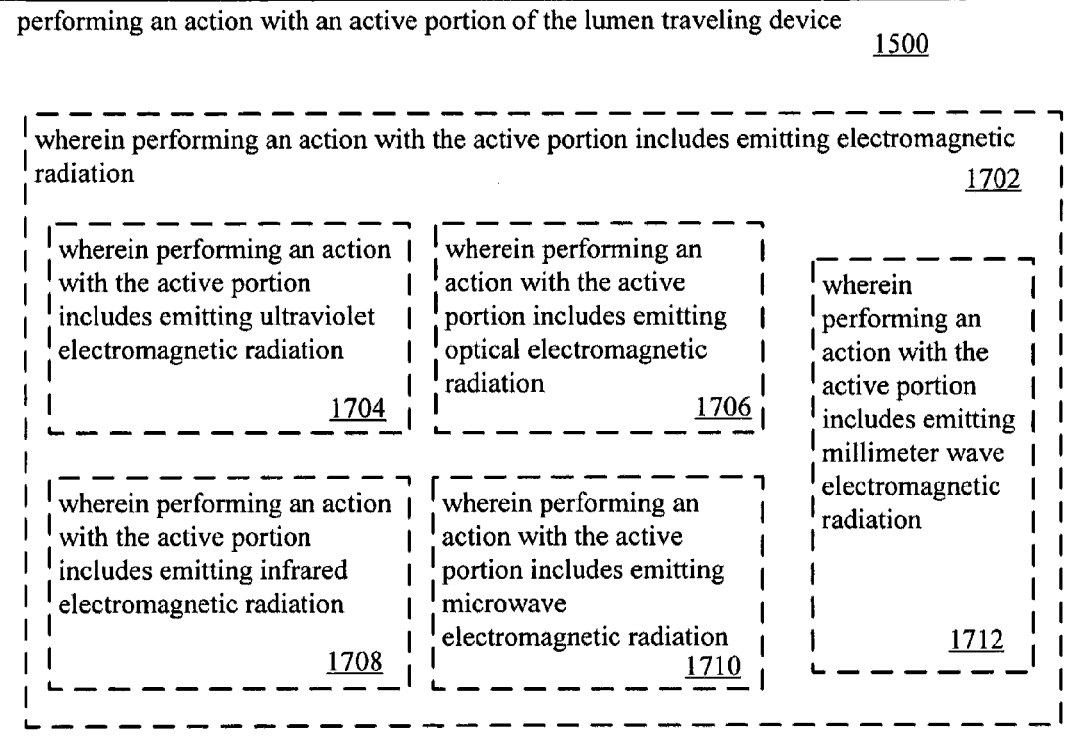
FIG. 17 illustrates embodiments of performing an action with an active portion of a lumen traveling device.

As shown in FIG. 17, performing an action with the active portion of the lumen traveling device 1500 can include emitting electromagnetic radiation, as shown at step 1702. The performing an action can include emitting ultraviolet, optical, infrared, microwave, or millimeter wave electromagnetic radiation, as indicated at steps 1704, 1706, 1708, 1710, and 1712, respectively.

As shown in step 1802 of FIG. 18, performing an action with the active portion of the lumen traveling device 1500 can include emitting acoustic energy, including, but not limited to, ultrasonic acoustic energy, as indicated in step 1804. As shown in FIG. 18, performing an action with the active portion of the lumen traveling device can include applying pressure to the body lumen (step 1806), by expansion of the active portion, or by release of a gas or fluid. Performing an action with the active portion of the lumen traveling device can include modulating the flow of fluid through at least a portion of the body lumen, as shown at step 1808, for example by blocking the flow of fluid through at least a portion of the body lumen (step 1810), modifying the direction of flow of fluid through at least a portion of the body lumen (step 1812), or modifying the amount of turbulent flow (step 1814). Modifying the direction of flow of fluid can include directing flow, toward a particular region and/or into a particular branch of a branching lumen, for example, with the use of various flow-directing structures as disclosed herein. Modifying the direction of flow of fluid can also include reversing the direction of flow, which can be accomplished, for example, by modifying the pressure within the lumen, as described herein.

As shown in FIG. 19, performing an action with the active portion of the lumen traveling device 1500 can include at least partly removing specific components from at least a portion of a fluid within the body lumen, as shown at step 1902, or exposing a catalyst, as shown at step 1904. Performing an action with the active portion can include generating a localized electric field, as shown at step 1906, generating a localized magnetic field, as shown at step 1908, or removing tissue from or cutting at least a portion of the body lumen, as indicated at steps 1910 and 1912, respectively. Performing an action with the active portion can include releasing a man-made structure from the lumen traveling device, as shown at step 1914, and, in some embodiments, attaching the man-made structure to a wall of the body lumen, as shown at step 1916. As further shown in FIG. 19, performing an action with the active portion of the lumen travel device at step 1500 can include delivering a material or structure to a receiving portion of a man-made device, as shown at 1918, receiving a material or structure from a delivery portion of a man-made device, as shown at 1920. Finally, performing an action can include one or more of transmitting power to the lumen traveling device, as shown in step 1922, transmitting a signal to the lumen traveling device, as shown in step 1924, receiving a signal from a remote source with the lumen traveling device, as shown in step 1926, or receiving power from a remote source with the lumen traveling device, as shown in step 1928. Performing an action can include transmitting an encrypted signal to the lumen traveling device (1925) or receiving an encrypted signal from a remote source (1927).

Figure 20A:
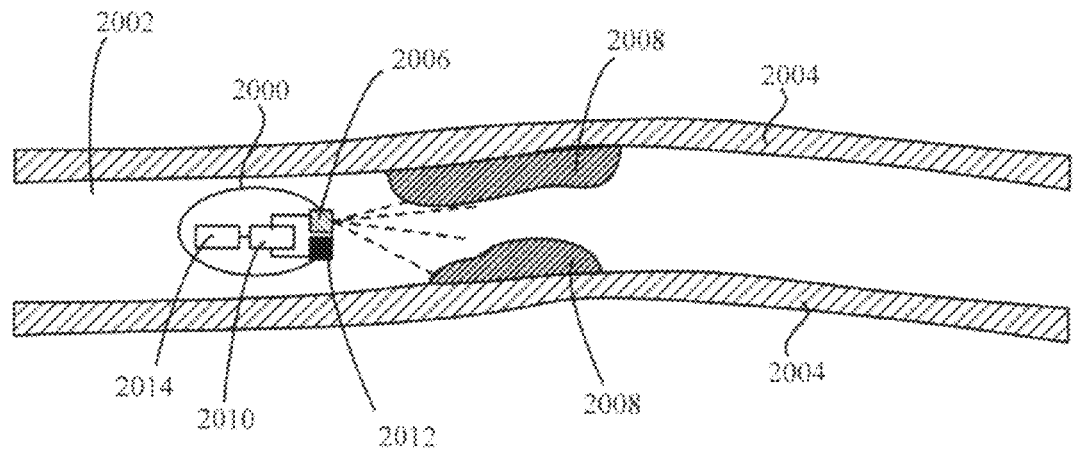
FIGS. 20A & 20B illustrate an example of the operation of a lumen traveling device in the lumen of a body tube tree.
Figure 20B:
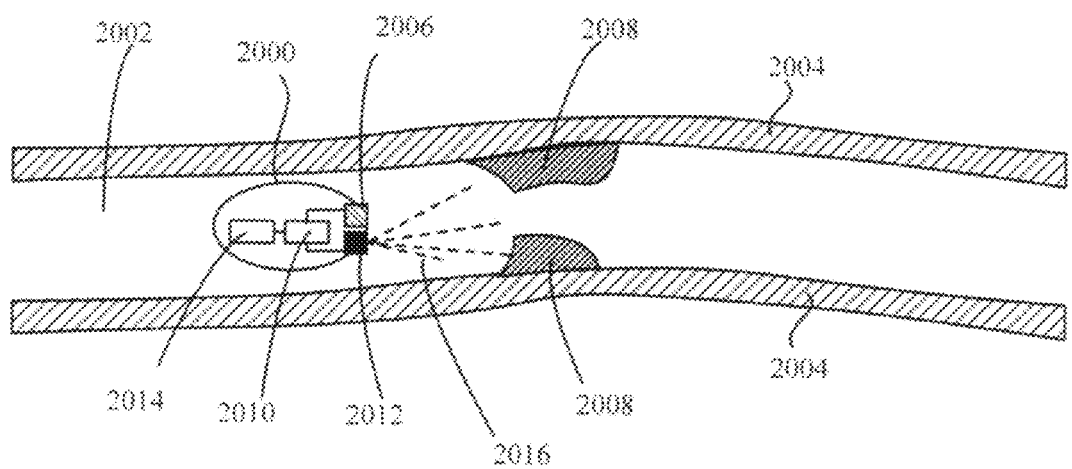

FIGS. 20A and 20B depict lumen traveling device 2000 moving through a lumen of a body tube tree 2002, sensing one or more local parameter value and performing an action with an active portion 2012. Lumen traveling device 2000 includes sensor 2006, response control circuitry 2010, and active portion 2012. Lumen traveling device 2000 also includes motion control circuitry 2014. As shown in FIG. 20A, sensor 2006 senses a local parameter value—in this case, material 2008 on the wall 2004 of the lumen of a body tube tree 2002. Material 2008 may be, for example, a plaque on the wall of an artery or a cancerous lesion in a bronchial airway. Sensor 2006 may be an optical sensor, an imaging device, or various other types of sensors, a number of which have been described herein. Upon detection of material 2008, active portion 2012 may be activated, as shown in FIG. 20B. In this example, active portion 2012 performs ablation of material 2008; for example, active portion 2012 may be an optical device which generates light 2016 to perform, for example, laser ablation of a plaque or cancerous lesion, or it may be an acoustic device for performing ultrasonic ablation of a plaque or cancerous lesion.

Figure 22A:
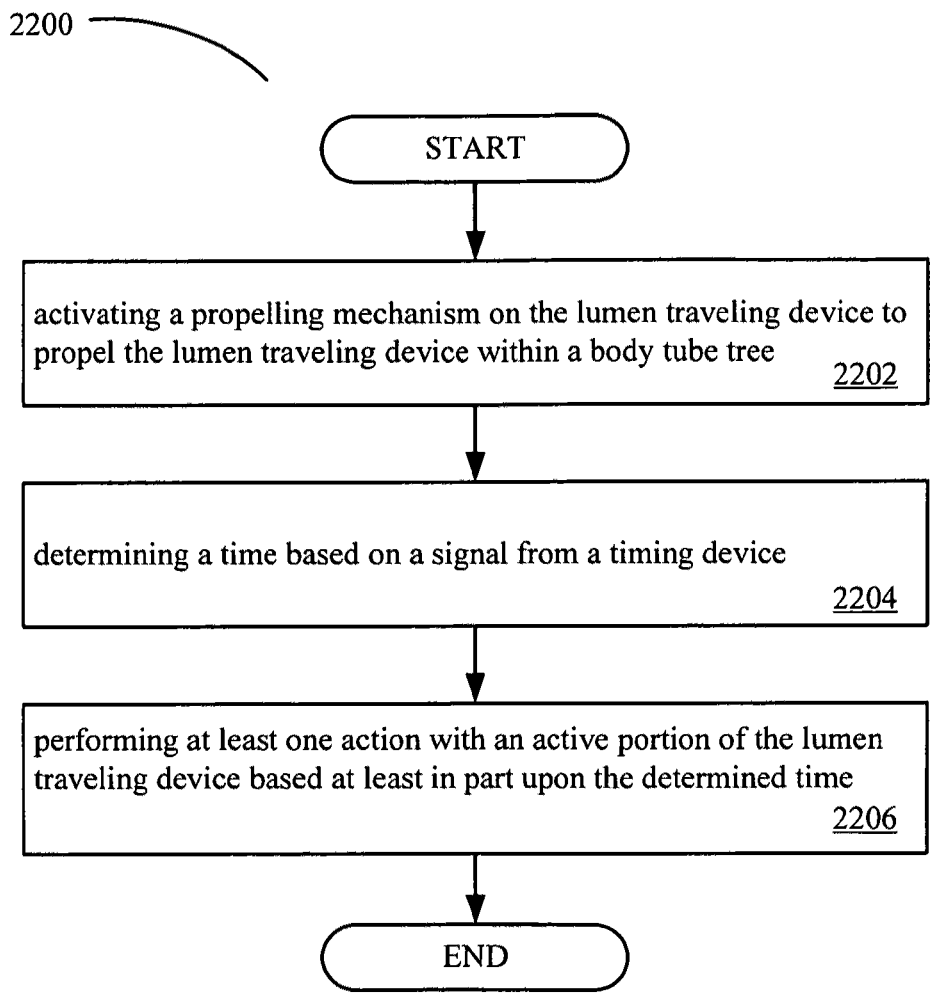
FIGS. 22A-22E illustrate a method of operating a lumen traveling-device and variants thereof.

FIG. 22A illustrates a method 2200 of operating a lumen traveling device in a lumen of a body tube tree including activating a propelling mechanism on the lumen traveling device to propel the lumen traveling device within a body tube tree at 2202, determining a time based on a signal from a timing device at 2204, and performing at least one action with an active portion of the lumen traveling device based at least in part upon the determined time at 2206. Variants of method 2200 are depicted in FIGS. 22B-22E.

Figure 22B:
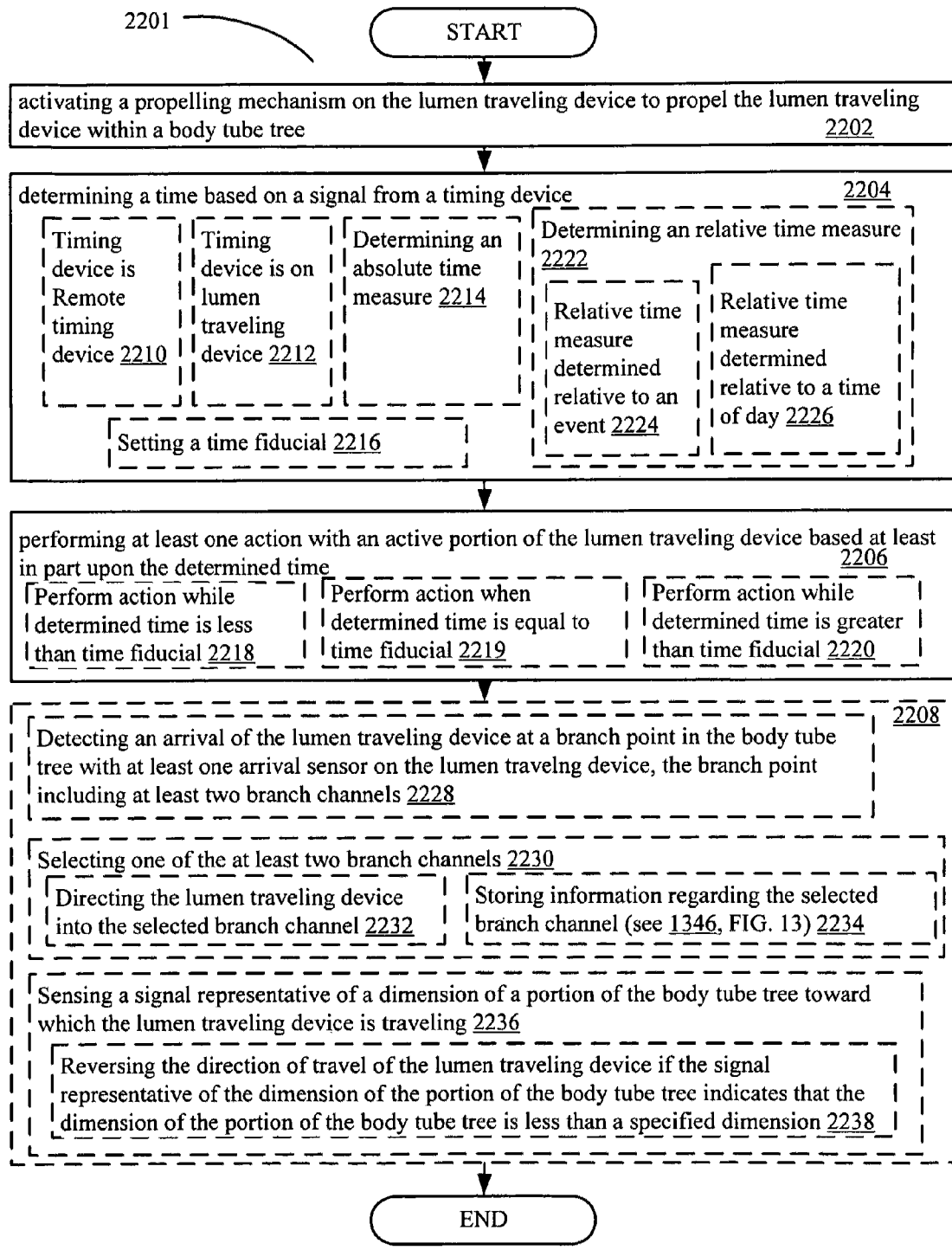

A signal from a timing device can be used to determine a time. The timing device for determining a time can be located on the lumen traveling device, or, alternatively, the timing device for determining a time can be a timing device associated with a remote device; see, for example FIGS. 7 and 8. Thus, as shown in FIG. 22B, method 2201 (a variant of method 2200) can include determining a time based on a signal from a timing device, wherein the timing device is a remote timing device (2210) or wherein the timing device is on a lumen traveling device (2212). The timing device can include an oscillator timing device such as, for example, quartz crystal oscillator, ceramic oscillator, a MEMS based CMOS timing circuit, film bulk acoustic resonator (FBAR), and surface acoustic-wave (SAW) timing devices (see, e.g., Nguyen, *IEEE Trans Ultrasonics Ferroelectrics Frequency Controls*, 54:251-270, 2007; U.S. Pat. No. 7,365,614, each of which is incorporated herein by reference.) The timing device can be a time processor unit (TPU), a semi-autonomous microcontroller designed for timing control. The TPU can operate simultaneously with an integrated central processing unit (CPU) and can schedule tasks, process microcode read only memory (ROM) instructions, access data shared with the CPU, and perform input and output (I/O) functions. See, e.g., U.S. Pat. No. 7,020,231 which is incorporated herein by reference. In an embodiment, the timing device is a MEMS based resettable timer as described in U.S. Pat. No. 7,398,734, which is incorporated herein by reference. In an embodiment, the lumen traveling device include a chip-based or microelectromechanical systems (MEMS) scale atomic clock such as those described by Knappe, "Emerging Topics: MEMS Atomic Clocks," in *Comprehensive Microsystems*, Y. Gianchandani, O. Tabata, and H. Zappe, (eds.), Volume 3, pp. 571-612, 2007, Elsevier, Netherlands; and by Kitching, "Time for a better receiver: Chip-scale atomic frequency references," *GPS World*, November 2007, pp. 52-57, each of which is incorporated herein by reference.

The lumen traveling device can be instructed to perform an action based on a time determined or measured by a timing device. For example, in method 2201, the method can including determining an absolute time measure (2214) based on a signal from the timing device. The lumen traveling device can be instructed to perform an action at a particular time (e.g. 2:00 p.m.), where the current time is tracked by a clock on the lumen traveling device or external to the lumen traveling device. It should be understood that the term "absolute time measure," as used herein, refers to a time measurement that is absolute with regard to the lumen traveling device system (that is, it is not changeable by the lumen traveling device system or determined relative to a lumen traveling device-specific event or events), which may, however, be determined relative to external world events or time measurements (including but not limited to local time of day, solar time, universal time (UTC or UT1), terrestrial time (TT), international atomic time (TAI), etc.). In an embodiment, the lumen traveling device can be instructed to perform an action at a particular 'count' on a continuously running timer device on or external to the lumen traveling device, where the timer device is incremented at regular, known intervals.

Alternatively, the method may include determining a relative time measure (2222). The relative time measure can be determined relative to an event (2224) or relative to a time of day (2226). The relative time determined by the timing device can be relative to an action or event performed by or occurring in relation to the lumen traveling device, including for example, and without limitation, arriving at a branch point, sensing a local parameter value, receiving a position indicator signal, traveling a specified distance, reaching a specific location in the body tube tree based on a map of at least a portion of a body tube tree, performing an action, or any combination thereof. The relative time measure can be set or reset, for example, when the lumen traveling device arrives and senses a branch point in the body tube tree. In an embodiment, the relative time can be set or reset by a remote signal, e.g. from a remote timing device. In an embodiment, the timing device can be external to the lumen traveling device, relaying specific instructions at specific times to the lumen traveling device through a transmitter. In an embodiment, the lumen traveling device is instructed to perform an action based on timing relative to one or more time fiducial. The method can include setting a time fiducial (2216). The time fiducial can be set at or relative to the time at which the lumen traveling device is introduced into the subject. Alternatively, the time fiducial can be set at or relative to the time of an event, e.g., arriving at a branch point, sensing a local parameter value, receiving a position indicator signal, reaching a specific location in the body tube tree, or performing an action. As shown at 2218, the lumen traveling device can be instructed to perform an action at a determined time that is less than the time fiducial (for example a lumen traveling device can be instructed to travel while less than an hour has passed since introduction of the lumen traveling device into the a subject's body). As shown at 2219, the lumen traveling device can be instructed to perform an action when the determined time is equal to the time fiducial (for example, a lumen traveling device can be instructed to release a bolus of a drug when the determined time is exactly 3:30 p.m.). In another example, as shown at 2220, a lumen traveling device can be instructed to perform an action at a determined time that is greater than the time fiducial (for example, the lumen traveling device can be instructed to begin gathering data regarding blood chemistry 30 minutes after delivery of a drug). The determined time can be a relative time measure, or it can be determined relative to an event or relative to a time of day. Similarly, the time fiducial can be set relative to an event (as in the first example) or relative to an absolute time measure (as in the second example).

Referring again to FIG. 22B, in an embodiment, a method of operating a lumen traveling device with a lumen traveling device control system can include activating a propelling mechanism on the lumen traveling device to propel the lumen traveling device within a body tube tree (2202); determining a time based on a signal from a timing device (2204); performing at least one action with the lumen traveling device based at least in part upon the determined time (2206). In further options shown in 2208, the method can include detecting an arrival of the lumen traveling device at a branch point in the body tube tree with at least one arrival sensor on the lumen traveling device, the branch point including at least two branch channels (2228); selecting one of the at least two branch channels (2230); and directing the lumen traveling device into the selected branch channel (2232). The method can include determining the time based on a signal from a remote timing device, or based on a signal from a timing device located on the lumen traveling device. The method can include setting a time fiducial (2216); for example, the time fiducial can be set relative to detection of an arrival of the lumen traveling device at the branch point. In an embodiment, an action can be performed while the determined time is less than the time fiducial (for example while less than some amount of time passed since reaching the branch point). Alternatively, the action can be performed when the determined time is equal to the time fiducial, or while the determined time is greater than the time fiducial. This approach can be used to ensure that the action is taken either when the lumen traveling device is close to the branch point (as in the first example) or when it has traveled away from the branch point for some minimum amount of time (as in the second and third examples).

Figure 22C:
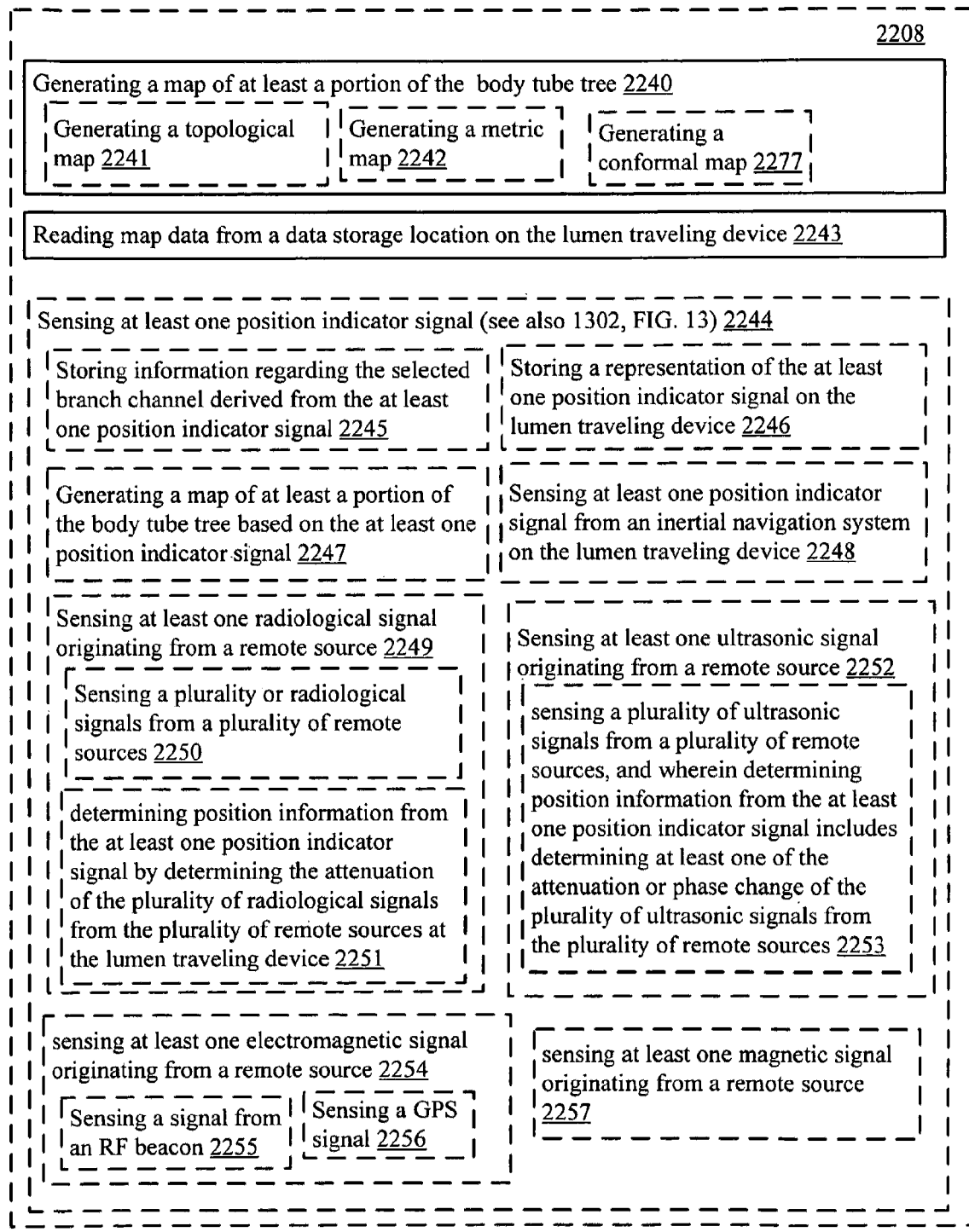

Method 2201 can include various additional steps, as represented by dashed box 2208 in FIG. 22B. Additional steps can include, for example, one or more of detecting an arrival of the lumen traveling device at a branch point in the body tube tree with at least one arrival sensor on the lumen traveling device, the branch point including at least two branch channels (2228), selecting one of the at least two branch channels (2230), directing the lumen traveling device into the selected branch channel (2232) and/or storing information regarding the selected branch channel (2234), sensing a signal representative of a dimension of a portion of the body tube tree toward which the lumen traveling device is traveling (2236), and reversing the direction of travel of the lumen traveling device if the signal representative of the dimension of the portion of the body tube tree indicates that the dimension of the portion of the body tube tree is less than a specified dimension (2238). Other examples of additional steps are shown in FIG. 22C. For example, the additional steps 2208 can include generating a map of at least a portion of the body tube tree 2240), which can include generating a topological map (2241), generating a metric map (2242), or generating a conformal map (2277), reading map data from a data storage location on the lumen traveling device (2243), or sensing at least one position indicator signal (see also 1302, FIG. 13) (2244), and can further include storing information regarding the selected branch channel derived from the at least one position indicator signal (2245), storing a representation of the at least one position indicator signal on the lumen traveling device (2246), or generating a map of at least a portion of the body tube tree based on the at least one position indicator signal (2247). Sensing at least one position indicator signal can include sensing at least one position indicator signal from an inertial navigation system on the lumen traveling device (2248), sensing at least one radiological signal originating from a remote source (2249), (which can include sensing a plurality or radiological signals from a plurality of remote sources (2250), and/or determining position information from the at least one position indicator signal by determining the attenuation of the plurality of radiological signals from the plurality of remote sources at the lumen traveling device (2251)). Sensing at least one position indicator signal can include sensing at least one ultrasonic signal originating from a remote source (2252), for example sensing a plurality of ultrasonic signals from a plurality of remote sources, and wherein determining position information from the at least one position indicator signal includes determining at least one of the attenuation or phase change of the plurality of ultrasonic signals from the plurality of remote sources (2253), sensing at least one electromagnetic signal originating from a remote source (2254), such as a signal from an RF beacon (2255) or GPS signal (2256), or sensing at least one magnetic signal originating from a remote source (2257).

Figure 22D:
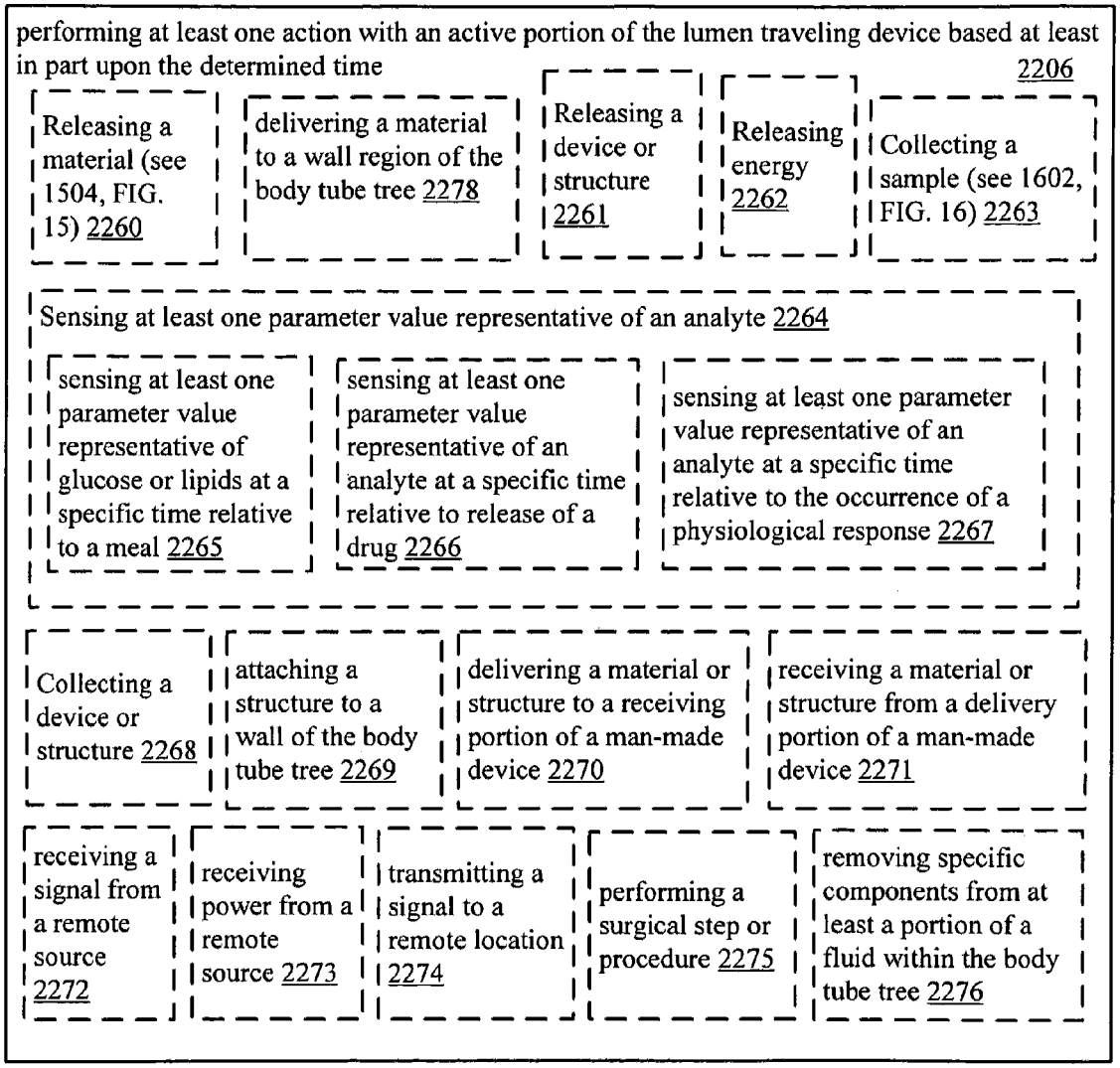

As shown in FIG. 22D, performing at least one action with an active portion of the lumen traveling device based at least in part upon the determined time (2206) can include releasing a material (2260), delivering a material to a wall region of the body tube tree (2278), releasing a device or structure (2261), releasing energy (2262), collecting a sample (2263), sensing at least one parameter value representative of an analyte (2264) (for example, sensing at least one parameter value representative of glucose or lipids at a specific time relative to a meal (2265), sensing at least one parameter value representative of an analyte at a specific time relative to release of a drug (2266), sensing at least one parameter value representative of an analyte at a specific time relative to the occurrence of a physiological response (2267), collecting a device or structure (2268), attaching a structure to a wall of the body tube tree (2269), delivering a material or structure to a receiving portion of a man-made device (2270), receiving a material or structure from a delivery portion of a man-made device (2271), receiving a signal from a remote source (2272), which may be an encrypted signal, as shown at 1927 in FIG. 19, receiving power from a remote source (2273), transmitting a signal to a remote location (2274), which may be an encrypted signal, as shown at 1925 in FIG. 19, performing a surgical step or procedure (2275), or removing specific components from at least a portion of a fluid within the body tube tree (2276).

Figure 22E:
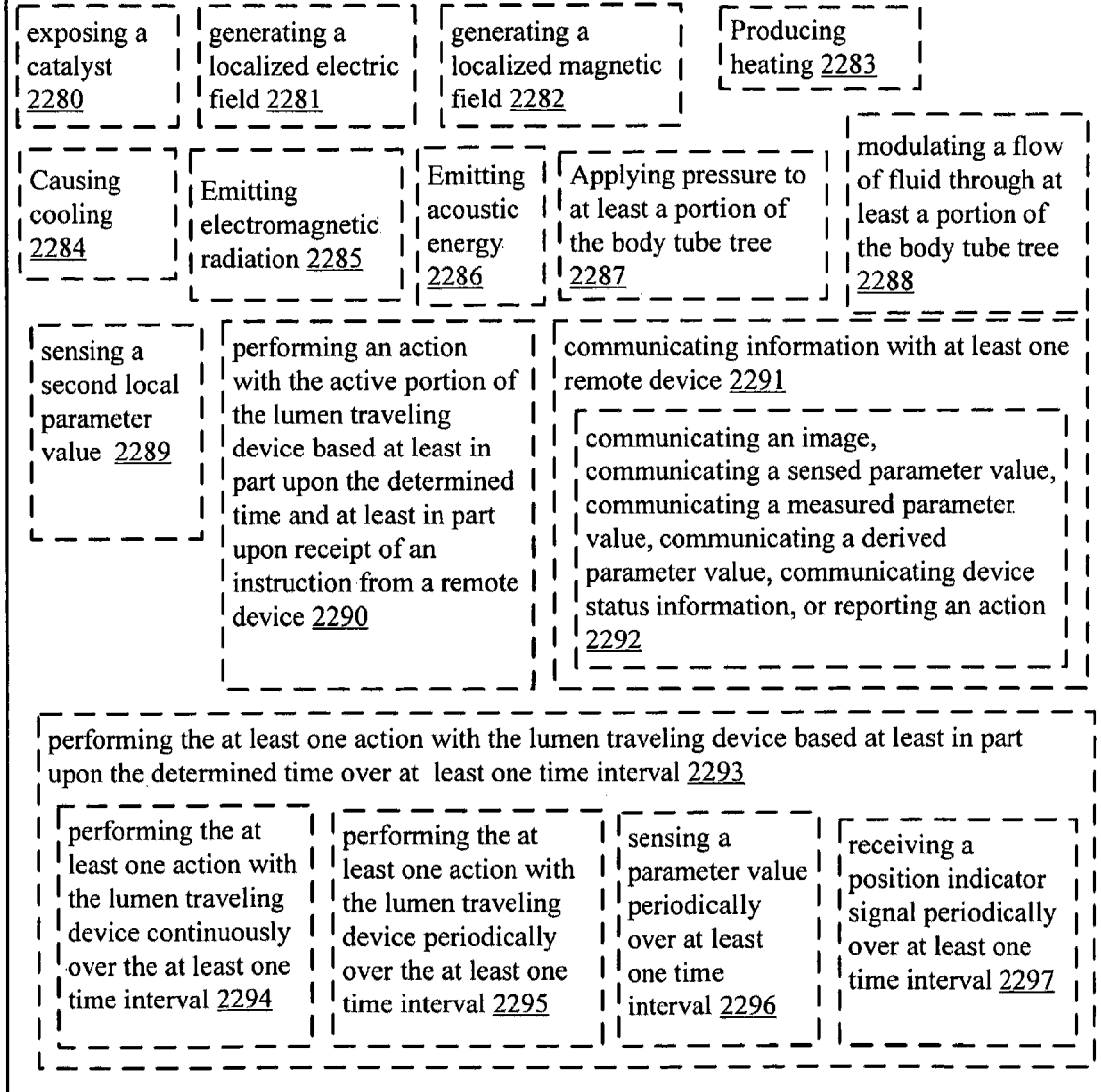

As further shown in FIG. 22E, the lumen traveling device can be instructed to perform various actions based at least in part on a determined time, including exposing a catalyst (2280), generating a localized electrical field (2281), generating a localized magnetic field (2282), producing heat (2283), causing cooling (2284), emitting electromagnetic radiation (2285), emitting acoustic energy (2286), applying pressure to a least a portion of the body tube tree (2287), modulating the flow of fluid through at least a portion of the body tube tree (2288), and/or sensing a second local parameter value (2289). In an embodiment, the lumen traveling device is instructed to perform an action based at least in part upon the determined time and at least in part upon receipt of an instruction from a remote device (2290).

The method can include communicating information with at least one remote device (2291), which may include, for example, communicating an image, communicating a sensed parameter value, communicating a measured parameter value, communicating a derived parameter value, communicating device status information, or reporting an action (2292).

The lumen traveling device can be instructed to perform an action based in part on a time if how or whether the action is performed is a function of both time and some additional parameter value or information; performance of the action can depend upon a time, as discussed herein above, and also upon the value of a sensed parameter value, an instruction from a user, etc. The additional parameter value or information may be used to determine whether or not the action will be performed (thus serving a gating or override function), or it may determine the nature or magnitude of the action (e.g., amplitude or duration of an electrical stimulus, quantity of drug released, etc.).

The lumen traveling device can be instructed to perform an action based at least in part upon the determined time, over one or more time interval, as shown at 2293. In an embodiment, the lumen traveling device can be instructed to perform an action continuously over a specified time interval (2294). In an embodiment, the lumen traveling device can be instructed to periodically perform an action (2295). For example, the lumen traveling device can be instructed to capture an image of the lumen of a body tube tree every second over a determined period of time as the lumen traveling device travels through the lumen. As another example, the lumen traveling device can be instructed to sense a parameter periodically over at least one time interval (2296). The method can include sensing a parameter such as a chemical analyte (e.g., pH) or physical parameter (e.g., lumen diameter) every second over a determined time interval. As a further example, the lumen traveling device can be instructed to receive a position indicator signal periodically over at least one time interval (2297), for example every second over a determined period of time to locate the position of the lumen traveling device in a body tube tree. In an embodiment, the instructions can include placing a chemical or physical marker or label as landmarks or indicators of the path of travel of the lumen traveling device. In the above example, the lumen traveling device performs an action at uniform intervals (i.e., once every second). In some embodiments, the lumen traveling device may be instructed to perform an action intermittently at non-uniform intervals or at random intervals.

Methods 2200 and 2201, and other variants thereof, can be performed, for example, with a device as depicted in and described in connection with FIGS. 1, 2, 7 and 8.

FIG. 21 illustrates a block diagram of a system 2100 that includes a set of instructions 2104 for operating a lumen traveling device. An embodiment of system 2100 is provided using non-transitory machine readable media 2102 including a set of instructions 2104 including one or more instructions that cause the lumen traveling device control system to activate a propelling mechanism on a lumen traveling device to propel the lumen traveling device within a body tube tree; one or more instructions that cause the lumen traveling device control system to determine a time based on a signal from a timing device; and one or more instructions that cause the lumen traveling device control system to direct the active portion of the lumen traveling device to perform at least one action based at least in part upon the determined time. The active portion of the lumen traveling device can be directed to perform various actions, as described elsewhere herein, for example. The one or more instructions can be, for example, computer executable and/or logic-implemented instructions. In an embodiment, the non-transitory machine readable media 2102 can include computer readable media 2106. In an embodiment, the non-transitory machine readable media 2102 can include recordable-type media 2108. A system as depicted in FIG. 21 can be used in implementation of the method of FIG. 22A, for example. It will be appreciated that while system 2100 is specifically shown to include instructions for performing method 2200 depicted in FIG. 21A, system 2100 can be modified to perform any of the variants of method 2200 and 2201 as depicted in FIGS. 22A-22E.

Figure 23A:
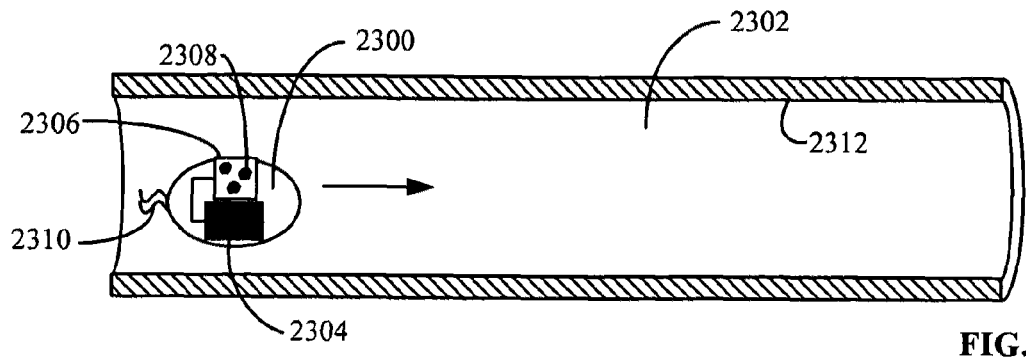
FIGS. 23A-23D illustrate an example of the operation of a lumen traveling device in the lumen of a body tube tree.
Figure 23B:
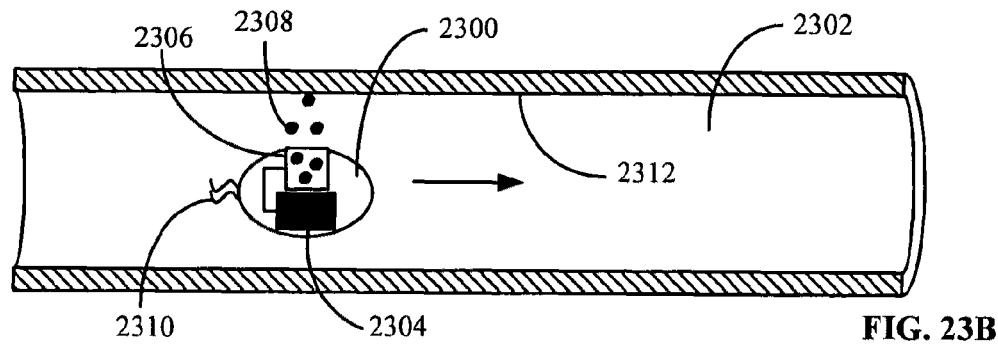
Figure 23C:
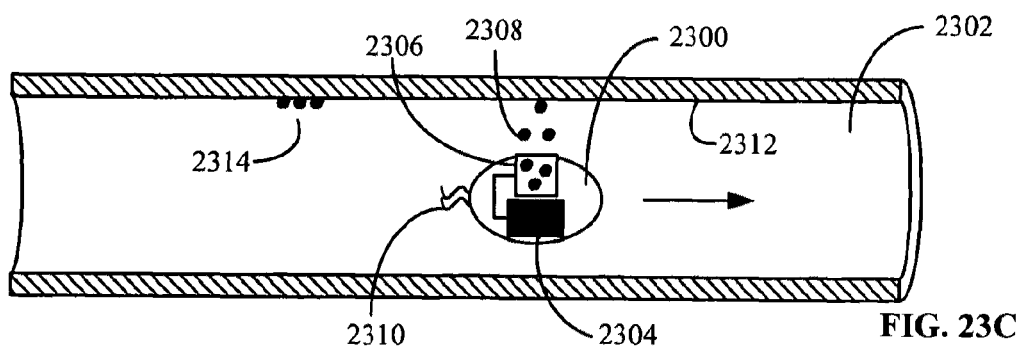
Figure 23D:
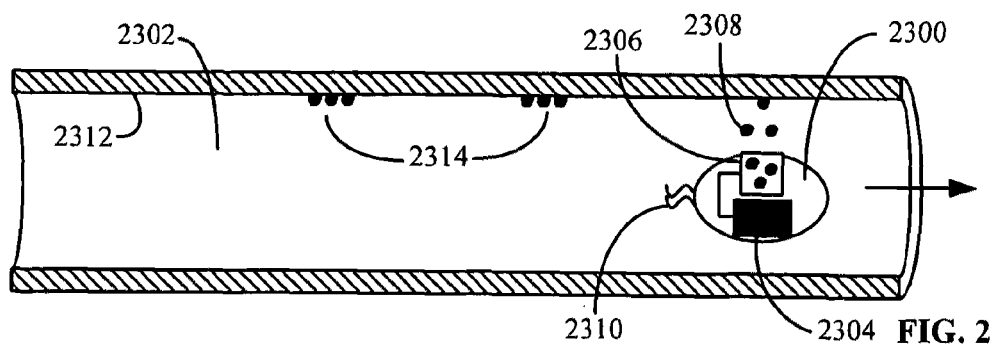

FIGS. 23A-23D provide an illustrative example of a lumen traveling device 2300 moving through a lumen of a body tube tree 2302 and periodically performing an action based at least in part upon a determined time. In FIG. 23A, lumen traveling device 2300 moving through a lumen of a body tube tree 2302 includes control circuitry 2304; an active portion 2306 for releasing a material 2308; and propelling mechanism 2310. Propelling mechanism 2310 is a flagella-like propelling mechanism used to move lumen traveling device 2300 through the lumen of a body tube tree 2302 as shown in FIG. 23B. The control circuitry 2304 of lumen traveling device 2300 is operationally connected to the active portion 2306 and includes motion control circuitry, response control circuitry and a timing device. The timing device of control circuitry 2304 periodically signals to the response control circuitry to activate an active portion 2306. Activation of active portion 2306 by the control circuitry 2304 results in release of material 2308 into the lumen of a body tube tree 2302. In this example, the material 2308 collects as deposits 2314 at discrete locations on the lumen wall 2312 as shown in FIG. 23C. After a period of time determined by the timing device, the response control circuitry of the control circuitry 2304 again causes activation of the active portion 2306 and release of material 2308. As lumen traveling device 2300 moves through a lumen of a body tube tree 2302, deposits 2314 of material 2308 are left by the lumen traveling device 2300 at periodic intervals on the lumen wall 2312 as shown in FIG. 23D.

The timing device can be used to determine an elapsed time between two events or actions, e.g., detection of a branch point, detection of specified value(s) of one or more sensed local parameter value(s), receipt of position indicator signals, or combinations thereof. Information regarding elapsed time can be combined with the speed of travel of the lumen traveling device to determined distance traveled. Conversely, information regarding time can be combined with distance traveled by the lumen traveling device to determine the speed of the lumen traveling device. Information regarding absolute and relative time measures is stored in one or more data storage locations of the lumen traveling device and/or in one or more remote devices. The stored information regarding time in combination with other measured parameters, e.g., position indicator signals, local parameter values, or properties of branches, can be used to generate a map of a body tube tree.

Figure 25A:
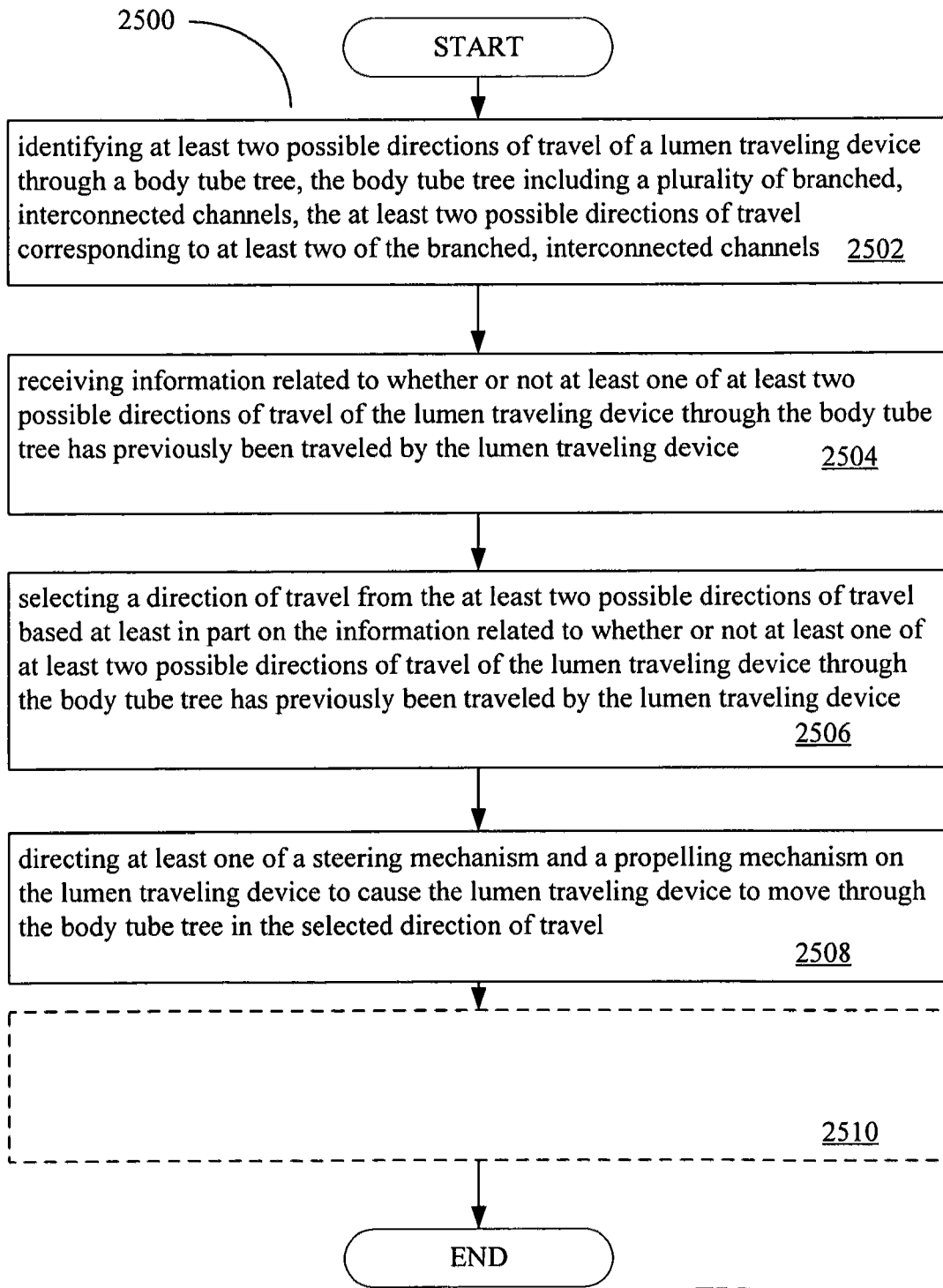

FIG. 25A shows a method 2500 of operating a lumen traveling device in a lumen of a body tube tree including identifying at least two possible directions of travel of a lumen traveling device through a body tube tree, the body tube tree including a plurality of branched, interconnected channels, the at least two possible directions of travel corresponding to at least two of the branched, interconnected channels at 2502; receiving information related to whether or not at least one of at least two possible directions of travel of the lumen traveling device through the body tube tree has previously been traveled by the lumen traveling device at 2504; selecting a direction of travel from the at least two possible directions of travel based at least in part on the information related to whether or not at least one of at least two possible directions of travel of the lumen traveling device through the body tube tree has previously been traveled by the lumen traveling device at 2506; and directing at least one of a steering mechanism and a propelling mechanism on the lumen traveling device to cause the lumen traveling device to move through the body tube tree in the selected direction of travel at 2508. Method 2500 can include various additional steps at 2510, as will be discussed herein. In an embodiment, the steps of method 2500 are performed by the lumen traveling device. In an embodiment, a portion of the steps of method 2500 are performed by the lumen traveling device and a portion of the steps of method 2500 are performed at least in part by a remote device. The steps outlined in FIG. 25A can be performed using systems as described elsewhere herein.

As shown in FIG. 25B, directing at least one of a steering mechanism and a propelling mechanism on the lumen traveling device to cause the lumen traveling device to move through the body tube tree in the selected direction of travel (2508) can be performed under the control of motion control circuitry located on-board the lumen traveling device (2509), under the control of motion control circuitry located in part on-board the lumen traveling device and in part on a remote device (2510), or under the control of motion control circuitry located on a remote device (2511). The method can include directing at least one of the steering mechanism and the propelling mechanism on the lumen traveling device to cause the lumen traveling device to move through the body tube tree in the selected direction of travel for a pre-determined distance (2512), directing at least one of the steering mechanism and the propelling mechanism on the lumen traveling device to cause the lumen traveling device to move through the body tube tree in the selected direction of travel for a pre-determined duration (2513), directing at least one of the steering mechanism and the propelling mechanism on the lumen traveling device to cause the lumen traveling device to move through the body tube tree in the selected direction of travel until a stop instruction is received from a remote device (2514), generating an instruction to turn the lumen traveling device (2515), directing at least one of the steering mechanism and the propelling mechanism on the lumen traveling device to cause the lumen traveling device to continue moving in a current direction of travel (2516), directing at least one of the steering mechanism and the propelling mechanism on the lumen traveling device to cause the lumen traveling device to continue moving in a current direction of travel until a branch point is reached (2517), and directing at least one of the steering mechanism and the propelling mechanism on the lumen traveling device to cause the lumen traveling device to reverse its direction of travel (2518).

Figure 25C:
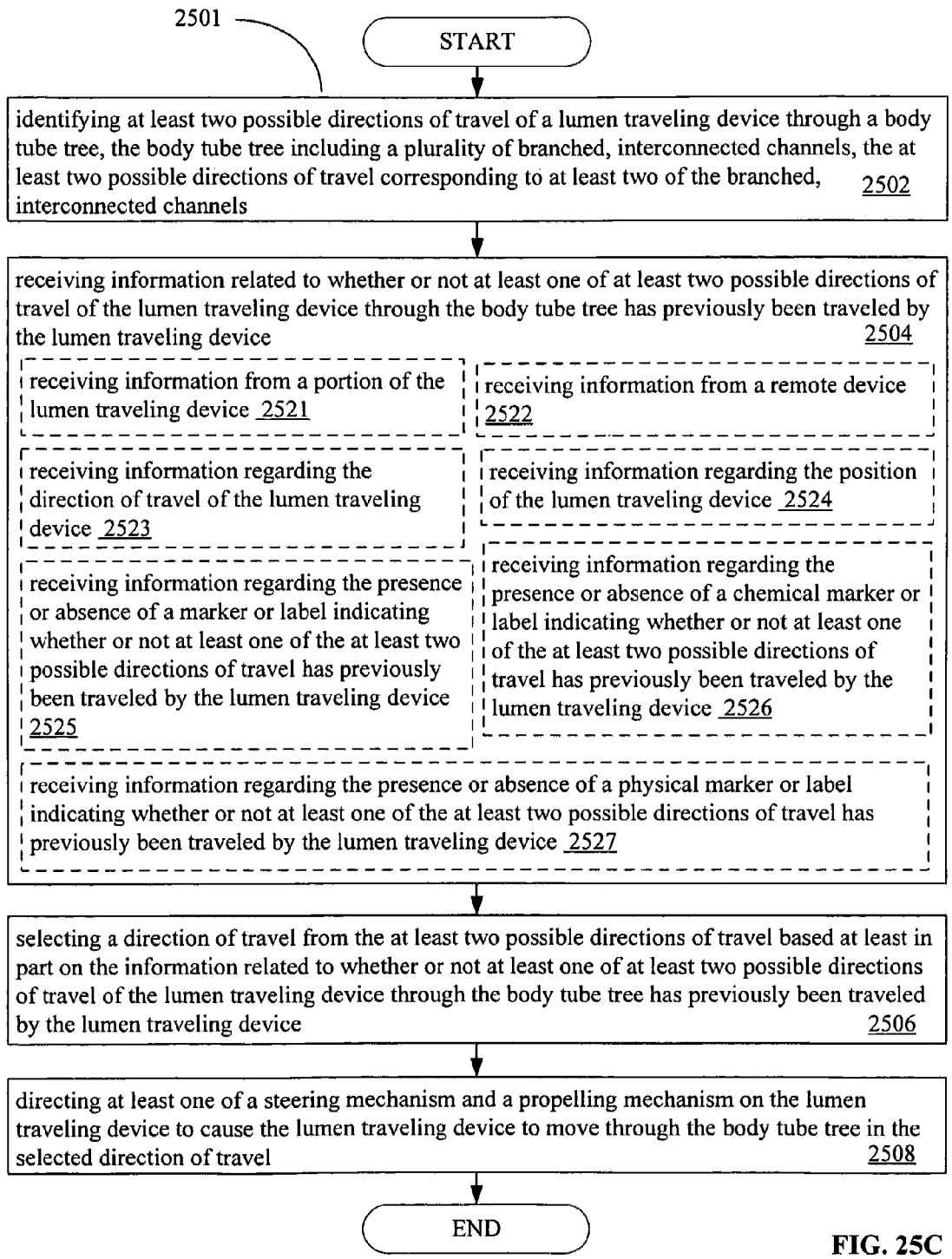

Arrival of the lumen traveling device at a decision point for identifying at least two possible directions of travel, e.g., a branch point, in the body tube tree can be identified by one or more arrival sensors as described elsewhere herein. The lumen traveling device is configured to receive additional information related to whether or not at least one of at least two possible directions of travel at the branch point has previously been traveled by the lumen traveling device. Receiving information related to whether or not at least one of at least two possible directions of travel of the lumen traveling device through the body tube tree has previously been traveled by the lumen traveling device can include information regarding current direction of travel of the lumen traveling device, the current location of the lumen traveling device, and the position of the lumen traveling device relative to a map of the body tube tree. The current direction of travel and location of the lumen traveling device can be determined based on one or more position indicator signals. The position indicator signals can be used to place the lumen traveling device on a previously generated portion of the map of a body tube tree or to aide in generating a map of unmapped portions of the body tube tree. As the lumen traveling device travels through the body tube tree, information regarding its path of travel relative to the map is collected and stored in the data storage location of the lumen traveling device or in a remote device. The current direction of travel and location of the lumen traveling device on the map is further compared with information gathered previously regarding positioning of the lumen traveling device on the map to determine if the lumen traveling device has taken this path in the past and, if so, when and/or how often. Method 2501 shown in FIG. 25C is a variant of method 2500 shown in FIG. 25A. In an embodiment, the information relating to a direction previously traveled is received from a portion of the lumen traveling device (2521). In an embodiment, the information relating to a direction previously traveled is received from a remote device (2522). The information received can include, but is not limited to, one or more of the direction of travel of the lumen traveling device (2523), the current position of the lumen traveling device (2524), and receiving information regarding the presence or absence of a marker or label indicating whether or not at least one of the at least two possible directions of travel has previously been traveled by the lumen traveling device (2525), for example the presence or absence of a chemical marker or label (2526) or a physical marker or label (2527).

Information related to whether or not at least one of at least two possible directions of travel of the lumen traveling device through the body tube tree has previously been traveled by the lumen traveling device can be information regarding one or more landmarks sensed in the lumen of a body tube tree. The one or more landmarks can be inherent chemical or physical markers or labels present at specific locations in the lumen of a body tube tree. An inherent chemical marker or label can include but is not limited to a specific protein, a nuclueic acid, an oligonucleotide, a polynucleotide, lipid, carbohydrate, a sugar, chemical compound, and the like, expressed on the surface of or excreted from specific cells at specific locations in the lumen of the body tube tree. An inherent physical landmark can include but is not limited to a branch point, a valve, a growth (e.g., polyp, plaque, fibroid, tumor), a discoloration, a lumen occlusion or expansion, an aneurysm or other measurable local alteration in the physical properties of a lumen. The inherent chemical or physical landmark can be represented by one or more of a variety of local parameters previously described herein. Alternatively, the one or more landmarks can be chemical or physical markers or labels previously placed in the lumen by an active portion of the lumen traveling device while traveling though the body tube tree.

Figure 26A:
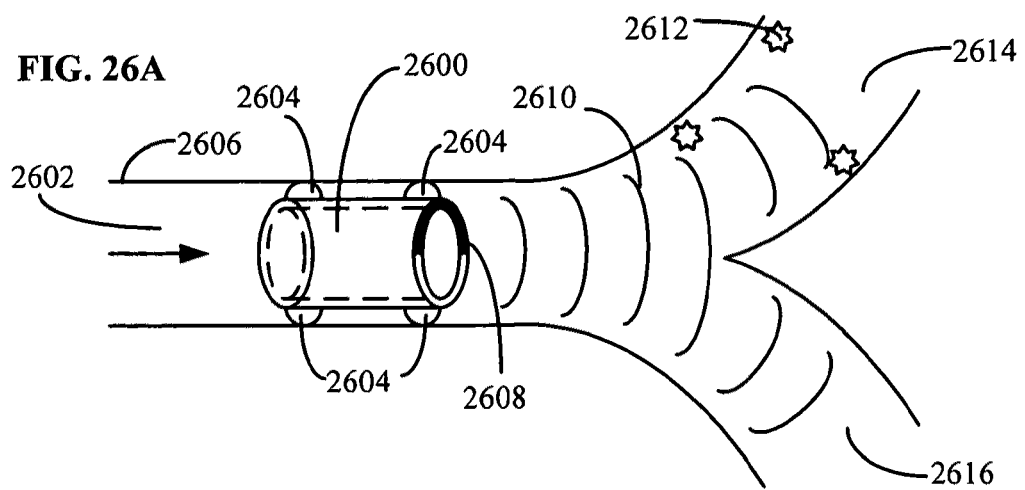
FIGS. 26A-26C illustrate an example of the operation of a lumen traveling device in the lumen of a body tube tree.
Figure 26B:
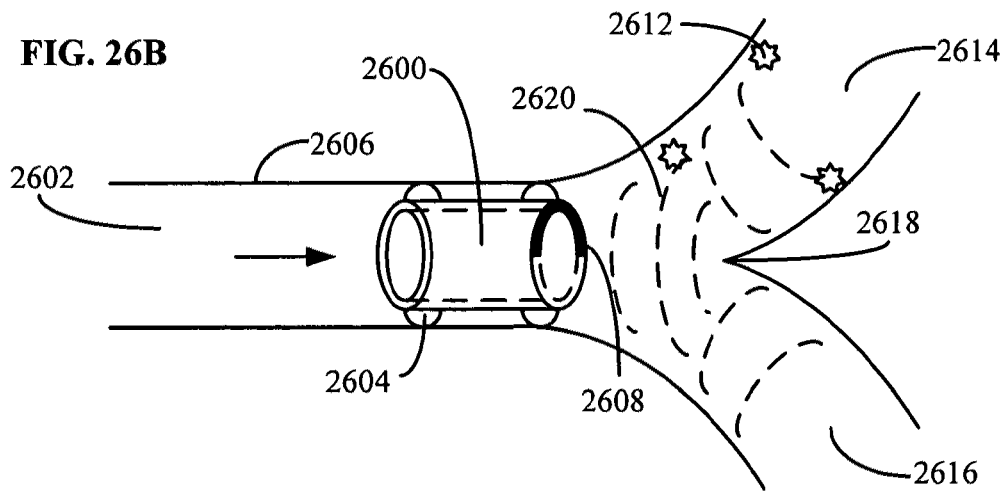
Figure 26C:
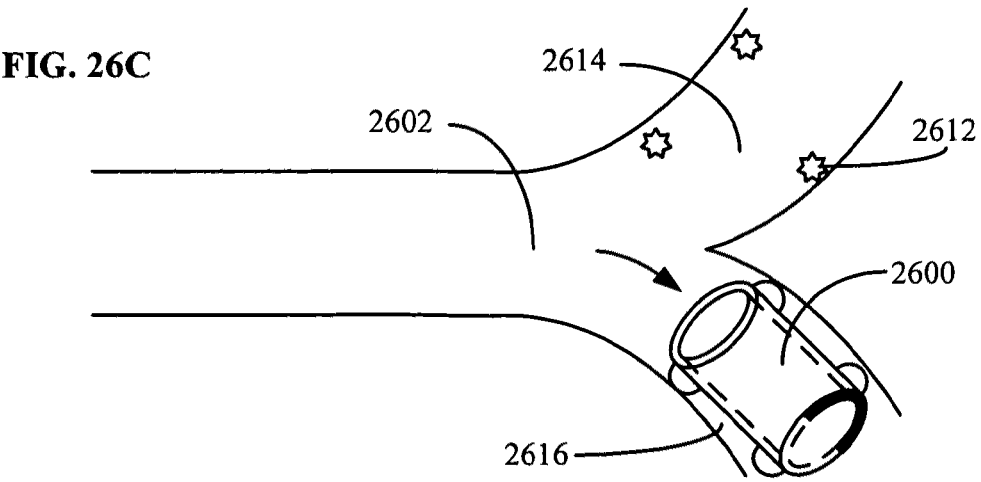

FIGS. 26A-26C depict lumen traveling device 2600 moving through a lumen of a body tube tree 2602 and selecting a direction of travel based on sensing one or more markers or labels. In this example, lumen traveling device 2600 includes one or more wall engaging elements 2604 for use in propelling lumen traveling device 2600 along the lumen wall 2606 of a lumen of a body tube tree 2602. The lumen traveling device 2600 further includes emitter/sensor system 2608, which emits electromagnetic energy 2610. In this example, a first branch channel 2614 has been previously marked or labeled with a chemical or physical marker or label, which in this example is fluorescent tag 2612, while a second branch channel 2616 lacks a chemical or physical marker or label. In FIG. 26B, lumen traveling device 2600 reaches a branch point 2618 and must select a direction of travel. Emitter/sensor system 2608 of lumen traveling device 2600 senses electromagnetic energy 2620 generated by fluorescent tag 2612 in response to emitted electromagnetic energy 2610 of FIG. 26A. Electromagnetic energy 2620 is indicative of the presence of fluorescent tag 2612 in first branch channel 2614 and the lack thereof in second branch channel 2616. In FIG. 26C, lumen traveling device 2600 is instructed to move into the second branch channel 2616, a branch channel not previously traveled by lumen traveling device 2600.

Information related to whether or not a direction of travel has been previously traveled by the lumen traveling device can be based on sensing one or more chemical marker or label previously placed in the lumen by an active portion of the lumen traveling device, as illustrated in FIG. 23. The chemical marker or label can be one or more of a detectable biomolecule including but not limited to a protein, a nuclueic acid, an oligonucleotide, a polynucleotide, a peptide, an antibody, a polysaccharide, an oligosaccharide, a carbohydrate, a sugar, a lectin, an oligonucleotide, an aptamer, and the like. The chemical marker or label can be periodically released from an active portion of the lumen traveling device and configured to bind to or associate with the lumen wall of the body tube tree, as illustrated in FIG. 23. For example, an antibody can be designed to specifically bind an antigen expressed on the surface of the lumen wall. In some instances, the chemical marker or label can be further modified with a physical marker or label, e.g., a fluorescent label, that can be detected using a physical sensor, e.g., a CCD imaging device in response to excitation by electromagnetic energy source.

In an embodiment, information related to whether or not a direction of travel has been previously traveled by the lumen traveling device can be based on sensing one or more physical marker or label previously placed in the lumen by an active portion of the lumen traveling device. The physical marker or label can be one or more of a light emitting marker, a radioactive marker, magnetic marker, a visible marker, or a radiofrequency identification (RFID) tag. The physical marker or label can be a light emitting marker or label that is either intrinsically light emitting or that reflects light or emits light (e.g., by fluorescence) in response to excitation from an electromagnetic energy source. An example of a light emitting marker or label includes a variety of quantum dots or semiconductor nanocrystals that fluoresce at various wavelengths in response to excitation energy (see, e.g., Jaiswal et al., *Nature Biotech.*, 2003, 21:47-51, which is incorporated herein by reference). Examples of other fluorescing dyes for use with biological samples include but are not limited to fluorescein (FITC), indocyanine green (ICG) and rhodamine B, red and near infrared emitting fluorophores (600-1200 nm) including cyanine dyes such as Cy5, Cy5.5, and Cy7 (Amersham Biosciences, Piscataway, N.J., USA) and/or a variety of Alexa Fluor dyes such as Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., USA; see, e.g., U.S. Pat. App. No.

2005/0171434 A1, which is incorporated herein by reference). Additional fluorophores include IRDye800, IRDye700, and IRDye680 (LI-COR, Lincoln, Nebr., USA), NIR-1 and 105-OSu (Dojindo, Kumamoto, Japan), La Jolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, CA), NIAD-4 (ICx Technologies, Arlington, Va.). Other fluorescing agents include BODIPY-FL, europium, green, yellow and red fluorescent proteins, luciferase. Alternatively, the light emitting marker or label can be a fluorescently labeled microsphere. Examples of fluorescently labeled microspheres ranging in diameter from 20 nanometers to 10 micrometers are available from commercial sources (e.g., Fluor Spheres® Fluorescent Microspheres, Invitrogen, Carlsbad, Calif.).

The physical marker or label can be one or more radioactive marker or label. The radioactive marker or label can include one or more radioisotope commonly used in nuclear medicine, examples of which include iodine-131, cobalt-60, cesium-137, technetium-99 m, carbon-11, nitrogen-13, oxygen-15, and fluorine-18. Other medical radioisotopes include but are not limited to, americium-241, arsenic-74, gold-198, boron-11, carbon-14, calcium-48, cerium-141, cobalt-55, cobalt-57, chromium-51, cesium-130, cesium-131, copper-61, copper-62, copper-64, copper-67, dysprosium-165, europium-155, gallium-67, gallium-68, gadolinium-153, germanium-68, hydrogen-3, iodine-122, iodine-123, iodine-124, iodine-125, iodine-132, indium-111, indium-115m, Iridium-191m, krypton-81m, manganese-51, manganese-52, Nb-95, osmium-194, phosphorous-32, phosphorous-33, lead-203, lead-82, ruthenium-97, ruthenium-103, sulfur-35, scandium-46, selenium-72, selenium-75, strontium-85, tantalum-178, tantalum-182, terbium-149, thallium-201, xenon-127, xenon-133.

The physical marker or label can be a magnetic marker or label such as, for example, magnetic beads, particles or carbon nanotubes. Magnetic particles and beads of various sub-millimeter size are available from commercial sources (from, e.g., Seradyn-Thermo Scientific, Indianapolis, Ind.; Dynal-Invitrogen, Carlsbad, Calif.). Carbon nanotubes with various functionalities can be synthesized de novo (see, e.g. Bianco et al., "Carbon nanotube-based vectors for delivering immunotherapeutics and drugs," in *Nanomaterials for Medical Diagnosis and Therapy, pp.* 85-142, *Nanotechnologies for the Live Sciences*, Vol. 10, Edited by Kumar, WILEY-VCH Verlag GmbH & Co. KGaA, Weinheim, 2007, which is incorporated herein by reference) or obtained from commercial sources (from, e.g., Nanolab, Newton, Mass.; Swan Chemical Inc., Lyndhurst, N.J.).

The physical marker or label can be a visual marker or label such as, for example, an ink or dye visible with ultraviolet, visible, near infrared, or infrared electromagnetic energy emitted by the lumen traveling device. Examples of vital dyes used to stain cells include but are not limited to acridin orange (stains DNA and RNA), DiOC (3,3'-dihexyloxacarbocyanine iodide; stains endoplasmic reticulum), rhodamine 123 (stains mitochondria), Nile red (stains lipid vesicles), DAPI (4',6-diamidino-2-phenylindole; stains DNA), Hoechst 33342 (stains DNA). Calcein AM and carboxyfluorescein diacetate are examples of membrane permeable dyes that are converted into membrane-impermeable dyes by cellular esterases, thereby trapping them inside live cells.

The physical marker or label can be one or more radiofrequency identification tags, sub-millimeter versions of which have been described (see, Hornyak, *Scientific American Magazine*, February 2008, pp. 68-71, which is incorporated herein by reference). Alternatively, the physical marker or label can be one or more bokodes, millimeter sized visual tags that can be captured with a camera as described by Mohan et al., "Bokode: Imperceptible visual tags for camera based interaction from a distance" *ACM Transactions on Graphics* (Proceedings of SIGGRAPH 2009, Aug. 3-7, 2009, New Orleans, which is incorporated herein by reference).

The chemical or physical marker or label is configured for attachment to or insertion into one or more cells and/or components of the basal lamina lining the lumen of a body tube tree. Examples of cells lining the lumen of body tube tree include but are not limited to endothelial cells (e.g., cells lining the vasculature) and epithelial cells (e.g., cells lining the respiratory system including the mouth and nose, the digestive tract including the anus, the urogenital tract, and the glands of the digestive tract, prostate, and breast). In an embodiment, the chemical or physical marker or label can be directly applied to the surface of the lumen by some means. For example, cell membranes can be readily labeled with a number of fluorescent lipophilic dyes, examples of which include DiI (1,1'-dioctadecyl-3,3,3',3'-tetramethylindocarbocyanine perchlorate), DiO (3,3'-dioctadecyl-oxacarbocyanine perchlorate) and DiA 4-(4-(dihexadecylamino) styryl)-N-methylpyridinium iodide.

In an embodiment, the physical marker or label is modified with a binding moiety to enable interaction of the chemical or physical marker or label with the wall of the lumen. For example, a physical marker or label, e.g., a fluorescent dye, a radioisotope, or a magnetic bead, can be linked to a binding moiety that selectively binds to the surface of a cell and/or a component of the basal lamina lining the lumen of a body tube tree. Examples of binding moieties include but are not limited to antibodies, aptamers, receptor binding ligands, peptide ligands. A further example of a binding moiety for linking a chemical or physical marker or label to the lumen is an antibody, aptamer or other binding moiety that selectively binds to a protein constitutively expressed on the surface of endothelial or epithelial cells, specific examples of which include intercellular adhesion molecule-1 (ICAM1) and epithelial cell adhesion molecule (EpCAM), respectively.

The chemical or physical marker or label can be conjugated to the binding moiety using one or more of a cross linking agent. In general, any of a number of cross linking agents can be used to conjugate an appropriately derivatized chemical or physical marker or label to an appropriately derivatized binding moiety. Examples of cross linking agents include, but are not limited to, primary amine/primary amine linkers such as DMS (dimethyl suberimidate), DMP (dimethyl pimelimidate), DSS (disuccinimidyl suberate), DST (disuccinimidyl tartate), Sulfo DST (sulfodisuccinimidyl tartate), DSP (dithiobis(succinimidyl propionate) and sulfhydryl/sulfhydryl linkers such as DPDPB (1,4-di-(3'[2' pyridyldithio]-propionamido) butane); primary amine/sulfhydryl linkers such as MBS (m-maleimidobenzoyl-N-hydroxysuccinimide ester), Sulfo MBS (m-maleimidobenzoyl-N-hydroxysulfosuccinimide), Sulfo GMBS (N-γ-maleimidobutyryloxysulfosuccinimide ester), EMCS(N-(epsilon-maleimidocaproyloxy) succinimide ester), Sulfo EMCS(N-(epsilon-maleimidocaproyloxy) sulfo succinimide), SMCC (succinimidyl 4-(N-maleimidomethyl)cyclohexane-1-carboxylate), SMPB (succinimidyl 4-(rho-maleimidophenyl) butyrate), Sulfo SIAB (N-sulfosuccinimidyl(4-iodoacetyl) aminobenzoate), cyclohexane-1-carboxylate), and MAL-PEG-NHS (maleimide PEG N-hydroxysuccinimide ester); sulfhydryl/hydroxyl linkers such as PMPI (N-rho-maleimidophenyl) isocyanate; sulfhydryl/carbohydrate linkers such as EMCH(N-(epsilon-maleimidocaproic acid) hydrazide);

and amine/carboxyl linkers such as EDC (1-ethyl-3-(3-dimethylaminopropyl) carbodiimide hydrochloride).

An antibody for use as a chemical or physical marker or label can be conjugated with one or more quantum dots via an amine-thiol linkage using amine-derivatized, poly-ethylene glycol coated quantum dots and the amine-thiol crosslinker SMCC with a commercially available kit (Qdot® Antibody Conjugation Kit, Invitrogen, Carlsbad, Calif.). Similarly, various methods are available for attaching quantum dots to the DNA backbone of an aptamer such as, for example, covalent linkage of amino-labeled DNA to carboxylated quantum dots and linkage of biotinylated DNA to streptavidin modified quantum dots. See, e.g., Cady et al., *Mol. Cell. Probes*, 21:116-124, 2007, which is incorporated herein by reference. For example, carboxy quantum dots (from, e.g., Quantum Dot Corporation, Hayward, Calif., USA) can be attached to an aptamer through a C6 amino modifier placed on either the 5 prime or 3 prime end of the aptamer sequence. Alternatively, streptavidin quantum dots (from, e.g., Quantum Dot Corporation, Hayward, Calif., USA) can be attached to an aptamer through a biotin attached to the 5-prime end of the aptamer sequence. Quantum dots, fluorescent dyes, and magnetic particles derivatized for cross-linking to antibodies, aptamers or other biomolecules are available from a number of commercial sources (from, e.g., Invitrogen, Carlsbad, Calif.; Seradyn-Thermo Scientific, Indianapolis, Ind.; Sigma-Aldrich, St. Louis, Mo.).

In an embodiment, a physical marker or label, e.g., radioactive or fluorescent, can be incorporated into the binding moiety at the time of synthesis. For example, radiolabeled nucleotides or radiolabeled amino acids can be incorporated into an oligonucleotide aptamer or protein antibody, respectively, during synthesis using standard methods. As another example, all or part of green fluorescent protein (GFP) derived from *Aequorea victoria* jellyfish or yellow, red and blue fluorescing derivatives thereof, can be fused with a binding moiety (e.g., an antibody) designed to bind to or associate with the surface of the lumen. A number of expression constructs for generating recombinant GFP fusion proteins are available from commercial sources (from, e.g., Invitrogen, Carlsbad, Calif.).

In an embodiment, the marker or label can be a DNA construct encoding a fluorescent protein and inserted into one or more cells lining the lumen of a body tube tree. For example, baculovirus expression constructs, e.g., Cellular Lights™ and Organelle Lights™ (from Invitrogen, Carlsbad, Calif.), can be inserted into a cell and induced to express specific fluorescent proteins.

In an embodiment, the chemical or physical marker or label can be inserted into one or more cells lining the lumen of the body tube tree. The marker or label can be inserted by direct injection, diffusion, fusion, or other means. For example, the lumen traveling device can include an active portion that includes one or more microneedles for direct injection of a chemical or physical marker or label into a cell. Alternatively, the lumen traveling device can include an active portion that includes a material release structure for releasing one or more chemical or physical marker or label into the lumen of a body tube tree. The chemical or physical marker or label can be periodically placed along the path of travel of the lumen traveling device by an active portion of the lumen traveling device, as described, for example, in connection with FIG. 23. The periodic placement can be based on distance traveled by the lumen traveling device, e.g., every one millimeter. The periodic placement of the chemical or physical marker or label by an active portion of the lumen traveling device can be completed based on time between placements, e.g., every second. The periodic placement of chemical or physical marker or labels in the lumen of the body tube tree can be used to inform selection of one of at least two possible directions of travel.

The selected direction of travel of the lumen traveling device can be selected based on information regarding whether or not at least one of at least two possible directions of travel have been previously traveled by the lumen traveling device. As shown in FIG. 25D, in an embodiment, the selected direction of travel can be a direction of travel not previously traveled by the lumen traveling device (2530). For example, the selected direction of travel may be the direction of travel devoid of chemical or physical markers or labels. In an embodiment, the selected direction of travel can be a direction of travel that is the least frequently traveled by the lumen traveling device of the at least two possible directions of travel (2531). In an embodiment, the selected direction of travel can be a direction of travel that is the most frequently traveled by the lumen traveling device of the at least two possible directions of travel (2532). For example, comparison of the current direction of travel of the lumen traveling device and the location of the lumen traveling device on a map of the body tube tree can be used to determined how frequently the lumen traveling device has traveled in the possible directions of travel. In an embodiment, the selected direction of travel can be a direction of travel that is the least recently traveled by the lumen traveling device of the at least two directions of travel (2533). In an embodiment, the selected direction of travel can be a direction of travel that is the most recently traveled by the lumen traveling device of the at least two directions of travel (2534). Information regarding the frequency of travel in one of at least two possible directions of travel can be stored in and/or retrieved from one or more data storage location associated with the lumen traveling device and/or a remote device. Information regarding the frequency of travel in one of at least two possible directions of travel is further correlated with a pre-existing map or an evolving map of the body tube tree and used to inform the selection of the direction of travel of the lumen traveling device. Selecting a direction of travel can also include avoiding at least one portion of the body tube tree having a dimension less than a specified minimum dimension (2535). Variants of the methods 2500 and 2501 can include additional steps 2510, which as shown in FIG. 25D, can include storing a record of the selected direction of travel 2536. In an embodiment, the method can include directing an active portion of the lumen traveling device to mark or label the selected direction of travel (2537), directing an active portion of the lumen traveling device to mark or label the selected direction of travel by marking or labeling a selected body lumen with a chemical marker or label (2538). A chemical marker or label may be a biochemical marker or label, which can include a nucleic acid (2540) or protein (2541). In an embodiment, a chemical marker or label includes a radioactive marker or label (2542). In an embodiment, the method includes directing an active portion of the lumen traveling device to mark or label the selected direction of travel by marking or labeling a selected body lumen with a physical marker or label (2543). A physical marker or label can include a magnetic marker or label (2544), optically detectable marker or label (2545), magnetically detectable marker or label (2546), or an electrically detectable marker or label (2548).

Further additional steps 2510 are depicted in FIG. 25E, and include sensing a local parameter value with a parameter sensor on the lumen traveling device (2550), identifying a stop condition based at least in part on the sensed local parameter value; and directing at least one of the steering mechanism and the propelling mechanism on the lumen traveling device to cause the lumen traveling device to stop movement of the lumen traveling device through the body tube tree based at least in part on the identified stop condition (2551), storing data representing the sensed local parameter value in a memory location on the lumen traveling device (2552), transmitting data representing the sensed local parameter value from the lumen traveling device to a remote device (2553), storing motion control instructions for directing operation of at least one of the steering mechanism and the propelling mechanism in a memory location on the lumen traveling device (2554), transmitting motion control instructions for directing operation of at least one of the steering mechanism and the propelling mechanism on the lumen traveling device to a remote device (2555), receiving at least one of instructions or data from a remote device (2556), wherein the method steps are performed by the lumen traveling device (2557), and wherein a portion of the method steps are performed by the lumen traveling device and a portion of the method steps are performed at least in part by a remote device (2558).

Motion control instructions are generated to cause movement of the lumen traveling device in the selected direction of travel. The motion control instructions are configured to instruct the lumen traveling device to go right, to go left, to turn a certain number of degrees, to go up, to go down, to continue moving in the current direction, or to reverse. In an embodiment, the motion control instructions can for directing operation of at least one of the steering mechanism and the propelling mechanism on the lumen traveling device to cause the lumen traveling device to move through the lumen of a body tube tree in the selected direction of travel for a pre-determined distance, for a pre-determined time, or until a branch point is reached, or until a combination of such distance, time and location criteria are attained. An arrival of the lumen traveling device at a branch point is detected using one or more arrival sensors as described elsewhere herein. In an embodiment, the motion control instructions are stored in a data storage location on the lumen traveling device. In another embodiment, the motion control instructions can be transmitted from the lumen traveling device to a remote device. In yet another embodiment, the motion control instructions are received at least in part from a remote device.

The motion control instruction can direct operation of at least one of the steering mechanism and the propelling mechanism on the lumen traveling device to cause the lumen traveling device to move through a body tube tree in the selected direction of travel until a stop instruction is received from a remote device. The stop instruction can be based on elapsed time, calculated distance of travel, or actual imaging or sensing of the location of the lumen traveling device in the body tube tree. For example, the stop instruction may be received after the lumen traveling device has traveled through the body tube tree for a specific period of time following receipt of the motion control instruction. As a further example, the stop instruction may be received after the lumen traveling device has reached a specific location. An arrival of the lumen traveling device at a specific location can be determined based on the location of the lumen traveling device on a map of the body tube tree.

An arrival of the lumen traveling device at a specific location can be determined by remote sensing using one or more medical imaging techniques. For example, an external medical imaging technique can be used to monitor in real time the movement of the lumen traveling device from outside the body and once the lumen traveling device has reached a specific location, a remote signal can be sent to the lumen traveling device to stop movement. The lumen traveling device can be labeled or can emit a signal (e.g., radiofrequency) while the body tube tree itself can be labeled with a contrast agent. As a further example, the lumen traveling device can be constructed from or coated with a radiopaque material and visualized relative to the vasculature using angiography or other imaging method.

The motion control instructions can direct operation of at least one of the steering mechanism and the propelling mechanism on the lumen traveling device to cause the lumen traveling device to move through a body tube tree in the selected direction of travel until a stop instruction is received based on sensing a local parameter value with one or more parameter sensors. Examples of sensors for sensing local parameter values have been described elsewhere herein. Information regarding the sensed local parameter value is stored in a data storage location on the lumen traveling device. Alternatively, or in addition, data regarding the sensed local parameter value may be transmitted to a remote device.

FIG. 24 illustrates a block diagram of a system 2400 that includes a set of instructions 2404 for operating a lumen traveling device. An embodiment of system 2400 is provided using non-transitory machine readable media 2402 including a set of instructions 2404 including one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of said branched, interconnected channels; one or more instructions that cause the lumen traveling device control system to receive information related to whether at least one of the at least two possible directions of travel of the lumen traveling device through the body tube tree has previously been traveled by the lumen traveling device; one or more instructions that cause the lumen traveling device control system to select a direction of travel from the at least two possible directions of travel based at least in part on the information related to whether or not at least one of the at least two possible directions of travel of the lumen traveling device through the body tube tree has previously been traveled by the lumen traveling device; and one or more instructions that cause the lumen traveling device control system to direct at least one of a steering mechanism and a propelling mechanism on the lumen traveling device to cause the lumen traveling device to move through the body tube tree in the selected direction of travel. The one or more instructions can be, for example, computer executable and/or logic implemented instructions. In an embodiment, the non-transitory machine readable media 2402 includes computer readable media 2406. In an embodiment, the non-transitory machine readable media 2402 includes recordable-type media 2408. A system as depicted in FIG. 24 can be used in implementation of the method of FIG. 25A, for example. It will be appreciated that while system 2400 is specifically shown to include instructions for performing method 2500 depicted in FIG. 25A, system 2400 can be modified to perform any of the variants of method 2500 and 2501 as depicted in FIGS. 25A-25E.

Figure 28A:
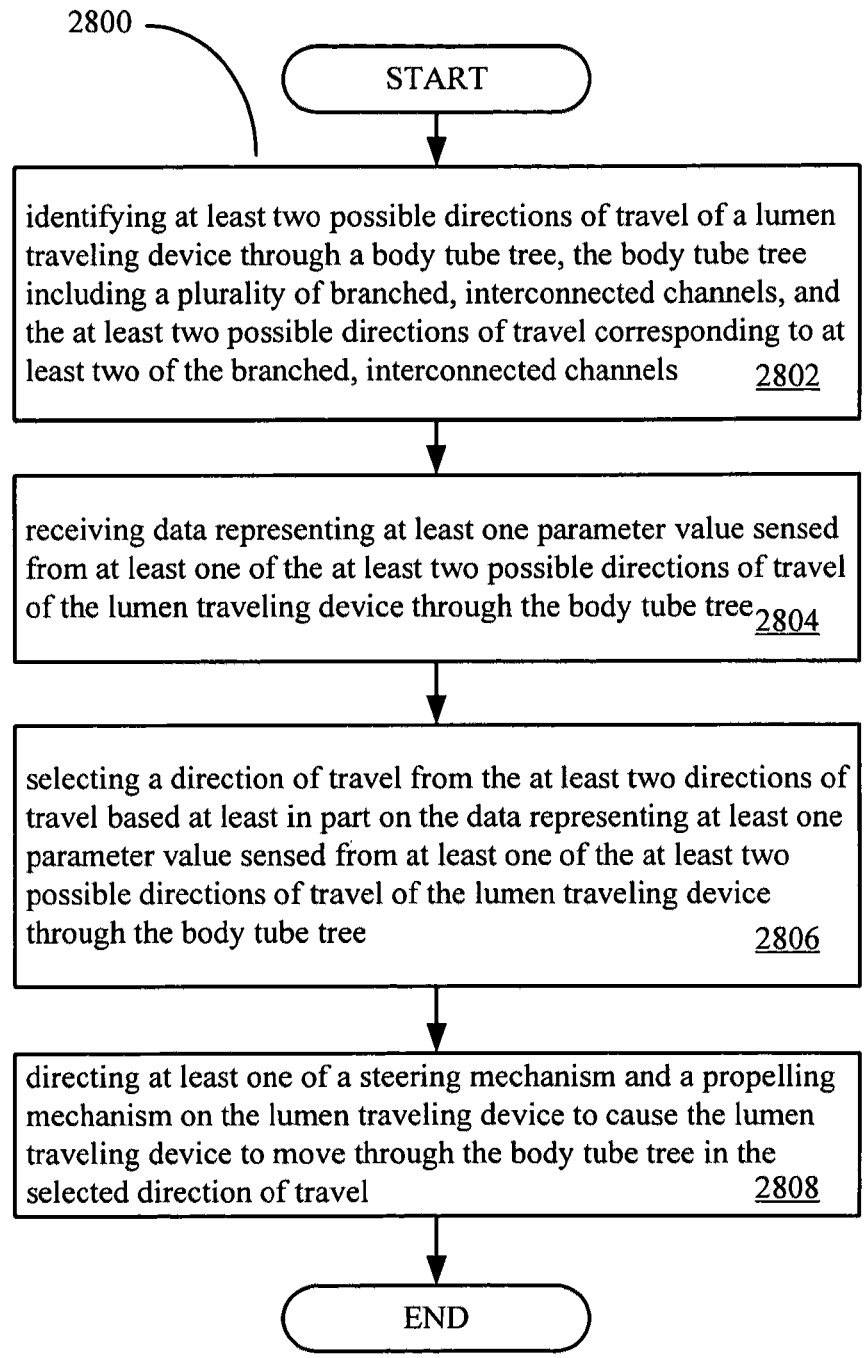

A further method 2800 of operating a lumen traveling device in the lumen of a body tube tree of a subject is illustrated in FIG. 28A and comprises identifying at least two possible directions of travel of a lumen traveling device through a body tube tree, the body tube tree including a plurality of branched, interconnected channels, and the at least two possible directions of travel corresponding to at least two of the branched, interconnected channels at 2802; receiving data representing at least one parameter value sensed from at least one of the at least two possible directions of travel of the lumen traveling device through the body tube tree at 2804; selecting a direction of travel from the at least two directions of travel based at least in part on the data representing at least one parameter value sensed from at least one of the at least two possible directions of travel of the lumen traveling device through the body tube tree at 2806; and directing at least one of the steering mechanism and the propelling mechanism on the lumen traveling device to cause the lumen traveling device to move through the body tube tree in the selected direction of travel at 2808. The steps outlined in FIG. 28 can be performed using systems as described elsewhere herein.

Figure 28B:
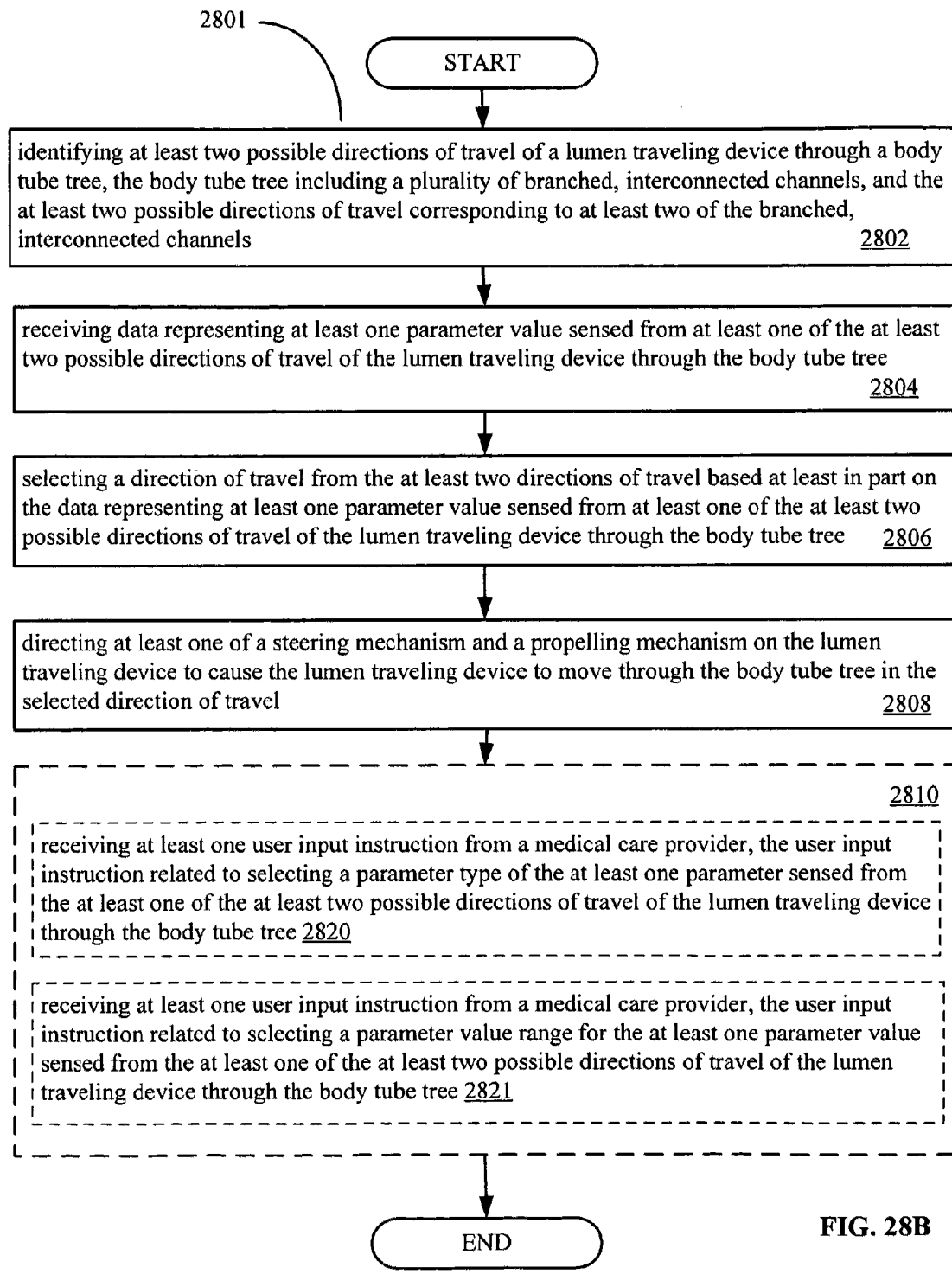

FIG. 28B illustrates method 2801, which is a variant of method 2800 depicted in FIG. 28A. Method 2801 includes steps 2802, 2804, 2806, and 2808 as described in connection with FIG. 28A, as well as additional steps 2810, which in the embodiment shown in FIG. 28B include receiving at least one user input instruction from a medical care provider, the user input instruction related to selecting a parameter type of the at least one parameter sensed from the at least one of the at least two possible directions of travel of the lumen traveling device through the body tube tree (2820) and/or receiving at least one user input instruction from a medical care provider, the user input instruction related to selecting a parameter value range for the at least one parameter value sensed from the at least one of the at least two possible directions of travel of the lumen traveling device through the body tube tree (2821).

FIG. 28C depicts variants of directing at least one of a steering mechanism and a propelling mechanism on the lumen traveling device to cause the lumen traveling device to move through the body tube tree in the selected direction of travel (2808), which can include directing at least one of the steering mechanism and the propelling mechanism on the lumen traveling device to cause the lumen traveling device to move through the body tube tree in the selected direction of travel for a pre-determined distance (2822), directing at least one of the steering mechanism and the propelling mechanism on the lumen traveling device to cause the lumen traveling device to move through the body tube tree in the selected direction of travel for a pre-determined duration (2823), directing at least one of the steering mechanism and the propelling mechanism on the lumen traveling device to cause the lumen traveling device to move through the body tube tree in the selected direction of travel until an stop instruction is received from a remote device by the lumen traveling device (2824), directing at least one of the steering mechanism and the propelling mechanism on the lumen traveling device to cause the lumen traveling device to turn (2825), directing at least one of the steering mechanism and the propelling mechanism on the lumen traveling device to cause the lumen traveling device to continue moving in a current direction of travel (2826), directing at least one of the steering mechanism and the propelling mechanism on the lumen traveling device to cause the lumen traveling device to reverse its direction of travel (2827), directing at least one of the steering mechanism and the propelling mechanism on the lumen traveling device to cause movement of the lumen traveling device based on a previous movement direction (2828), directing at least one of the steering mechanism and the propelling mechanism on the lumen traveling device to cause the lumen traveling device to move in a different direction the direction it was previously instructed to move (2829), directing at least one of the steering mechanism and the propelling mechanism on the lumen traveling device to cause the lumen traveling device to move in the same direction it was previously directed to move (2830).

The lumen traveling device is configured to receive data representing at least one parameter value sensed from at least one of at least two possible directions of travel. The at least two possible directions of travel can be at a branch point with two or more branches representing two or more possible directions of travel. Arrival of the lumen traveling device at a branch point in the body tube tree can be sensed by one or more arrival sensors. The at least two possible directions of travel can also be in any direction of travel away from the current location of the lumen traveling device, e.g., up, down, right, left, forward, backward, diagonal, etc. A direction of travel away from the current location can be selected based on data regarding one or more local parameters of interest in the lumen of the body tube tree. Data regarding one or more local parameters can be obtained from one or more sensors. The one or more sensors can be configured to measure at least one parameter value, including, but not limited to, a temperature, a pressure, a fluid flow, an optical absorption, optical emission, fluorescence, or phosphorescence, an index of refraction, an electrical resistivity, a density or sound speed, a pH, an osmolality, the presence of an embolism, the presence (or absence) of an object (such as a blood clot, a thrombus, an embolus, a plaque, a lipid, a kidney stone, a dust particle, a pollen particle, a gas bubble, an aggregate, a cell, a specific type of cell, a cellular component or fragment, a collection of cells, a gamete, a pathogen, or a parasite), and/or the presence (or absence) of a substance such as a biological marker, an antibody, an antigen, a peptide, a polypeptide, a protein, a complex, a signaling material, a nuclueic acid, an oligonucleotide, a polynucleotide, a cell (and, in some cases, a cell of a particular type, e.g. by methods used in flow cytometry), a cellular component, an organelle, a gamete, a pathogen, a lipid, a lipoprotein, an alcohol, an acid, an ion, an immunomodulator, a sterol, a steroid, a carbohydrate, a sugar, a polysaccharide, a glycoprotein, a metal, an electrolyte, a metabolite, an organic compound, an organophosphate, a drug, a therapeutic, a gas, a pollutant, or a tag (e.g., chemical or physical marker or label), for example. Specific examples of sensors include one or more of a pressure sensor, a flow sensor, a temperature sensor, an optical sensor, a biosensor, or a chemical sensor. The selection of a suitable sensor for a particular application or use site is considered to be within the capability of a person having skill in the art. In some aspects, a sensor can include signal processing or pre-processing capability integrated therewith.

In an embodiment, the sensed parameter is electromagnetic energy emitted by the lumen traveling device. For example, the lumen traveling device can be configured to sense autofluorescence emitted from cells of the lumen wall, to differentiate between normal and diseased cells, and to move in the direction of the diseased tissue based on the sensed autofluorescence parameter. The lumen traveling device can be configured to sense autofluorescence emitted from lumen wall tissue that has been illuminated with specific wavelengths of electromagnetic energy from, for example, one or more of a microscale light-emitting diode or quantum dot. Endogenous fluorophores associated with the lumen wall absorb the electromagnetic energy delivered from the lumen traveling device and re-emit it as fluoresced light at a longer wavelength. The autofluorescence can be sensed with one or more of a light or image capture device, e.g., CCD, CMOS, or other similar device. Tissue autofluorescence can originate from aromatic amino acids such as tryptophan, tyrosine, and phenylalanine (excitation wavelengths of 200-340 nm, emission wavelengths of 360-370, 455 nm), from reduced pyridine nucleotides such as nicotinamide adenine dinucleotide (NADH, excitation wavelength of 360 nm, emission wavelength of 460 nm), from flavins and flavin nucleotides such as riboflavin and flavin mononucleotide (excitation wavelengths of 360 nm, 445-470 nm, emission wavelengths of 440 nm, 520 nm), from structural proteins such as collagen, and from lipopigments such as ceroid and lipofuscin. See, e.g., Chung et al., *Current Surgery*, 62:365-370, 2005, and Dacosta et al., *J. Clin. Path.*, 58:766-774, 2005, each of which is incorporated herein by reference. Differences in the properties of emitted autofluorescence can be used to distinguish between normal and cancerous cells in a variety of epithelial organ systems, including the cervix, colon, bladder, bronchus and oral mucosa (See, e.g., Breslin et al., *Ann. Surg. Oncol.*, 2004, 11:65-70; Weingandt et al., *BJOG* 2002, 109:947-951; Chiyo et al., *Lung Cancer*, 2005, 48:307-313; Eker et al., *Gut*, 1999, 44:511-518, each of which is incorporated herein by reference). For example, changes in autofluorescence emission (350 to 700 nm) of premalignant or malignant lesions in the oral cavity relative to normal tissue can be detected using excitation wavelengths of 337 nm, 365 nm, and 410 nm (see, e.g., Gillenwater et al., *Arch. Otolaryngol. Head Neck Surg.*, 1998, 124:1251-1258, which is incorporated herein by reference). Cervical intraepithelial neoplasia can be differentiated from normal tissue by autofluorescence using an excitation wavelength of 355 nm (see, e.g., Nordstrom et al., *Lasers Surg. Med.*, 2001, 29:118-127, which is incorporated herein by reference). Autofluorescence in combination with reflected light can be used to differentiate between normal, inflamed and pre-invasive lesions in the lung see, e.g., Gabrecht et al., *Diagnostic Optical Spectroscopy in Biomedicine IV: Proc. SPIE-OSA Biomedical Optics*, 2007, Vol. 6628, 66208C-1-8; U.S. Pat. No. 5,507,287, each of which is incorporated herein by reference). Autofluorescence associated with macrophages in a plaque can be used to characterize an atherosclerotic lesion as described by Marcu et al., *Atherosclerosis*, 2005, 181:295-303, which is incorporated herein by reference. The accumulation of macrophages in the fibrous cap of an atherosclerotic plaque are indicative of inflammation as well as instability of the plaque and can be detected by irradiation of the lumen wall with electromagnetic energy at a wavelength of 337 nm and sensing autofluorescence at specific maxima wavelengths of 395 nm and 450 nm or over a range of wavelengths from 300-600 nm.

As shown in FIG. 28D, additional step 2810 can include receiving data representing at least one parameter value sensed from at least one of the at least two possible directions of travel of the lumen traveling device through the body tube tree (2831), which may include receiving data representing an analyte (2832), for example, receiving data representing an analyte selected from the list consisting of a chemical, a biomaterial, an ion, an electrolyte, a biological marker, an antibody, a polypeptide, a protein, a nucleic acid, an oligonucleotide, a polynucleotide, a complex, a pathogen, a signaling material, a lipid, an alcohol, a sterol, a steroid, a carbohydrate, a sugar, a drug, a therapeutic, a gas, a metabolite, a cytokine, a chemokine, a hormone, an inflammatory molecule, a cell, and a cell fragment (2833). Data representative of an analyte can be data representative of the presence or concentration of an analyte, for example.

In an embodiment, the sensed parameter can be one or more analytes released from a target location within a body tube tree. The target location can be a tumor or localized site of inflammation from which analytes such as tumor markers and/or inflammatory mediators are secreted. Examples of tumor markers found in blood include but are not limited to prostate-specific antigen (PSA), cancer antigen 125 (CA 125), CA19-9 antigen, calcitonin, alpha-fetoprotein (AFP), human chorionic gonadotropin (HCG). Examples of inflammatory mediators include but are not limited to cytokines, interferons, interleukins, chemokines, leukotrienes, prostaglandins, growth factors, soluble receptors, and the like. Tumor markers and inflammatory mediators may also be found in expired breath condensate. A number of analytes are detected in the expired breath of cancer patients, examples of which include but are not limited to volatile organic compounds (VOCs), interleukin 6 (IL-6), and endothelin-1 (see, e.g., Dweik & Amann, *J Breath Res.*, 2008, 030301 (3 pp) and Phillips et al., *Chest*, 2003, 123:2115-2123, each of which is incorporated herein by reference). Analytes associated with inflammation of the lungs have also been detected in expired breath and include 8-isoprostane and nitric oxide (see, e.g., Psathakis et al., *Chest*, 2004, 125:1005-1011, which is incorporated herein by reference). A number of specific volatile organic compounds are elevated in the expired breath of subjects with cancer, including but not limited to butane, 3-methyl tridecane, 7-methyl tridecane, 4-methyl octane, 3-methyl hexane, heptane, 2-methyl hexane, pentane, and 5-methyl decane. Exhaled analytes associated with various diseases and/or lesions of the lungs can include nitric oxide, other volatile gases (e.g. carbon monoxide, ethan, pentane), and endogenous substances (e.g., inflammatory mediators, cytokines, oxidants) (see, e.g., Kharitonov et al., *Am. J. Respir. Crit. Care Med.*, Vol. 163, pp. 1693-1722, 2001, which is incorporated herein by reference).

Information regarding a local parameter can be collected using one or more of a sensing or information gathering devices or structures. The lumen traveling device can include one or more sensors of the same or different types including but not limited to, pressure sensors, temperature sensors, flow sensors, viscosity sensors, shear sensors (e.g., for measuring the effective shear modulus of the fluid at a frequency or strain-rate), pH sensors, chemical sensors for determining the presence or concentration of a chemical compound or species, optical sensors, acoustic sensors, biosensors, electrical sensors, magnetic sensors, clocks or timers. Examples of a variety of sensors that can be used in embodiments described herein are provided in U.S. Pat. Nos. 5,522,394; 5,873,835; 6,053,873; 6,409,674; 6,111,520; 6,278,379; 6,475,639; 6,802,811; and 6,855,115, and U.S. Patent Applications 2005/0277839 and 2005/0149170, each of which is incorporated herein by reference. In some aspects, an imaging device (e.g., a CCD array) can be operatively connected to the lumen traveling device. Information regarding one or more local parameter sensed by the lumen traveling device while traveling through a body tube tree can be stored in one or more data storage locations within the lumen traveling device or in one or more remote devices. As shown in FIG. 28D, additional step 2810 can include receiving data representing a temperature (2834), receiving data representing a pressure (2835), receiving data representing a fluid flow (2836), receiving data representing a structural parameter of at least one of the plurality of branched interconnected channels (2837), for example, receiving data representing a length, width, diameter, thickness, direction, orientation, structural configuration, branching pattern, distance from a branch point, proximity to a valve, or proximity to a channel restriction of at least one of the plurality of branched interconnected channels (2838), receiving data representing an electrical field (2839), receiving data representing a magnetic field (2840), receiving data representing an electromagnetic signal (2841), receiving data representing an acoustic signal (2842), receiving data representing an optical signal (2843), receiving data from at least one parameter sensor on the lumen traveling device (2844), receiving data from a remote device (2845), receiving data representing at least one parameter value sensed from at least one of the at least two possible directions of travel at least two different times, and wherein selecting a direction of travel from the at least two directions of travel based at least in part on the data includes selecting the direction of travel based on the value of a function of the at least one parameter at the at least two different times (2846).

In an embodiment, a medical provider or other caregiver can input one or more instructions that cause the lumen traveling device control system to select a parameter type to be sensed by the lumen traveling device. The parameter type to be sensed can be selected based on data received from the lumen traveling device or from a remote device regarding a condition of the subject. For example, if diagnostic medical imaging indicates the presence of a tumor at a location within a body tube tree, the lumen traveling device can be instructed by the medical provider or other caregiver to seek out the tumor by sensing one or more parameters, e.g., tumor markers, associated with the tumor and to move in the direction of the tumor. A medical provider or other caregiver can further input one or more instructions that cause the lumen traveling device control system to select a parameter value range. The selection of one or more parameters to be sensed by the lumen traveling device can be programmed into the lumen traveling device prior to insertion into the body tube tree of a subject. Alternatively, the selection of one or more parameters to be sensed can be sent wirelessly to a lumen traveling device already residing in the lumen of a body tube tree. For example, a signal can be transmitted from a remote device to a receiver on the lumen traveling device to instruct the lumen traveling device to utilize (receive information from) specific on-board sensors. The remote device can include a computer terminal or other device configured to interface with a medical provider or caregiver.

The direction of travel of the lumen traveling device can be selected based on one or more parameters sensed in the lumen of the body tube tree. The direction of travel can be selected such that the lumen traveling device will move along a gradient of one or more parameters, so that movement of the lumen traveling device along the gradient will move the lumen traveling device toward or away from a location or region of interest, e.g. a source of a chemical marker, a source or area of high fluid flow, a larger or smaller channel dimension, etc. Motion control instructions are generated to cause movement of the lumen traveling device in the selected direction of travel. The motion control instructions can direct movement of the lumen traveling device through the lumen of a body tube tree in the selected direction of travel for a pre-determined distance and/or a pre-determined time. In a embodiment, the motion control instructions can direct the propelling mechanism and the steering mechanism to cause movement of the lumen traveling device through a body tube tree in the selected direction of travel until a stop instruction is received from a remote device. The stop instruction can be based on elapsed time, calculated distance of travel, or actual imaging or sensing of the lumen traveling device location in the body tube tree. For example, the stop instruction may be received after the lumen traveling device has traveled through the body tube tree for a prescribed period of time since receipt of the motion control instruction. As a further example, the stop instruction may be received after the lumen traveling device has reached a specific location. Alternatively, the motion control instruction can cause movement of the lumen traveling device through a body tube tree in the selected direction of travel until a stop instruction is received based on sensing a local parameter value with a parameter sensor. The motion control instructions can cause the lumen traveling device to turn, to continue moving in the current direction, or reverse its direction. In an embodiment, the motion control instructions can cause at least one of the steering mechanism and the propelling mechanism on the lumen traveling device to cause the lumen traveling device to move in the selected direction of travel until a branch point is reached. Arrival at a branch point is detected using one or more arrival sensor as described elsewhere herein.

FIG. 28E depicts further variants of selecting a direction of travel from the at least two directions of travel based at least in part on the data representing at least one parameter value sensed from at least one of the at least two possible directions of travel of the lumen traveling device through the body tube tree (2806). These include avoiding at least one direction of travel if the data representing the at least one parameter value sensed from the at least one direction of travel indicates that the at least one direction of travel is non-navigable by the lumen traveling device (2850). Selecting the direction of travel can include selecting the direction of travel based on the value of a function of the at least one parameter (2851), which can include selecting the direction of travel having the lowest value of the function of the at least one parameter (2852), the highest value of the function of the at least one parameter (2853), or having a value of the function of the at least one parameter that falls within a specified range of values (2854). The method can include selecting a direction of travel from the at least two directions of travel based at least in part on the data representing parameter values sensed at two or more times by comparing a rate of change of at least one parameter from the at least two possible directions of travel and selecting the direction of travel having the lowest rate of change of the at least one parameter (2855). In an embodiment, the method can include selecting a direction of travel from the at least two directions of travel based at least in part on the data representing parameter values sensed at two or more times by comparing a rate of change of at least one parameter from the at least two possible directions of travel and selecting the direction of travel having the highest rate of change of the at least one parameter (2856).

FIG. 28F depicts further additional steps (2810) which can be included in method (2801). In an embodiment, additional step (2810) can include identifying a stop condition based at least in part on the data representing at least one parameter value sensed from at least one of the at least two possible directions of travel of the lumen traveling device through the body tube tree; and directing at least one of the steering mechanism and the propelling mechanism on the lumen traveling device to cause the lumen traveling device to stop moving through the body tube tree (2860). In an embodiment, additional step (2810) can include storing the data representing at least one parameter value sensed from at least one of the at least two possible directions of travel of the lumen traveling device through the body tube tree in a memory location on the lumen traveling device (2861) storing instructions related to directing at least one of the steering mechanism and the propelling mechanism on the lumen traveling device to cause movement of the lumen traveling device in a memory location on the lumen traveling device (2862) transmitting the data representing at least one parameter value sensed from at least one of the at least two possible directions of travel of the lumen traveling device through the body tube tree from the lumen traveling device to a remote device (2863) transmitting instructions related to directing at least one of the steering mechanism and the propelling mechanism on the lumen traveling device to cause movement of the lumen traveling device from the lumen traveling device to a remote device (2864) receiving at least one of instructions or data from a remote device (2865). In another embodiment, method (2801) can include receiving information related to whether or not at least one of at least two possible directions of travel of the lumen traveling device through the body tube tree has previously been traveled by the lumen traveling device; and selecting the direction of travel from the at least two possible directions of travel based at least in part on the information related to whether or not at least one of at least two possible directions of travel of the lumen traveling device through the body tube tree has previously been traveled by the lumen traveling device (2866).

FIG. 27 illustrates a block diagram of a system 2700 that includes a set of instructions 2704 for operating a lumen traveling device. While system 2700 is shown to include instructions for performing method 2800 as described in connection with FIG. 28A, system 2700 can be modified to perform any method as depicted in FIGS. 28A-28F. An embodiment of system 2700 is provided using non-transitory machine readable media 2702 including a set of instructions 2704 including one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of the branched, interconnected channels; one or more instructions that cause the lumen traveling device control system to receive data representing at least one parameter value sensed from at least one of the at least two possible directions of travel of the lumen traveling device through the body tube tree; one or more instructions that cause the lumen traveling device control system to select a direction of travel from the at least two directions of travel based at least in part on the data; and one or more instructions that cause the lumen traveling device control system to direct at least one of the steering mechanism and the propelling mechanism on the lumen traveling device to cause the lumen traveling device to move through the body tube tree in the selected direction of travel. The one or more instructions can be, for example, computer executable and/or logic implemented instructions. In an embodiment, the non-transitory machine readable media 2702 may include computer readable media 2706. In an embodiment, the non-transitory machine readable media 2702 can include recordable-type media 2708.

Figure 30A:
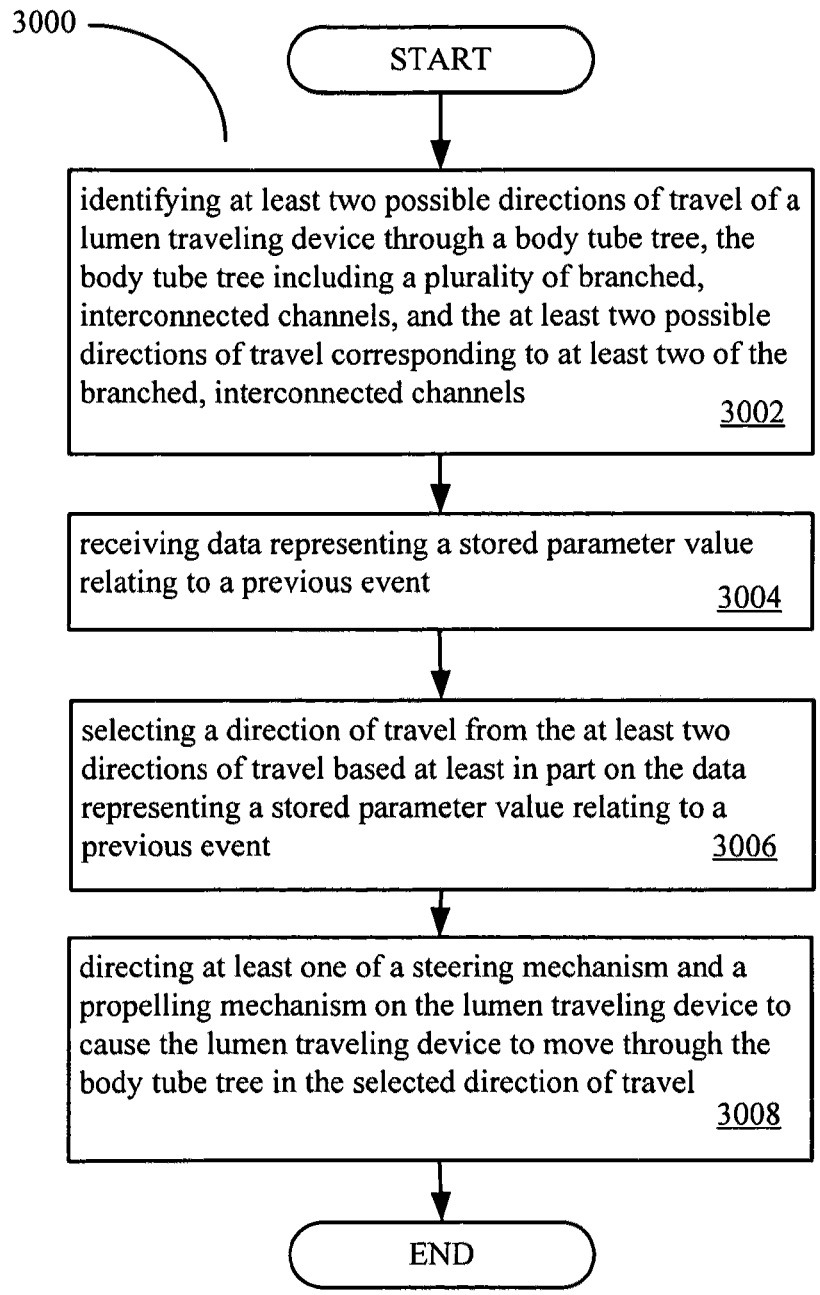

FIG. 30A illustrates a method 3000 of operating a lumen traveling device in a lumen of a body tube tree including identifying at least two possible directions of travel of a lumen traveling device through a body tube tree, the body tube tree including a plurality of branched, interconnected channels, and the at least two possible directions of travel corresponding to at least two of the branched, interconnected channels at 3002; receiving data representing a stored parameter value relating to a previous event at 3004; selecting a direction of travel from the at least two directions of travel based at least in part on the data representing a stored parameter value relating to a previous event at 3006; and directing at least one of a steering mechanism and a propelling mechanism on the lumen traveling device to cause the lumen traveling device to move through the body tube tree in the selected direction of travel at 3008. This method can be performed, for example, with a device as depicted in and described in connection with FIGS. 1, 2, 7 and 8.

Figure 30B:
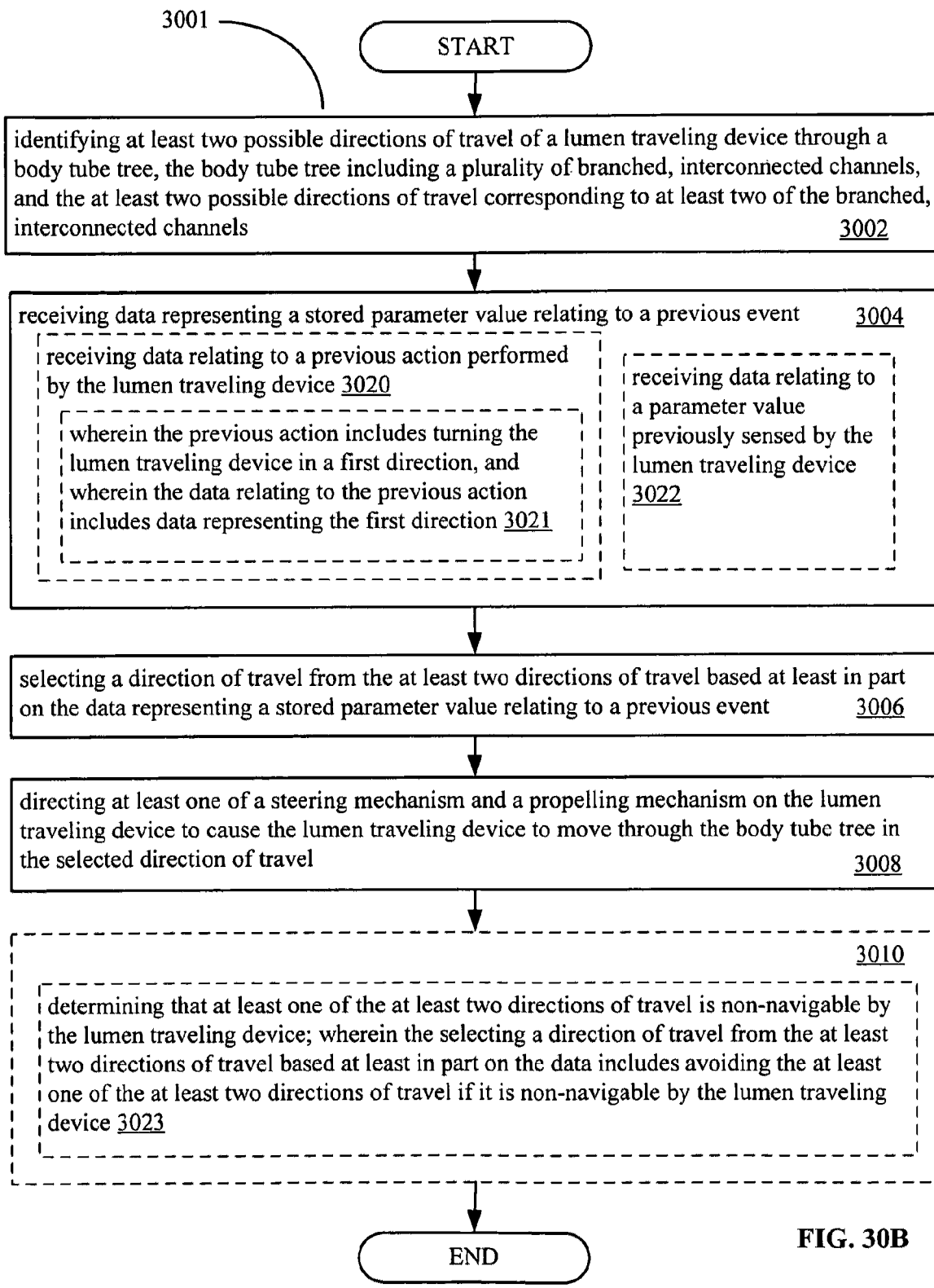

FIG. 30B depicts method 3001, which is a variant of method 3000 depicted in FIG. 30A. In method 3001, step 3004 further can include receiving data relating to a previous action performed by the lumen traveling device (3020). In some embodiments this can further include wherein the previous action includes turning the lumen traveling device in a first direction, and wherein the data relating to the previous action includes data representing the first direction (3021). Step 3004 can include receiving data relating to a parameter value previously sensed by the lumen traveling device (3022). Method 3001 can also include an additional step 3010, which in the example of FIG. 30B includes determining that at least one of the at least two directions of travel is non-navigable by the lumen traveling device; wherein the selecting a direction of travel from the at least two directions of travel based at least in part on the data includes avoiding the at least one of the at least two directions of travel if it is non-navigable by the lumen traveling device (3023).

As depicted in FIG. 30C, in further variants of the method 3001, additional step 3010 can include identifying a stop condition based at least in part on the data; and directing at least one of the steering mechanism and the propelling mechanism on the lumen traveling device to cause to cause the lumen traveling device to stop moving through the body tube tree (3030). In an embodiment, additional step 3010 can include storing the data in a memory location on the lumen traveling device (3031), storing motion control instructions for directing operation of at least one of the steering mechanism and the propelling mechanism in a memory location on the lumen traveling device (3032), transmitting the data from the lumen traveling device to a remote device (3033), transmitting motion control instructions for directing operation of at least one of the steering mechanism and the propelling mechanism from the lumen traveling device to a remote device (3034), and/or receiving at least one of instructions or data from a remote device (3035). In another variant, additional step 3010 can include receiving information related to whether or not at least one of at least two possible directions of travel of the lumen traveling device through the body tube tree has previously been traveled by the lumen traveling device; and selecting the direction of travel from the at least two possible directions of travel based at least in part on the information related to whether or not at least one of at least two possible directions of travel of the lumen traveling device through the body tube tree has previously been traveled by the lumen traveling device (3036).

As shown in FIG. 30D, directing at least one of the steering mechanism and the propelling mechanism on the lumen traveling device to cause the lumen traveling device to move through the body tube tree in the selected direction of travel for a pre-determined duration (3008) can include directing at least one of the steering mechanism and the propelling mechanism on the lumen traveling device to cause the lumen traveling device to move through the body tube tree in the selected direction of travel for a pre-determined distance (3040), directing at least one of the steering mechanism and the propelling mechanism on the lumen traveling device to cause the lumen traveling device to move through the body tube tree in the selected direction of travel for a pre-determined duration (3041), directing at least one of the steering mechanism and the propelling mechanism on the lumen traveling device to cause the lumen traveling device to move through the body tube tree in the selected direction of travel until an stop instruction is received from a remote device by the lumen traveling device (3042), directing at least one of the steering mechanism and the propelling mechanism on the lumen traveling device to cause the lumen traveling device to turn (3043), directing at least one of the steering mechanism and the propelling mechanism on the lumen traveling device to cause the lumen traveling device to continue moving in a current direction of travel (3044), and/or directing at least one of the steering mechanism and the propelling mechanism on the lumen traveling device to cause to cause the lumen traveling device to reverse its direction of travel (3045).

In an embodiment, the lumen traveling device can be instructed to select a direction of travel based on receiving data representing a stored parameter value relating to a previous event. The stored parameter value relating to a previous event can be a parameter value previously sensed by the lumen traveling device and can include values representative of an anatomical feature of the lumen such as a branch point, a valve, a polyp, an aneurysm, growth, a tumor, obstruction; a man-made structure such as an implantable device of some sort, potentially including another lumen traveling device; or other parameters such as an electrical field, magnetic field, temperature, flow condition, time, location, pressure, pH, presence or concentration of a chemical compound or species. The stored parameter value can also include data regarding the characterization of the branching elements of the body tube tree and position indicator signals that have been used to inform development of a map of at least a portion of the body tube tree. The stored parameter value relating to a previous event can include data regarding previous travel of the lumen traveling device along one or more portions of a pre-existing and/or evolving map of a least a portion of the body tube tree.

In some embodiments, the previous event can be an action previously performed by the lumen traveling device. Examples of performing an action include but are not limited to releasing a material, releasing a device or structure, releasing an energy, collecting a sample, collecting a device or structure, attaching a structure to a wall of the body tube tree, delivering a material of structure to a receiving portion of a man-made device, receiving a material or structure from a delivery portion of a man-made device, receiving a signal from a remote source, receiving power from a remote source, transmitting a signal to a remote location, performing a surgical step or procedure, removing tissue from at least a portion of the body tube tree, removing specific components of at least a portion of a fluid from a body tube tree, exposing a catalyst, generating a localized electric field, generating a localized magnetic field, producing heat, causing cooling, emitting electromagnetic radiation, emitting acoustic energy, applying pressure to at least a portion of the body tube tree, modulating the flow of a fluid through at least a portion of the body tube tree. An example of a previous event can include placement of one or more chemical or physical markers or labels which are now detectable by the lumen traveling device and are used to inform the selection of a direction of travel of the lumen traveling device.

The direction of travel of the lumen traveling device can be selected based on one or more stored parameter values. For example, the lumen traveling device may reach a branch point in the body tube tree and select a direction of travel into the two or more branch channels based on one or more stored parameter values indicating whether a particular channel has been previously traveled. As another example, the lumen traveling device may reach a location in the lumen of the body tube tree where one or more stored parameter values indicate that an action was previously performed, and may select a direction of travel based on that information. Motion control instructions are generated to cause movement of the lumen traveling device in the selected direction of travel as described herein.

FIG. 29 illustrates a block diagram of a system 2900 that includes a set of instructions 2904 for operating a lumen traveling device. While system 2900 is shown to include instructions for performing method 3000 as described in connection with FIG. 30A, system 2900 can be modified to perform any method as depicted in FIGS. 30A-30D. An embodiment of the system 2900 is provided using non-transitory machine readable media 2902 including a set of instructions 2904 including one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of the branched, interconnected channels; one or more instructions that cause the lumen traveling device control system to receive data representing a stored parameter value relating to a previous event associated with at least one of the at least two possible directions of travel; one or more instructions that cause the lumen traveling device control system to select a direction of travel from the at least two directions of travel based at least in part on the data representing a stored parameter value relating to a previous event associated with at least one of the at least two possible directions of travel; and one or more instructions that cause the lumen traveling device control system to direct at least one of a steering mechanism and a propelling mechanism on the lumen traveling device to cause the lumen traveling device to move through the body tube tree in the selected direction of travel. The one or more instructions may be, for example, computer executable and/or logic implemented instructions. In an embodiment, the non-transitory machine readable media 2902 can include computer readable media 2906. In an embodiment, the non-transitory machine readable media 2902 can include recordable-type media 2908.

Figure 32A:
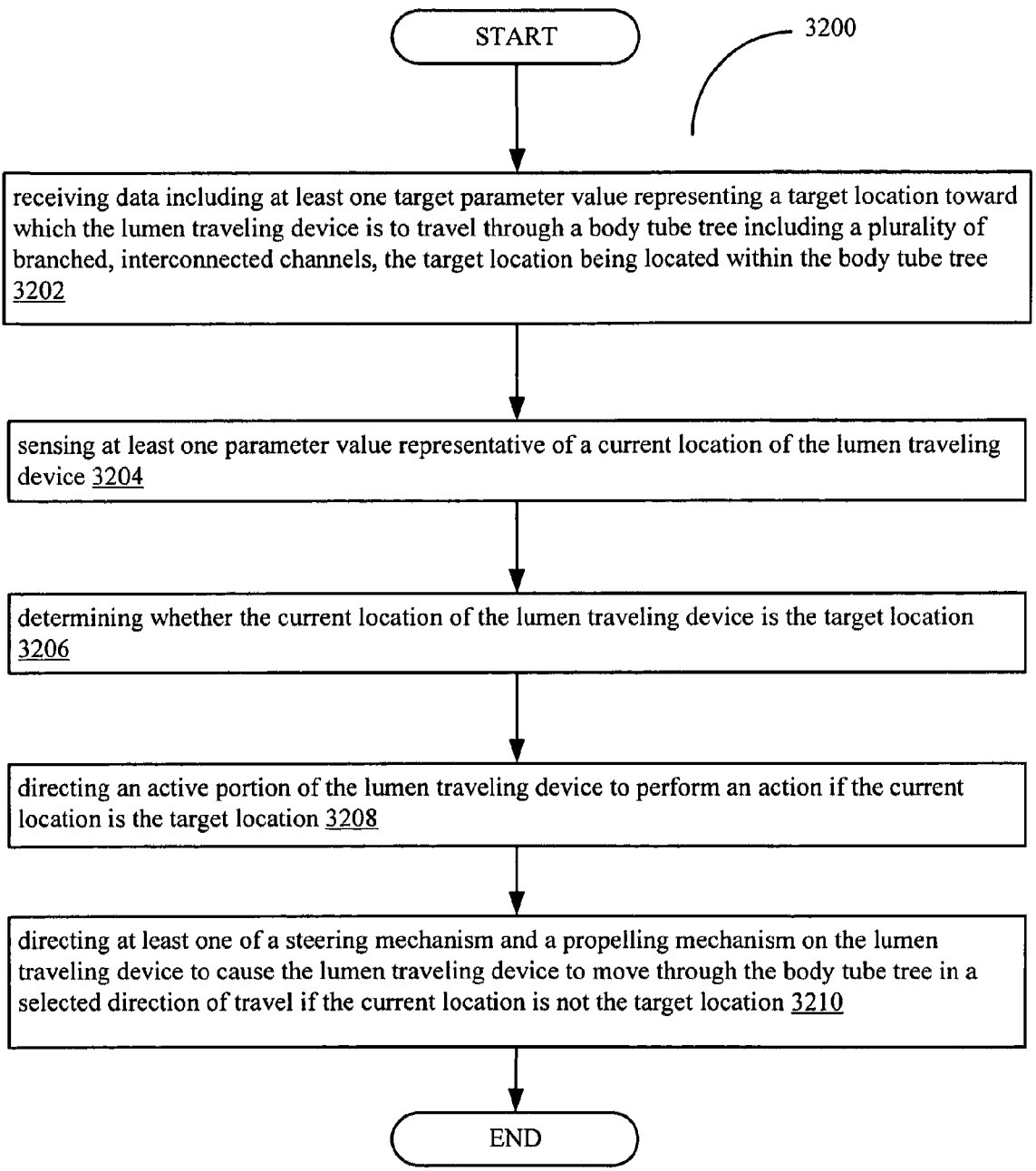

FIG. 32A illustrates a method 3200 of operating a lumen traveling device in a lumen of a body tube tree including receiving data including at least one target parameter value representing a target location toward which the lumen traveling device is to travel through a body tube tree including a plurality of branched, interconnected channels, the target location being located within the body tube tree at 3202; sensing at least one parameter value representative of a current location of the lumen traveling device at 3204; determining whether the current location of the lumen traveling device is the target location at 3206; directing an active portion of the lumen traveling device to perform an action if the current location is the target location at 3208; or directing at least one of a steering mechanism and a propelling mechanism on the lumen traveling device to cause the lumen traveling device to move through the body tube tree in a selected direction of travel if the current location is not the target location at 3210.

Figure 32B:
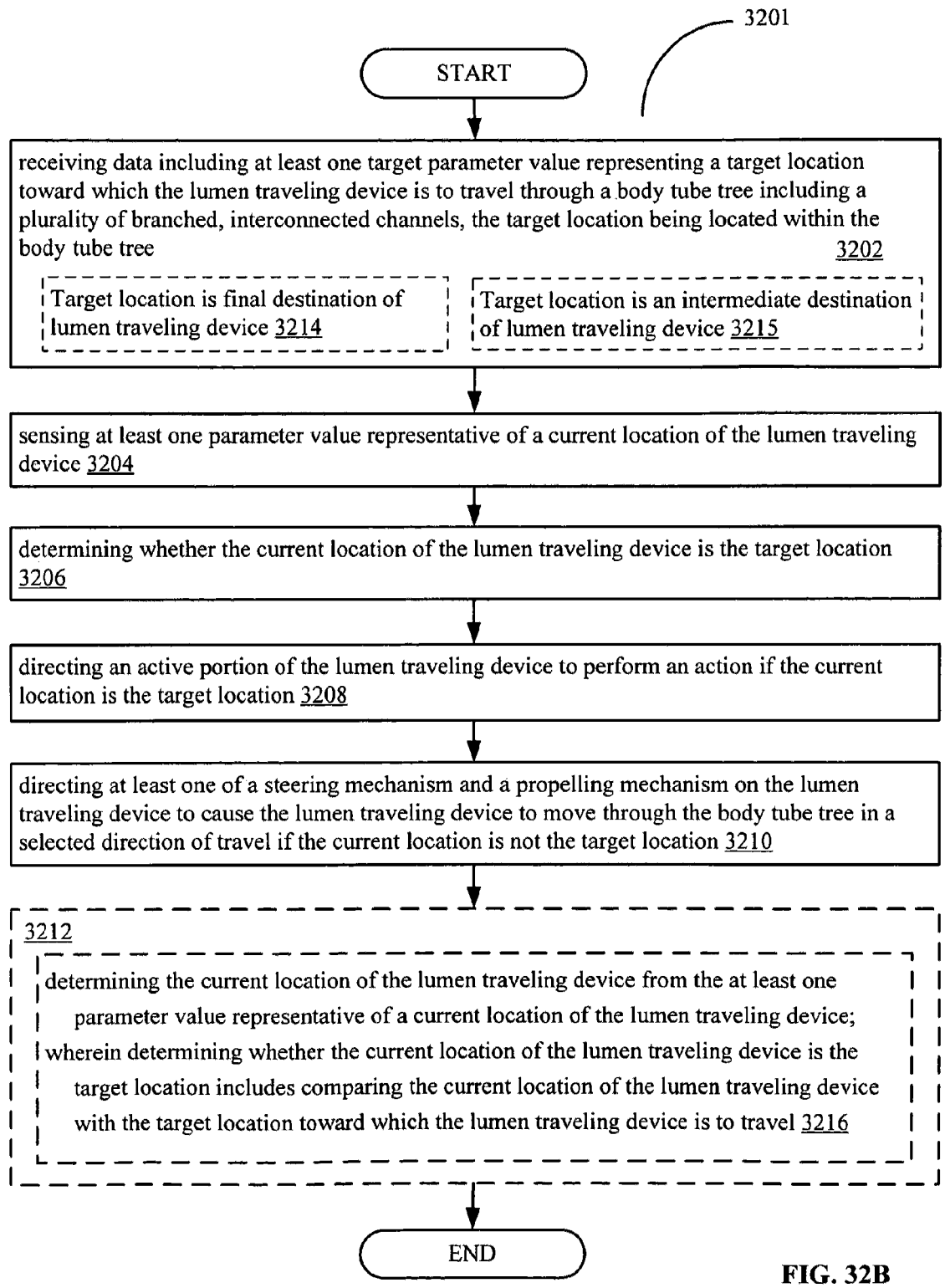

FIG. 32B depicts method 3201, a variant of the method depicted in FIG. 32A. As indicated generally at 3212, method 3201 can include one or more additional steps 3212.

In an embodiment, a lumen traveling device travels along a controlled path that leads to a specific target location. The lumen traveling device receives information regarding a target parameter value representing a target location towards which the lumen traveling device travels through a body tube tree. The lumen traveling device further senses at least one parameter value representative of the current location of the lumen traveling device. Sensors for sensing one or more local parameter values representative of a current location have been described herein. One or more parameter values representative of the current location are compared with the one or more target parameter values representative of the target location to determine whether or not the lumen traveling device has arrived at the target location. If the current location is the target location, the lumen traveling device may be instructed to perform an action. If the current location is not the target location, motion control instructions are generated to move the lumen traveling device in a selected direction of travel towards the target location. In a further embodiment, the steps of the method of FIG. 32 comprise an iterative process in which parameter values representative of a current location are measured and compared with the target parameter values representative of the target location, and the lumen traveling device is instructed to move to a new current location whereupon another set of parameter values representative of a current location are measured and compared with the target parameter values. This iterative process may continue until the lumen traveling device reaches the target location.

The lumen traveling device can receive data including at least one target parameter value representative of a target location. A target location can be a final destination of the lumen traveling device, as indicated at 3214 in FIG. 32B. Alternatively, a target location can be an intermediate destination of the lumen traveling device, as indicated at 3215 in FIG. 32B. The target location can include a location of anatomical interest (e.g., a branching point, a valve), a location near an organ, a tumor, an injury, etc., a diseased or damaged region (e.g. a fistula or aneurysm), area of scar tissue, a polyp, a blockage or constriction formed by a atherosclerotic plaque, blood clot, or vasospasm, for example. In an embodiment, the target location is a specific location on a stored map of the body tube tree.

The target parameter representative of a target location can include, but is not limited to, a temperature, a pressure, a fluid flow, an optical absorption, optical emission, fluorescence, or phosphorescence, an index of refraction, an electrical resistivity, a density or sound speed, a pH, an osmolality, or a concentration, e.g., of an analyte. The parameter can be representative of the presence or absence of an embolism, the presence or absence of an object (such as a blood clot, a thrombus, an embolus, a plaque, a lipid, a kidney stone, a dust particle, a pollen particle, a gas bubble, an aggregate, a cell, a specific type of cell, a cellular component or fragment, a collection of cells, a gamete, a pathogen, or a parasite), and/or the presence or absence of a substance such as a biological marker, an antibody, an antigen, a peptide, a polypeptide, a protein, a complex, a nuclueic acid, an oligonucleotide, a polynucleotide, a cell (and, in some cases, a cell of a particular type, e.g. by methods used in flow cytometry), a cellular component, an organelle, a gamete, a pathogen, a signaling-material, a lipid, a lipoprotein, an alcohol, an acid, an ion, an immunomodulator, a sterol, a steroid, a carbohydrate, a sugar, a polysaccharide, a glycoprotein, a metal, an electrolyte, a metabolite, an organic compound, an organophosphate, a drug, a therapeutic, a gas, a pollutant, a tag (e.g., chemical or physical marker or label), or a combination thereof.

The target location can be detected by sensing a target parameter value representative of the target location. The target parameter can include one or more chemical markers or labels, chemical fingerprints, altered mechanical, optical, thermal, electrical or acoustic properties, an image, and by other detectable parameter. In an embodiment, the target parameter representative of a target location can be a change in autofluorescence or other optically detectable signal associated with a cancer, an atherosclerotic plaque, other lesion or pathology. See, e.g., Koenig et al., *J. Fluoresc.*, 1994, 4:17-40; Chiyo et al., *Lung Cancer* 2005, 48:307-313; and Weingandt et al., *BJOG,* 2002, 109:947-951, each of which is incorporated herein by reference. In an embodiment, the target parameter value representative of a target location may be an increase and/or decrease in one or more chemical analytes associated with cancer, plaque, infection, or other lesion or pathology. As an example, the target parameter value may be an increase in magnetic properties of an atherosclerotic plaque relative to normal lumen wall due to increased levels of iron $Fe(II)$ and $Fe(III)$ cations associated with the plaque. See, e.g., Raman et al., *JACC Cardiovasc., Imaging* 2008, 1:49-57, which is incorporated herein by reference. In an embodiment, the target parameter can be a lesion along the lumen of the body tube tree visible with visible light imaging and an image capture device. In an embodiment, the target parameter can be a change in the diameter of the lumen of a body tube tree indicative of an occluding lesion such as, for example, an atherosclerotic plaque, a polyp, or a cancerous lesion. In a further embodiment, the target parameter can be a signal from a chemical or physical marker or label previously placed at the target location. As used herein, the term "lesion" refers not only to cancerous lesions, but to various other types of tissue damage or abnormality, e.g., scar tissue, granuloma, infiltration, etc. A lesion may be caused by injury or disease, for example. In some cases, a lesion may be bacterial or viral in origin.

As indicated at 3216 in FIG. 32B, in an embodiment, the method can include determining the current location of the lumen traveling device from the at least one parameter value representative of a current location of the lumen traveling device, wherein determining whether the current location of the lumen traveling device is the target location includes comparing the current location of the lumen traveling device with the target location toward which the lumen traveling device is to travel.

The current location of the lumen traveling device can be determined based upon one or more sensed parameter values representative of the current location. The parameter values representative of the current location of the lumen traveling device can include chemical markers or labels, chemical fingerprints, altered mechanical, optical, thermal, electrical or acoustic properties, an image, or other detectable parameters. Other parameters representative of a current location can include but are not limited to rate of fluid flow, direction of fluid flow, presence or concentration of a chemical or other analyte, concentration gradient, temperature, temperature gradient, luminal dimension, material in or on a lumen wall, lumen wall mechanical property, a position indicator signal, an electromagnetic field, markers, or labels. As depicted in FIG. 32C, sensing at least one parameter value representative of a current location of the lumen traveling device (3204) can include sensing at least one parameter value representative of an orientation of at least a portion of the body tube tree (3221), sensing at least one parameter value representative of an orientation of at least a portion of the body tube tree within a absolute coordinate system (3222), sensing at least one parameter value representative of an orientation of at least a portion of the body tube tree within a relative coordinate system (3223), sensing at least one parameter value representative of an orientation of at least a portion of the body tube tree relative to at least one other portion of the body tube tree (3224), sensing at least one parameter value representative of an orientation of at least a portion of the body tube tree relative to at least one other portion of the body tube tree (3225), sensing at least one parameter value representative of a rate of fluid flow through of at least a portion of the body tube tree (3226), sensing at least one parameter value representative of a direction of fluid flow through of at least a portion of the body tube tree (3227), sensing at least one parameter value representative of a chemical (3228), sensing at least one parameter value representative of at least one of a biological marker, a biomaterial, a carbohydrate, a sugar, a cell, a cell fragment, a chemical, a chemokine, a hormone, a complex, a cytokine, a drug, a gas, a lipid, a metabolite, a pathogen, a signaling-material, a polypeptide, a protein, a nuclueic acid, an oligonucleotide, a polynucleotide, a sterol, a steroid, a therapeutic, an alcohol, an antibody, an electrolyte, an inflammatory molecule, or an ion (3229). A parameter value representative of an analyte can be a parameter value representative of the presence or concentration of the analyte, for example. In addition, as shown in FIG. 32D, sensing at least one parameter value representative of a current location of the lumen traveling device (3204) can include sensing at least one parameter value representative of a concentration gradient of at least one of a biological marker, a biomaterial, a carbohydrate, a sugar, a cell, a cell fragment, a chemical, a chemokine, a hormone, a complex, a cytokine, a drug, a gas, a lipid, a metabolite, a pathogen, a signaling-material, a polypeptide, a protein, a nucleic acid, an oligonucleotide, a polynucleotide, a sterol, a steroid, a therapeutic, an alcohol, an antibody, an electrolyte, an inflammatory molecule, or an ion (3230). Sensing at least one parameter value representative of a current location of the lumen traveling device (3204) can include sensing at least one parameter value representative of a temperature (3231) sensing at least one parameter value representative of a temperature gradient (3232), sensing at least one parameter value representative of a lumenal dimension (3233), sensing at least one parameter value representative of a material in or on a lumen wall (3234), sensing at least one parameter value representative of a lumen wall mechanical property (3235), sensing at least one parameter value representative of a position signal (3236), sensing at least one parameter value representative of an electromagnetic field (3237), and/or sensing at least one parameter value representative of a the presence of a marker or label (3238).

Sensors for sensing one or more local parameter values representative of a current location have been described herein. Sensing at least one parameter value representative of a current location of the lumen traveling device can further include one or more instructions that cause the lumen traveling device control system to direct the sensing of at least one parameter value representative of an orientation of at least a portion of the body tube tree within an absolute coordinate system, a relative coordinate system, and/or relative to at least one other portion of the body tube tree.

In an embodiment, the method as depicted in FIG. 32A and variants thereof can further include receiving data representing at least one parameter value sensed from at least one of at least two possible directions of travel of the lumen traveling device through the body tube tree; and selecting a direction of travel from the at least two directions of travel based at least in part on the data representing at least one parameter value sensed from at least one of the at least two possible directions of travel of the lumen traveling device through the body tube tree. The method can also include receiving information indicating whether or not at least one of at least two possible directions of travel of the lumen traveling device through the body tube tree has previously been traveled by the lumen traveling device and selecting a direction of travel from the at least two directions of travel based at least in part on the information indicating whether or not at least one of at least two possible directions of travel of the lumen traveling device through the body tube tree has previously been traveled by the lumen traveling device.

As shown in FIG. 32E, determining whether the current location of the lumen traveling device is the target location (3206) can include comparing the at least one parameter value representative of a current location of the lumen traveling device with the at least one target parameter value representing a target location toward which the lumen traveling device is to travel (3239). For example, the target parameter value representing the target location can include a temperature (3240), a pressure (3241), a fluid flow (3242), an optical absorption (3243), an optical emission (3244), a fluorescence (3245), a phosphorescence (3246), an index of refraction (3247), an electrical resistivity (3248), a density (3249), a sound speed (3250), a pH (3251), an osmolality or concentration (3252). In an embodiment, the target parameter value representing the target location can include at least one of temperature, pressure, fluid flow, optical absorption, optical emission, fluorescence, phosphorescence, index of refraction at least one wavelength, electrical resistivity, density, sound speed, pH, osmolality, or concentration (3253).

The value of one or more parameter values representative of the current location can be compared with the value of one or more target parameter values indicative of a target location to determine whether the current location is the target location. The value of a parameter can include but is not limited to a number, an image, a spectrum, a color, a profile, a fingerprint, or a combination thereof. A mathematical algorithm, pattern recognition algorithm, pattern matching algorithm, microprocessor, software program, analog or digital comparator or logic circuitry, and/or look-up table, for example, can be used to compare parameter values representative of a current location and parameter values representative of a target location. Comparison of parameter values representative of a current location and a target location can be performed at least in part by the lumen traveling device. Alternatively, comparison of parameter values representative of a current location and a target location can be performed by a remote device and the results of the comparison transmitted back to the lumen traveling device.

If the current location is determined to be the target location, instructions can be sent to the active portion of the lumen traveling device to initiate performing an action. As shown in FIG. 32F, directing an active portion of the lumen traveling device to perform an action if the current location is the target location (3208) can include directing the active portion of the lumen traveling device to perform various different actions. Actions to be performed at the target location can include but are not limited to releasing a material (3255), releasing a device or structure (3257), releasing energy (3258), collecting a sample (3259) (which can include collecting at least one of a fluid sample or a sample from a wall region of the body tube tree (3260)), collecting a device or structure (3261), attaching a structure to a wall of the body tube tree (3262), delivering a material or structure to a receiving portion of a man-made device (3263), receiving a material or structure from a delivery portion of a man-made device (3264), receiving a signal from a remote source (3265), which can be an encrypted signal, as shown at 1927 in FIG. 19, receiving power from a remote source (3266), transmitting a signal to a remote location (3267), which can be an encrypted signal, as shown at 1925 in FIG. 19, and performing a surgical step or procedure (3268). An action to be performed at a target location can include delivering a material to a wall region of the body tube tree (3298). As further shown in FIG. 32G, actions to be performed at the target location can include but are not limited to, removing tissue from at least a portion of the body tube tree (3269), removing specific components of at least a portion of a fluid from a body tube tree (3270), exposing a catalyst (3271), generating a localized electric field (3272), generating a localized magnetic field (3273, producing heat (3274), causing cooling (3275), emitting electromagnetic radiation (3276), emitting acoustic energy (3277), applying pressure to at least a portion of the body tube tree (3278), modulating the flow of a fluid through at least a portion of the body tube tree (3279).

The method can further include sensing a second local parameter value, stopping performance of an action if the local parameter value is within a specified range, and initiating performance of an action if the local parameter value is within a specified range. For example, arrival of the lumen traveling device at a target location that is a cancerous lesion may result in instructions being sent to an active portion of the lumen traveling device to perform an action that includes emitting an ablating energy or cutting and/or scraping to remove the cancerous lesion.

If the parameter value representative of the current location differs from the target parameter value representative of the target location, motion control instructions are generated to move the lumen traveling device in a selected direction of travel until the target location is reached. In an embodiment, the lumen traveling device randomly searches for the target location by comparing one or more parameter values representative of the current location of the lumen traveling device with one or more parameter values representative of the target location. In this instance, the lumen traveling device moves through the body tube tree scanning the environment with one or more sensors and comparing parameter values representative of a current location with parameter values representative of a target location until the target location is found. Upon arriving at the target location, the lumen traveling device may be instructed to perform one or more actions, examples of which have been described herein.

As shown in FIG. 32H, directing at least one of a steering mechanism and a propelling mechanism on the lumen traveling device to cause the lumen traveling device to move through the body tube tree in a selected direction of travel if the current location is not the target location (3210) can include directing at least one of the steering mechanism and the propelling mechanism on the lumen traveling device to cause the lumen traveling device to stop (3280), directing at least one of the steering mechanism and the propelling mechanism on the lumen traveling device to cause the lumen traveling device to advance (3281), directing at least one of the steering mechanism and the propelling mechanism on the lumen traveling device to cause the lumen traveling device to reverse direction (3282), or directing at least one of the steering mechanism and the propelling mechanism on the lumen traveling device to cause the lumen traveling device to turn (3283).

As shown in FIG. 32H, addition step 3212 can include receiving map data representing a map of at least a portion of the body tube tree (3284), which can include receiving map data from a data storage location on the lumen traveling device (3285) or receiving map data from a remote source (3286). Map data from a remote source can be encrypted, as indicated at 3297. In an embodiment, additional step (3212) can include receiving data representing at least one parameter value sensed from at least one of at least two possible directions of travel of the lumen traveling device through the body tube tree and selecting a direction of travel from the at least two directions of travel based at least in part on the data (3287). In this embodiment, selecting the direction of travel from the at least two directions of travel based at least in part on the data can include avoiding at least one of the at least two directions of travel if at least one of the at least two directions of travel is non-navigable by the lumen traveling device (3288). In an embodiment, additional step (3212) can include receiving information indicating whether or not at least one of at least two possible directions of travel of the lumen traveling device through the body tube tree has previously been traveled by the lumen traveling device; and selecting a direction of travel from the at least two directions of travel based at least in part on the information indicating whether or not at least one of at least two possible directions of travel of the lumen traveling device through the body tube tree has previously been traveled by the lumen traveling device (3289). FIG. 32J includes still further additional steps that may be included in methods 3200 or 3201. Further additional steps 3212 include storing the data in a memory location on the lumen traveling device (3289), storing motion control instructions for directing operation of at least one of the steering mechanism and the propelling mechanism in a memory location on the lumen traveling device (3290), transmitting the data from the lumen traveling device to a remote device (3291), transmitting motion control instructions for directing operation of at least one of the steering mechanism and the propelling mechanism from the lumen traveling device to a remote device (3292), receiving at least one of instructions or data from a remote device (3293), determining the current location of the lumen traveling device on a map of at least a portion of a body tube tree, the lumen traveling device located within the body tube tree represented by the map; and planning a path of travel for the lumen traveling device, the path of travel leading at least a portion of the way between the current location and the target location, wherein directing at least one of a steering mechanism and a propelling mechanism on the lumen traveling device to cause the lumen traveling device to move through the body tube tree in a selected direction of travel if the current location is not the target location along the planned path of travel (3294). Instructions or data received from a remote device can be encrypted, as indicated at 3299.

FIG. 31 illustrates a block diagram of a system 3100 that includes a set of instructions 3104 for operating a lumen traveling device such as that depicted in and described in connection with FIGS. 1, 2, 7 and 8. While system 3100 is shown to include instructions for performing method 3200 as described in connection with FIG. 32A, system 3100 can be modified to perform any method as depicted in FIGS. 32A-32J. An embodiment of system 3100 is provided using non-transitory machine readable media 3102 including a set of instructions 3104 including one or more instructions that cause the lumen traveling device control system to receive data including at least one target parameter value representing a target location in a body tube tree, the body tube tree including a plurality of branched, interconnected channels, the target location being located within the body tube tree; one or more instructions that cause the lumen traveling device control system to direct the sensing of at least one parameter value representative of a current location of the lumen traveling device within the body tube tree; one or more instructions that cause the lumen traveling device control system to determine whether the current location of the lumen traveling device is the target location; one or more instructions that cause the lumen traveling device control system to direct an active portion of the lumen traveling device to perform an action if the current location is the target location; and one or more instructions that cause the lumen traveling device control system to direct at least one of a steering mechanism and a propelling mechanism on the lumen traveling device to cause the lumen traveling device to move through the body tube tree in a selected direction of travel if the current location is not the target location. The one or more instructions may be, for example, computer executable and/or logic implemented instructions. In an embodiment, the non-transitory machine readable media 3102 can include computer readable media 3106. In an embodiment, the non-transitory machine readable media 3102 can include recordable-type media 3108.

Figure 34A:
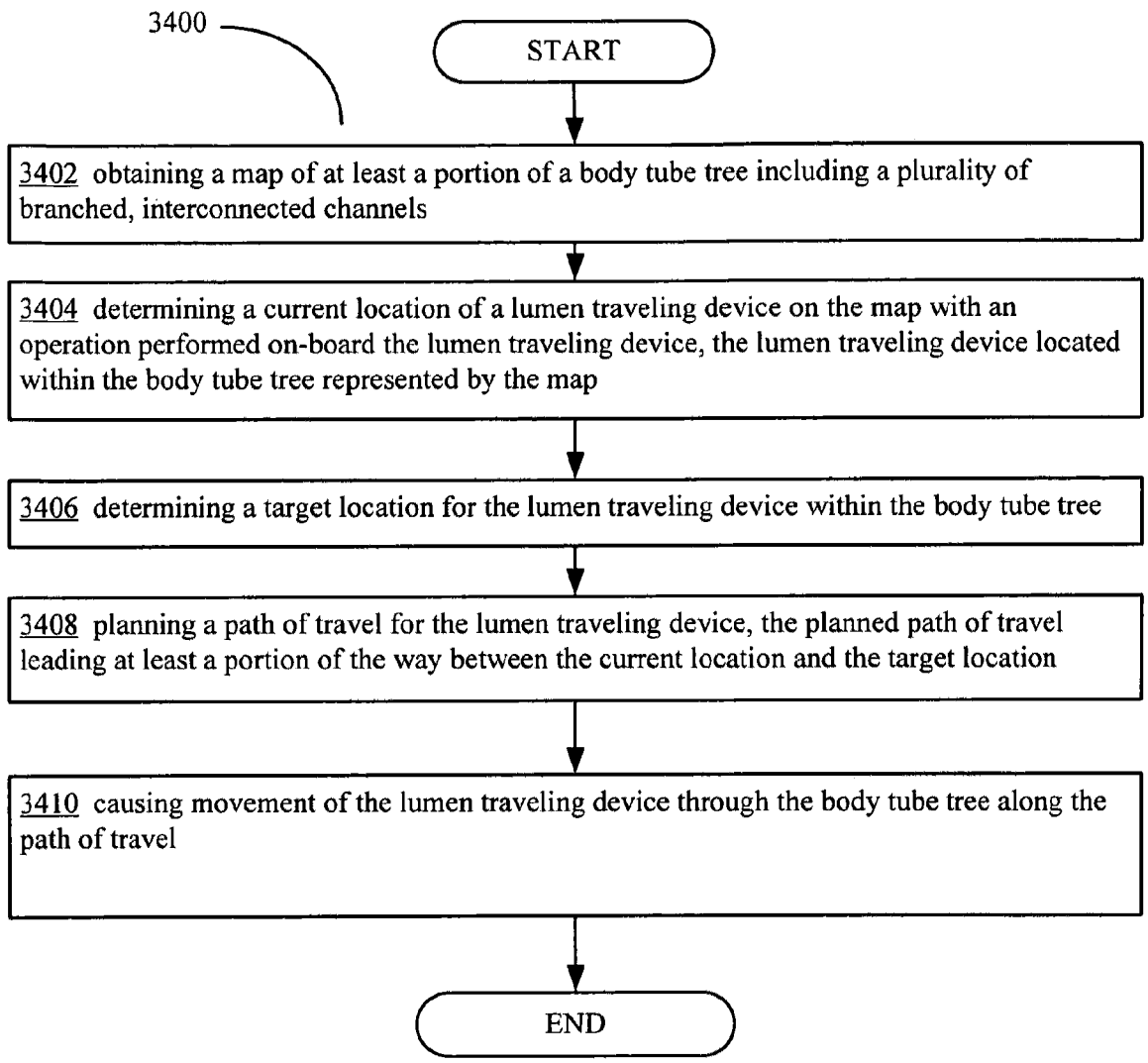

FIG. 34A illustrates a method 3400 of operating a lumen traveling device in the lumen of a body tube tree including obtaining a map of at least a portion of a body tube tree including a plurality of branched, interconnected channels at

3402; determining a current location of a lumen traveling device on the map with an operation performed on-board the lumen traveling device, the lumen traveling device located within the body tube tree represented by the map at 3404; determining a target location for the lumen traveling device within the body tube tree at 3406; planning a path of travel for the lumen traveling device, the planned path of travel leading at least a portion of the way between the current location and the target location at 3408; and causing movement of the lumen traveling device through the body tube tree along the path of travel at 3410. This method can be performed, for example, with a device as depicted in and described in connection with FIGS. 1, 2, 7 and 8.

Figure 34B:
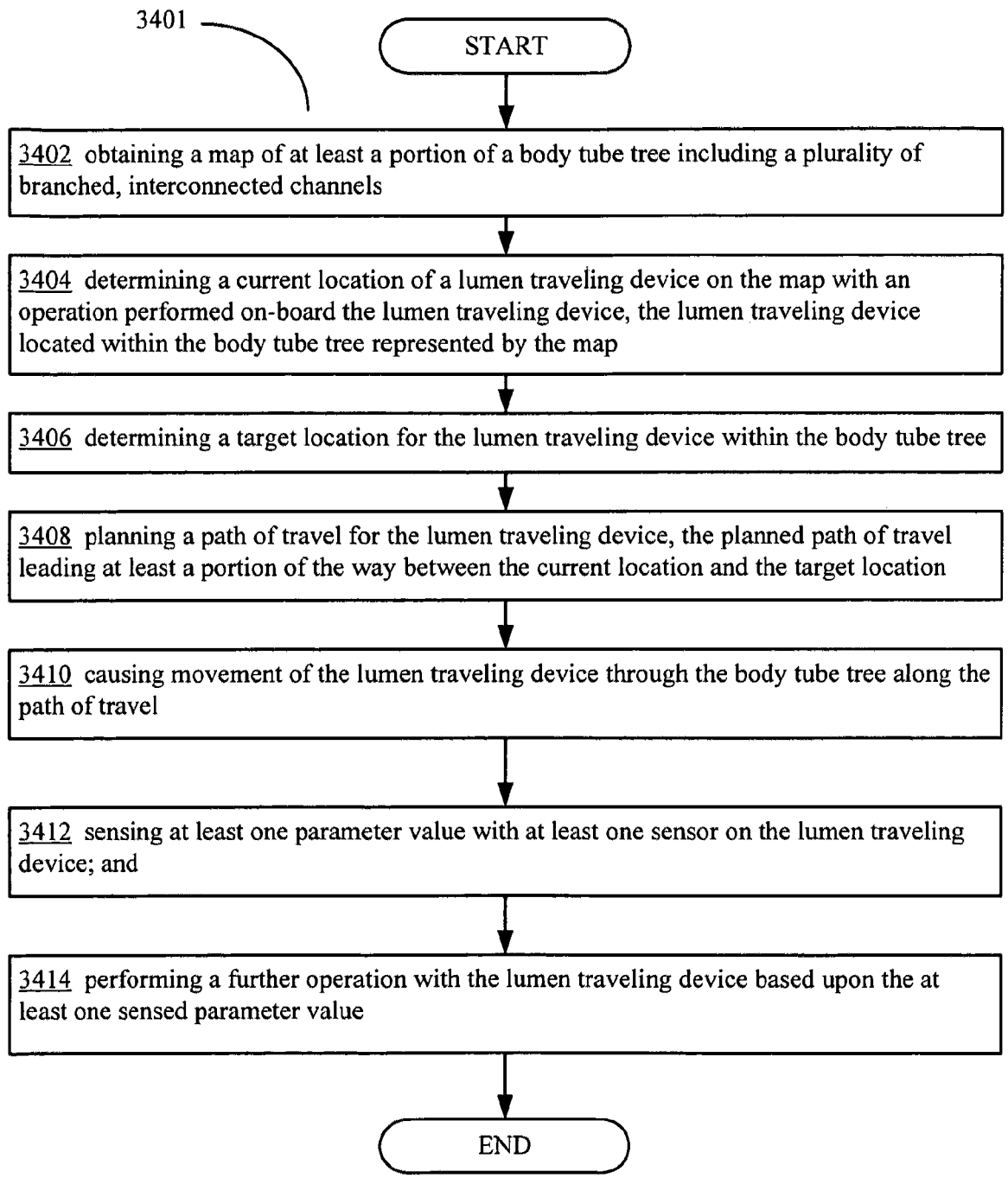

A variant of this method is shown in FIG. 34B. FIG. 34B illustrates method 3401 of operating a lumen traveling device in the lumen of a body tube tree including obtaining a map of at least a portion of a body tube tree including a plurality of branched, interconnected channels at 3402; determining a current location of a lumen traveling device on the map with an operation performed on-board the lumen traveling device, the lumen traveling device located within the body tube tree represented by the map at 3404; determining a target location for the lumen traveling device within the body tube tree at 3406; planning a path of travel for the lumen traveling device, the planned path of travel leading at least a portion of the way between the current location and the target location at 3408; and causing movement of the lumen traveling device through the body tube tree along the path of travel at 3410, as described in connection with FIG. 34A. Method 3401 further includes sensing at least one parameter value with at least one sensor on the lumen traveling device at 3412; and performing a further operation with the lumen traveling device based upon the at least one sensed parameter value at 3414.

Figure 34C:
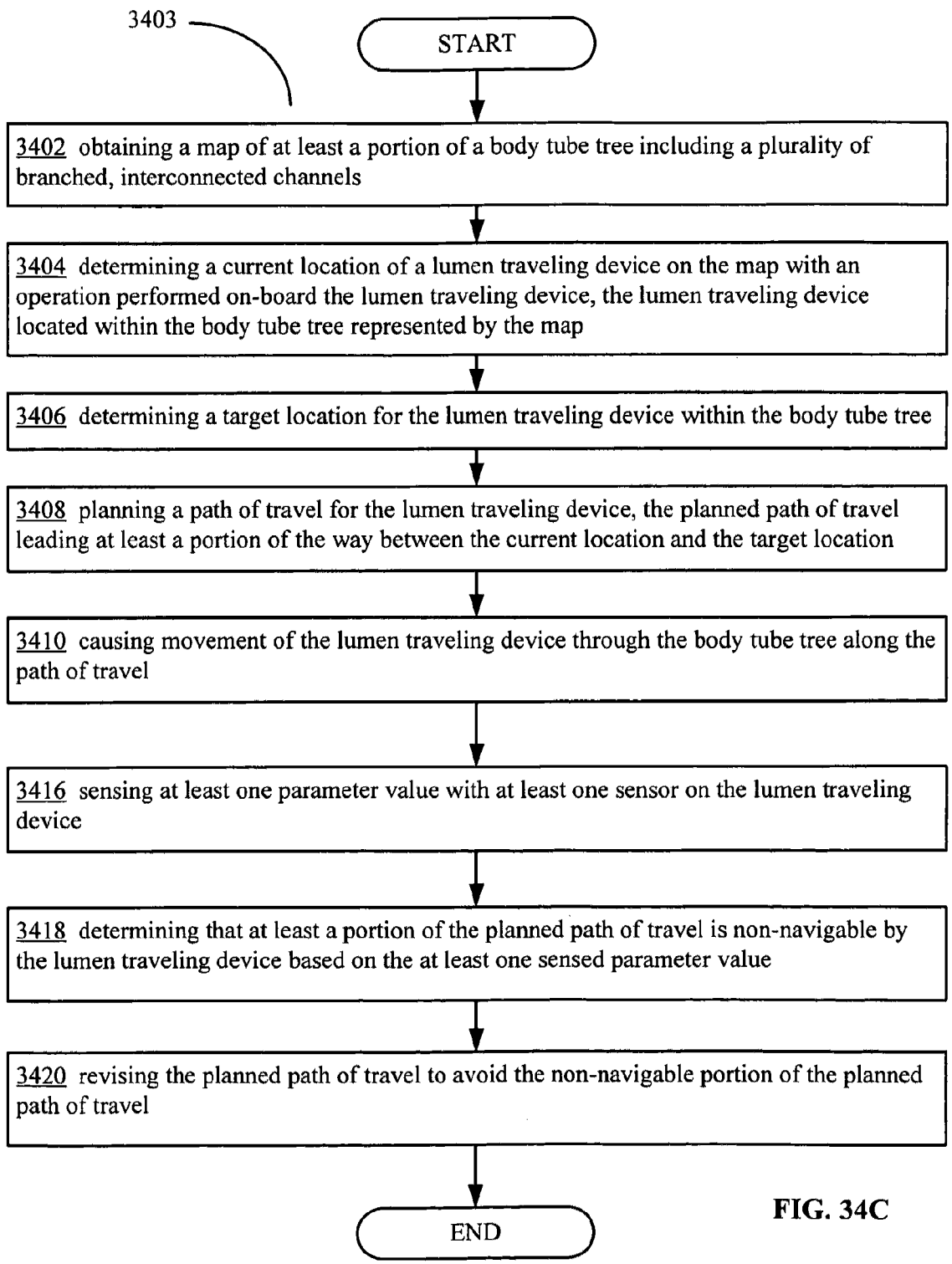

A further variant of this method is shown in FIG. 34C. FIG. 34C illustrates method 3403 of operating a lumen traveling device in the lumen of a body tube tree including obtaining a map of at least a portion of a body tube tree including a plurality of branched, interconnected channels at 3402; determining a current location of a lumen traveling device on the map with an operation performed on-board the lumen traveling device, the lumen traveling device located within the body tube tree represented by the map at 3404; determining a target location for the lumen traveling device within the body tube tree at 3406; planning a path of travel for the lumen traveling device, the planned path of travel leading at least a portion of the way between the current location and the target location at 3408; and causing movement of the lumen traveling device through the body tube tree along the path of travel at 3410, as described in connection with FIG. 34A. Method 3403 further includes sensing at least one parameter value with at least one sensor on the lumen traveling device at 3416; determining that at least a portion of the planned path of travel is non-navigable by the lumen traveling device based on the at least one sensed parameter value at 3418; and revising the planned path of travel to avoid the non-navigable portion of the planned path of travel at 3420.

In some aspects the lumen traveling device navigates through the body tube tree of a subject based on the current location of the lumen traveling device relative to a map of the body tube tree. The location of the lumen traveling device can be correlated with a pre-existing map of the body tube tree of the subject, or used to construct a map of the body tube tree of the subject. In an embodiment, a pre-existing map of the body tube tree of a subject is stored within a data storage location of the lumen traveling device. The pre-existing map can be loaded into the data storage location of the lumen traveling device prior to introducing the lumen traveling device into a body tube tree of a subject, or it can be transmitted from a data storage location of a remote device through a wireless communication link to the data storage location of the lumen traveling device already residing in the lumen of a body tube tree of a subject. In an embodiment, the pre-existing map of the body tube tree can reside entirely in the data storage location of a remote device.

As shown in FIG. 34D, with regard to obtaining a map of at least a portion of a body tube tree including a plurality of branched, interconnected channels at 3402, the map can include a topological map (3421), a metric map (3422), or a conformal map (3440), for example. Obtaining a map can include generating a map of at least a portion of the body tube tree through exploration of the body tube tree with the lumen traveling device 3423, receiving a map of at least a portion of the body tube tree from a remote source 3424, or receiving a map of at least a portion of the body tube tree from another lumen traveling device 3425. As also shown in FIG. 34D, methods 3400, 3401, and 3403 as shown in FIGS. 34A, 34B, and 34C, respectively, can include determining a target location for the lumen traveling device within the body tube tree (3406), wherein determining a target location for the lumen traveling device within the body tube tree includes receiving at least one instruction regarding a target location from a remote device (3426).

In an embodiment, a map Of the body tube tree can be generated on the basis of information gathered as the lumen traveling device travels through the body tube tree of the subject. The map can be generated either with the use of logic on the lumen traveling device, logic in a remote device, or a combination thereof. The map thus generated can be stored in a memory location on the lumen traveling device or elsewhere.

FIG. 34E illustrates various aspects of, planning a path of travel for the lumen traveling device, the planned path of travel leading at least a portion of the way between the current location and the target location (at 3408). In an embodiment, planning a path of travel for the lumen traveling device can include planning a path between the current location and the target location (3427), where, for example, the target location is a selected anatomical location (3428). In an embodiment, planning a path of travel for the lumen traveling device can include planning a path between the current location and a second location in the body tube tree, the second location intermediate between the current location and the target location on a map of the body tube tree (3429), e.g., planning a path between a first branch point at the current location and a second branch point at the second location (3430).

In an embodiment, planning a path of travel can include planning a first path of travel leading between the current location and an intermediate location and a planning a second path of travel leading between the intermediate location and the target location and wherein causing movement of the lumen traveling device through the body tube tree along the path of travel includes causing the lumen traveling device to move along the first path of travel leading between the current location and an intermediate location and causing the lumen traveling device to move along the second path of travel leading between the intermediate location and the target location (3431). In an embodiment, causing the lumen traveling device to move along the first path of travel can include controlling the movement of the lumen traveling device according to a first algorithm and causing the lumen traveling device to move along the second path of travel includes controlling the movement of the lumen traveling device according to a second algorithm, wherein the first algorithm is different than the second algorithm (3432); for example, the first algorithm can be a Markov localization algorithm and the second algorithm can be a Kalman filtering algorithm (3433). In a method including step 3431, obtaining a map of at least a portion of a body tube tree can include receiving the map of at least a portion of a body tube tree from a remote device (3434), receiving the map of at least a portion of a body tube tree from a data storage location on the lumen traveling device (3435), or wherein obtaining a map of at least a portion of a body tube tree includes generating a map of at least a portion of the body tube tree through exploration of the body tube tree with the lumen traveling device (3436).

FIG. 33 illustrates a block diagram of a system 3300 that includes a set of instructions 3304 for operating a lumen traveling device, such as a device as depicted in and described in connection with FIGS. 1, 2, 7 and 8. While system 3300 is shown to include instructions for performing method 3400 as described in connection with FIG. 34A, system 3400 can be modified to perform any method as depicted in FIGS. 34A-34E. An embodiment of system 3300 is provided using non-transitory machine readable media 3302 including a set of instructions 3304 including one or more instructions that cause the lumen traveling device control system to obtain a map of at least a portion of a body tube tree including a plurality of branched, interconnected channels; one or more instructions that cause the lumen traveling device control system to determine a current location of a lumen traveling device on the map with an operation performed on-board the lumen traveling device, the lumen traveling device located within the body tube tree represented by the map; one or more instructions that cause the lumen traveling device control system to determine a target location for the lumen traveling device within the body tube tree; one or more instructions that cause the lumen traveling device control system to determine a path of travel for the lumen traveling device, the path of travel leading at least a portion of the way between the current location and the target location; and one or more instructions that cause the lumen traveling device control system to direct at least one of a steering mechanism and a propelling mechanism on the lumen traveling device to cause the lumen traveling device to move through the body tube tree along the path of travel. The one or more instructions may be, for example, computer executable and/or logic implemented instructions. In an embodiment, the non-transitory machine readable media 3302 can include computer readable media 3306. In an embodiment, the non-transitory machine readable media 3302 can include recordable-type media 3308. The non-transitory machine readable media 3302 can further include instructions that cause the lumen traveling device control system to read map data from a data storage location on the lumen traveling device.

Figure 35:
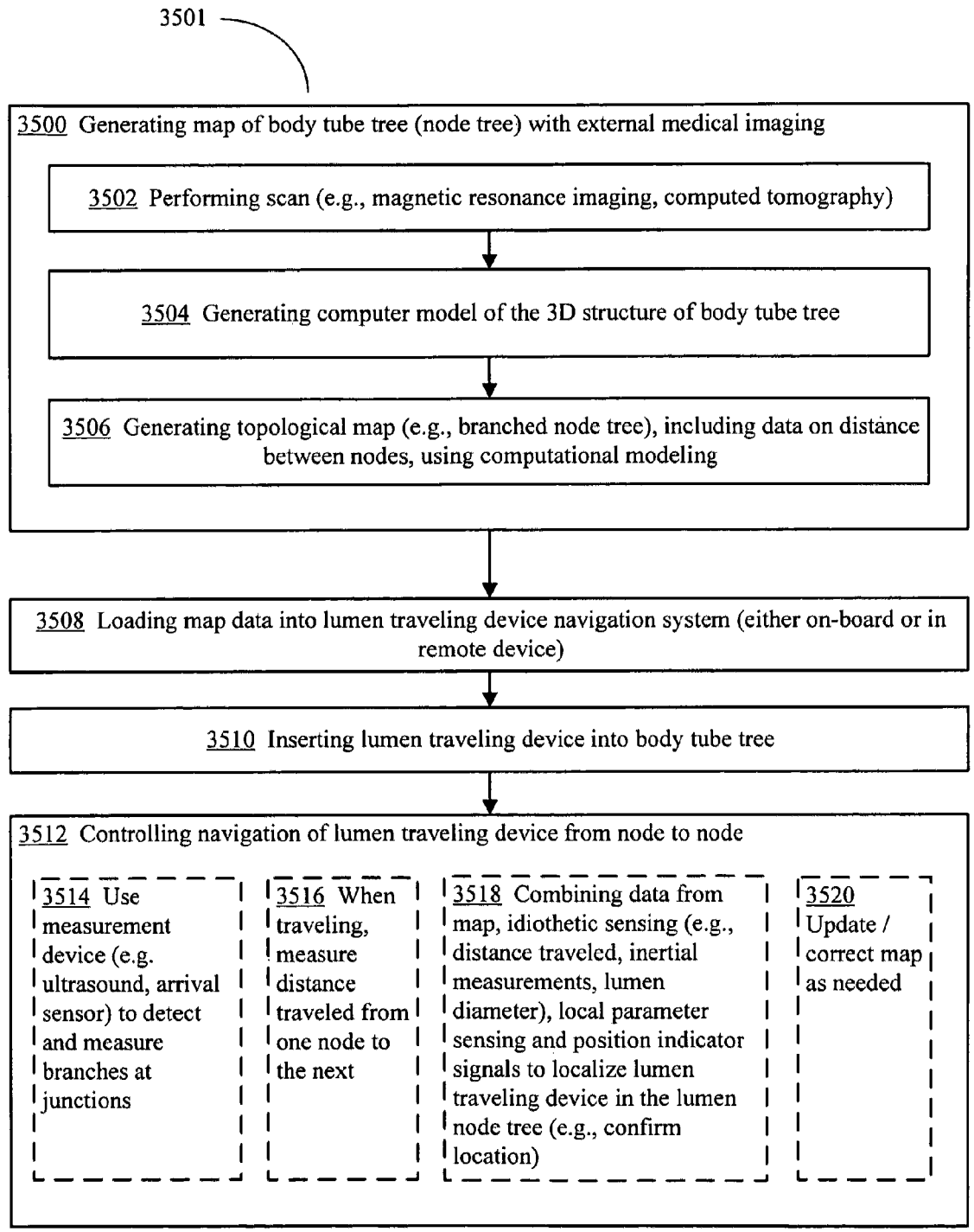
FIG. 35 illustrates steps for generating a map of a body tube tree.

A map of at least a portion of the body tube tree can be obtained by the lumen traveling device itself using a combination of exploration, localization and mapping as outlined in FIG. 14. Alternatively, a map of at least a portion of the body tube tree can be obtained through a combination of external imaging of the body tube tree and computational analysis to develop a three-dimensional structure and map of the body tube tree. FIG. 35 outlines the steps for generating a map of a body tube tree with external medical imaging 3500 including performing a scan (e.g., magnetic resonance imaging, computed tomography) at step 3502; generating a computer model of the three-dimensional structure of the body tube tree at step 3504; generating a topological map (e.g., branched node tree), including data on distance between nodes, using computational modeling at step 3506; loading the map data into the lumen traveling device navigation system (either on-board or in remote device) at step 3508, inserting the lumen traveling device into the body tube tree at step 3510; and controlling navigation of the lumen traveling device from node to node at step 3512. Controlling navigation of the lumen traveling device from node to node at step 3512 can further include using a measurement device (e.g., ultrasound, arrival sensor) to sense and measure branches at junctions at step 3514; measuring distance traveled from one node to the next while traveling through the body tube tree at step 3516; combining data from map, idiothetic sensing (e.g., distance traveled, inertial measurements, lumen diameter), local parameter sensing and position indicator signals to localize lumen traveling device in the lumen node tree (e.g., confirm location) at step 3518; and updating and correcting the map as needed at step 3520.

A map of a body tube tree can be based on two-dimensional and/or three-dimensional renderings of images of a body tube tree generated by external medical imaging. Examples of medical imaging for use in generating two-dimensional and three-dimensional images of a body tube tree include but are not limited to X-ray, gamma camera, computed tomography (CT), magnetic resonance imaging (MRI), and ultrasound. Additional imaging methods include diffuse optical tomography, elastography, electrical impedance tomography, optoacoustic imaging, optical coherence tomography and scanning laser ophthalmoscopy.

A three-dimensional rendering of the vasculature, for example, can be generated using magnetic resonance imaging. A variety of magnetic resonance angiography imaging techniques can be used to generate images of the vasculature, based on flow effects or on inherent or pharmaceutically induced contrast. Examples of magnetic resonance angiography (MRA) techniques include but are not limited to contrast enhanced MRA, time-of-flight (TOF) or inflow angiography, phase-contrast MRA, and fresh blood imaging. For contrast enhanced MRA, a contrast agent is injected into a vein and images are acquired during the first pass of the agent through the arteries. Alternatively, the contrast agent can be a compound that resides for some time in the blood allowing for imaging of both arteries and veins. Examples of contrast agents used for this purpose include but are not limited to gadolinium chelates, iron oxide (e.g., superparamagnetic and ultra-small superparamagnetic iron oxide), and manganese chelates. As an example, Nowinski et al., describe using magnetic resonance angiographic data to create a three dimensional atlas of the cerebral vasculature (Nowinski et al., *RadioGraphics,* 2005, 25:263-271, which is incorporated herein by reference).

The scanned images of a body tube tree (e.g., vasculature) derived from medical imaging can be compiled to generate a three-dimensional map of the body tube tree. The three-dimensional rendering can be transformed into a nodal map system. For example, Tang & Chung describe using a centerline extraction technique to generate a branch map of the vasculature from a pre-segmented, three-dimensional rotational angiography dataset (Tang & Chung, "Cerebral vascular tree matching of 3D-RA data based on tree edit distance," In, *Medical Imaging and Augmented Reality,* G. Z. Yang et al. (Eds): MIAR 2006, LNCS 4091, pp. 116-123, Springer-Verlag Berlin Heidelberg, 2006, which is incorporated herein by reference). Methods have also been described for defining vessel "trees" from three-dimensional image data captured by computed tomography, three-dimensional digital subtraction angiography, ultrasound, and confocal microscopy (see, e.g., Bullitt & Aylward, "Anaylsis of time-varying images using 3D vascular models," *Proceedings* 30*th Applied Imagery Pattern Recognition Workshop* (AIPR 2001), Bilof, R. and Palagi, L. (eds), IEEE Computer Society, Piscataway N.J., pp. 9-14, which is incorporated herein by reference).

Figure 36:
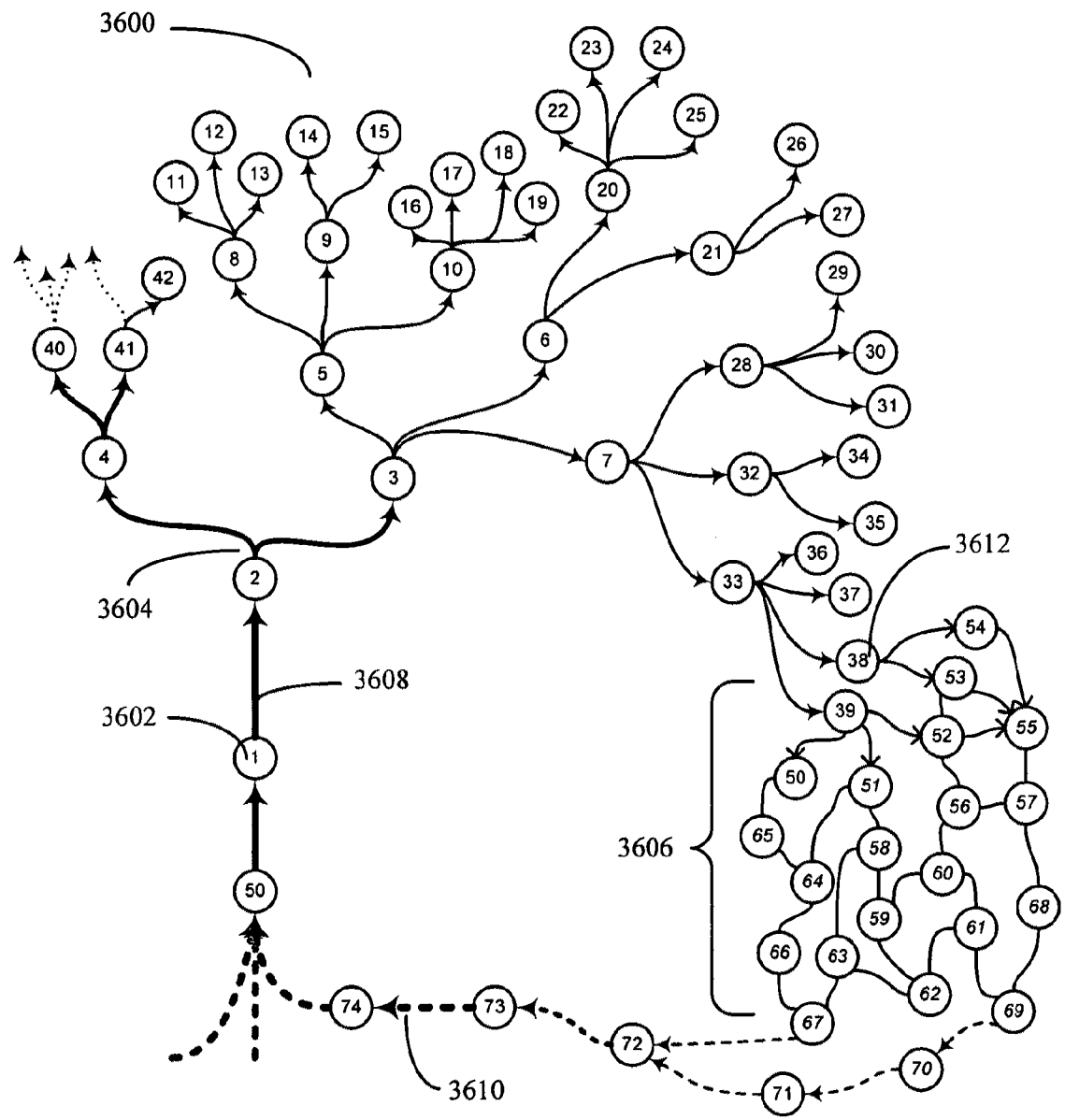
FIG. 36 is an illustration of a map system.

FIG. 36 illustrates an example of a closed loop nodal map system 3600 representative of the vasculature system in which a continuous path of travel eventually leads back to node 1 at the "root" of the tree 3602. In this example, the "root" of the tree 3602 is the heart. Nodal map system 3600 begins at the "root" of the tree 3602 and goes through progressive branches (e.g., nodes 3604) eventually reaching the nodes 3604 representative of a capillary bed 3606 at which point the branches begin to converge and lead back to the "root" of the tree 3602. In this example, solid arrows 3608 represent flow away from the "root" of the tree 3602 (e.g., arterial blood flow) and dashed arrows 3610 represent flow towards the "root" of the tree 3602 (e.g., venous blood flow). For a lumen traveling device configured to fit into the capillary bed 3606, the "end" nodes for the out-bound (e.g., arterial) flow can be connected to nodes of the in-bound (e.g., venous) flow. As an example, planning a path using the nodal map system 3600 from the "root" of the tree 3602 to target location 3612 would involve following a path from node 1, to node 2, to node 3, to node 7 to node 33, to node 38 at target location 3612.

Similarly, a three-dimensional volume rendering of the bronchial tree can be generated by using three-dimensional reconstruction software to stack multiple scanned images (e.g., slices) of the lung. For example, Yu et al. describe a system for complete definition and quantitative analysis of anatomical trees contained in high-resolution three-dimensional digital images (Yu et al., *Comput. Biol. Med.*, 2007, 37:1802-1820, which is incorporated herein by reference). Software packages for 3D reconstruction of medical images are available from commercial sources (e.g., Amira® 5, Visage Imaging™ La Jolla, Calif.; Voxar 3D, Toshiba Medical Visualization Systems Europe, Ltd., Edinburgh, UK). Skeletonizing or thinning algorithms can be used to generate a skeleton or straight line central axis tree from the three-dimensional volume rendering of the bronchial tree. This in turn can be used to generate a branched nodal map. As an example, Pisupati et al. describe using a two pass algorithm to compute the central axis tree and to obtain accurate centroid points that lie along the axes of the branches (Pisupati et al., "A central axis algorithm for 3D bronchial tree structures," ISCV, pp. 259-264, *Proceedings of the International Symposium on Computer Vision,* 1995, which is incorporated herein by reference). The centroid points at each bifurcation are used to compute the branch points and three direction vectors along the branches. The central axis tree is formed by connecting the computed branch points at each bifurcation with straight lines. Also see, e.g., Kitaoka et al., *J. Appl. Physiol.*, 1999, 87:2207-2217; Schertler et al., *AJR* 2004, 183:83-89; and Zrimec & Busayarat, "3D Modeling and Visualization of the Human Lung" 3dpvt, pp. 110-115, *Second International Symposium on 3D Data Processing, Visualization and Transmission* (3DPVT'04), 2004, each of which is incorporated herein by reference.

Figure 37:
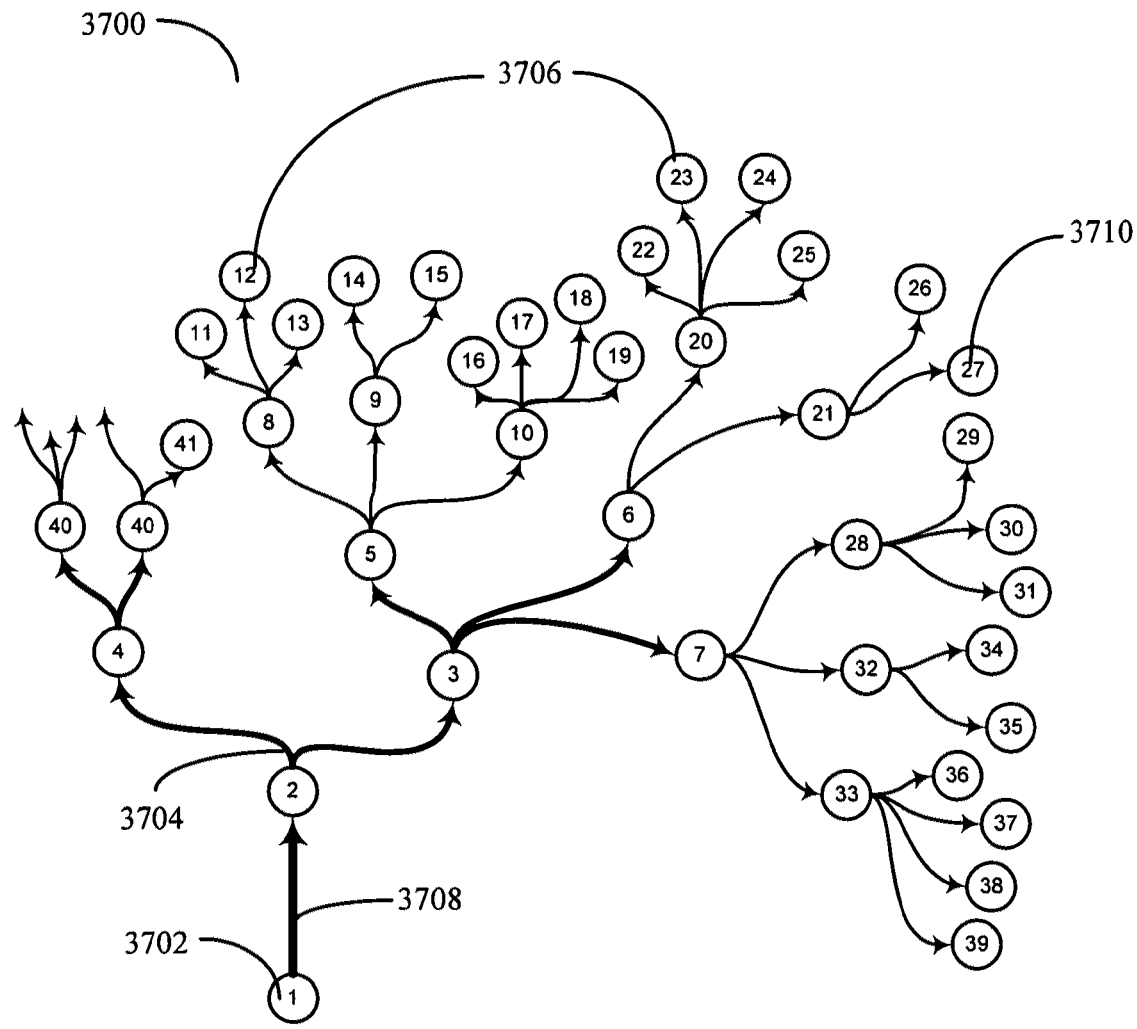
FIG. 37 is an illustration of a map system.

FIG. 37 illustrates an example of an open nodal map system 3700 representative of the bronchial system in which a path of travel begins at the "root" of the tree 3702 and goes through progressive branches (e.g., nodes 3704) eventually reaching "end nodes" 3706 at which point travel must continue in the reverse direction. In this example, the "root" of the tree 3702 can be the trachea, mouth or other entry way into the bronchial airways while the "end nodes" 3706 can be the terminal portion of the alveoli. Solid arrows 3708 indicate direction of flow from the "root" of the tree 3702 to the "end nodes" 3706. As an example, planning a path using the nodal map system 3700 from the "root" of the tree 3702 to target location 3710 would involve following a path from node 1, to node 2, to node 3, to node 6 to node 21, to node 27 at target location 3710. The open nodal map system 3700 can also be representative of other maps of body tube trees in which the branching pattern eventually reaches a dead-end, such as the case in which the lumen traveling device is not configured to travel into the capillaries of the vasculature and must reverse direction to continue moving.

A map generated using medical imaging can be stored on the lumen traveling device in a data storage location. Alternatively, the map can be stored in a remote device, which is in communication with the lumen traveling device through a wireless transmitter/receiver system. As the lumen traveling device moves through the lumen of the body tube tree, one or more position indicator signals can be used to locate the lumen traveling device on the map. In addition, as the lumen traveling device explores and senses the local environment, information regarding specific characteristics of the branch channels as well as sensed local parameter values can be added to the map.

Information regarding the current location of the lumen traveling device within the body tube tree can be determined using an operation performed on-board the lumen traveling device. For example, the lumen traveling device can receive one or more position indicator signals that indicate where the current location of the lumen traveling device is on the stored map. Similarly, the lumen traveling device can receive information from one or more sensors regarding local parameter values that are correlated with specific locations on the stored map.

The lumen traveling device can be instructed to navigate from a current location to a target location within the body tube tree of a subject, whereupon the lumen traveling device performs one or more actions. A target location can be the final destination of the lumen traveling device. Alternatively, a target location can be an intermediate destination of the lumen traveling device. A target location can include a location of anatomical interest (e.g., a branching point, a valve), a location near an organ, a tumor, an injury, etc., a diseased or damaged region (e.g. a fistula or aneurysm), an area of scar tissue, a polyp, or a blockage or constriction formed by a atherosclerotic plaque, blood clot, or vasospasm, for example. In an embodiment, the target location is a specific location on a stored map of the body tube tree which can be identified by the lumen traveling device or by using an external imaging technique. For example, the target location may be a suspicious lesion in the bronchial body tube tree detected using chest radiography, computed tomography, magnetic resonance imaging, positron emission tomography, or combinations thereof (see, e.g., Hollings & Shaw, *Eur. Respir. J.*, 2002, 19:772-742, which is incorporated herein by reference). The target location, as identified by an external imaging technique, can be located on the stored map.

The map of the body tube tree obtained by exploration of the lumen traveling device and or by external medical imaging can be used to plan a path of travel between a current location of the lumen traveling device and a target location. The lumen traveling device can be configured to receive instructions regarding the planned path of travel from on-board control circuitry or from a remote device. The lumen traveling device is instructed to move through the body tube tree along the planned path of travel. The current location of the lumen traveling device is determined at intervals and compared with the map of the body tube tree, the planned path of travel and the target location. Corrections can be made in the planned path of travel and/or in the movements of the lumen traveling device to keep the lumen traveling device moving on course towards the target location. When the current location of the lumen traveling device on the map is the target location, the lumen traveling device may be instructed to stop and perform an action.

FIG. 38 shows various strategies for planning a path of travel 3800 of a lumen traveling device through a body tube tree including planning a path to a specific location 3802 by planning an optimal path to a target location based on known graph-search-based planning techniques (i.e., a map) 3804; planning a path along a gradient of a specific parameter 3806 by choosing a local branch and or a direction that leads in the desired direction along a gradient of specific parameter 3808; planning a path based on previous event 3810 by planning a path based on whether the direction has been previously traveled 3812 and/or by planning a path based on previous action, movement, and or previously sensed parameter 3814; and in some instances, planning a 'random' walk 3816 by choosing branch and or direction of travel substantially at random 3818.

In an embodiment, rather than generating and/or storing a map, the lumen traveling device and/or remote device thereof can be configured to store other positional or locational information that can be used to control the route taken by the lumen traveling device through the body tube tree. In an embodiment, the lumen traveling device can be configured to cover some statistical distribution of lumen sizes or locations during its travels, but not necessarily travel a specific route through the body. The size and location information for already-visited sites can be stored and used in selection of the route to be taken by the lumen traveling device.

FIG. 39 illustrates a block diagram of a system 3900 that is a variant of the system shown in FIG. 33, and that includes a set of instructions 3904 for operating a lumen traveling device. An embodiment of system 3900 is provided using non-transitory machine readable media 3902 including a set of instructions 3304 as in FIG. 33, including one or more instructions that cause the lumen traveling device control system to obtain a map of at least a portion of a body tube tree including a plurality of branched, interconnected channels; one or more instructions that cause the lumen traveling device control system to determine a current location of a lumen traveling device on the map with an operation performed on-board the lumen traveling device, the lumen traveling device located within the body tube tree represented by the map; one or more instructions that cause the lumen traveling device control system to determine a target location for the lumen traveling device within the body tube tree; one or more instructions that cause the lumen traveling device control system to plan a path of travel for the lumen traveling device, the path of travel leading at least a portion of the way between the current location and the target location; and one or more instructions that cause the lumen traveling device control system to direct at least one of a steering mechanism and a propelling mechanism on the lumen traveling device to cause the lumen traveling device to move through the body tube tree along the path of travel. As shown in FIG. 39, the non-transitory machine readable media further includes instructions 3904 specifying wherein the one or more instructions that cause the lumen traveling device control system to plan a path of travel for the lumen traveling device include one or more instructions that cause the lumen traveling device control system to determine a first path of travel leading between the current location and an intermediate location; and one or more instructions that cause the lumen traveling device control system to determine a second path of travel leading between the intermediate location and the target location. The one or more instructions may be, for example, computer executable and/or logic implemented instructions. In an embodiment, the non-transitory machine readable media 3902 can include computer readable media 3906. In an embodiment, the non-transitory machine readable media 3902 can include recordable-type media 3908.

Figure 40:
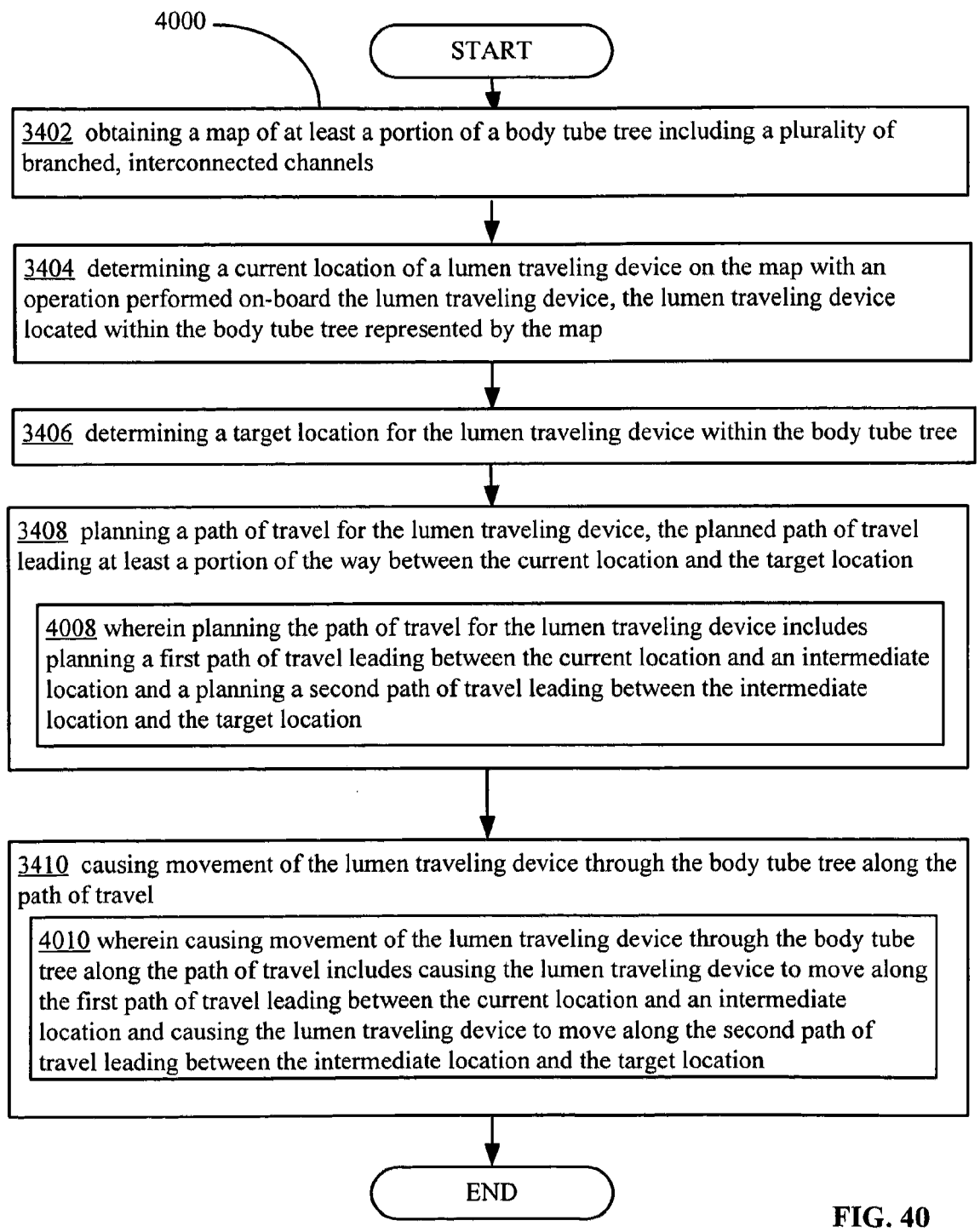
FIG. 40 illustrates a method of operating a lumen traveling device.

FIG. 40 illustrates a method 4000 including obtaining a map of at least a portion of a body tube tree including a plurality of branched, interconnected channels at 3402; determining a current location of a lumen traveling device on the map with an operation performed on-board the lumen traveling device, the lumen traveling device located within the body tube tree represented by the map at 3404; determining a target location for the lumen traveling device within the body tube tree at 3406; planning a path of travel for the lumen traveling device, the planned path of travel leading at least a portion of the way between the current location and the target location at 3408; and causing movement of the lumen traveling device through the body tube tree along the path of travel at 3410, where it is further specified at 4008 wherein planning the path of travel for the lumen traveling device includes planning a first path of travel leading between the current location and an intermediate location and a planning a second path of travel leading between the intermediate location and the target location and wherein causing movement of the lumen traveling device through the body tube tree along the path of travel includes causing the lumen traveling device to move along the first path of travel leading between the current location and an intermediate location and causing the lumen traveling device to move along the second path of travel leading between the intermediate location and the target location.

Controlling the movement of the lumen traveling device along a first path between the current location and an intermediate location can include controlling the movement of the lumen traveling device according to a first algorithm. Controlling the movement of the lumen traveling device along a second path between the intermediate location and a target location can include controlling the movement of the lumen traveling device according to a second algorithm. In an embodiment, the first algorithm and the second algorithm for controlling movement of the lumen traveling device along a first and a second path are the same. In an embodiment, the first algorithm and the second algorithm for controlling movement of the lumen traveling device along a first and a second path differ. For example, the first algorithm can be a Markov localization algorithm and the second algorithm can be a Kalman filtering algorithm.

The first and second algorithms for controlling movement of a lumen traveling device based on a map of a body tube tree can include probabilistic frameworks, Bayesian frameworks, artificial neural networks, Cartesian symbolic-oriented approaches, Markov localization, simultaneous localization and mapping (SLAM), concurrent mapping and localization (CML), and expectation maximization. See, e.g., Thrun, "Robotic Mapping: A Survey," In *Exploring Artificial Intelligence in the New Millenium*, eds. Lakemeyer, G & Nebel, B, published by Morgan Kaufmann, 2002; Thrun, *AI Magazine*, 2000, 21:93-109; Pfister et al., "Weighted line fitting algorithms for mobile robot map building and efficient data representation," *Proceedings of the* 2003 *IEEE International Conference on Robotics and Automation*, Taipei, Taiwan, Sep. 14-19, 2003; Thrun et al., "A real-time algorithm for mobile robot mapping with applications to multi-robot and 3D mapping," *Proceedings of the* 2000 *IEEE International Conference on Robotics and Automation*, San Francisco, Calif., April 2000, each of which is incorporated herein by reference.

PROPHETIC EXAMPLES

Prophetic Example 1

Detecting and Treating Atherosclerotic Plaques in the Vasculature with a Lumen Traveling Device.

A method for detecting and treating atherosclerotic plaques in the vasculature of a mammalian subject may be performed with a system including at least one lumen traveling device configured to travel through the vasculature, sense an atherosclerotic plaque, and controllably perform, an action to treat the atherosclerotic plaque. Atherosclerotic plaques constitute focal accumulation of lipid, smooth muscle cells, foamy macrophages, other inflammatory cells, and cholesterol crystals. Atherosclerotic plaque formation occurs predominantly in arteries and disproportionately in large arteries at points in the lumen where blood flow slows or is more turbulent such as, for example, at branch points or curved portions of the vasculature. As the plaque grows, the lumen of the arterial vessel is gradually occluded, restricting the flow of blood through the vessel. In some instances, the plaque may rupture, inducing the formation of a thrombus at the site of the rupture that further occludes the vessel. Alternatively, debris associated with the ruptured plaque can travel downstream and form an embolus that blocks an artery, e.g., a coronary artery, leading to myocardial infarction and other acute coronary syndromes. The ability to detect and treat vulnerable atherosclerotic plaques prior to rupture is of benefit to the subject.

The method of detecting and treating an atherosclerotic plaque includes introducing one or more lumen traveling devices into one or more blood vessels of a subject. In this example, a lumen traveling device is initially placed into a large artery, e.g., the femoral artery, coronary artery, or carotid artery, by directly injecting the lumen traveling device into the artery with a syringe fitted with a needle. The gauge of needle used for injection should be sufficient to allow passage of the lumen traveling device. Needles commonly used in medical practice range in size from 10 gauge (nominal inner diameter of 2.69 millimeters) to 33 gauge (nominal inner diameter of 0.11 millimeters). For example, the standard nominal inner diameter of a 14 gauge needle is 1.6 millimeters.

Figure 41A:
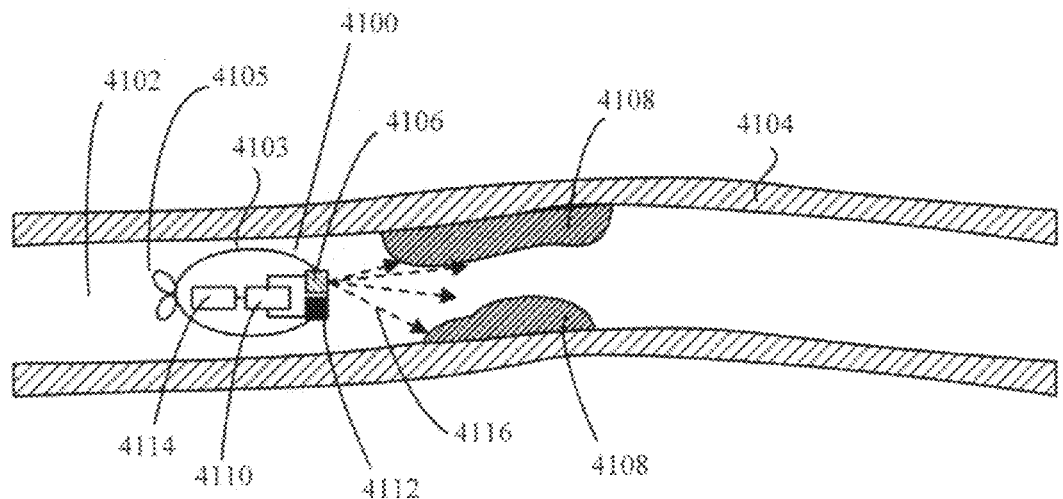
FIGS. 41A & 41B illustrate placement of a lumen traveling device in a body tube tree.
Figure 41B:
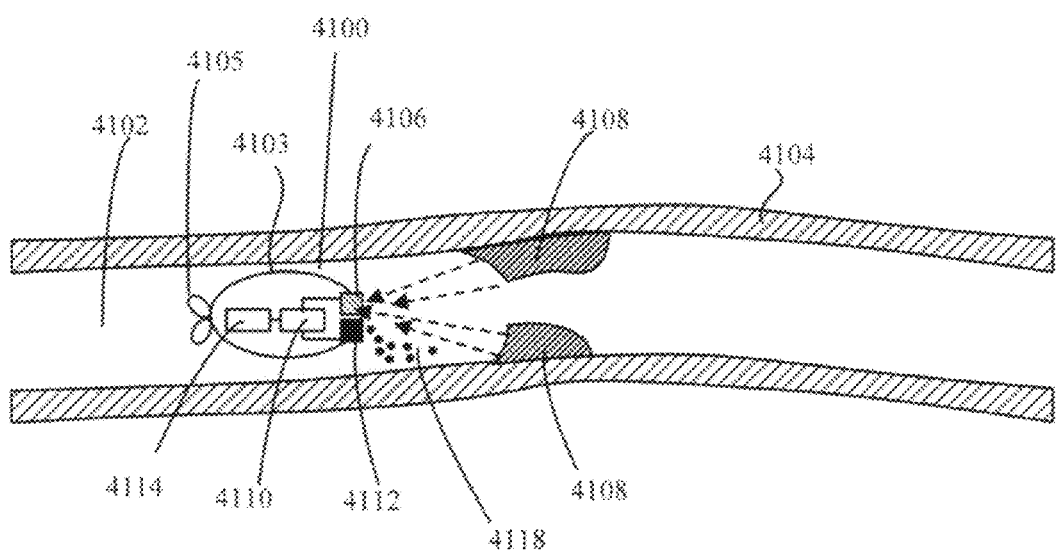

FIG. 41A provides an illustrative example of a lumen traveling device moving through the vasculature body tube tree sensing the presence of atherosclerotic plaques. FIG. 41B further provides an illustrative example of a lumen traveling device performing an action to eliminate an atherosclerotic plaque. In this example, lumen traveling device 4100 moving through a body lumen 4102 can have a capsule-like body structure 4103 and include a propelling mechanism 4105. Lumen traveling device 4100 can include a sensor 4106, response control circuitry 4110, and reservoir 4112, the active portion of the lumen traveling device which releases a therapeutic agent for treatment of an atherosclerotic plaque. Lumen traveling device 4100 can also include motion control circuitry 4114 to control movement of the lumen traveling device through the vasculature body tube tree. The sensor 4106 of the lumen traveling device can include a light emitting diode, which serves as an electromagnetic radiation source that emits a first wavelength(s) of electromagnetic radiation 4116 to induce autofluorescence of a plaque 4108 associated with the lumen wall 4104. The autofluorescence emitted by the plaque 4108 can be detected by an image capturing portion of sensor 4106. Upon detection of the plaque 4108, reservoir 4112 can be activated as shown in FIG. 41B. In this example, reservoir 4112 releases a plaque stabilizing agent 4118, e.g., everolimus, which serves a therapeutic agent for treatment of an atherosclerotic plaque, in this case, by stabilizing the plaque 4108.

The lumen traveling device travels to a target location within the vasculature guided by a map. A map of the arterial vasculature can be generated using external imaging as exemplified by magnetic resonance angiography (MRA). In preparation for magnetic resonance angiography, the subject can be injected intravenously with a gadolinium-based contrast agent, e.g., gadodiamide (Omniscan™; dosed at 0.05 to 0.2 mmol/kg). Magnetic resonance imaging can be performed using standard methodologies. A stack of image slices can be generated representing a unique 3D volume of the subject's body. Computational analysis can be used to generate a topological map of the vasculature. At least a portion of the map is incorporated into the data storage location within the lumen traveling device with the remainder of the map incorporated into a remote device in wireless communication with the lumen traveling device.

The location of the lumen traveling device within the vascular body tube tree of a subject can be determined relative to the map of the vascular body tube tree. In this example, a position indicator signal is produced by a radiofrequency identification (RFID) tag associated with the lumen traveling device. The RFID tag produces (reflects or transmits) a signal that is detected by an external receiver in response to an interrogation signal generated by the remote device.

The lumen traveling device is configured with one or more light emitting diodes in sensor 4106 to induce autofluorescence of the lumen surface. The LED is configured to emit electromagnetic energy at a wavelength of about 340 nm. Ultraviolet LEDs constructed of quaternary AlGaInN on small area devices (<100 um diameter) and operating in the range of 340 nm wavelength are described by Peng et al., in Applied Physics Letters, 85:1436-1438, 2004, which is incorporated herein by reference. Autofluorescence emitted from an atherosclerotic plaque can be distinguished from that of the normal luminal surface of the vasculature, using response control circuitry 4110. Autofluorescence associated with the lumen wall is detected at specific peak wavelengths, e.g., 395 nm and 450 nm, using a CMOS (complementary metal-oxide semiconductor) imaging sensor in sensor 4106. Differences in the autofluorescence spectra are used to differentiate between normal, collagen thick and macrophage thick plaques. See, e.g., Marcu et al., Atherosclerosis, 2005, 181: 295-303, which is incorporated herein by reference.

Upon detection of an atherosclerotic plaque, the lumen traveling device can be instructed by response control circuitry 4110 to release a therapeutic agent, everolimus, which either stabilizes or causes regression of the plaque without catastrophic rupture. Everolimus [40-O-(2-hydroxyethyl)-rapamycin] is a rapamycin derivative that inhibits the activity of mammalian target of rapamycin (mTOR) and selectively clears macrophages in vulnerable plaques without altering the viability of plaque-stabilizing smooth muscle cells. See, e.g., Verheye, et al., *J. Am. Coll. Cardiol.* 2007, 49:706-715, which is incorporated herein by reference. The lumen traveling device can include a reservoir containing everolimus. Upon detection of an atherosclerotic plaque, the lumen traveling device is instructed to release the everolimus in the immediate vicinity of the plaque. Alternative or additional plaque stabilizing agents can be incorporated into reservoir 4112 or additional reservoirs (not shown). Examples of additional plaque stabilizing agents include but are not limited to HMG-CoA-reductase inhibitors (statins), angiotensin-converting enzyme (ACE) inhibitors, antihypertensive agents, beta-blocking agents, and antiplatelet agents.

Figure 42:
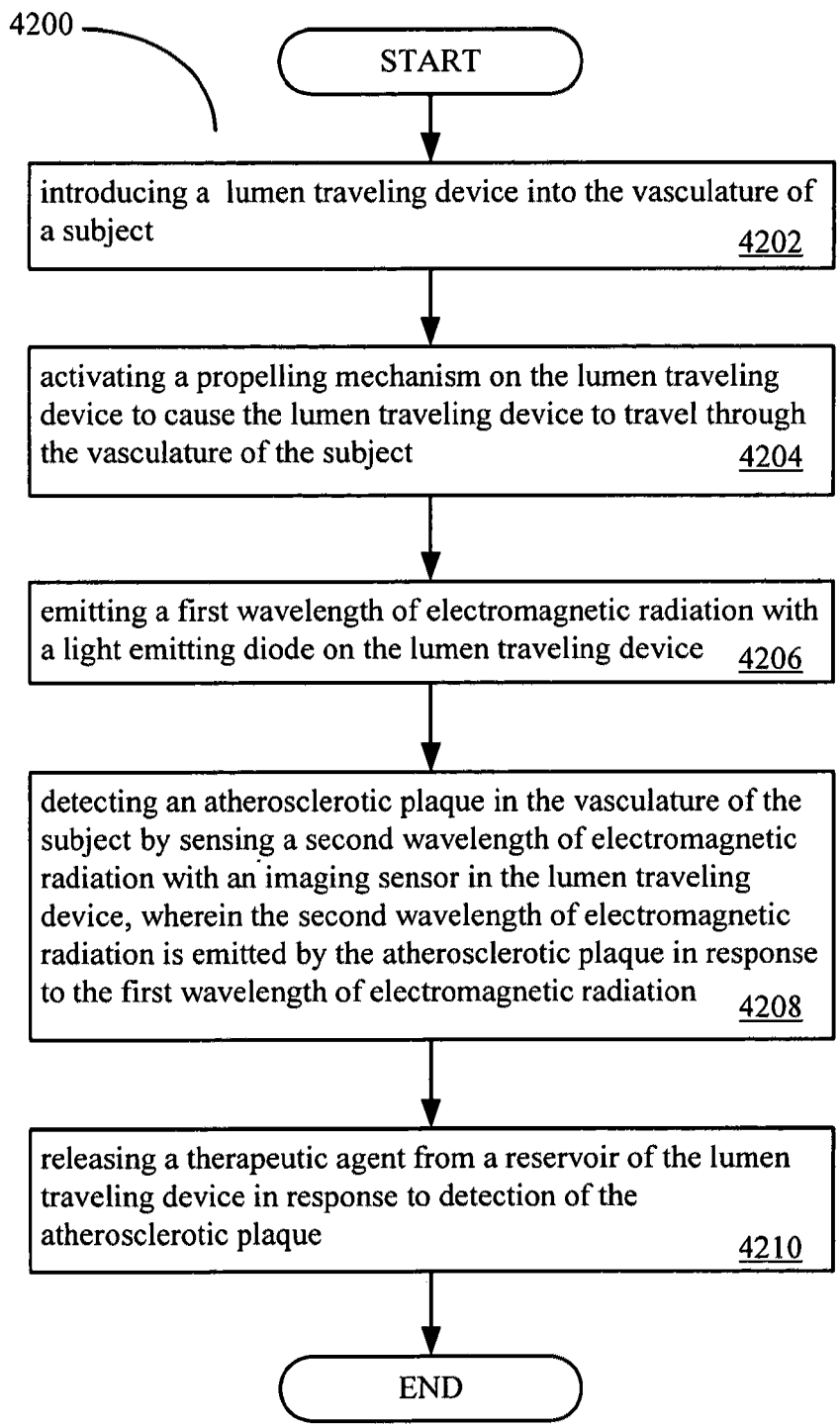
FIG. 42 illustrates a method of operating a lumen traveling device.

As shown in FIG. 42, a method for detecting and treating atherosclerotic plaques in the vasculature of a mammalian subject can thus include introducing a lumen traveling device into the vasculature of a subject at 4202; activating a propelling mechanism on the lumen traveling device to cause the lumen traveling device to travel through the vasculature of the subject at 4204; emitting a first wavelength of electromagnetic radiation with a light emitting diode on the lumen traveling device at 4206; detecting an atherosclerotic plaque in the vasculature of the subject by sensing a second wavelength of electromagnetic radiation with an imaging sensor in the lumen traveling device, wherein the second wavelength of electromagnetic radiation is emitted by the atherosclerotic plaque in response to the first wavelength of electromagnetic radiation at 4208; and releasing a therapeutic agent from a reservoir of the lumen traveling device in response to detection of the atherosclerotic plaque at 4210.

FIG. 43, illustrates a block diagram of a system 4300 that includes a set of instructions 4304 for operating a lumen traveling device. An embodiment of system 4300 is provided using non-transitory machine readable media 4302 for use in a lumen traveling device control system for controlling a lumen traveling device including a light emitting diode, an imaging sensor, a reservoir containing a therapeutic agent for treatment of an atherosclerotic plaque, and a propelling mechanism. Non-transitory machine readable media 4302 including a set of instructions 4304, including one or more instructions that cause the lumen traveling device control system to activate the propelling mechanism to cause the lumen traveling device to travel through the vasculature of the subject; one or more instructions that cause the lumen traveling device control system to direct the light emitting diode to emit a first wavelength of electromagnetic radiation; one or more instructions that cause the lumen traveling device control system to direct the detection of an atherosclerotic plaque by sensing a second wavelength of electromagnetic radiation emitted by the atherosclerotic plaque with the imaging sensor; and one or more instructions that cause the lumen traveling device control system to release the therapeutic agent from the reservoir of the lumen traveling device in response to detection of an atherosclerotic plaque. The one or more instructions may be, for example, computer executable and/or logic implemented instructions. In an embodiment, the non-transitory machine readable media 4302 can include computer readable media 4306. In an embodiment, the non-transitory machine readable media 4302 can include recordable-type media 4308.

Prophetic Example 2

Detecting and Treating Lung Cancer in the Bronchial Tree with a Lumen Traveling Device.

A method for detecting and treating a cancerous lesion in the bronchial airways of a mammalian subject can be performed with a system including at least one lumen traveling device configured to travel through the bronchial body tube tree up a concentration gradient of one or more cancer-associated analytes in the exhaled breath to reach the cancerous lesion and to controllably perform an action to treat the cancerous lesion. The vast majority of primary lung cancers are carcinomas of the lung, derived from bronchial epithelial cells lining the bronchial airways. The main types of lung cancer are small cell lung carcinoma and non-small cell lung carcinoma. Small cell lung carcinoma tends to arise in the larger airways (e.g., primary and secondary bronchi), and grows rapidly. Non-small cell carcinoma includes squamous cell lung carcinoma (originating primarily near a central bronchus), adenocarcinoma (originating primarily in peripheral lung tissue), and large cell carcinoma. The diagnosis of lung cancer often occurs at the first signs of symptoms (e.g., weight loss, coughing blood, difficulty breathing), a point at which the cancer may have already spread extensively within the lung and possibly metastasized. As such, early diagnosis is critical to early treatment and survival.

Figure 44:
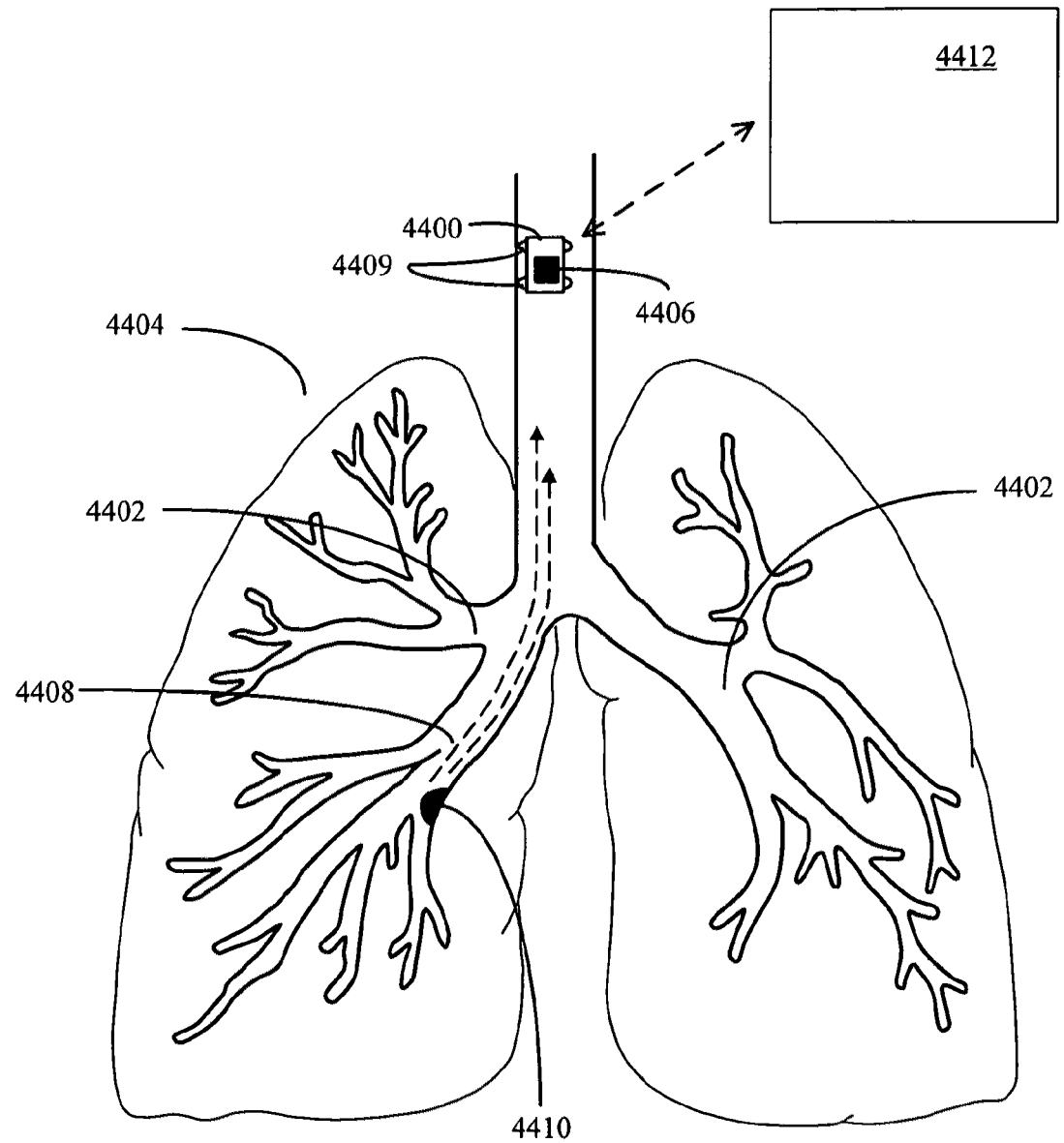
FIG. 44 illustrates an example of the operation of a lumen traveling device in the lumen of a body tube tree.

In this prophetic example, as depicted in FIG. 44, a lumen traveling device 4400 containing one or more sensors for sensing analytes such as volatile organic compounds associated with lung cancer can be introduced into the lungs 4404 of a subject. Lumen traveling device 4400 is used in combination with remote device 4412, which includes a portion of the control circuitry used for controlling lumen traveling device 4400 and provides power to lumen traveling device 4400. Data and power signals are transmitted between remote device 4412 and lumen traveling device 4400 as indicated by the dashed line. Lumen traveling device 4400 is introduced into the bronchial body tube tree 4402 either through direct inhalation or with a bronchoscope using methods similar to those described for placement of a tracheobronchial stent (see, e.g., Herth, et al., *Chest,* 2001, 119:1910-1912, which is incorporated herein by reference).

Lumen traveling device 4400 can travel through the bronchial body tube tree 4402 following the concentration gradient of one or more analytes, e.g., volatile organic compounds, sensed in the exhaled breath of a subject. The lumen traveling device 4400 includes sensor 4406 with an electronic nose configured to sense one or more cancer-associated analytes 4408 (e.g., volatile organic compound) in the exhaled breath of a subject, wheeled propelling mechanism 4409 (as depicted in FIG. 1), and an active portion (not shown in FIG. 44, but is an electromagnetic energy source of the type depicted in FIG. 6C). Lumen traveling device 4400 also includes control circuitry, including response control circuitry, operating in cooperation with control circuitry on remote device 4412. A cancer-associated analyte 4408 originates from and is at its highest concentration at a cancerous lesion 4410 residing in the lumen of the bronchial body tube tree 4402. The sensor 4406 of the lumen traveling device 4400 can continuously sense the exhaled breath as it moves through the bronchial body tube tree 4402. Response control circuitry on lumen traveling device 4400 can compare the concentration of the cancer-associated analyte 4408 at a current location with the highest concentration sensed so far. The lumen traveling device can select a path of travel based on the concentration gradient of a sensed cancer-associated analyte 4408 and ultimately reaches the source of the analyte, the cancerous lesion 4410. Upon reaching the source of the cancer-associated analyte 4408, the lumen traveling device can be instructed to perform an action designed to eliminate the cancerous lesion 4410 by activating the electromagnetic energy source to emit electromagnetic energy.

The lumen traveling device can be configured with one or more sensors for sensing one or more cancer-specific analytes in the bronchial tree of a subject. As an example, the one or more sensed cancer-specific parameters can be one or more analytes expired in the breath of the subject. A number of analytes have been detected in the expired breath of cancer patients, examples of which include but are not limited to, volatile organic compounds (VOCs), interleukin 6 (IL-6), and endothelin-1 (see, e.g., Dweik & Amann, *J. Breath Res.,* 2008; 030301 (3 pp) and Phillips et al., *Chest,* 2003; 123: 2115-2123, each of which is incorporated herein by reference). A number of specific volatile organic compounds are elevated in the expired breath of subjects with cancer, including but not limited to butane, 3-methyl tridecane, 7-methyl tridecane, 4-methyl octane, 3-methyl hexane, heptane, 2-methyl hexane, pentane, and 5-methyl decane. Sensor 4206 can sense one or more volatile organic compounds in the exhaled breath of a subject. The sensor is a form of electronic nose capable of detecting volatile organic compounds in exhaled breath (see, e.g., Machado et al., *Am. J. Respir. Crit. Care Med.*, 2005; 171:1286-1291, which is incorporated herein by reference). The sensor can include one or more polymer composite sensors which undergo a reversible change in electrical resistance when exposed to a target vapor or analyte. The resistance change of each sensor is unique because of the chemical diversity of the sensor materials. The pattern of resistance changes obtained from the sensor array constitutes a "smellprint". A particular smellprint is indicative of a pathological state, e.g., cancer. Examples of micro and nanoscale electronic noses are described in Rolfe, B., "Toward Nanometer-Scale Sensing Systems: Natural and Artificial Noses as Models for Ultra-Small, Ultra-Dense Sensing Systems," in *Advances in Computers*, Volume 71, ed. M Zelkowitz, Elsevier, B. V., 2007.

Figure 45:
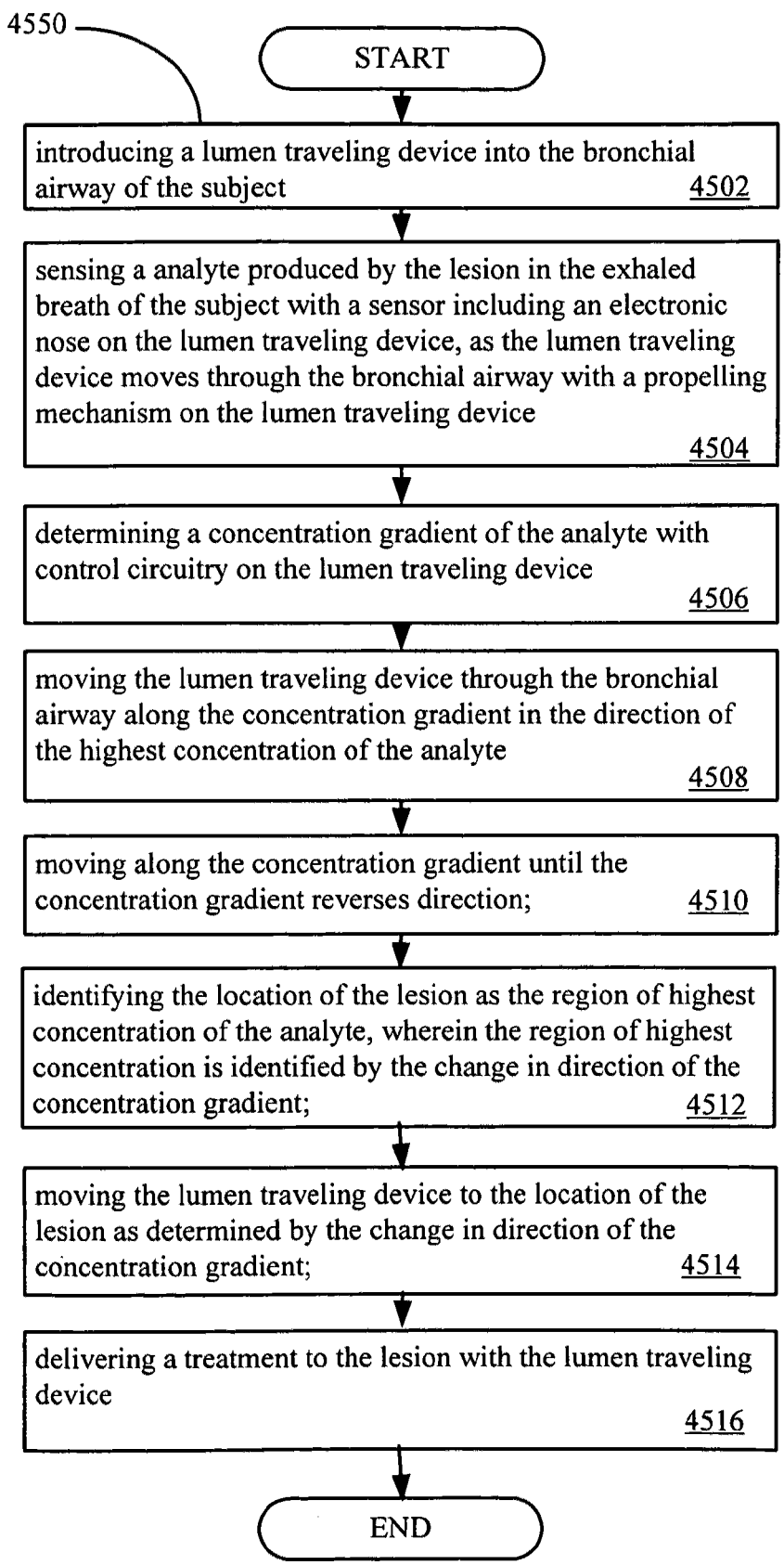
FIG. 45 illustrates a method of operating a lumen traveling device.

As shown in FIG. 45, the method of detecting and treating a lesion in the bronchial airways of a subject using a lumen traveling device thus includes introducing a lumen traveling device into the bronchial airway of the subject at 4502; sensing a analyte produced by the lesion in the exhaled breath of the subject with a sensor including an electronic nose on the lumen traveling device, as the lumen traveling device moves through the bronchial airway with a propelling mechanism on the lumen traveling device at 4504; determining a concentration gradient of the analyte with control circuitry on the lumen traveling device at 4506; moving the lumen traveling device through the bronchial airway along the concentration gradient in the direction of the highest concentration of the analyte at 4508; moving along the concentration gradient until the concentration gradient reverses direction at 4510; identifying the location of the lesion as the region of highest concentration of the analyte, wherein the region of highest concentration is identified by the change in direction of the concentration gradient at 4512; moving the lumen traveling device to the location of the lesion as determined by the change in direction of the concentration gradient at 4514; and delivering a treatment to the lesion with the lumen traveling device at 4516. Upon reaching the origin of a sensed cancer-associated analyte, the lumen traveling device is instructed by the control circuitry to perform a treatment action, specifically delivering electromagnetic energy to ablate the lesion.

In related embodiments, the lumen traveling device can release one or more chemotherapeutic agent, such as cisplatin, etoposide, carboplatin, cyclophosphamide, doxorubicin, vincristine, gemcitabine, topotecan, instead of or in addition to electromagnetic energy to treat the lesion.

As shown in FIG. 46, instructions for performing the method can be provided on non-transitory machine readable media as described elsewhere herein, which can be carried fully or in part on the lumen traveling device, or which can be provided on various other types of media. An embodiment of system 4600 is provided using non-transitory machine readable media 4602 including a set of instructions 4604 including one or more instructions that cause the lumen traveling device control system to direct a sensor including an electronic nose on a lumen traveling device to sense a analyte indicative of a lesion in a bronchial airway of a subject while the lumen traveling device moves through the bronchial airway; one or more instructions that cause the lumen traveling device control system to determine a concentration gradient of the analyte; one or more instructions that cause the lumen traveling device control system to direct at least one of a steering mechanism and a propelling mechanism on the lumen traveling device to move the lumen traveling device through the bronchial airway along the concentration gradient in the direction of the highest concentration of the analyte with a propelling mechanism on the lumen traveling device; one or more instructions that cause the lumen traveling device control system to detect when the concentration gradient reverses direction; one or more instructions that cause the lumen traveling device control system to reverse the direction of movement of the lumen traveling device when the concentration gradient changes direction; one or more instructions that cause the lumen traveling device control system to direct at least one of the steering mechanism and the propelling mechanism on the lumen traveling device to move the lumen traveling device to the location of the lesion as determined by the change in direction of the concentration gradient; and one or more instructions that cause the lumen traveling device control system to direct the lumen traveling device to deliver a treatment to the lesion. The one or more instructions may be, for example, computer executable and/or logic implemented instructions. In an embodiment, the non-transitory machine readable media 4602 can include computer readable media 4606. In an embodiment, the non-transitory machine readable media 4602 can include recordable-type media 4608.

Prophetic Example 3

Detecting and Treating a Meningeal Malignancy in the Cerebrospinal Fluid with a Lumen Traveling Device.

In another prophetic example, a method is provided for detecting and treating a meningeal malignancy in the central nervous system of a mammalian subject. The method includes using at least one lumen traveling device configured to travel through the cerebrospinal fluid, sense one or more analyte associated with the meningeal malignancy, and controllably perform an action to treat the meningeal malignancy. Meningeal malignancy results from metastasis of intracranial or extracranial tumors to the leptomeninges (the arachnoid membrane and the pia mater). The cerebrospinal fluid (CSF) flows in the subarachnoid space between the pia and the arachnoid and may provide a route for metastasis along the entire neuraxis. In many instances, the chemotherapeutic drugs used to treat extracranial tumors do not readily cross the blood brain barrier and as such the central nervous system can become a sanctuary for metastasizing tumor cells. Examples of tumors that can metastasize to the meninges include leukemia, lymphoma, melanoma, breast and lung carcinoma, Ewing's sarcoma, rhabdomyosarcoma, retinoblastoma, and brain tumors. Various manifestations of meningeal malignancy are referred to as carcinomatous meningitis, leptomeningeal cancer, leptomeningeal carcinoma, leptomeningeal metastasis, meningeal carcinomatosis, and neoplastic meningitis.

The lumen traveling device can include one or more sensors for sensing parameters associated with meningeal malignancy in the flow route of the CSF, e.g., the subarachnoid space and the ventricles. Examples of parameters associated with meningeal malignancy that can be measured in the CSF include but are not limited to circulating tumor cells, elevated protein, reduced glucose and increase in specific biomarkers. See, e.g., Pavlidis, *Ann. Oncol.*, 2004, 15 (Suppl 4):iv285-iv291, which is incorporated herein by reference. The gold standard for diagnosis of meningeal malignancy is the presence of circulating tumor cells in the CSF and as such, the one or more sensors associated with the lumen traveling device are configured to sense circulating tumor cells. A circulating tumor cell derived from metastasis of a solid tumor will be considerably larger in volume than the limited number of blood cells normally found in the CSF and can be differentiated from other cells based on size using filtration and/or electrical impedance. A circulating tumor cell can be as large as 2000 fL or 2.5 to 5 times larger than white blood cells the latter of which range in volume range from 100 to 450 fL. Circulating tumor cells can be detected based on size using electrical impedance. The lumen traveling device can be configured to include a microelectromechanical system (MEMS) miniaturized Coulter counter for differentiating cells based on volume as described (see, e.g., Zheng et al., "Design and fabrication of a micro coulter counter with thin film electronics," *Proceedings of* 2006 *International Conference on Microtechnologies in Medicine and Biology, IEEE*, Okinawa, Japan, 9-12 May, 2006 and Gao et al., "A micro sensing probe for detecting individual biological cells," *Proceedings of the 25th Annual International Conference of the IEEE EMBS*, Cancun, Mexico, Sep. 17-21, 2003, each of which is incorporated herein by reference).

Figure 47:
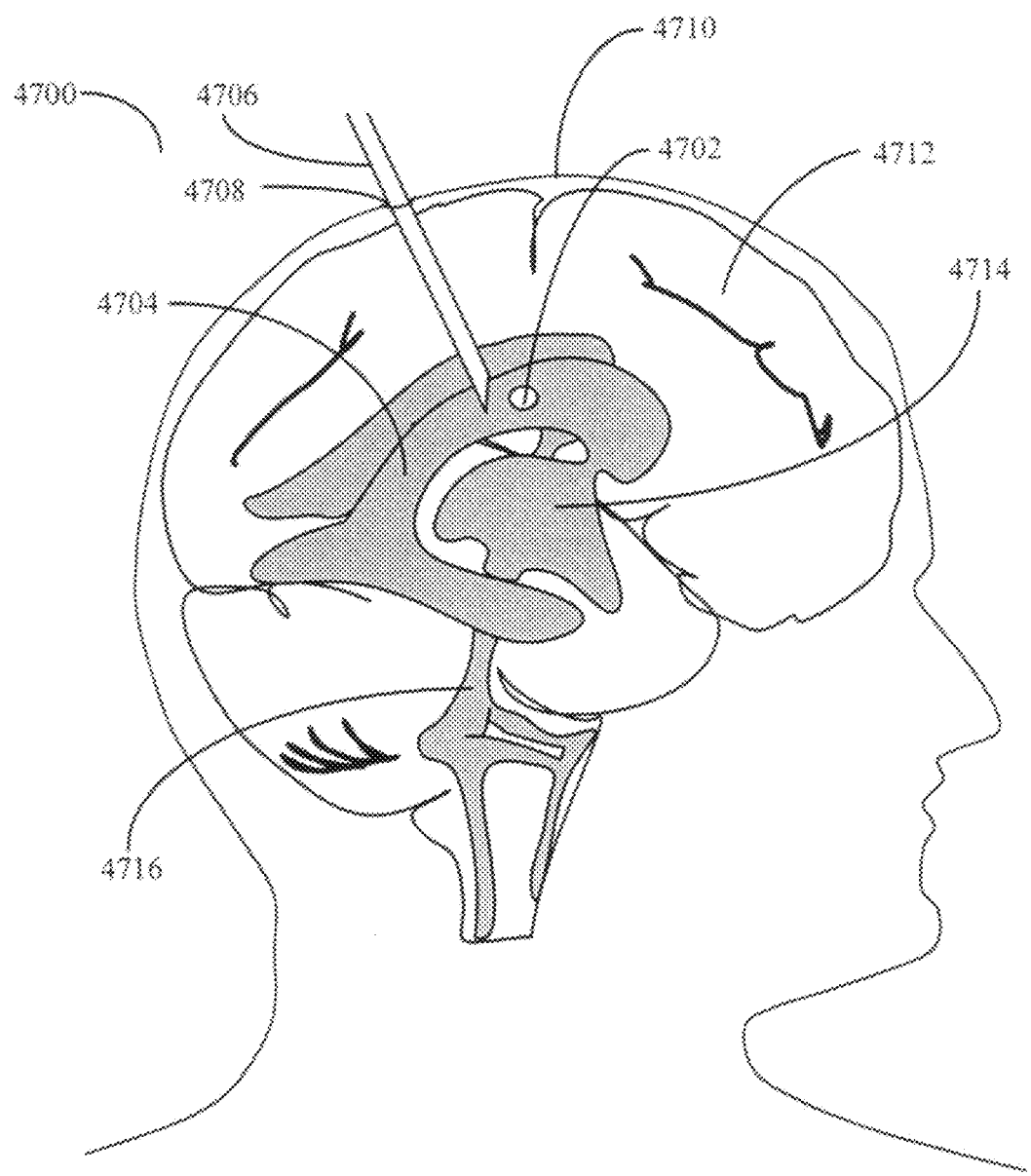
FIG. 47 illustrates a method of operating a lumen traveling device.

A method of detecting and treating meningeal malignancy can include intraventricular placement of one or more lumen traveling devices into the CSF flow route of a subject as illustrated in FIG. 47. As shown in FIG. 47, lumen traveling device 4702 can be introduced into the lateral ventricle 4704 of subject 4700, from which it can travel through the CSF flow route. Lumen traveling device 4702 can be introduced into the lateral ventricle 4704 using a ventricular catheter 4706. The subject 4700 can be given a local anesthetic at insertion site 4708. A hole can be drilled in the skull 4710 at the insertion site 4708. The ventricular catheter 4706 can be inserted through the skull 4710 at insertion site 4708 and through the cerebral cortex 4712 to a depth of about six centimeters to reach the lateral ventricle 4704. The lumen traveling device 4702 can be released into the lateral ventricle 4704 from which it may travel into other parts of the CSF flow route including the third ventricle 4714 and the fourth ventricle 4716. Alternatively, the lumen traveling device 4702 can be placed in the CSF flow route by intrathecal injection into the central canal of the spinal cord.

In response to sensing a circulating tumor cell and or a meningeal malignancy biomarker in the CSF, the lumen traveling device can be instructed to release a chemotherapeutic agent from a reservoir on the lumen traveling device. Chemotherapeutic agents commonly used to treat meningeal malignancy include but are not limited to methotrazate, cyarabine, thiotepa, diaziquone, 6-mercaptopurine, mafosfamide/4HC, or topotecan.

Figure 48:
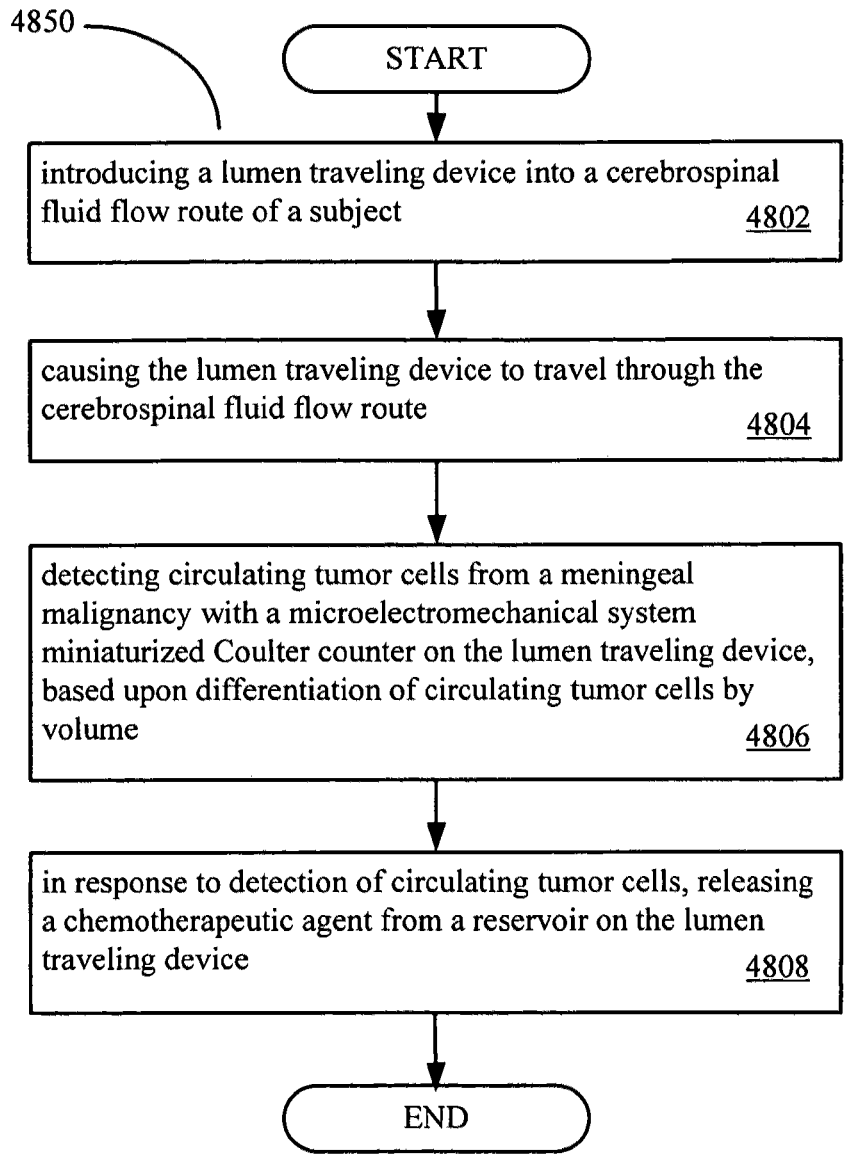
FIG. 48 illustrates a method of operating a lumen traveling device.

As shown in FIG. 48, a method of detecting and treating a meningeal malignancy can thus include introducing a lumen traveling device into a cerebrospinal fluid flow route of a subject at 4802 causing the lumen traveling device to travel through the cerebrospinal fluid flow route at 4804; detecting circulating tumor cells from a meningeal malignancy with a microelectromechanical system miniaturized Coulter counter on the lumen traveling device, based upon differentiation of circulating tumor cells by volume at 4806; and in response to detection of circulating tumor cells, releasing a chemotherapeutic agent from a reservoir on the lumen traveling device at 4808.

FIG. 49 illustrates a block diagram of a system 4900 that includes non-transitory machine readable media 4902 including a set of instructions 4904 including: one or more instructions that cause the lumen traveling device control system to direct at least one of a steering mechanism and a propelling mechanism on the lumen traveling device to cause a lumen traveling device to travel through a cerebrospinal fluid flow route of a subject; one or more instructions that cause the lumen traveling device control system to detect circulating tumor cells from a meningeal malignancy with a microelectromechanical system miniaturized Coulter counter on the lumen traveling device; and one or more instructions that cause the lumen traveling device control system to release a chemotherapeutic agent from a reservoir on the lumen traveling device in response to detect circulating tumor cells with the microelectromechanical system miniaturized Coulter counter on the lumen traveling device. The one or more instructions may be, for example, computer executable and/or logic implemented instructions. In an embodiment, the non-transitory machine readable media 4902 can include computer readable media 4906. In an embodiment, the non-transitory machine readable media 4902 can include recordable-type media 4908.

Prophetic Example 4

Detecting and Treating HIV Infection in the Central Nervous System Using a Lumen Traveling Device.

A method for detecting and treating acquired immunodeficiency syndrome (AIDS) dementia complex in the central nervous system of a mammalian subject can be implemented using at least one lumen traveling device designed to travel through the cerebrospinal fluid, sense one or more analyte indicative of infection with human immunodeficiency virus (HIV), and controllably perform an action to treat the infection and or the dementia. AIDS dementia complex is a metabolic encephalopathy caused by HIV infection of brain macrophages and microglia and is a common neurological disorder associated with AIDS. The infected cells secrete neurotoxins of both host and viral origin which cause disabling cognitive impairment accompanied by motor dysfunction, speech problems and behavioral changes. In some individuals, the central nervous system (CNS) may be a reservoir for HIV with viral replication occurring relatively independently from systemic infection. In addition, a number of commonly used HIV drugs do not efficiently pass in to the CNS. See, e.g., Groothuis & Levy, *J. Neurovirol.*, 1997, 3:387-400, which is incorporated herein by reference. AIDS dementia is confirmed in those HIV positive subjects experiencing cognitive impairment by testing the cerebrospinal fluid (CSF) for the presence of HIV antibodies or HIV RNA. A lumen traveling device can be configured to monitor the CSF of an HIV positive subject for infection in the CNS and to directly administer one or more drugs into the CSF.

A method for detecting and treating AIDS dementia complex in the CNS of an HIV positive subject can include use of a lumen traveling device with one or more sensors configured to sense one or more markers of HIV infection in the CNS. In this example, the sensors are configured to detect HIV antibodies in the CSF generated by the body's immune response to HIV infection. The sensors are one or more carbon nanotube-field effect transistors as described by Kim et al., *Anal. Biochem.*, 2008, 381:193-198, which is incorporated herein by reference. Carbon nanotubes are functionalized with all or part of the HIV surface glycoprotein 41 (gp41) and are incorporated into one or more fluid contacting surfaces of the lumen traveling device. Binding of the target HIV antibodies in the CSF to the gp41 fragments on the carbon nanotubes can be detected by monitoring the gating effects induced by the charges associated with the bound HIV antibodies. A similar approach can be used to detect HIV RNA in which the carbon nanotubes are functionalized with an RNA binding moiety such as, for example, anti-sense RNA/DNA, an aptamer, or a peptide nucleic acid (PNA).

The lumen traveling device containing one or more sensors for sensing one or more markers of HIV infection can be placed into the CSF flow route of a subject by intraventricular insertion as described in FIG. 43. Ideally, the lumen traveling device is placed into one of the cerebral ventricles using a ventricular catheter. The subject can be given a local anesthetic on the scalp at the site of insertion. An incision can be made in the skin and the skull can be drilled to create a hole in the skull through which the catheter can pass. The catheter can be inserted to a depth of about 6 centimeters to reach the lateral ventricle and the lumen traveling device released into the ventricular space.

In response to sensing HIV antibodies or HIV RNA in the CSF, the lumen traveling device can be instructed by the response control circuitry to perform an action. In this instance, the action performed is release of one or more antiretroviral drugs for treatment of HIV infection. The lumen traveling device can administer one or more antiviral drugs directly into the CSF. Examples of antiviral drugs commonly used for treating HIV/AIDS include but are not limited nucleoside analog reverse transcriptase inhibitors (e.g., AZT, stavudine, didanosine, zalcitabin, almivudine, abacavir, emtricitabine), nucleotide analog reverse transcriptase inhibitors (e.g., tenofovir, adefovir), non-nucleoside reverse transcriptase inhibitors (e.g., efavirenz, nevirapine, delavirdine, etravirine), protease inhibitors (e.g., ritonavir, indinavir, nelfinavir, saquinavir, fosamprenavir, lopinavir, atazanavir, tipranavir, darunavir), integrase inhibitors (e.g., raltegravir), entry or fusion inhibitors (e.g., enfuvirtide, maraviroc). Optionally, the lumen traveling device controllably releases drugs used to treat the symptoms of AIDS dementia. These include but are not limited to antidepressants (e.g., fluoxetine, sertraline, citalopram, duloxetine) to improve symptoms of depression and antipsychotics (e.g., haloperidol, chlorpromazine, flupenthixol, clozapine, aripiprazole) to improve symptoms of severe agitation or aggression, hallucinations, or delusions.

As shown in FIG. 50, a method for detecting and treating acquired immunodeficiency syndrome dementia complex in the central nervous system of a subject thus can include introducing a lumen traveling device into a cerebral ventricle of a subject at 5002; activating the propelling mechanism to propel the lumen traveling device through the ventricle at 5004; detecting the binding of human immunodeficiency virus marker to one or more carbon nanotube-field effect transistors functionalized with an human immunodeficiency virus marker binding moiety on a fluid-contacting surface of the lumen traveling device at 5006; and in response to detection of human immunodeficiency virus marker in the cerebrospinal fluid, releasing the one or more antiretroviral drugs from a reservoir in the lumen traveling device 5008; wherein the activating a propelling mechanism, detecting the binding of human immunodeficiency virus mark, and releasing the one or more antiretroviral drugs in response to detection of human immunodeficiency virus marker are performed under the control of control circuitry on the lumen traveling device.

As shown in the block diagram of FIG. 51, an associated system 5100 can include non-transitory machine readable media 5102 including a set of instructions 5104 including one or more instructions that cause the lumen traveling device control system to activate a propelling mechanism on a lumen traveling device to propel the lumen traveling device through a cerebral ventricle of a subject, the cerebral ventricle containing cerebrospinal fluid; one or more instructions that cause the lumen traveling device control system to detect the binding of a disease marker to one or more carbon nanotube-field effect transistors functionalized with a disease marker binding moiety on a fluid-contacting surface of the lumen traveling device; and one or more instructions that cause the lumen traveling device control system to release the one or more drugs from a reservoir in the lumen traveling device in response to detection of the disease marker in the cerebrospinal fluid. The one or more instructions may be, for example, computer executable and/or logic implemented instructions. In an embodiment, the non-transitory machine readable media 5102 can include computer readable media 1506. In an embodiment, the non-transitory machine readable media 5102 can include recordable-type media 5108.

Examples of Alternative and Combined Functionality

With respect to the appended claims, the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-incluion of specific components (e.g., operations), devices, and objects should not be taken limiting. Different numbers and combinations of components and operations disclosed herein can be used in different embodiments. It is contemplated that more than one instance of a particular component or operation can be included in an embodiment, and the different exemplars of such components or operations presented herein are not considered mutually exclusive unless context clearly dictates that this is the case. For example, a lumen traveling device can include several instances of an "active portion," and these instances can be the same, or different—e.g., a sample collector, a material release structure (e.g. for releasing a medication or drug), and a heating element. Different instances of a particular component or operation can operate independently or in cooperation. As further examples, a lumen traveling device can include several instances of propelling mechanisms, e.g., it can include both appendages and a paddle; a lumen traveling device can perform multiple operations relating to selecting a direction of travel, e.g. selecting a direction of travel based on determining whether a particular direction has been previously traveled and determining whether a certain concentration of an analyte is sensed from the direction of travel.

FIGS. 52-71 provide examples of methods and corresponding systems that including various combinations of steps that can be performed with lumen traveling devices as described herein.

Figure 52:
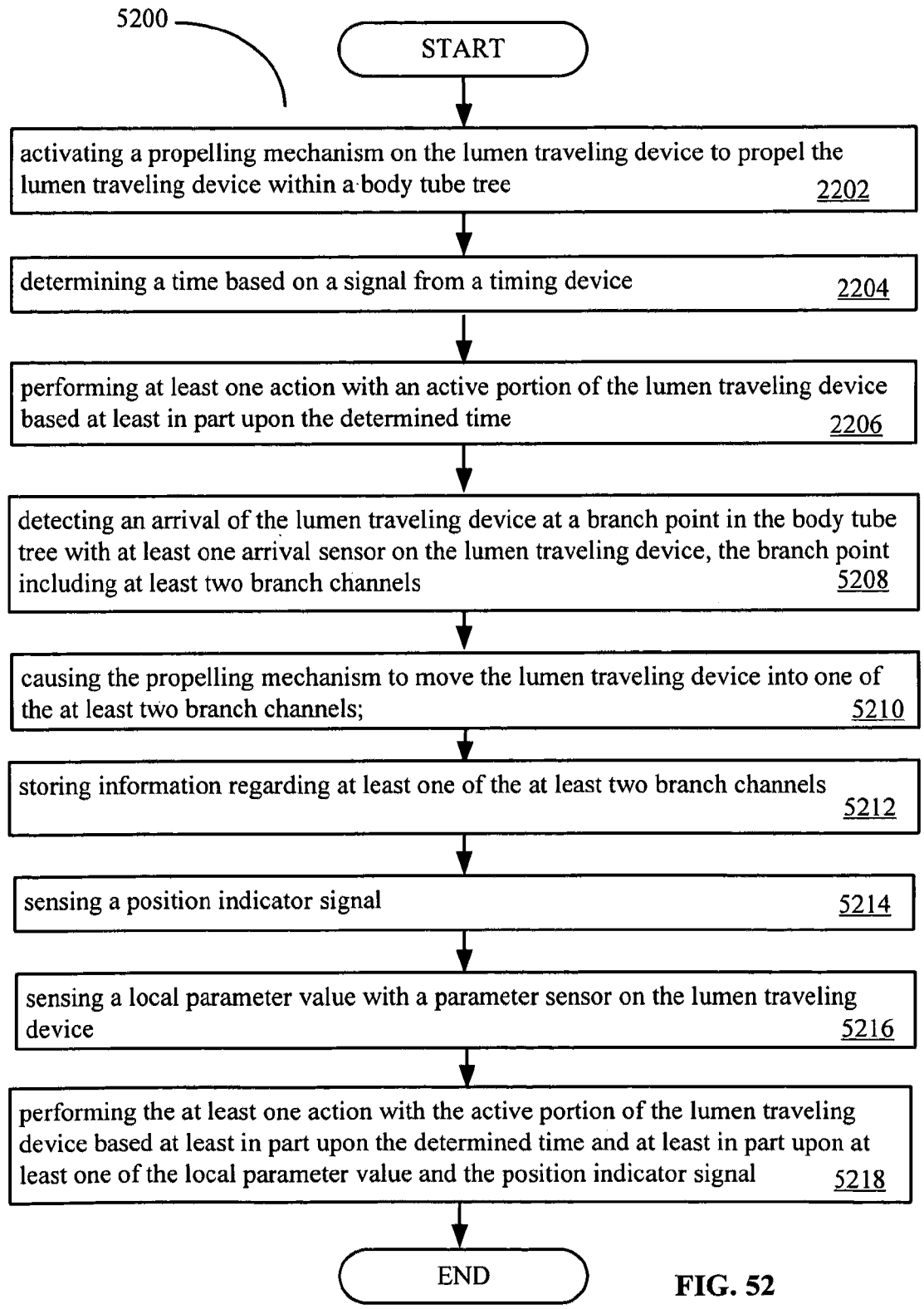
FIG. 52 illustrates a method of operating a lumen traveling device.

FIG. 52 is a flow diagram of a method 5200 of operating a lumen traveling device in a lumen of a body tube tree including activating a propelling mechanism on the lumen traveling device to propel the lumen traveling device within a body tube tree at 2202, determining a time based on a signal from a timing device at 2204, and performing at least one action with an active portion of the lumen traveling device based at least in part upon the determined time at 2206, as in the method shown in FIG. 22, and further including detecting an arrival of the lumen traveling device at a branch point in the body tube tree with at least one arrival sensor on the lumen traveling device, the branch point including at least two branch channels at 5208; causing the propelling mechanism to move the lumen traveling device into one of the at least two branch channels at 5210, storing information regarding at least one of the at least two branch channels at 5212, sensing a position indicator signal at 5214, sensing a local parameter value with a parameter sensor on the lumen traveling device at 5216 and performing the at least one action with the active portion of the lumen traveling device based at least in part upon the determined time and at least in part upon at least one of the local parameter value and the position indicator signal at 5218.

FIG. 53 illustrates a block diagram of a system 5300 that is a variant of the system depicted in FIG. 21. System 5300 includes non-transitory machine readable media 5302, including instructions 2104 as shown in FIG. 21 and further instructions 5304, including: one or more instructions that cause the lumen traveling device control system to detect an arrival of the lumen traveling device at a branch point in the body tube tree with at least one arrival sensor on the lumen traveling device, the branch point including at least two branch channels; one or more instructions that cause the lumen traveling device control system to direct the propelling mechanism on the lumen traveling device to move the lumen traveling device into one of the at least two branch channels; one or more instructions that cause the lumen traveling device control system to store information regarding at least one of the at least two branch channels; one or more instructions that cause the lumen traveling device control system to direct the sensing of a position indicator signal; one or more instructions that cause the lumen traveling device control system to direct the sensing of a local parameter value with a parameter sensor on the lumen traveling device; and one or more instructions that cause the lumen traveling device control system to direct the active portion of the lumen traveling device to perform the action based at least in part upon at least one of the local parameter value and the position indicator signal. The one or more instructions may be, for example, computer executable and/or logic implemented instructions. In an embodiment, the non-transitory machine readable media 5302 can include computer readable media 5306. In an embodiment, the non-transitory machine readable media 5302 can include recordable-type media 5308.

Figure 54:
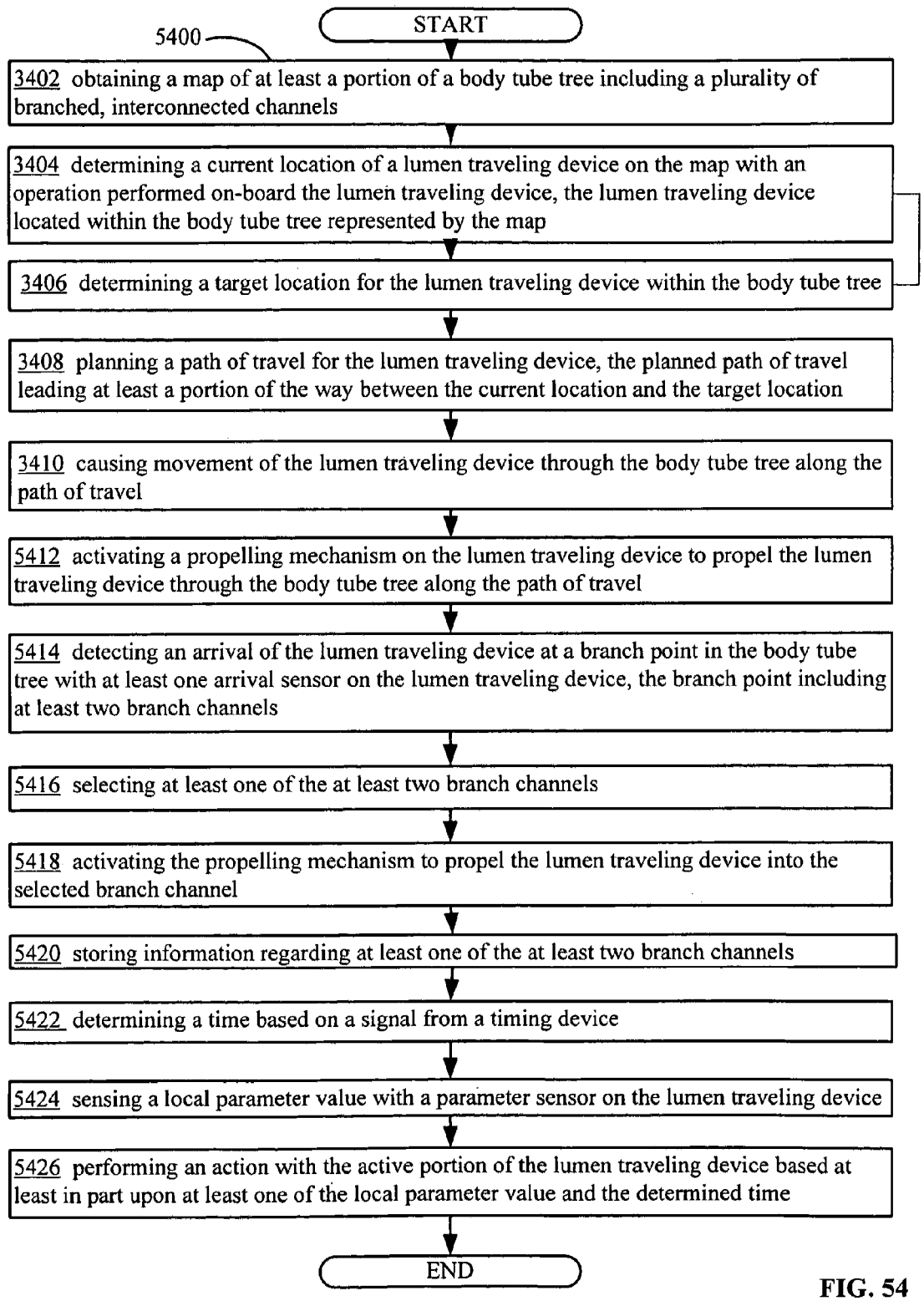
FIG. 54 illustrates a method of operating a lumen traveling device.

FIG. 54 is a flow diagram of a method 5400 of operating a lumen traveling device, which is an expansion of the method of FIG. 34, including obtaining a map of at least a portion of a body tube tree including a plurality of branched, interconnected channels at 3402, determining a current location of a lumen traveling device on the map with an operation performed on-board the lumen traveling device, the lumen traveling device located within the body tube tree represented by the map at 3404, determining a target location for the lumen traveling device within the body tube tree at 3406, planning a path of travel for the lumen traveling device, the planned path of travel leading at least a portion of the way between the current location and the target location at 3408, and causing movement of the lumen traveling device through the body tube tree along the path of travel at 3410 causing movement of the lumen traveling device through the body tube tree along the path of travel, as in FIG. 34, and further including activating a propelling mechanism on the lumen traveling device to propel the lumen traveling device through the body tube tree along the path of travel at 5412, detecting an arrival of the lumen traveling device at a branch point in the body tube tree with at least one arrival sensor on the lumen traveling device, the branch point including at least two branch channels at 5414, selecting at least one of the at least two branch channels at 5416, activating the propelling mechanism to propel the lumen traveling device into the selected branch channel at 5418, storing information regarding at least one of the at least two branch channels at 5420, determining a time based on a signal from a timing device at 5422, sensing a local parameter value with a parameter sensor on the lumen traveling device at 5424, and performing an action with the active portion of the lumen traveling device based at least in part upon at least one of the local parameter value and the determined time at 5426.

FIG. 55 illustrates a block diagram of a system 5500 that is a variant of system 3300 depicted in FIG. 33. System 5500 is provided using non-transitory machine readable media 5502, and includes a set of instructions 3304, as shown in FIG. 33, including one or more instructions that cause the lumen traveling device control system to obtain a map of at least a portion of a body tube tree including a plurality of branched, interconnected channels; one or more instructions that cause the lumen traveling device control system to determine a current location of a lumen traveling device on the map with an operation performed on-board the lumen traveling device, the lumen traveling device located within the body tube tree represented by the map; one or more instructions that cause the lumen traveling device control system to determine a target location for the lumen traveling device within the body tube tree; one or more instructions that cause the lumen traveling device control system to determine a path of travel for the lumen traveling device, the path of travel leading at least a portion of the way between the current location and the target location; and one or more instructions that cause the lumen traveling device control system to direct at least one of a steering mechanism and a propelling mechanism on the lumen traveling device to cause the lumen traveling device to move through the body tube tree along the path of travel. Non-transitory machine readable media 5502 further includes a set of instructions 5504, including one or more instructions that cause the lumen traveling device control system to detect an arrival of the lumen traveling device at a branch point in the body tube tree with at least one arrival sensor on the lumen traveling device, the branch point including at least two branch channels; one or more instructions that cause the lumen traveling device control system to select at least one of the at least two branch channels; one or more instructions that cause the lumen traveling device control system to activate the propelling mechanism to propel the lumen traveling device into the selected branch channel; one or more instructions that cause the lumen traveling device control system to store information regarding at least one of the at least two branch channels; one or more instructions that cause the lumen traveling device control system to determine a time based on a signal from a timing device; one or more instructions that cause the lumen traveling device control system to direct the sensing of a local parameter value with a parameter sensor on the lumen traveling device; and one or more instructions that cause the lumen traveling device control system to direct the active portion of the lumen traveling device to perform an action based at least in part upon at least one of the local parameter value and the determined time. In an embodiment, the non-transitory machine readable media 5502 can include computer readable media 5506. In an embodiment, the non-transitory machine readable media 5502 can include recordable-type media 5508.

Figure 56:
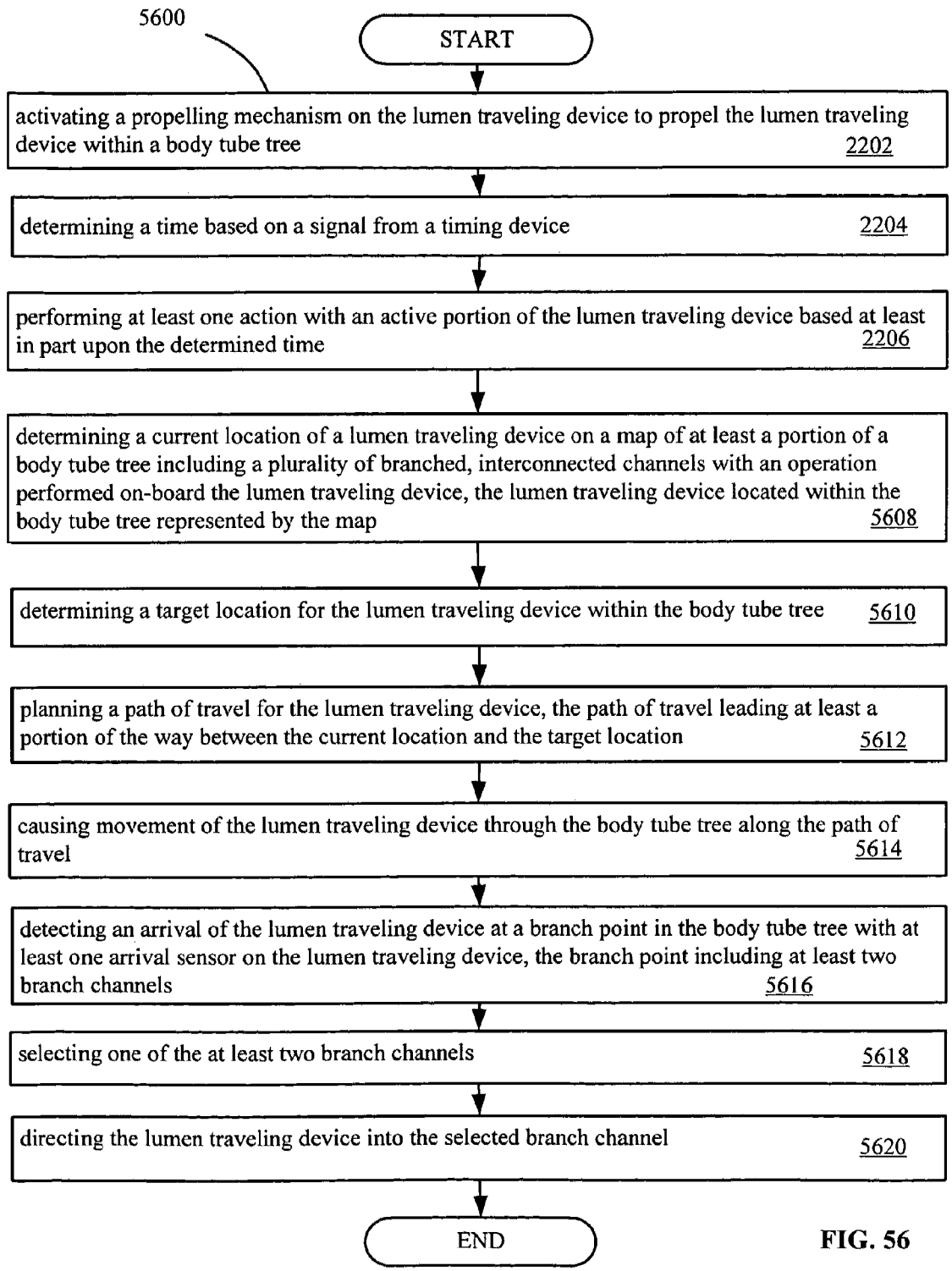
FIG. 56 illustrates a method of operating a lumen traveling device.

FIG. 56 is a flow diagram of a method 5600 of operating a lumen traveling device, based on the method shown in FIG. 22, and similarly including activating a propelling mechanism on the lumen traveling device to propel the lumen traveling device within a body tube tree at 2202, determining a time based on a signal from a timing device at 2204, and performing at least one action with an active portion of the lumen traveling device based at least in part upon the determined time at 2206. The method further includes determining a current location of a lumen traveling device on a map of at least a portion of a body tube tree including a plurality of branched, interconnected channels with an operation performed on-board the lumen traveling device, the lumen traveling device located within the body tube tree represented by the map at 5608, determining a target location for the lumen traveling device within the body tube tree at 5610, planning a path of travel for the lumen traveling device, the path of travel leading at least a portion of the way between the current location and the target location at 5612, causing movement of the lumen traveling device through the body tube tree along the path of travel at 5614, detecting an arrival of the lumen traveling device at a branch point in the body tube tree with at least one arrival sensor on the lumen traveling device, the branch point including at least two branch channels at 5616, selecting one of the at least two branch channels at 5618, and directing the lumen traveling device into the selected branch channel at 5620.

FIG. 57 illustrates a block diagram of a system 5700 that is a variant of the system shown in FIG. 21. System 5700 is provided using non-transitory machine readable media 5702, and includes a set of instructions 2104 for operating a lumen traveling device, as shown in FIG. 21, including one or more instructions that cause the lumen traveling device control system to activate a propelling mechanism on a lumen traveling device to propel the lumen traveling device within a body tube tree; one or more instructions that cause the lumen traveling device control system to determine a time based on a signal from a timing device; and one or more instructions that cause the lumen traveling device control system to direct the active portion of the lumen traveling device to perform at least one action based at least in part upon the determined time. 5700 further includes a set of instructions 5704, including one or more instructions that cause the lumen traveling device control system to determine a current location of a lumen traveling device on a map of at least a portion of a body tube tree including a plurality of branched, interconnected channels with an operation performed on-board the lumen traveling device, the lumen traveling device located within the body tube tree represented by the map; one or more instructions that cause the lumen traveling device control system to determine a target location for the lumen traveling device within the body tube tree; one or more instructions that cause the lumen traveling device control system to plan a path of travel for the lumen traveling device, the path of travel leading at least a portion of the way between the current location and the target location; one or more instructions that cause the lumen traveling device control system to detect an arrival of the lumen traveling device at a branch point in the body tube tree with at least one arrival sensor on the lumen traveling device, the branch point including at least two branch channels; one or more instructions that cause the lumen traveling device control system to select one of the at least two branch channels; one or more instructions that cause the lumen traveling device control system to direct at least one of a steering mechanism on the lumen traveling device and the propelling mechanism to cause the lumen traveling device to move into the selected branch channel. The one or more instructions may be, for example, computer executable and/or logic implemented instructions. In an embodiment, the non-transitory machine readable media 5702 can include computer readable media 5706. In an embodiment, the non-transitory machine readable media 5702 can include recordable-type media 5708.

Figure 58:
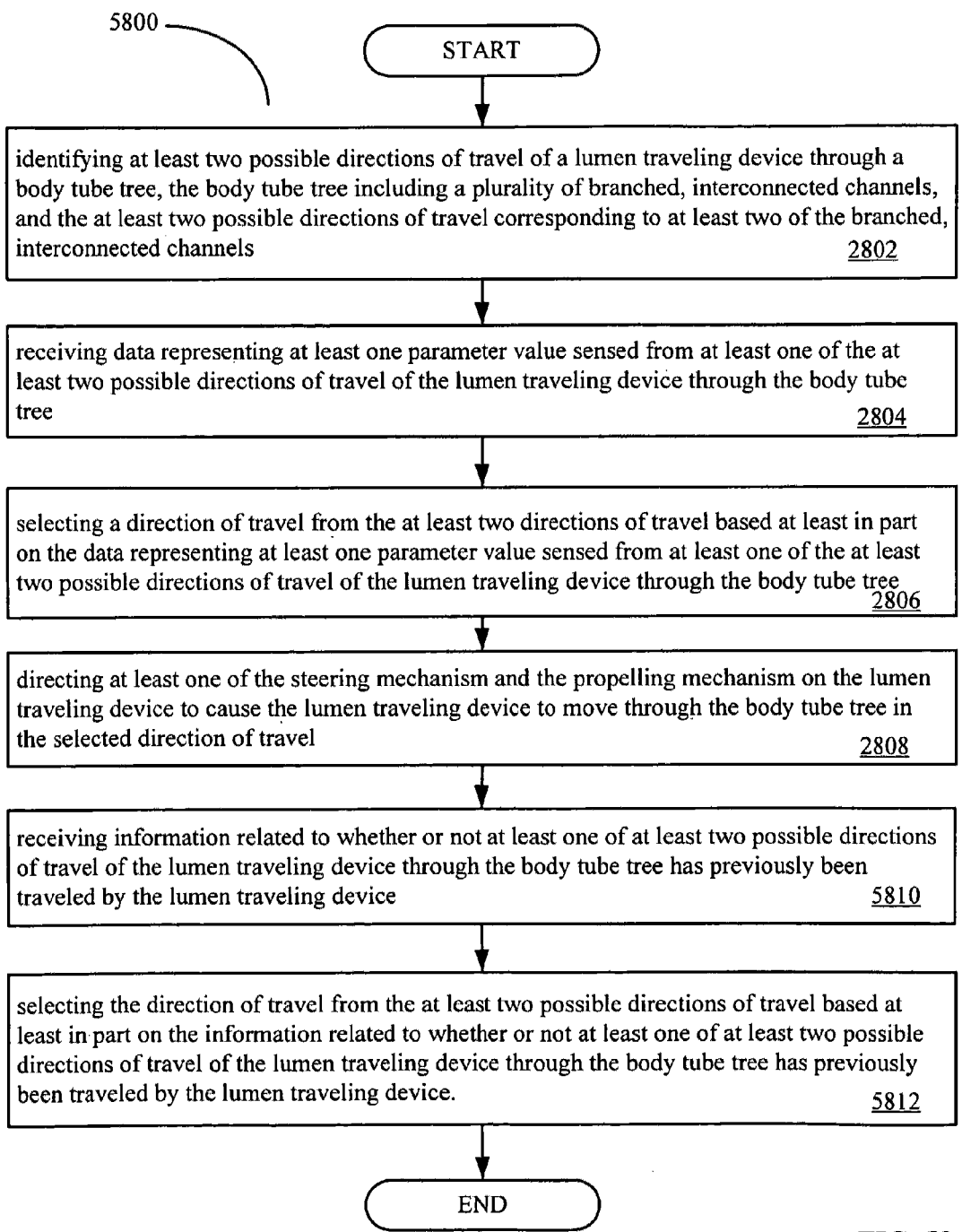
FIG. 58 illustrates a method of operating a lumen traveling device.

FIG. 58 is a flow diagram of a method 5800 of operating a lumen traveling device, which is a variant of the method of FIG. 28, and includes identifying at least two possible directions of travel of a lumen traveling device through a body tube tree, the body tube tree including a plurality of branched, interconnected channels, and the at least two possible directions of travel corresponding to at least two of the branched, interconnected channels at 2802; receiving data representing at least one parameter value sensed from at least one of the at least two possible directions of travel of the lumen traveling device through the body tube tree at 2804; selecting a direction of travel from the at least two directions of travel based at least in part on the data representing at least one parameter value sensed from at least one of the at least two possible directions of travel of the lumen traveling device through the body tube tree at 2806; and directing at least one of the steering mechanism and the propelling mechanism on the lumen traveling device to cause the lumen traveling device to move through the body tube tree in the selected direction of travel at 2808. The method further includes receiving information related to whether or not at least one of at least two possible directions of travel of the lumen traveling device through the body tube tree has previously been traveled by the lumen traveling device at 5810 and selecting the direction of travel from the at least two possible directions of travel based at least in part on the information related to whether or not at least one of at least two possible directions of travel of the lumen traveling device through the body tube tree has previously been traveled by the lumen traveling device at 5812.

FIG. 59 illustrates a block diagram of a system 5900 that is a variant of the system shown in FIG. 27. An embodiment of system 5900 is provided using non-transitory machine readable media 5902 including a set of instructions 2704, including one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of the branched, interconnected channels; one or more instructions that cause the lumen traveling device control system to receive data representing at least one parameter value sensed from at least one of the at least two possible directions of travel of the lumen traveling device through the body tube tree; one or more instructions that cause the lumen traveling device control system to select a direction of travel from the at least two directions of travel based at least in part on the data representing at least one parameter value sensed from at least one of the at least two possible directions of travel of the lumen traveling device through the body tube tree; and one or more instructions that cause the lumen traveling device control system to direct at least one of the steering mechanism and the propelling mechanism on the lumen traveling device to cause the lumen traveling device to move through the body tube tree in the selected direction of travel. Non-transitory machine readable media 5902 further includes instructions 5904, including one or more instructions that cause the lumen traveling device control system to receive information related to whether or not at least one of at least two possible directions of travel of the lumen traveling device through the body tube tree has previously been traveled by the lumen traveling device; and one or more instructions that cause the lumen traveling device control system to select a direction of travel from the at least two possible directions of travel based at least in part on the information related to whether or not at least one of at least two possible directions of travel of the lumen traveling device through the body tube tree has previously been traveled by the lumen traveling device. The one or more instructions may be, for example, computer executable and/or logic implemented instructions. In an embodiment, the non-transitory machine readable media 5902 can include computer readable media 5906. In an embodiment, the non-transitory machine readable media 5902 can include recordable-type media 5908.

Figure 60:
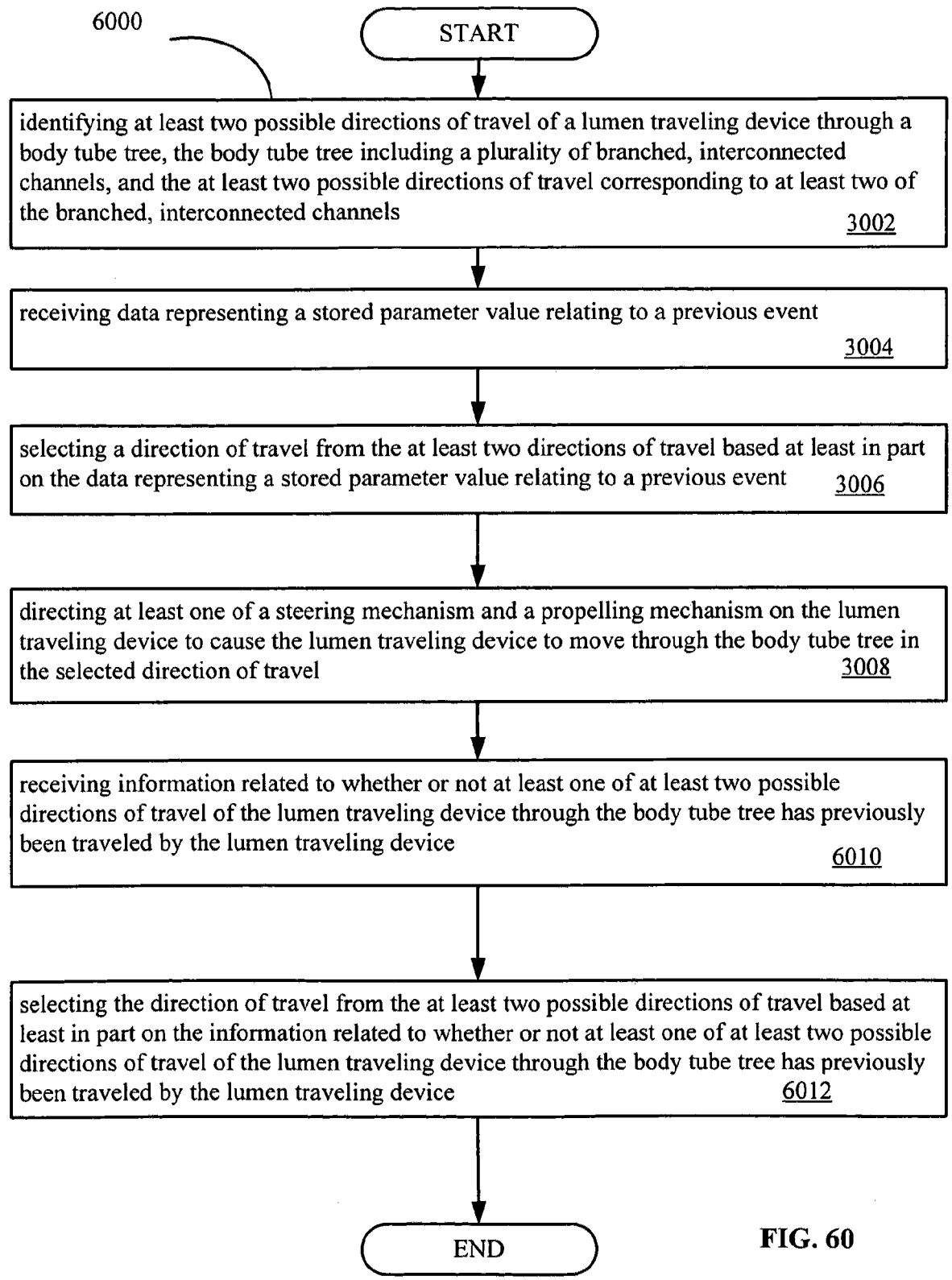
FIG. 60 illustrates a method of operating a lumen traveling device.

FIG. 60 is a flow diagram of a method 6000 of operating a lumen traveling device that is a variant of the method of FIG. 30, and includes identifying at least two possible directions of travel of a lumen traveling device through a body tube tree, the body tube tree including a plurality of branched, interconnected channels, and the at least two possible directions of travel corresponding to at least two of the branched, interconnected channels at 3002; receiving data representing a stored parameter value relating to a previous event at 3004; selecting a direction of travel from the at least two directions of travel based at least in part on the data representing a stored parameter value relating to a previous event at 3006; and directing at least one of a steering mechanism and a propelling mechanism on the lumen traveling device to cause the lumen traveling device to move through the body tube tree in the selected direction of travel at 3008. The method further includes receiving information related to whether or not at least one of at least two possible directions of travel of the lumen traveling device through the body tube tree has previously been traveled by the lumen traveling device at 6010, and selecting the direction of travel from the at least two possible directions of travel based at least in part on the information related to whether or not at least one of at least two possible directions of travel of the lumen traveling device through the body tube tree has previously been traveled by the lumen traveling device at 6012.

FIG. 61 illustrates a block diagram of a system 6100 that is a variant of the system depicted in FIG. 29 and includes a non-transitory machine readable media 6102 bearing instructions for operating a lumen traveling device. Non-transitory machine readable media 6102 includes a set of instructions 2904 including one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of the branched, interconnected channels; one or more instructions that cause the lumen traveling device control system to receive data representing a stored parameter value relating to a previous event associated with at least one of the at least two possible directions of travel; one or more instructions that cause the lumen traveling device control system to select a direction of travel from the at least two directions of travel based at least in part on the data representing a stored parameter value relating to a previous event associated with at least one of the at least two possible directions of travel; and one or more instructions that cause the lumen traveling device control system to direct at least one of a steering mechanism and a propelling mechanism on the lumen traveling device to cause the lumen traveling device to move through the body tube tree in the selected direction of travel. Non-transitory machine readable media 6102 further includes set of instruction 6104 including one or more instructions that cause the lumen traveling device control system to receive information related to whether or not at least one of at least two possible directions of travel of the lumen traveling device through the body tube tree has previously been traveled by the lumen traveling device; and one or more instructions that cause the lumen traveling device control system to select a direction of travel from the at least two possible directions of travel based at least in part on the information related to whether or not at least one of at least two possible directions of travel of the lumen traveling device through the body tube tree has previously been traveled by the lumen traveling device. The one or more instructions may be, for example, computer executable and/or logic implemented instructions. In an embodiment, the non-transitory machine readable media 6102 can include computer readable media 6106. In an embodiment, the non-transitory machine readable media 6102 can include recordable-type media 6108.

Figure 62:
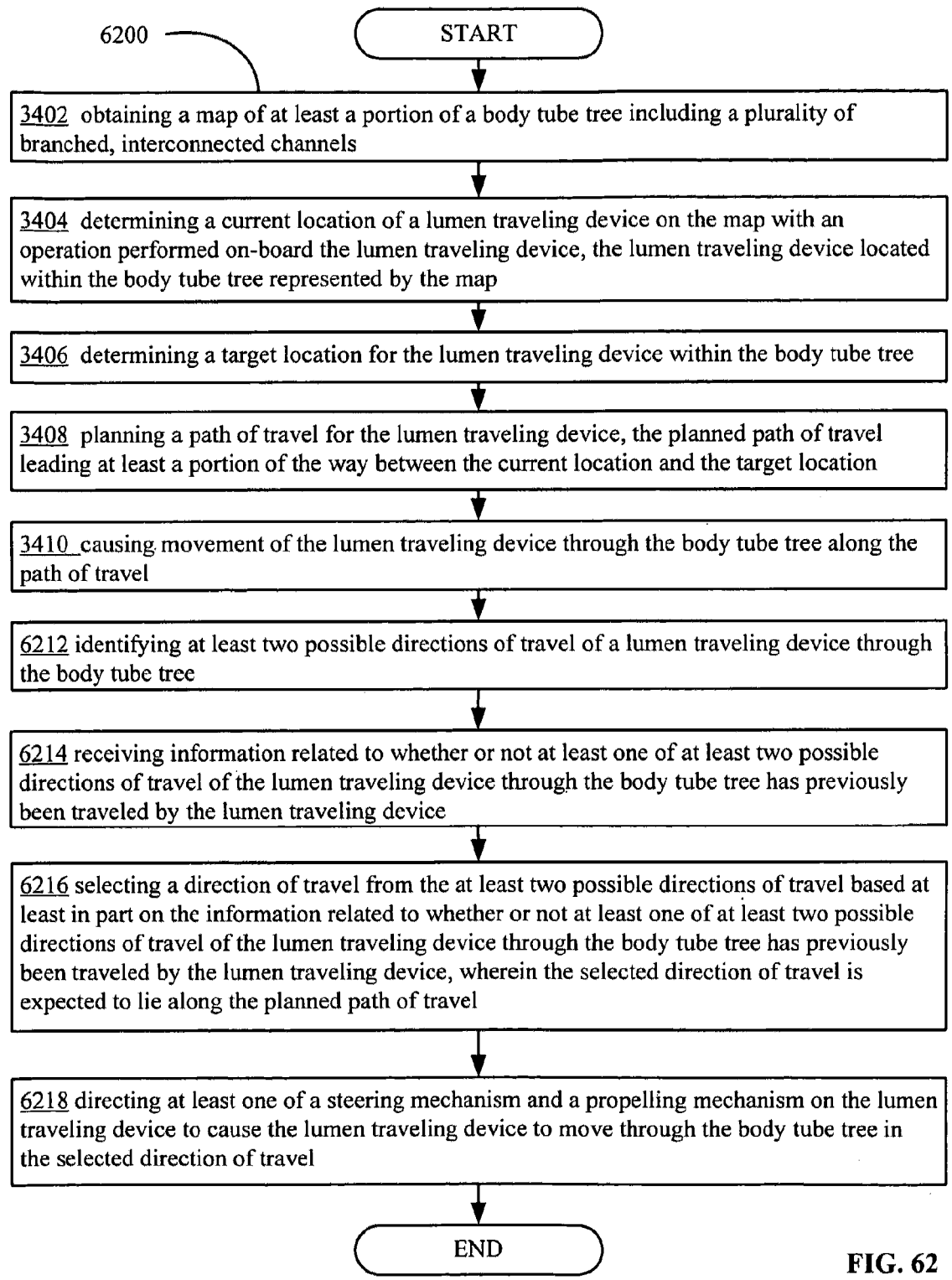
FIG. 62 illustrates a method of operating a lumen traveling device.

FIG. 62 is a flow diagram of a method 6200 of operating a lumen traveling device, that is a variant of the method of FIG. 34, and includes obtaining a map of at least a portion of a body tube tree including a plurality of branched, interconnected channels at 3402; determining a current location of a lumen traveling device on the map with an operation performed on-board the lumen traveling device, the lumen traveling device located within the body tube tree represented by the map at 3404; determining a target location for the lumen traveling device within the body tube tree at 3406; planning a path of travel for the lumen traveling device, the planned path of travel leading at least a portion of the way between the current location and the target location at 3408; and causing movement of the lumen traveling device through the body tube tree along the path of travel at 3410. The method further includes identifying at least two possible directions of travel of a lumen traveling device through the body tube tree at 6212, receiving information related to whether or not at least one of at least two possible directions of travel of the lumen traveling device through the body tube tree has previously been traveled by the lumen traveling device at 6214, selecting a direction of travel from the at least two possible directions of travel based at least in part on the information related to whether or not at least one of at least two possible directions of travel of the lumen traveling device through the body tube tree has previously been traveled by the lumen traveling device, wherein the selected direction of travel is expected to lie along the planned path of travel at 6216, and directing at least one of a steering mechanism and a propelling mechanism on the lumen traveling device to cause the lumen traveling device to move through the body tube tree in the selected direction of travel at 6218.

FIG. 63 illustrates a block diagram of a system 6300 that includes non-transitory machine readable media 6302 bearing instructions for operating a lumen traveling device. System 6300 is a variant of the system shown in FIG. 33. Non-transitory machine readable media 6302 including a set of instructions 3304 including one or more instructions that cause the lumen traveling device control system to obtain a map of at least a portion of a body tube tree including a plurality of branched, interconnected channels; one or more instructions that cause the lumen traveling device control system to determine a current location of a lumen traveling device on the map with an operation performed on-board the lumen traveling device, the lumen traveling device located within the body tube tree represented by the map; one or more instructions that cause the lumen traveling device control system to determine a target location for the lumen traveling device within the body tube tree; one or more instructions that cause the lumen traveling device control system to plan a path of travel for the lumen traveling device, the path of travel leading at least a portion of the way between the current location and the target location; and one or more instructions that cause the lumen traveling device control system to direct at least one of a steering mechanism and a propelling mechanism on the lumen traveling device to cause the lumen traveling device to move through the body tube tree along the path of travel. Non-transitory machine readable media 6302 further includes set of instructions 6304 including one or more instructions that cause the lumen traveling device control system to identify at least two possible directions of travel of a lumen traveling device through a body tube tree, the body tube tree including a plurality of branched, interconnected channels, and the at least two possible directions of travel corresponding to at least two of the branched, interconnected channels; one or more instructions that cause the lumen traveling device control system to receive information related to whether or not at least one of at least two possible directions of travel of the lumen traveling device through the body tube tree has previously been traveled by the lumen traveling device; one or more instructions that cause the lumen traveling device control system to select a direction of travel from the at least two possible directions of travel based at least in part on the information related to whether or not at least one of at least two possible directions of travel of the lumen traveling device through the body tube tree has previously been traveled by the lumen traveling device, wherein the selected direction of travel is expected to lie along the planned path of travel; and one or more instructions that cause the lumen traveling device control system to direct at least one of a steering mechanism and a propelling mechanism on the lumen traveling device to cause the lumen traveling device to move through the body tube tree in the selected direction of travel. The one or more instructions may be, for example, computer executable and/or logic implemented instructions. In an embodiment, the non-transitory machine readable media 6302 can include computer readable media 6306. In an embodiment, the non-transitory machine readable media 6302 can include recordable-type media 6308.

Figure 64:
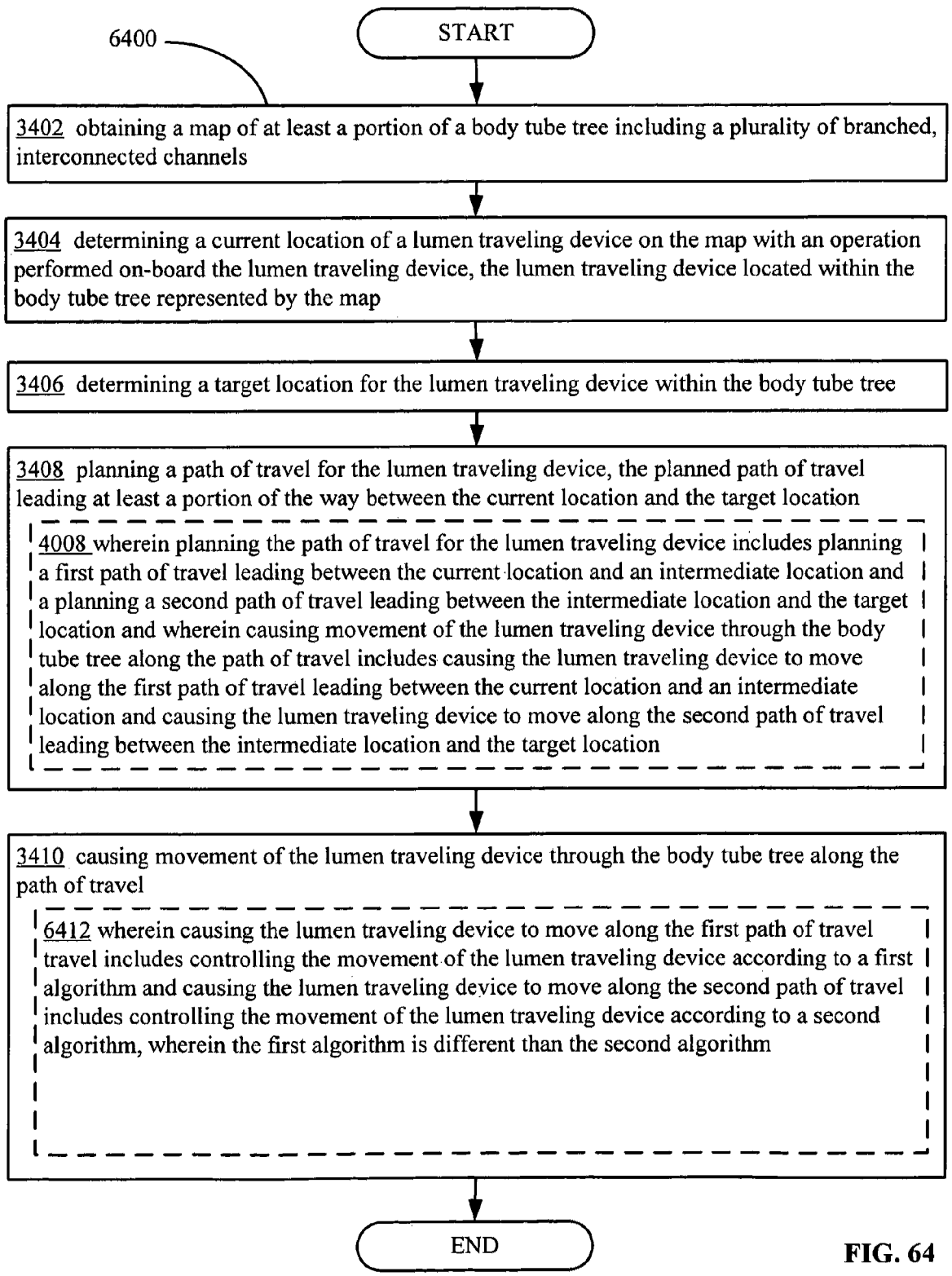
FIG. 64 illustrates a method of operating a lumen traveling device.

FIG. 64 is a flow diagram of a method 6400 of operating a lumen traveling device, that is a variant of the method shown in FIG. 40, and includes obtaining a map of at least a portion of a body tube tree including a plurality of branched, interconnected channels at 3402; determining a current location of a lumen traveling device on the map with an operation performed on-board the lumen traveling device, the lumen traveling device located within the body tube tree represented by the map at 3404; determining a target location for the lumen traveling device within the body tube tree at 3406; planning a path of travel for the lumen traveling device, the planned path of travel leading at least a portion of the way between the current location and the target location at 3408; and causing movement of the lumen traveling device through the body tube tree along the path of travel at 3410, where it is further specified at 4008 wherein planning the path of travel for the lumen traveling device includes planning a first path of travel leading between the current location and an intermediate location and a planning a second path of travel leading between the intermediate location and the target location and wherein causing movement of the lumen traveling device through the body tube tree along the path of travel includes causing the lumen traveling device to move along the first path of travel leading between the current location and an intermediate location and causing the lumen traveling device to move along the second path of travel leading between the intermediate location and the target location. In addition, it is further specified at 6412 wherein planning the path of travel for the lumen traveling device includes planning a first path of travel leading between the current location and an intermediate location and a planning a second path of travel leading between the intermediate location and the target location and wherein causing movement of the lumen traveling device through the body tube tree along the path of travel includes causing the lumen traveling device to move along the first path of travel leading between the current location and an intermediate location and causing the lumen traveling device to move along the second path of travel leading between the intermediate location and the target location.

FIG. 65 illustrates a block diagram of a system 6500 that includes a non-transitory machine readable media 6502 including a set of instructions 3304, as shown in FIG. 33, wherein it is specified wherein the one or more instructions that cause the lumen traveling device control system to plan a path of travel for the lumen traveling device include one or more instructions that cause the lumen traveling device control system to determine a first path of travel leading between the current location and an intermediate location; and one or more instructions that cause the lumen traveling device control system to determine a second path of travel leading between the intermediate location and the target location, at 3904, as in the system of FIG. 39. It is further specified wherein the one or more instructions that cause the lumen traveling device control system determine the first path of travel include: one or more instructions that cause the lumen traveling device control system to identify at least two possible directions of travel of the lumen traveling device through the body tube tree; one or more instructions that cause the lumen traveling device control system to receive information related to whether or not at least one of at least two possible directions of travel of the lumen traveling device through the body tube tree has previously been traveled by the lumen traveling device; and one or more instructions that cause the lumen traveling device control system to select a direction of travel from the at least two possible directions of travel based at least in part on the information related to whether or not at least one of at least two possible directions of travel of the lumen traveling device through the body tube tree has previously been traveled by the lumen traveling device, wherein the selected direction of travel is along the first path, as shown at 6504. The one or more instructions may be, for example, computer executable and/or logic implemented instructions. In an embodiment, the non-transitory machine readable media 6502 can include computer readable media 6506. In an embodiment, the non-transitory machine readable media 6502 can include recordable-type media 6508.

Figure 66:
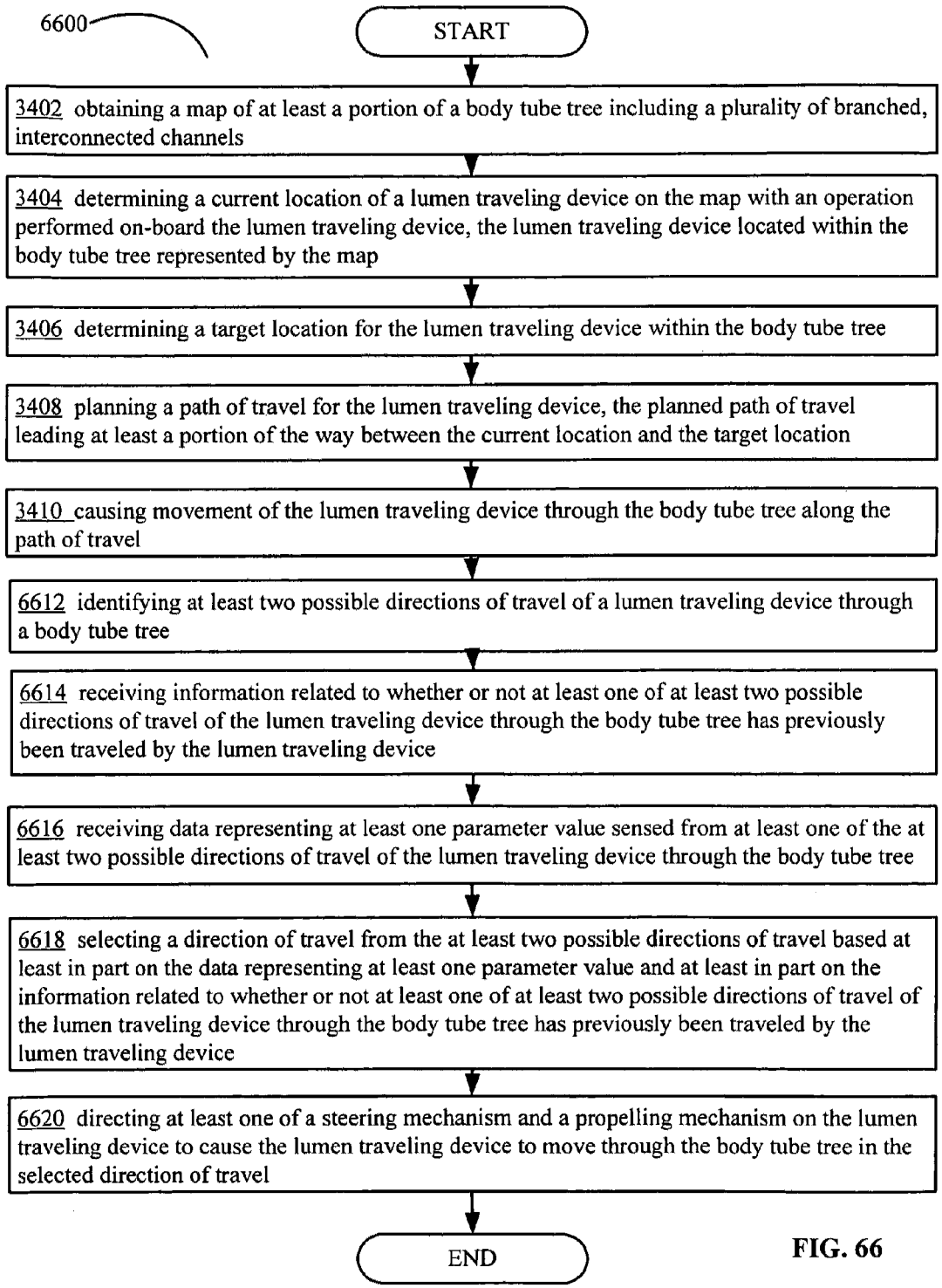
FIG. 66 illustrates a method of operating a lumen traveling device.

FIG. 66 is a flow diagram of a method 6600 of operating a lumen traveling device, which is a variant of the method shown in FIG. 34. Method 6600 includes obtaining a map of at least a portion of a body tube tree including a plurality of branched, interconnected channels at 3402; determining a current location of a lumen traveling device on the map with an operation performed on-board the lumen traveling device, the lumen traveling device located within the body tube tree represented by the map at 3404; determining a target location for the lumen traveling device within the body tube tree at 3406; planning a path of travel for the lumen traveling device, the planned path of travel leading at least a portion of the way between the current location and the target location at 3408; and causing movement of the lumen traveling device through the body tube tree along the path of travel at 3410. Method 6600 further includes identifying at least two possible directions of travel of a lumen traveling device through a body tube tree at 6612; receiving information related to whether or not at least one of at least two possible directions of travel of the lumen traveling device through the body tube tree has previously been traveled by the lumen traveling device at 6614; receiving data representing at least one parameter value sensed from at least one of the at least two possible directions of travel of the lumen traveling device through the body tube tree at 6616; selecting a direction of travel from the at least two possible directions of travel based at least in part on the data representing at least one parameter value and at least in part on the information related to whether or not at least one of at least two possible directions of travel of the lumen traveling device through the body tube tree has previously been traveled by the lumen traveling device at 6618; and directing at least one of a steering mechanism and a propelling mechanism on the lumen traveling device to cause the lumen traveling device to move through the body tube tree in the selected direction of travel at 6620. This method can be performed, for example, with a device as depicted in and described in connection with FIGS. 1, 2, 7 and 8.

FIG. 67 illustrates a block diagram of a system 6700 that includes non-transitory machine readable media 6702 including instruction for use in a lumen traveling device control system. Non-transitory machine readable media 6702 includes a set of instructions 3304, as shown in FIG. 33, for operating a lumen traveling device, including one or more instructions that cause the lumen traveling device control system to obtain a map of at least a portion of a body tube tree including a plurality of branched, interconnected channels; one or more instructions that cause the lumen traveling device control system to determine a current location of a lumen traveling device on the map with an operation performed on-board the lumen traveling device, the lumen traveling device located within the body tube tree represented by the map; one or more instructions that cause the lumen traveling device control system to determine a target location for the lumen traveling device within the body tube tree; one or more instructions that cause the lumen traveling device control system to plan a path of travel for the lumen traveling device, the path of travel leading at least a portion of the way between the current location and the target location; and one or more instructions that cause the lumen traveling device control system to direct at least one of a steering mechanism and a propelling mechanism on the lumen traveling device to cause the lumen traveling device to move through the body tube tree along the path of travel. Non-transitory machine readable media 6702 further includes one or more instructions that cause the lumen traveling device control system to identify at least two possible directions of travel of a lumen traveling device through a body tube tree; one or more instructions that cause the lumen traveling device control system to receive information related to whether or not at least one of at least two possible directions of travel of the lumen traveling device through the body tube tree has previously been traveled by the lumen traveling device; one or more instructions that cause the lumen traveling device control system to receive data representing at least one parameter value sensed from at least one of the at least two possible directions of travel of the lumen traveling device through the body tube tree; one or more instructions that cause the lumen traveling device control system to select a direction of travel from the at least two possible directions of travel based at least in part on the data representing at least one parameter value and at least in part on the information related to whether or not at least one of at least two possible directions of travel of the lumen traveling device through the body tube tree has previously been traveled by the lumen traveling device; and one or more instructions that cause the lumen traveling device control system to direct at least one of the steering mechanism and the propelling mechanism on the lumen traveling device to cause the lumen traveling device to move through the body tube tree in the selected direction of travel, shown at 6704. The one or more instructions may be, for example, computer executable and/or logic implemented instructions. In an embodiment, the non-transitory machine readable media 6702 can include computer readable media 6706. In an embodiment, the non-transitory machine readable media 6702 can include recordable-type media 6708.

FIG. 68 illustrates a block diagram of a system 6800 that includes non-transitory machine readable media 6802. Non-transitory machine readable media 6802 includes a set of instructions 3304 including one or more instructions that cause the lumen traveling device control system to obtain a map of at least a portion of a body tube tree including a plurality of branched, interconnected channels; one or more instructions that cause the lumen traveling device control system to determine a current location of a lumen traveling device on the map with an operation performed on-board the lumen traveling device, the lumen traveling device located within the body tube tree represented by the map; one or more instructions that cause the lumen traveling device control system to determine a target location for the lumen traveling device within the body tube tree; one or more instructions that cause the lumen traveling device control system to plan a path of travel for the lumen traveling device, the path of travel leading at least a portion of the way between the current location and the target location; and one or more instructions that cause the lumen traveling device control system to direct at least one of a steering mechanism and a propelling mechanism on the lumen traveling device to cause the lumen traveling device to move through the body tube tree along the path of travel, wherein as indicated at 3904, the one or more instructions that cause the lumen traveling device control system to plan a path of travel for the lumen traveling device include: one or more instructions that cause the lumen traveling device control system to determine a first path of travel leading between the current location and an intermediate location; and one or more instructions that cause the lumen traveling device control system to determine a second path of travel leading between the intermediate location and the target location. Non-transitory machine readable media 6802 further includes set of instructions 6804 including wherein the non-transitory machine readable media includes: one or more instructions that cause the lumen traveling device control system to identify at least two possible directions of travel of a lumen traveling device through the body tube tree; one or more instructions that cause the lumen traveling device control system to receive information related to whether or not at least one of at least two possible directions of travel of the lumen traveling device through the body tube tree has previously been traveled by the lumen traveling device; one or more instructions that cause the lumen traveling device control system to receive data representing at least one parameter value sensed from at least one of the at least two possible directions of travel of the lumen traveling device through the body tube tree; one or more instructions that cause the lumen traveling device control system to select a direction of travel from the at least two possible directions of travel based at least in part on the data representing at least one parameter value sensed from at least one of the at least two possible directions of travel of the lumen traveling device through the body tube tree and at least in part on the information related to whether or not at least one of at least two possible directions of travel of the lumen traveling device through the body tube tree has previously been traveled by the lumen traveling device; and one or more instructions that cause the lumen traveling device control system to direct at least one of a steering mechanism and a propelling mechanism on the lumen traveling device to cause the lumen traveling device to move through the body tube tree in the selected direction of travel. The one or more instructions may be, for example, computer executable and/or logic implemented instructions. In an embodiment, the non-transitory machine readable media 6802 can include computer readable media 6806. In an embodiment, the non-transitory machine readable media 6802 can include recordable-type media 6808.

Figure 69:
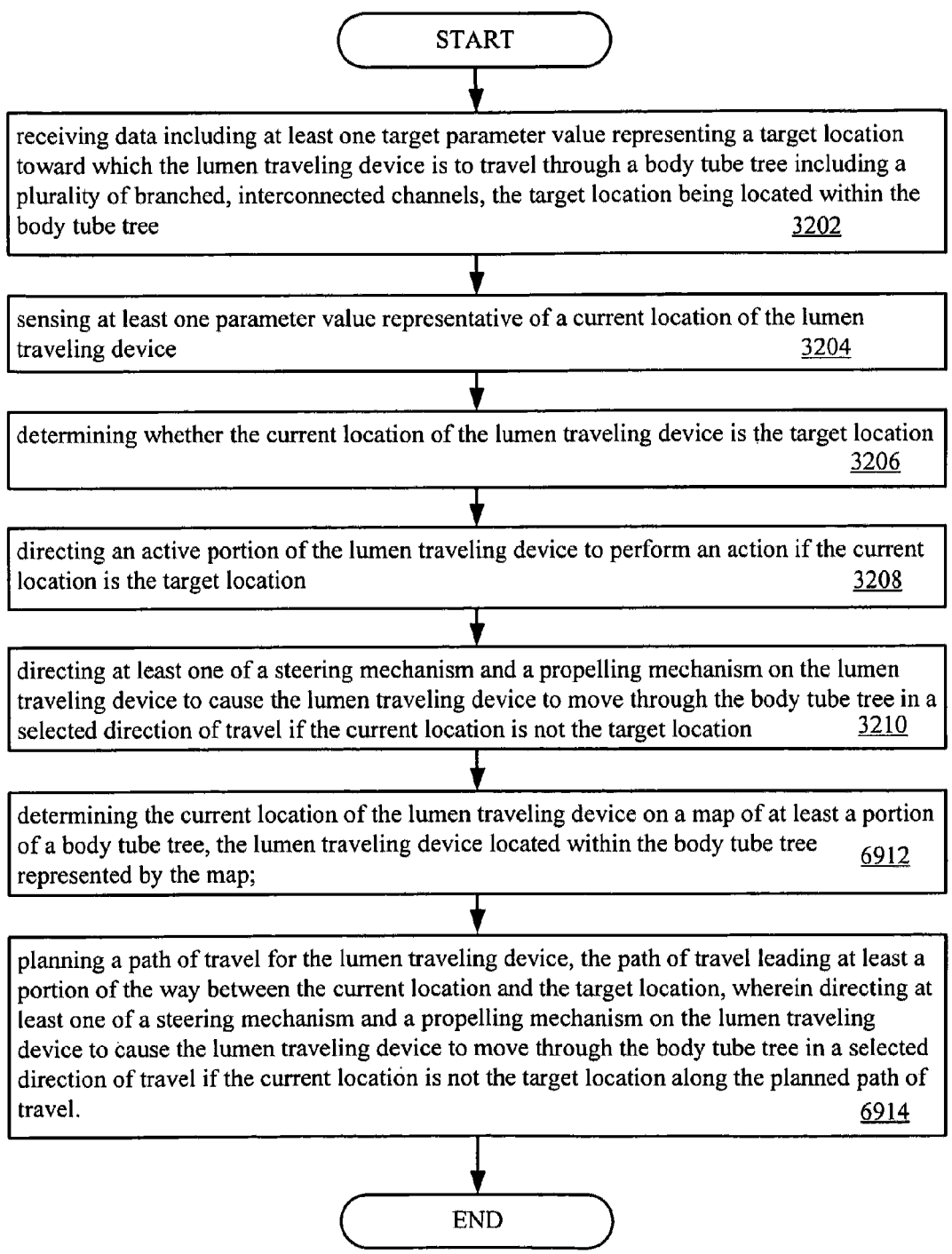
FIG. 69 illustrates a method of operating a lumen traveling device.

FIG. 69 is a flow diagram of a method 6900 that is a variant of the method shown in FIG. 32. Method 6900 includes receiving data including at least one target parameter value representing a target location toward which the lumen traveling device is to travel through a body tube tree including a plurality of branched, interconnected channels, the target location being located within the body tube tree at 3202; sensing at least one parameter value representative of a current location of the lumen traveling device at 3204; determining whether the current location of the lumen traveling device is the target location at 3206; directing an active portion of the lumen traveling device to perform an action if the current location is the target location at 3208; or directing at least one of a steering mechanism and a propelling mechanism on the lumen traveling device to cause the lumen traveling device to move through the body tube tree in a selected direction of travel if the current location is not the target location at 3210. The method further includes determining the current location of the lumen traveling device on a map of at least a portion of a body tube tree, the lumen traveling device located within the body tube tree represented by the map at 6912; and planning a path of travel for the lumen traveling device, the path of travel leading at least a portion of the way between the current location and the target location, wherein directing at least one of a steering mechanism and a propelling mechanism on the lumen traveling device to cause the lumen traveling device to move through the body tube tree in a selected direction of travel if the current location is not the target location along the planned path of travel at 6914.

FIG. 70 illustrates a block diagram of a system 7000 that includes non-transitory machine readable media 7002. System 7000 is a variant of the system shown in FIG. 31. Non-transitory machine readable media 7002 includes a set of instructions 3104 including one or more instructions that cause the lumen traveling device control system to receive data including at least one target parameter value representing a target location in a body tube tree, the body tube tree including a plurality of branched, interconnected channels, the target location being located within the body tube tree; one or more instructions that cause the lumen traveling device control system to direct the sensing of at least one parameter value representative of a current location of the lumen traveling device within the body tube tree; one or more instructions that cause the lumen traveling device control system to determine whether the current location of the lumen traveling device is the target location; one or more instructions that cause the lumen traveling device control system to direct an active portion of the lumen traveling device to perform an action if the current location is the target location; and one or more instructions that cause the lumen traveling device control system to direct at least one of a steering mechanism and a propelling mechanism on the lumen traveling device to cause the lumen traveling device to move through the body tube tree in a selected direction of travel if the current location is not the target location. Non-transitory machine readable media 7002 further includes set of instructions 7004 including one or more instructions that cause the lumen traveling device control system to receive data including at least one target parameter value representing a target location in a body tube tree, the body tube tree including a plurality of branched, interconnected channels, the target location being located within the body tube tree; one or more instructions that cause the lumen traveling device control system to direct the sensing of at least one parameter value representative of a current location of the lumen traveling device within the body tube tree; one or more instructions that cause the lumen traveling device control system to determine whether the current location of the lumen traveling device is the target location; one or more instructions that cause the lumen traveling device control system to direct an active portion of the lumen traveling device to perform an action if the current location is the target location; and one or more instructions that cause the lumen traveling device control system to direct at least one of a steering mechanism and a propelling mechanism on the lumen traveling device to cause the lumen traveling device to move through the body tube tree in a selected direction of travel if the current location is not the target location. The one or more instructions may be, for example, computer executable and/or logic implemented instructions. In an embodiment, the non-transitory machine readable media 7002 can include computer readable media 7006. In an embodiment, the non-transitory machine readable media 7002 can include recordable-type media 7008.

Any of the methods described herein, including, e.g., the methods of FIGS. 12-19, 22, 25, 28, 30, 32, 34, 40, 42, 45, 48, 50, 52, 54, 56, 58, 60, 62, 64, 66, 68 and 70, may be implemented using the devices as depicted and described herein, e.g., in conjunction with FIGS. 1, 2, 3, 4A-4E, 5, 7, 8, 20A-20B, 23A-23D, 26A-26C, 41A-41B, 44 and 47.

The various embodiments described herein may be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer or a microprocessor), electrical circuitry forming a memory device (e.g., forms of memory (e.g., random access, flash, read only, etc.)), electrical circuitry forming a communications device (e.g., a wireless communication device, communications switch, optical-electrical equipment, etc.), and/or any non-electrical analog thereto, such as optical or other analogs.

The various aspects of the embodiments for methods, processes, apparatus and systems as described herein can be implemented, individually and/or collectively, by a wide range of hardware, software, firmware, or any combination thereof. The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of non-transitory machine readable media used to actually carry out the distribution. Examples of a non-transitory machine readable media include, but are not limited to, the following: non-transitory machine readable media such as a floppy disk, a hard disk drive, a Compact Disc (CD), a Digital Video Disk (DVD), a digital tape, a computer memory, etc.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by that the reader that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended as (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent. The various aspects and embodiments disclosed herein are for purposes of illustration and are not intended to be limiting, with the true scope and spirit being indicated by the following claims.

What is claimed is:

1. A method of operating a lumen traveling device with a lumen traveling device control system, comprising:
    identifying at least two possible directions of travel of an untethered lumen traveling device through a body tube tree with control circuitry in the lumen traveling device control system located at least in part on the lumen traveling device, the body tube tree including a plurality of branched, interconnected channels, and the at least two possible directions of travel corresponding to at least two of the branched, interconnected channels;
    receiving data with the control circuitry, the data representing at least one parameter value sensed with a sensor within the body tube tree on the lumen traveling device from at least one of the at least two possible directions of travel of the lumen traveling device through the body tube tree;
    selecting a direction of travel with the control circuitry, the direction of travel selected from the at least two directions of travel based at least in part on the data representing at least one parameter value sensed with the sensor from at least one of the at least two possible directions of travel of the lumen traveling device through the body tube tree; and
    directing at least one of a steering mechanism and a propelling mechanism within the body tube tree on the lumen traveling device with the control circuitry to cause the lumen traveling device to move through the body tube tree in the selected direction of travel;
    wherein selecting the direction of travel with the control circuitry from the at least two directions of travel based at least in part on the data representing at least one parameter value sensed with the sensor from at least one of the at least two possible directions of travel of the lumen traveling device through the body tube tree includes selecting a direction of travel from the at least two directions of travel based at least in part on the data representing parameter values sensed at two or more times by comparing a rate of change of at least one parameter from the at least two possible directions of travel and selecting the direction of travel from the group consisting of the direction of travel having a lowest rate of change of the at least one parameter and the direction of travel having a highest rate of change of the at least one parameter.

2. The method of claim 1, including
    identifying a stop condition based at least in part on the data representing at least one parameter value sensed from the at least two possible directions of travel of the lumen traveling device through the body tube tree; and
    directing at least one of the steering mechanism and the propelling mechanism to cause the lumen traveling device to stop moving through the body tube tree.

3. The method of claim 1, including
    storing the data representing at least one parameter value sensed with the sensor from the at least two possible directions of travel of the lumen traveling device through the body tube tree in a memory location within the body tube tree on the lumen traveling device.

4. The method of claim 1, including
    storing instructions related to directing at least one of the steering mechanism and the propelling mechanism to cause movement of the lumen traveling device in a memory location within the body tube tree on the lumen traveling device.

5. The method of claim 4, including receiving the instructions from a remote device.

6. The method of claim 1, including
    transmitting the data representing at least one parameter value sensed with the sensor from at least one of the at least two possible directions of travel of the lumen traveling device through the body tube tree from the lumen traveling device to a remote device.

7. The method of claim 1, including
    transmitting instructions related to directing at least one of the steering mechanism and the propelling mechanism to cause movement of the lumen traveling device from the lumen traveling device to a remote device.

8. The method of claim 1, including
    receiving information related to whether or not at least one of the at least two possible directions of travel of the lumen traveling device through the body tube tree has previously been traveled by the lumen traveling device; and
    selecting the direction of travel with the control circuitry from the at least two possible directions of travel based at least in part on the information related to whether or not the at least one of the at least two possible directions of travel of the lumen traveling device through the body tube tree has previously been traveled by the lumen traveling device.

9. The method of claim 1, wherein directing the at least one of the steering mechanism and the propelling mechanism within the body tube tree on the lumen traveling device with the control circuitry to cause the lumen traveling device to move through the body tube tree in the selected direction of travel includes directing the at least one of the steering mechanism and the propelling mechanism within the body tube tree on the lumen traveling device to cause the lumen traveling device to move through the body tube tree in the selected direction of travel for a pre-determined distance, for a pre-determined duration, or until a stop instruction is received from a remote device by the lumen traveling device.

10. The method of claim 1, including receiving at least one user input instruction from a medical care provider, the user input instruction related to selecting at least one of a parameter type or a parameter value range for the at least one parameter value sensed with the sensor from the at least two possible directions of travel of the lumen traveling device through the body tube tree.

11. The method of claim 1, wherein receiving the data representing at least one parameter value sensed with the sensor from the at least two possible directions of travel of the lumen traveling device through the body tube tree includes receiving data representing at least one of an analyte, a temperature, a pressure, a fluid flow, a structural parameter of at least one of the plurality of branched interconnected channels, an electrical field, a magnetic field, an electromagnetic signal, an acoustic signal, or an optical signal.

12. The method of claim 1, wherein receiving the data with the control circuitry further includes receiving data from a remote device.

13. The method of claim 1, wherein directing the at least one of the steering mechanism and the propelling mechanism within the body tube tree on the lumen traveling device to cause the lumen traveling device to move through the body tube tree in the selected direction of travel includes directing at least one of the steering mechanism and the propelling mechanism within the body tube tree on the lumen traveling device to cause the lumen traveling device to turn, cause the lumen traveling device to continue moving in a current direction of travel, cause the lumen traveling device to reverse its direction of travel, cause movement of the lumen traveling device based on a previous movement direction, cause the lumen traveling device to move in a different direction than the direction it was previously instructed to move, or cause the lumen traveling device to move in the same direction it was previously directed to move.

14. The method of claim 1, further comprising detecting an arrival of the lumen traveling device at a branch point in the body tube tree based on a signal from at least one arrival sensor on the lumen traveling device, the branch point including the at least two of the branched, interconnected channels corresponding to the at least two possible directions of travel.

15. The method of claim 1, wherein receiving data representing at least one parameter value sensed from at least one of the at least two possible directions of travel of the lumen traveling device through the body tube tree includes receiving data representing an analyte, the analyte selected from a list consisting of a chemical, a biomaterial, an ion, an electrolyte, a biological marker, an antibody, a polypeptide, a protein, a nuclueic acid, an oligonucleotide, a polynucleotide, a complex, a pathogen, a signaling-material, a lipid, an alcohol, a sterol, a steroid, a carbohydrate, a sugar, a drug, a therapeutic, a gas, a metabolite, a cytokine, a chemokine, a hormone, an inflammatory molecule, a cell, and a cell fragment.

16. The method of claim 1, wherein selecting the direction of travel with the control circuitry from the at least two directions of travel based at least in part on the data representing at least one parameter value sensed with the sensor from the at least two possible directions of travel of the lumen traveling device through the body tube tree further includes avoiding at least one direction of travel if the data representing the at least one parameter value sensed with the sensor from the at least one direction of travel indicates that the at least one direction of travel is non-navigable by the lumen traveling device.

17. An untethered lumen traveling device system comprising: a sensor, a steering mechanism and/or a propelling mechanism, and a lumen traveling device control system including non-transitory machine readable media including:
- one or more instructions that cause the lumen traveling device control system to identify at least two possible directions of travel of the untethered lumen traveling device through a body tube tree, the body tube tree including a plurality of branched, interconnected channels, and the at least two possible directions of travel corresponding to at least two of the branched, interconnected channels;
- one or more instructions that cause the lumen traveling device control system to receive data representing at least one parameter value sensed with the sensor within the body tube tree on the lumen traveling device from the at least two possible directions of travel of the lumen traveling device through the body tube tree;
- one or more instructions that cause the lumen traveling device control system to select a direction of travel from the at least two directions of travel based at least in part on the data representing at least one parameter value sensed with the sensor from at least one of the at least two possible directions of travel of the lumen traveling device through the body tube tree; and
- one or more instructions that cause the lumen traveling device control system to direct at least one of the steering mechanism and the propelling mechanism within the body tube tree on the lumen traveling device to cause the lumen traveling device to move through the body tube tree in the selected direction of travel; wherein the one or more instructions that cause the lumen traveling device control system to select the direction of travel from the at least two directions of travel based at least in part on the data representing at least one parameter value sensed with the sensor from at least one of the at least two possible directions of travel of the lumen traveling device through the body tube tree include one or more instructions for comparing a rate of change of at least one parameter from the at least two possible directions of travel and selecting the direction of travel from the group consisting of the direction of travel having a lowest rate of change of the at least one parameter and the direction of travel having a highest rate of change of the at least one parameter.

* * * * *